United States Patent
Allen et al.

(10) Patent No.: US 12,130,230 B2
(45) Date of Patent: *Oct. 29, 2024

(54) NON-DESTRUCTIVE ASSAY FOR SOYBEAN SEEDS USING NEAR INFRARED ANALYSIS

(71) Applicant: PIONEER HI-BRED INTERNATIONAL, INC., Johnston, IA (US)

(72) Inventors: Ross M Allen, Des Moines, IA (US); John D Everard, Grimes, IA (US); Min Ren, Johnston, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/305,333

(22) Filed: Apr. 22, 2023

(65) Prior Publication Data

US 2024/0060886 A1 Feb. 22, 2024

Related U.S. Application Data

(63) Continuation of application No. 17/655,190, filed on Mar. 17, 2022, now Pat. No. 11,668,651, which is a continuation of application No. 16/490,261, filed as application No. PCT/US2018/019683 on Feb. 26, 2018, now Pat. No. 11,307,139.

(60) Provisional application No. 62/466,575, filed on Mar. 3, 2017.

(51) Int. Cl.
| | | |
|---|---|---|
| *G01N 21/84* | (2006.01) | |
| *B07C 5/342* | (2006.01) | |
| *C12N 15/82* | (2006.01) | |
| *G01N 21/3563* | (2014.01) | |
| *G01N 21/359* | (2014.01) | |
| *G01N 33/02* | (2006.01) | |

(52) U.S. Cl.
CPC ......... *G01N 21/359* (2013.01); *B07C 5/3425* (2013.01); *C12N 15/8245* (2013.01); *C12N 15/8247* (2013.01); *G01N 21/3563* (2013.01); *G01N 21/84* (2013.01); *G01N 33/025* (2013.01); *G01N 2021/8466* (2013.01)

(58) Field of Classification Search
CPC .. G01N 21/359; G01N 21/3563; G01N 21/84; G01N 33/025; B07C 5/3425; C12N 15/8245; C12N 15/8247
See application file for complete search history.

(56) References Cited

U.S. PATENT DOCUMENTS

| | | | |
|---|---|---|---|
| 4,752,689 A | 6/1988 | Satake | |
| 6,646,264 B1 * | 11/2003 | Modiano | G01N 21/3563 356/326 |
| 7,600,642 B2 | 10/2009 | Deppermann | |
| 9,227,230 B2 * | 1/2016 | Bensley-Bromilow | G01N 21/3563 |
| 9,387,518 B2 * | 7/2016 | Deppermann | B07C 5/361 |
| 11,307,139 B2 * | 4/2022 | Allen | B07C 5/3425 |
| 11,668,651 B2 * | 6/2023 | Allen | C12N 15/8245 209/587 |
| 2013/0040826 A1 * | 2/2013 | Braun, III | C12Q 1/6809 506/2 |
| 2018/0010142 A1 * | 1/2018 | Davies | A23L 25/30 |
| 2023/0200322 A1 * | 6/2023 | Bettis | C12Q 1/6895 800/276 |

FOREIGN PATENT DOCUMENTS

| | | |
|---|---|---|
| CN | 109211784 A | 1/2019 |
| CN | 110018134 A | 7/2019 |

OTHER PUBLICATIONS

Hollung, Kristin et al.: Evaluation of Nonstarch Polysaccharides and Oligosaccharide Content of Different Soybean Varieties (Glycine max) by Near-Infrared Spectroscopy and Proteomics, J. Agric. Food Chem., Oct. 14, 2005 (Oct. 14, 2005), vol. 53, pp. 9112-9121 (Year: 2005).*

Choung, Myoung-Gun; Determination of Sucrose Content in Soybean Using Near-infrared Reflectance Spectroscopy; J. Korean Soc. Appl. Biol. Chem., 2010. (Year: 2010).*

Hollung, Kristin; et al.: "Evaluation of Nonstarch Polysaccharides and Oligosaccharide Content of Different Soybean Varieties (Glycine max) by Near-Infrared Spectroscopy and Proteomics", J. Agric. Food Chem., Oct. 14, 2005 (Oct. 14, 2005), vol. 53, pp. 9112-9121.

Poysa, V.; et al.: "Stability of soybean seed composition and its effect on soymilk and tofu yield and quality", Food Research International, 2002, vol. 35, No. 4, pp. 337-345.

International Search Report and Written Opinion, International Application No. PCT/US2018/019683, mailed May 2, 2018.

* cited by examiner

*Primary Examiner* — Patrick H Mackey

(57) ABSTRACT

Disclosed are methods and systems for spectral imaging of soybean samples to accurately and non-destructively measure the amount of sucrosyl-oligosaccharide in the soybean samples. Populations containing modified and unmodified soybean seeds and having varying amounts of sucrosyl-oligosaccharides, oil or protein can be sorted and separated and further used in soybean processing or breeding.

20 Claims, No Drawings

Specification includes a Sequence Listing.

NON-DESTRUCTIVE ASSAY FOR SOYBEAN SEEDS USING NEAR INFRARED ANALYSIS

REFERENCE TO SEQUENCE LISTING SUBMITTED ELECTRONICALLY

The official copy of the sequence listing is submitted electronically via Patent Center as an XML formatted sequence listing with a file named BB2225_SequenceListing created on Oct. 30, 2023, and having a size of 149,262 bytes and is filed concurrently with the specification. The sequence listing comprised in this XML formatted document is part of the specification and is herein incorporated by reference in its entirety.

BACKGROUND

Soybeans are the world's foremost provider of vegetable protein and oil. Soybean oil is used in food and industrial products. Soybean flakes remaining after the removal of oil can be processed into various edible soy protein products or used to produce soybean meal for animal feeds.

Soybean seed reserves can be repartitioned through plant research and breeding techniques. Analytical techniques facilitate research by permitting assessment of the composition of the soybean seed, soybean flakes and soybean meal.

SUMMARY

Non-destructive methods for accurately measuring the amount of a sucrosyl-oligosaccharide, such as stachyose, or a combination of stachyose and raffinose, in a soybean seed are provided which include steps of directing near infrared light from a light source onto a soybean seed to form modified light from the soybean seed, receiving the modified light in an imaging device, and measuring the amount of a sucrosyl-oligosaccharide in the soybean seed based on the received modified light. The amount of the sucrosyl-oligosaccharide can be measured to an accuracy that is within 0.2 wt. %, 0.3 wt. %, 0.4 wt. %, 0.5 wt. %, 0.6 wt. %, 0.7 wt. %, 0.8 wt. %, 0.9 wt. %, 1 wt. %, 1.1 wt. %, 1.2 wt. %, 1.3 wt. %, 1.4 wt. %, or 1.5 wt. % of the amount measured using a standard reference analytical method. Following measurements, the seed can be optionally transported to a first or second location depending on whether the amount of sucrosyl-oligosaccharide measured is above or below a threshold value. The threshold value for stachyose can be selected to be, for example, 1 wt. %, 0.9 wt. %, 0.8 wt. %, 0.7 wt. %, 0.6 wt. %, 0.5 wt. %, 0.4 wt. %, 0.3 wt. %, 0.2 wt. % or 0.1 wt. %.

The methods can be used with a single seed or a plurality of seeds in a batch and the method steps can be repeated multiple times. The sucrosyl-oligosaccharide can be accurately measured in at least 80%, 85%, 90%, 95%, 96%, 97%, 98% or 99% of the measurements taken. The methods are non-destructive and preserve the viability of the seed or otherwise permit other compositional analyses or processing to be undertaken. For stachyose measurements, the imaging device can be calibrated using a plurality of soybean seeds having variable stachyose contents falling in a range that includes values of less than 0.1 wt. %, 0.2 wt. %, or 0.3 wt. % stachyose and more than 4.5 wt. %, 5 wt. % or 5.5 wt. % stachyose. In some embodiments, the seed is genetically modified to overexpress a diglyceride acyltransferase.

Provided are methods for measuring stachyose in a population of soybean seeds by directing near infrared light from a light source onto a first and second subsample of a population of soybean seeds to form a first and second modified light, which is received in an imaging device and used to measure the amount of a sucrosyl-oligosaccharide in the first and second subsamples. The first and second subsamples are separated when the amount of stachyose measured differs by at least 1 percentage point between the subsamples and are combined when the amount of stachyose differs by less than 0.2 percentage points between the first and second subsamples. The population can, for example include genetically modified and unmodified soybean seeds, such as a modified diacylglycerol transferase and the oil content of the modified beans may be at least 1 percentage point higher than of the unmodified soybean seeds.

Provided are methods for processing soybean seeds which have been genetically modified to contain high oil, high protein, or a combination thereof compared with unmodified soybean seeds which include the steps of directing near infrared light from a light source onto a sample comprising or being a soybean seed to form modified light from the soybean seed which is received in an imaging device and used to measure the amount of a sucrosyl-oligosaccharide, such as stachyose or a combination of stachyose and raffinose, in the sample. The method steps can be repeated for at least 10 samples and soybean seeds above a threshold value, which indicates high oil, high protein, or a combination thereof, can be separated from soybean seeds below the threshold value. The method is sufficiently robust such that at least 90% of the soybean seeds below the threshold value are modified soybean seeds or at least 90% of the seeds above the threshold value are unmodified soybean seeds. The amount of sucrosyl-oligosaccharide can be measured to an accuracy that is within 0.2 wt. %, 0.3 wt. %, 0.4 wt. %, 0.5 wt. %, 0.6 wt. %, 0.7 wt. %, 0.8 wt. %, 0.9 wt. %, 1 wt. %, 1.1 wt. %, 1.2 wt. %, 1.3 wt. %, 1.4 wt. %, or 1.5 wt. % of the amount measured using a standard reference analytical method. In some embodiments, at least one of the modified seeds that is separated is grown and crossed with the same or a different soybean plant to produce progeny seed. The progeny seed can be grown and crossed with another plant having a genetic modification, such as a recombinant construct incorporated into its genome, to produce further progeny seed, the genetic modification optionally providing one or more traits such as herbicide tolerance, disease resistance, insect resistance, increased grain yield, increased nutritional content, increased growth rate, enhanced stress tolerance, altered maturity. The method can include an initial step of separating the sample comprising the soybean seed from the plurality of seeds such as in an automated method. The method can include the step of measuring the amount of oil in the seed based on the received modified light.

Provided are methods for processing soybean seeds which include seeds genetically modified to contain increased oil and increased protein and unmodified soybean seeds. The methods include the steps of directing near infrared light from a light source onto a sample comprising a soybean seed to form modified light from the soybean seed which is received in an imaging device and used to measure the amount of a sucrosyl-oligosaccharide, such as stachyose or a combination of stachyose and raffinose, in the soybean seed. The method steps are repeated for at least 100 samples or seeds. The amount of sucrosyl-oligosaccharide measured below a threshold value indicates high oil and high protein in the soybean seed and the measurements taken are such that at least 90% of the soybean seeds below the threshold value are the modified soybean seeds or at least 90% of the seeds above the threshold value are the unmodified soybean seeds. The seeds above the threshold value can differ by a least 1 wt. % stachyose from the seeds below the threshold value. The seeds can be further processed for removal of oil and production of soy flakes or meal.

Provided are methods for measuring the amount of a sucrosyl-oligosaccharide, such as stachyose, or a combination of stachyose and raffinose, in soybean meal or soybean flakes. The methods include the steps of directing near infrared light from a light source onto a soybean meal sample to form modified light from the soybean meal sample which is received in an imaging device and used to measure the amount of a sucrosyl-oligosaccharide in the soybean meal sample. The amount of the sucrosyl-oligosaccharide can be measured to an accuracy that is within 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, 1 wt. %, 1.1 wt. %, 1.2 wt. %, 1.3 wt. %, 1.4 wt. %, or 1.5 wt. % of the amount measured using a standard reference analytical method.

DETAILED DESCRIPTION

Systems and methods for the sampling of soybean seeds and measurement of soybean seed components are provided, which permit individual seed analysis, soybean meal, flake or powder analysis, or analysis of bulk seeds in an accurate, non-destructive and efficient manner. The term "soybean" refers to the species *Glycine max, Glycine soja*, or any species or line that is sexually cross compatible with *Glycine max*. Unless indicated to the contrary, seed as used herein means soybean seed. Following analysis, the soybean seeds can be grown and allowed to self or be crossed with genetically different soybean plants to produce progeny seed that can be used in a plant breeding program. The systems and methods further permit efficient processing of the soybeans according to their composition, such as to produce oil and protein flakes or meal. The analysis includes accurate measurement of one or more sucrosyl-oligosaccharides. A sucrosyl-oligosaccharide is generally understood to be a short-chain, non-digestible oligosaccharide such as stachyose, raffinose and verbascose. Because verbascose and other minor sucrosyl-oligosaccharides are present in very low amounts, as used in this application, a sucrosyl-oligosaccharide means one or more of stachyose and raffinose.

Destructive analytical methods for the measurement of seed components such as oil, fatty acids, protein and sucrosyl-oligosaccharides are those which directly measure the component including steps such as powdering the material, extraction of the sucrosyl-oligosaccharide, and detection of the amount or concentration of sucrosyl-oligosaccharide using chromatographic methods. Certain of these methods are accredited by professional associations (e.g., American Oil Chemists Society (AOCS); the American Association of Analytical Chemists (AOAC); American Association of Cereal Chemists (AACC) or international standards accreditation agencies, e.g., The Codex Alimentarius, International Organization for Standards (ISO) and the International Union of Pure and Applied Chemistry (IUPAC)). While accurate, such methods are time consuming and typically require a large sample size; for example, 60 g or more of whole soybeans, a portion of which may be used to determine the moisture contents of the samples, to enable compositional reporting on a defined moisture basis. For example, an accredited method for oil content is AOCS Official Method Ba 3-38 which gravimetrically measures the oil content of powdered seed material after extraction with petroleum ether. An example of an accredited method for protein content is AOAC 990.03 or AOCS Ba 4e-93 which determine the protein content of ground soybean powders by combustion analysis.

Destructive analytical methods for analysis of raffinose and stachyose can be based on methods that have been validated for quantitation of simple sugars in cereal products (e.g., AACC Method 80-04 Determination of Simple Sugars (fructose, glucose, sucrose, maltose and lactose) in Cereal Products-HPLC Method; AOAC Official Method 982.14 Glucose, Fructose, Sucrose, and Maltose in Presweetened Cereals; Black, L. T., and Glover, J. D., 1980. A Simple and rapid HPLC analysis of sugars in soybeans and the factors affecting their standardization. Journal of the American Oil Chemists Society 1980; 143. However, a harmonized cross-validated method is not available.

Methods, systems and devices provided herein measure the amount of one or more sucrosyl-oligosaccharides in a soybean seed using non-destructive methods to an accuracy that is representative of the amount measured using standard reference analytical methods. The term "accuracy" refers to the degree to which the result of a measurement, calculation, or specification conforms to the correct value, a standard, or reference value. Useful examples of such values which may be achieved are accuracies within at least 25%, 20%, 19%, 18%, 17%, 16%, 15%, 14%, 13%, 12%, 11%, 10%, 9%, 8%, 7%, 6%, 5%, 4%, 3%, 2%, or 1% of the amount measured using a standard reference analytical method as described herein, such as by weight. The accurate measurements may be achieved for at least 75%, 80%, 85%, 90%, 95%, 96%, 97%, 98%, 99%, 99.5%, or 99.9% of a population of seeds, a plurality of seeds, a plurality of individual or a plurality of seed samples measured. The size of the population or plurality of seeds can be at least 1, 2, 3, 4, 5, 10, 15, 20, 25, 30, 35, 40, 45, 50, 60, 70, 80, 90, 100, 150, 200, 250, 300, 400, 500, 750, 1000, 2000, 3000, 5000, 10000, 100000, or 1,000,000 individual seeds or seed batches. The term "reference chemistry" refers to the benchmark values obtained for the measurements of the compositions analyzed herein, using standard reference analytical methods. As used herein, the "standard reference analytical method" used for measuring stachyose, raffinose or a combination thereof is a chromatographic (wet-chemistry) technique performed as follows. One of skill in the art will understand that certain substitutions in the components and steps used in the following methods may be made without affecting the results of the analysis:

Grinding

Analysis is performed on soybeans, ground into fine powders with a particle size ranging between 0.5 to 0.9 mm. For single soybean seed, grinding is performed in Spex Certiprep ½×2" polycarbonate vials with cap (cat #3116PC). A ⅜" stainless steel ball bearing is used to pulverize the seed using a Spex Certiprep 2000 Geno/Grinder at 1500 strokes/min for three, 30 second bursts, with a 1-minute rest between each cycle. Samples are retained in the grinding vial at room temperature, in the dark, to minimize moisture loss prior to further analysis.

For bulk samples, approximately seventy-five gram batches of beans are ground in a Foss Knifetec 1095 grinder (commercially available from FOSS North America, Eden Prairie, MN). The grinding chamber is cooled prior to and during the process by a circulating chiller set to 14° C. Samples are ground for 6×10 second bursts using a standard rotor blade. At the conclusion of each 10 second grinder burst the chamber is opened and the powder in the chamber is loosened and any material adhering to the chamber wall is returned to the center of the chamber, using a small rubber spatula. After grinding the powders are quantitatively recovered from the chamber and transferred to plastic specimen cups fitted with airtight lids (Fisher Brand, part number 14828321) to ensure minimal moisture loss prior to analysis. The sample chamber and blade are cleaned thoroughly with a soft brush and pneumatic air prior to introduction of the next sample. Sample cups were stored at room temperature in the dark prior to further analysis. Ground samples were not sieved or otherwise treated prior to further analysis, this ensured that the sub-aliquot analyzed is fully representative of the original bulk sample and allows small subsamples to be used to provide data that is representative of the whole.

Powder Moisture Content Determination

The moisture contents of the ground soybean powders are determined according to AOCS Official Method Ba 2a-38, which can be modified for small samples as described below. In order to standardize analytical results for moisture content, 100-200 mg samples are weighed (recorded to an accuracy of 0.1 mg) into 13×100 mm sample tubes (VWR part number 53283-800). The samples are placed in a forced draft oven, set to 130° C. for two hours and are then allowed to equilibrate to room temperature, in a desiccator, prior to reweighing. Moisture contents are calculated according to the following formula:

$$\text{Moisture} = \frac{(\text{wt. tube} + \text{tissue as is} - \text{wt. tube}) - (\text{wt. tube} + \text{tissue dry} - \text{wt. tube})}{(\text{wt. tube} + \text{tissue as is} - \text{wt. tube})} \times 100$$

Moisture contents are used to adjust analytical results to a common moisture content using the following formula:

Analyte at desired moisture content, % =

$$\frac{F(100 - \% \text{ moisture content desired})}{(100 - \% \text{ moisture content of ground sample})}$$

Where F is the measured wt. % of the analyte in the ground sample.

Extraction of Soluble Carbohydrates

Prior to carbohydrate analysis samples are de-fatted as follows: Weigh powdered sample (approximately 20-30 mg; to an accuracy of 0.1 mg) into 13×100 mm tube (with Teflon® lined cap; VWR (53283-800)) and record weight. Add 2 mL Heptane, vortex and place into an ultrasonic bath (VWR Scientific Model 750D) at 60° C. for 15 min at full sonification-power (~360 W). Centrifuge for 5 min at 1700×g at room temperature. Decant the supernatant to a clean 13×100 mm glass tube; this sample is used to determine fatty acid profiles of the extracted oil. Add 1 mL acetone to the de-fatted pellet, vortex mix to disperse the material into the acetone and dry in a SpeedVac (Thermo Fisher Scientific 275 Aiken Road, Ashville, NC 28804). To the dry pellet add 2 mL of 80% ethanol. Vortex to break up pellet as much as possible. Extract on sonicator for 15 min at 60° C. Centrifuge for 5 min at 1700×g. Transfer supernatant to a clean 13×100 mm tube. Repeat the ethanol extraction two more times, combining all of the supernatants. Add 100 µL of phenyl-β-D glucopyranoside internal standard (phenyl-β-D glucopyranoside stock 0.5000+/−0.0010 g in 100 ml water) to the combined supernatant. Dry the extract in the SpeedVac and analyze for soluble carbohydrates as described below. Add 1 ml acetone to the extracted pellets and dry in the SpeedVac.

Starch Digestion and Extraction

The starch digestion is performed directly on the acetone dried pellets from soluble carbohydrate extraction. Add 100 units of α-Amylase (α-amylase; Heat Stable from *Bacillus licheniformis* Sigma-Aldrich A-4551) in 0.9 mL 50 mM MOPS (3-(N-Morpholino) propane sulfonic acid) buffer pH 7.0, containing 5 mM $CaCl_2$ and mix. Place tubes into a heating block at 90° C. for 75 minutes. Mix several times during hydrolysis. Allow the tubes to cool to room temperature and add 5 units of Amyloglucosidase (commercially available from Roche 11 202 367 001) in 0.6 mL of 285 mM acetate buffer, pH 4.5 and incubate in a reciprocating water bath at 55° C. for 15-18 hours. Remove rack of tubes and bring to room temperature. Add 4.5 mL of absolute ethanol to each tube, to attain a final ethanol concentration 80% and vortex mix. Extract on sonicator for 15 min at 60° C. Centrifuge 5 min at 1700×g and decant supernatant to a 13×100 mm tube and immediately place tube in SpeedVac to reduce the volume. Extract pellet a further 2 times with 2 mL 80% ethanol, combining supernatant with above each time. Add 100 µL of phenyl-β-D glucopyranoside (see above) to the combined supernatant before it is fully dry. Once the extract in the SpeedVac is dry analyze for soluble carbohydrates as described below.

Total Soluble Carbohydrate Derivatization and Analysis

The dried samples from the soluble and starch extractions described above along with sets of sugar standard mixtures (containing; pinitol, sorbitol, fructose, glucose, myo-inositol, sucrose, raffinose and stachyose; at 0, 0.05, 0.1, 0.5, 1.00, 2.00, and 3.00 mg/tube; each containing the same amount (0.5 mg) of phenyl-β-D glucopyranoside internal standard) were solubilized in 1 ml anhydrous pyridine (Sigma-Aldrich P57506) containing 30 mg/ml of hydroxylamine HCl (Sigma-Aldrich 159417). Samples were placed on an orbital shaker (350 rpm) overnight and were then heated for 1 hr (75° C.) with vigorous vortex mixing applied every 15 min. After cooling to room temperature 1 ml hexamethyldisilazane (Sigma-Aldrich H-4875) and 100 µL trifluoroacetic acid (Sigma-Aldrich T-6508) are added. The samples are vortex mixed and the precipitates are allowed to settle prior to transferring the supernatants to GC sample vials.

Samples are analyzed on an Agilent 6890 gas chromatography system fitted with a DB-17MS capillary column (30 m×0.32 mm×0.25 um film). Inlet and detector temperatures are both 275° C. After injection (2 µL, 20:1 split) the initial column temperature (150° C.) was increased to 180° C. at a rate 3° C./min and then at 25° C./min to a final temperature of 320° C. The final temperature is maintained for 10 min. Hydrogen gas is used as the carrier at a linear velocity of 51 cm/sec. Detection is by flame ionization. A 1 m length of plain 0.320 mm capillary tube (Agilent; 160-2325-5) is inserted between the inlet and the analytical column to act as a guard column. The two column sections are connected using a push-fit connector. Prior to all analytical runs three injections of a standard mixture containing 3 mg of each sugar is made to passivate the chromatography system. This process was found to enable full recovery of stachyose from the analytical samples, especially as the column aged. Ultra-Inert Inlet Liners (Agilent; 5190-3164) are used and are routinely changed based on indications of loss in stachyose recovery from the lowest concentration standard.

Data analysis is performed using Agilent ChemStation software. Each sugar is quantified relative to its own calibration curve, after dividing each individual peak by the area of the internal standard in each sample and standard. Final carbohydrate concentrations are expressed corrected for moisture content (see above). Residual sucrose, raffinose and stachyose recovered in the starch digestions are included in the total values reported for each sugar.

Soybean samples with a wide range in the amount sucrosyl-oligosaccharide, such as raffinose, stachyose, or a combination thereof can be accurately measured using these standard reference chemistry methods, facilitating the development spectroscopic techniques for accurate non-destructive measurements.

As used herein, the standard reference analytical method used for measuring the moisture content of whole beans is AOCS Official Method Ac 2-41, which measures the weight loss of a sample after a defined period in a forced draft oven heated to 130° C.

As used herein, the standard reference analytical method used for measuring the moisture content of soybean powders is AOCS Official Method Ba 2a-38, which measures the weight loss of a sample after a defined period in a forced draft oven heated to 130° C.

As used herein, the standard reference analytical method used for measuring oil is AOCS Official Method Ba 3-38 which gravimetrically measures the oil content of powdered seed material after extraction with petroleum ether.

As used herein, the standard reference analytical method used for measuring protein content is AOCS Ba 4e-93 which determines the protein content of ground soybean powders by combustion analysis.

As used herein, the standard reference analytical method used for measuring PROIL is the addition of the oil and protein contents determined by the standard reference analytical methods defined above.

As used herein, the standard reference analytical method used for determining fatty acid profiles is AOCS Official Method Ce 1e-91 on methyl esters derived from oil samples extracted from soybean powders.

The amount of sucrosyl-oligosaccharide such as stachyose, raffinose or a combination thereof in intact, whole, single or pooled soybean seeds can be measured using optical interrogation devices employing near infrared spectroscopy to an amount that is within at least 15%, 14%, 13%, 12%, 11%, 10%, 9%, 8%, 7%, 6%, 5%, 4%, 3%, 2%, or 1% of the amount measured using the standard reference analytical method described herein. Accuracy can be contrasted with precision, which refers to the closeness of two or more measurements to each other. Accurate and precise measurements of sucrosyl-oligosaccharides are achievable according to methods described herein. Precision with respect to the composition of soybean seed sample under analysis refers how closely replicate measurements of the same sample result in similar concentration or amounts being measured each time. Accuracy, with respect to the composition of soybean seed sample under analysis refers to the measured concentration or measured amount of the component of interest being similar to or the same as that obtained when running the standard reference analytical method on the same sample.

The accuracy obtained using the methods described herein is reproducible across multiple seeds or seed samples and facilitates high-throughput assessment on the composition of soybean seeds. For example, if a population of at least 10, 20, 50, 100, 250, 500, 1,000, 5,000, 10,000, 1,000,000, or 1,000,000 soybean seeds are measured using individual single-seed analysis, the amount of raffinose or stachyose may be accurately determined to within parameters described herein for at least 75%, 80%, 85%, 90%, 91%, 92%, 93%, 94%, 95%, 96%, 97%, 98%, 99%, 99.5% or 99.9% of the population of seeds.

Near Infrared Spectroscopy (NIRS) is a non-destructive tool for analyzing seed composition, with measurements based on the absorption of light energy (about 780 to 2500 nm) by H2O, C—C, C—H, O—H, N—H, S—H and C═O bonds in the organic constituents of the materials being analyzed. The present disclosure provides methods which are based on NIRS and on the absorption of light energy, in the near-infrared spectrum range (780 to 2500 nm), in the organic constituents of the materials being analyzed. Near infrared reflectance (NIR) and near infrared transmittance (NIT) light spectra can be collected and used. For example, methods described herein can be carried out as single-seed NIR (SS-NIR), bulk NIT or FT-NIR. The absorption of the light energy is proportional to the concentration of the constituent of interest and the modified light comprising one or more of transmitted and reflected light spectra from the seed can be converted to accurately measure the amounts or concentrations of the constituent of interest, such as a sucrosyl-oligosaccharide. "Modified light" as used in the context of this disclosure means light that is transmitted (transmitted light) and/or reflected (reflected light) from a seed or other object such as soybean meal or defatted soybean flakes after receiving light from a light source. Transflected light is a combination of reflected and transmitted light and is included in modified light.

In some embodiments, such as when single seed NIR (SS-NIR) is used, a suitable spectral range for a sucrosyl-oligosaccharide such as stachyose includes one or more values at or about 850 nm, 866 nm, 880 nm, 890 nm, 902 nm, 910 nm, 920 nm, 930 nm, 944 nm, 952 nm, 964 nm, 978 nm, 990 nm, 1004 nm, 1016 nm, 1032 nm, and 1042 nm, such as one or more values falling within 850-852 nm, 862-868 nm, 876-884 nm, 888-892 nm, 900-904 nm, 908-912 nm, 918-922 nm, 930-934 nm, 940-944 nm, 950-954 nm, 962-968 nm, 976-982 nm, 988-996 nm, 1000-1008 nm, 1012-1020 nm, 1026-1036 nm and 1040-1046 nm. In some embodiments, such as when FT-NIR is used, a suitable spectral region for a sucrosyl-oligosaccharide such as stachyose includes values at or about 1157-1283 nm and 1437-2254 nm. In some embodiments, such as when NIT is used for whole soybeans, a suitable spectral range for a sucrosyl-oligosaccharide such as stachyose includes values at or about 918, 930, 940, 950, 964, 980, and 996 nm.

In some embodiments, spectrometers are used to collect spectra from samples of soybeans, such as single seeds (e.g., SS-NIR), batches of seed from a single plant (e.g., FT-NIR), bulk samples from a field plot (e.g., NIT) or protein compositions such as protein meal and defatted soybean flakes (NIR). Protein meal can be produced by extracting oil from dried cleaned soybeans to produce dried defatted soy flakes, and processing the defatted soy flakes to produce soybean meal. Measurements taken are compared to the standard reference analytical method for samples sizes (single seeds or bulk samples). In some embodiments a diverse array of soybean samples grown in different seasons and different environments that display a wide range in the concentrations of the components are used to generate calibrations that provide for reliable and accurate measurements of the components.

In the methods provided, the conversion from modified light spectra from the soybean to the concentration of the constituent of interest is determined by a referencing to spectra from seeds where the constituent of interest has been measured using the standard reference analytical method for the component of interest as disclosed herein. Interpreting the near infrared spectral region (780-2500 nm) of seeds is complex for a number of reasons. Absorption in this region contains weaker overtones or harmonics of the fundamental frequencies and in combination bands, where absorption occurs in two or more overlapping fundamental bond energies. The energy absorption and resulting spectra are therefore composite vibrational signals of all of the resonating bonds within the organic components and water in the seed being analyzed. The spectral signal from any specific component is deciphered from the background and is influenced by the matrix that it is embedded in. For example, the molecular specific signal within an intact seed can be influenced by the environment such as geographic location, growing season, storage conditions and conditions during measurement, the genetic background, and the presence of similar molecules.

In some embodiments, accurate measurements of sucrosyl-oligosaccharides in a seed are achieved by utilizing a broad array of samples in which compounds with similar chemical compositions, such as sucrose, stachyose and raffinose, differ in a reciprocal manner. The sucrosyl-oligosaccharide specific signal is detected in the seed by having the sucrosyl-oligosaccharide present in a reciprocal concentration series of related molecules and visa-versa. A collection of mature soybean seeds that have significant differences in the concentrations of the sucrosyl-oligosaccharides facilitates this approach. The amount or concentration of sucrosyl-oligosaccharides can also be measured in seeds having the same or similar genetics that have been grown in multiple environments and over multiple seasons.

The measurements may be taken at any moisture content of the soybean. The moisture content of the soybean affects the weight percentages of components of the soybean, with drier beans generally having a higher weight percent of the component, such as oil, protein or sucrosyl-oligosaccharide. When comparing NIR-based measurements with standard reference analytical methods, measurements may be taken in each case at the same moisture content of soybean, or if measurements are taken at different moisture contents, the values obtained can be corrected to the same moisture content. Measurements can, for example, be taken at or standardized to a moisture content by weight of at least or at least about 0.01%, 0.1%, 0.5%, 1%, 2%, 3%, 4%, 5%, 6%, 7%, 8%, 9%, 10%, 11%, 12%, 13%, 14%, 15% or 20% and less than or less than about 35%, 30%, 25%, 20%, 19%, 18%, 17%, 16%, 15%, 14%, 13%, 12%, 11%, 10%, 9% or 8%. Unless indicated to the contrary, measurements described herein are at or about 13% by weight moisture content.

Provided are accurate non-destructive analytical NIRS-based methods for accurately measuring soluble carbohydrates such as sucrose and the sucrosyl-oligosaccharides raffinose and stachyose, which are appropriate for both single soybeans as well as bulk batches of soybeans and soybean meal. Following measurement, the seed remains viable and can be crossed with the same or different plant such as in a plant breeding program to produce progeny seed or processed for extraction of components such as oil and protein meal.

In the methods and systems provided, the amount or concentration of one or more sucrosyl-oligosaccharides in the seed can be accurately and non-destructively measured by interrogating a seed using an optical interrogation device, such as a spectrophotometer, which directs near-infrared light onto the seed, and using the reflected, transmitted or transflected (a combination of transmitted and reflected light) light spectra from the seed and detected by the optical interrogation device in combination with measurements used to generate calibration models obtained from previously assayed seed. In some embodiments, the seed is sorted or selected based on the amount or concentration of sucrosyl-oligosaccharide present in the seed. The seed can be a whole seed, an intact seed, a viable seed, an individual seed or a population of individual, whole, viable or intact seeds. In some embodiments, sorting decisions can be made following measurement and analysis of a single seed or following measurement and analysis of a population of seeds or a defined number of seeds assayed together in a seed sample. When a number of seeds are assayed together, an average for the measured values across the population of seeds may be obtained either by pooling the data collected from individual seeds from that population or by using methods in which a pooled sample of the soybean seeds are measured simultaneously. Following analysis, the seed remains viable and may be planted and grown to produce a soybean plant. The seeds remain whole, intact or viable before and following the analysis process. Protein meal from soybeans can be similarly analyzed.

By plotting values from the standard reference analytical method against the measurements taken by non-destructive analysis for a particular constituent, the $R^2$ value can be used to indicate the proportion of the data that is accounted for by an ideal line plotted through it. A value of 1 indicates highest accuracy. The root mean square error of calibration (RMSEC) indicates the resolving power of the measured values and can give an indication of the statistical confidence as to whether two values differ significantly from each other. Typically, values differing by 2×the RMSEC differ from each other at the 95% confidence level. The root mean square error of cross validation (RMSECV) is another statistical parameter that is used to assess the quality of the calibrations Once a model (calibration) is created, the data for a group of samples are removed and the influence of their omission is assessed. In robust models the RMSECV is similar to RMSEC. The cross validation also allows aberrant values which may incorrectly influence a model to be identified for further analysis. The RMSECV also gives an estimate of the potential of the models to predict the composition of samples outside the range represented in the calibration set.

Using the methods disclosed herein seeds, such as unmodified seeds and modified seeds in one or more populations of seeds, differing in stachyose content by at least 0.5%, 1.0%, 1.25%, 1.5%, 1.75%, 2.0%, 2.5% or 3.0% and less than 6.0%, 5.0%, 4.0%, 3.5%, 3.0% 2.5%, 2.0% or 1.5% (values are percentage points by weight) can be correctly identified for at least or at least about 80%, 85%, 90%, 91%, 92%, 93%, 94%, 95%, 96%, 97% or 98% of the population of seeds containing differing stachyose content.

The term "percentage point" (pp) difference, change, increase or decrease refers to the arithmetic difference of two percentages, e.g. [transgenic or genetically modified value (%)−control value (%)]=percentage points. For example, a modified seed may contain 20% by weight of a component and the corresponding unmodified control seed may contain 15% by weight of that component. The difference in the component between the control and transgenic seed would be expressed as 5 percentage points.

"Percent increase" or "percent decrease" refers to a change or difference expressed as a fraction of the control value, e.g. {[modified/transgenic/test value (%)−control value (%)]/control value (%)}×100%=percent change, or {[value obtained in a first location (%)−value obtained in second location (%)]/value in the second location (%)}×

100=percent change. The term "total fatty acid content" refers to the sum of the five major fatty acid components found in soybeans, namely C16:0, C18:0, C18:1, C18:2, and C18:3. The term "total polyunsaturated fatty acid content" refers to the total C18:2 plus C18:3 content. The term "total saturated fatty acid content" refers to the total C16:0 plus C18:0 content.

Using the methods disclosed herein seeds, such as unmodified seeds and modified seeds, differing in raffinose content by at least 0.1%, 0.2%, 0.3%, 0.4%, 0.5%, 0.6%, 0.7%, 0.8%, 0.9%, 1% or 1.5% and less than 3%, 2.5%, 2%, 1.5%, 1%, 0.5%, 0.3% or 0.2% (values are percentage points by weight) in one or more populations of seeds can be correctly identified for at least or at least about 80%, 85%, 90%, 91%, 92%, 93%, 94%, 95%, 96%, 97% and 98% of the population of seeds.

The population can include at least or at least about 2, 5, 10, 15, 20, 25, 30, 35, 40, 35, 50, 55, 60, 65, 70, 75, 80, 85, 90, 95, 100, 125, 150, 175, 200, 250, 300, 350, 400, 450, 500, 600, 750, 1000, 5,000, 10,000 or 50,000 seeds and less than or less than about 5,000,000, 1,000,000, 500,000, 400,000, 250,000, 100,000, 50,000, 10,000, 5,000, 2,500, 1,000, 750, 600, 500, 400, 300, 200, 150, 100, 75, 50 or 25 seeds.

In some embodiments, single individual intact soybeans are analyzed one seed at a time, such as with single-seed NIR techniques (SS-NIR) utilizing reflected light, transmitted light or a combination thereof. Such methods are useful, for example, to identify an individual seed carrying the desired trait, such as a transgene, edited gene or mutant allele, which results in a desired composition. Following analysis according the methods described herein, the seed can be used in research and plant breeding programs. For example, the seed can be grown to produce a plant which is crossed with itself or another different plant to produce progeny seed.

In some embodiments, small bulk quantities of seed, such as the amount of seed harvested from a single soybean plant (about 50-300 seeds) which may be homozygous, are analyzed together. FT-NIR, which utilizes reflectance NIR, can be used as in methods described herein for soybean samples harvested from individual plants. Such methods are useful, for example, in assessing or ranking trait performance at the single plant level, and can be used to make selections of plants for their use in further research or breeding. Such assessments may be used in evaluations of transgenic events in controlled environment and field studies.

In some embodiments, bulk seed analysis (bulk NIT methods) are provided which typically require a mass of at least or at least about 100 g, 200 g, 250 g, 300 g, 350 g, or 400 g and less than or less than about 2000 g, 1000 g, 900 g, 800 g, 700 g or 500 g of sample. Such methods are useful, for example, in the analysis of seed grown in field test plots and yield trials or from a bulk harvest and the identification of modified seed from unmodified seed. Such methods can be used, for example, at grain receiving sites such as grain elevators to determine the composition and quality of seeds delivered and the value of the grain shipment. Such methods may include a step of sampling the seed using a sampling system such as AOCS Official Method Ac 1-45.

Commercial soybean cultivars are homozygous for most traits and may be modified to have additional traits introduced by backcrossing (e.g., introgression of the trait of interest can be achieved by crossing to a second line containing the trait and repeated backcrossing to the original line while selecting for the trait of interest), genetic modification, mutation or transformation. Such additional traits can include one or more transgenes or gene modifications which alter the composition of the soybean seed or provide other agronomic characteristics such as herbicide or insect resistance. Selection of lines can include, for example, selections based on one or more of the performance of the line which produced the seed being measured, determining the presence or absence of a transgene, mutation or genetic modification in the seed, and assessing whether a transgene, genetic modification or mutant gene or coding sequence has been inherited by a seed, for example, by introgression through crossing and breeding steps.

Soybean seeds used in the methods and systems described herein can be generated using one or more techniques disclosed herein that facilitate integration or expression of a target sequence in the plant or seed. Examples include one or more of a particle gun, *Agrobacterium*, single-site integration, CRISPR-Cas (clustered, regularly interspaced, short, palindromic repeats-Cas) technology, TALENs (transcription activator-like effector nucleases), zinc-finger proteins (ZNF) or combination thereof.

Modified seed means seed that contains a genetic modification that results in an alteration of the composition of the seed. Examples of altered composition includes one or more of an increase or decrease in oil, protein, one or more fatty acids, one or more amino acids, one or more sucrosyl-oligosaccharides, sucrose, one or more carbohydrates, cell wall polysaccharides, cell wall monosaccharide components, fiber, starch, fermentable starch, cellulose, biopolymers, pharmaceuticals, secondary compounds, metabolites and combinations thereof.

Examples of genetic modifications in modified seed include transformation, such as with a recombinant construct containing a target sequence of interest operably connected to heterologous promoter, natural or induced mutations, and genome editing which may encompass altering one or more soybean genomic DNA sequences or a pre-existing transgenic sequence including regulatory elements, coding and non-coding sequences. The modification can be a single nucleotide deletion, substitution, a full or partial gene deletion, or insertion or alteration of an enhancer sequence, such as a promoter or promoter element, to increase expression. Deletions may include deletion of one or more exon coding sequences of the gene or deletion of one or more regulatory elements of the gene.

As an example, the modified seed, cell or plant described herein can be generated using "custom" or engineered endonucleases such as meganucleases produced to modify plant genomes (see e.g., WO 2009/114321; Gao et al. (2010) Plant Journal 1:176-187). Another site-directed engineering is through the use of zinc finger domain recognition coupled with the restriction properties of restriction enzyme. See e.g., Urnov, et al., (2010) Nat Rev Genet. 11(9):636-46; Shukla, et al., (2009) Nature 459 (7245):437-41. A transcription activator-like (TAL) effector-DNA modifying enzyme (TALE or TALEN) is also used to engineer changes in plant genome. See e.g., U.S. 20110145940, Cermak et al., (2011) Nucleic Acids Res. 39(12) and Boch et al., (2009), Science 326(5959): 1509-12. Site-specific modification of plant genomes can also be performed using the bacterial type II CRISPR (clustered regularly interspaced short palindromic repeats)/Cas (CRISPR-associated) system. See e.g., Belhaj et al., (2013), Plant Methods 9: 39; The Cas9/guide RNA-based system allows targeted cleavage of genomic DNA guided by a customizable small noncoding RNA in plants (see e.g., WO 2015026883A1, incorporated herein by reference). These methods are also useful in targeting nucleic acids to pre-engineered target recognition sequences in the genome. A "mutation", which is possessed by a mutant, refers to a detectable and heritable genetic change (either spontaneous or induced) not caused by segregation or genetic recombination.

Unmodified seed is seed which is similar to the modified seed but which lacks the genetic modification which alters the composition of the seed.

In some embodiments, the methods include measuring a different seed constituent, in combination with measuring a sucrosyl-oligosaccharide to provide additional compositional information, such as a compositional profile, about the seed. Such measurements can be carried out simultaneously with the measurements of sucrosyl-oligosaccharide and may be used to evaluate lines or seeds therefrom, such as modified lines or seeds. A "line" when referring to soybean, is a group of plants of similar parentage that display little or no genetic variation between individuals for a least one trait. Soybean lines are generally homozygous for almost all traits. Lines may be created by one or more generations of self-pollination and selection, or vegetative propagation from a single parent including by tissue or cell culture techniques.

Non-limiting examples of seed constituents which may be measured in the methods provided herein, including processing or sorting seeds, include proteins, oils, carbohydrates, fatty acids (such as one or more of oleic acid, palmitic acid, stearic acid, linoleic acid, linolenic acid, arachidic acid, erucic acid, behenic acid, lignoceric acid and myristic acid) and fatty acid profiles, amino acids, biopolymers, pharmaceuticals, starch, fermentable starch, secondary compounds, sucrosyl-oligosaccharides, metabolites and combinations thereof. For example, alterations, such as increases or decreases, in these constituents can be measured in combination with measuring the amount or concentration of one or more sucrosyl-oligosaccharides in a target or modified soybean seed and compared with a comparable control or unmodified soybean seed which does contain the modification contributing to the altered phenotype.

Soybean seeds that can be used in the methods and systems provided may be transgenic for one or more traits, for example through suppression or over-expression, and/or may have one or more mutations or genetic modifications, that result in a seed having a composition sufficiently different from comparable commodity, non-mutant, non-modified or non-transgenic soybean seeds to enable identification, separation and/or sorting of the transgenic, mutant or genetically modified seed from the comparable or control seed. For example, a low amount or concentration of sucrosyl-oligosaccharide in a soybean seed may indicate that the soybean seed is a modified seed containing one or more traits, such as one or more transgenic events or genetic modifications, that result in a high oil, high protein and/or altered fatty acid profile phenotype in the soybean seed compared with a comparable soybean seed not containing the trait or modification. Soybean seeds that have an amount or concentration of sucrosyl-oligosaccharide below a desired threshold (i.e., below a desired maximal amount) of sucrosyl-oligosaccharide and above a desired threshold (i.e. above a desired minimal amount) of oil content, protein content, or both oil and protein content can be selected and used in plant breeding or industrial processing. The methods described herein can also be used with modified soybean seeds that have an amount or concentration of sucrosyl-oligosaccharide below a desired threshold (i.e., below a desired maximal amount) of sucrosyl-oligosaccharide and above or below a desired threshold for one or more fatty acids. The threshold is selected to enable sorting or separation of modified seeds from the comparable seeds not containing the transgenic trait or genetic modification. Protein meal can also be analyzed rapidly and non-destructively using the methods described herein, and protein meal produced from soybeans containing one or more genetic modifications such as the modifications described herein can be identified from meal produced from non-modified soybeans.

In some embodiments, the genetic modifications include one or more mutations or modifications that result in reduced amounts of stachyose, raffinose or a combination thereof in the soybean seed, such as the low1, low2, low3, low4 mutations described in U.S. Pat. Nos. 5,710,365, 6,147,193 and 6,653,451, mutations in stachyose synthase such as in the PI 603176A and PI 594012 soybean lines (Qui et al., Theor Appl Genet 2015, 128:2167), the mutations in raffinose synthase such as the RS2 or RS3 genes described in U.S. Pat. No. 8,728,726 and U.S. Patent Publication No. 20130318660, the SG-ULRFO mutation described in U.S. Patent Publication No. 20110003045, and the low phytate, low stachyose mutations described in U.S. Pat. No. 8,003,856.

In some embodiments, the genetic modifications include one or more mutations or modifications that result in increased oleic acid, such as in one or more FAD2 alleles, see, e.g. U.S. Pat. Nos. 9,198,365, 9,185,826, 7,531,718, 7,205,457, 7,067,722, 6,426,448, 6,229,033, 5,981,781 and U.S. Patent Publication Nos. 20160186195, 20130219565.

The oleic acid may be increased to about 50%, 55%, 60%, 65%, 70%, 75%, 80%, 85% or 90% (such as at least about or at least 50%, 55%, 60%, 65%, 70%, 75%, 80% or 85% and less than or less than about 95%, 90%, 85%, 80%, 75%, 70%, or 65%; measured as a proportion of the total fatty acids) by suppressing or inhibiting expression of one or more FAD2 genes, such as by mutation, genome editing or transgenes, alone or in combination with other modifications described herein.

In some embodiments, the genetic modifications include one or more mutations or modifications that result in reduced linolenic acid, such as one or more FAD3 or fan (e.g. fan1, fan2, fan3) alleles found, for example, in mutant lines, A5, C1640, RG10, A16, A17, A23, A29 and in soybean lines having such alleles modified by genome editing or transformation. See, e.g. U.S. Pat. Nos. 8,901,375, 7,943,818, 7,205,457, 7,067,722, 6,133,509, 5,850,030, 5,710,369, 5,714,670, 5,763,745, 5,714,668, 5,534,425 and 5,714,670 and U.S. Patent Publication Nos. 20160186195, 20130219565.

The linolenic acid may be decreased to about 6%, 5.5%, 5%, 4.5%, 4%, 3.5%, 3.0%, 2.9%, 2.8%, 2.7%, 2.6%, 2.5%, 2.4%, 2.3%, 2.3%, 2.1%, 2.0%, 1.9%, 1.8%, 1.7%, 1.6%, 1.5%, 1.4%, 1.3%, 1.2%, 1.1% or 1.0% (such as at least about or at least 0.5%, 0.6%. 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.5%, 2.9% or 3.0% and less than or less than about 6%, 5.5%, 5.0%, 4.5%, 4.0%, 3.5%, 3.4%, 3.3%, 3.2%, 3.1%, 3.0%, 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1% or 1.0% measured as a proportion of the total fatty acids) by suppressing or inhibiting expression of one or more FAD3 genes, such as those disclosed herein and such as by mutation, genome editing or use of transgenes, alone or in combination with other modifications described herein.

In some embodiments, for example, components that can be used to modify the composition of the seed include increased expression of a DGAT (diglyceride acyltransferase; e.g. U.S. Pat. Nos. 8,153,859; 8,399,736; 9,187,736), such as DGAT1 (e.g. a soy DGAT1 or a modified soy DGAT1 expressing a polypeptide with one or more amino acid substitutions, e.g. U.S. Pat. Nos. 7,524,945, 8,497,362, 8,101,819, 8,455,714; 9,447,386) or DGAT2 (e.g. a *Yarrowia lipolytica* DGAT2, e.g. U.S. Pat. No. 9,574,207, 8,927, 809; 8,993,840), suppression of one or more galactinol synthases (GAS; such as GAS1, GAS2 and GAS3, e.g. U.S. Pat. Nos. 9,574,207; 7,294,756; 6,967,262; 5,648,210; 5,773,699; 5,710,365; 6,147,193; 6,653,451), increased expression of a sucrose transporter, such as SUT2 or SUT4 (e.g. U.S. Pat. No. 8,993,840), expression of transcription factors such as ovule development protein (ODP; also known as Wrinkled1, see, e.g. U.S. Pat. Nos. 8,404,926 and 9,284,571), LEC1 or FUSCA3 (e.g. U.S. Patent Publication No. 20160186195), phosphoglucomutase (PGM; U.S. Pat. Nos. 8,143,476, 8,829,273), fatty acid desaturase FAD3 (e.g. U.S. Pat. Nos. 7,081,564; 8,609,935; 5,981,781; U.S. Patent Publication No. 20130219565) am iRNA fragments of fad2-1b, fatBF, or fad3c (e.g. U.S. Patent Publication No. 20130219565), carbonic anhydrase (e.g. U.S. Patent Publication No. 20170029836), pectin acetyl esterase (PAE; e.g. U.S. Pat. No. 9,574,204), aldolase such as HpaIL aldolases (e.g. U.S. Pat. No. 9,347,066), cytosolic pyrophosphatase (PPiase; e.g. U.S. Patent Publication No. 20120174261), oxidoreductase and oxidoreductase motifs (ORMs; e.g. U.S. Patent Publication No. 20110219474), or combinations thereof. Promoters that can be used include, for example, one or more of annexin promoter, beta-conglycinin α'-subunit promoter, glycinin 1 promoter, Kunitz trypsin Inhibitor 3 Promoter, albumin 2S promoter, s-adenosylmethionine synthetase promoter, sucrose synthase promoter such as a SUS2 promoter, late embryogensis abundant gene promoter. Other components which can be used include a yeast FLP-Recombinase to facilitate recombination at short flippase recognition target (FRT) sites. Further examples of components are provided in Table 1, which constructs can be used to generate modified or transgenic seeds having a wide range of amounts or concentrations of one or more sucrosyl-oligosaccharides. Any combination if these components described in this paragraph and in Table 1 may be expressed together. One or more of these components may also be combined with one or more of the modifications or mutations described herein, such as mutations or modifications affecting the fatty acid profile such as oleic acid, linolenic acid, linoleic acid, stearic acid or palmitic acid. Sequences disclosed herein include sequences that have at least or at least about 50%, 55%, 60%, 65%, 70%, 75%, 80%, 85%, 90%, 95%, 96%, 97%, 98%, 99% or 100% identity to the disclosed sequences, provided that the sequence functions for its intended purpose.

TABLE 1

List of promoters and gene/amiRNA/RNAi cassettes and their abbreviations

| Feature Name | Description | Reference |
| --- | --- | --- |
| ANN | Soy annexin promoter | U.S. Pat. No. 8,084,074 (e.g. the sequence identified as number 3) |
| BC | Soy beta-conglycinin α'-subunit promoter | Beachy et al., *EMBO J.* 4, 3047-3053 (1985) |
| FAD2 RNAi | RNAi construct containing fragments of soy fatty acid desaturase 2 genes and designed to silence them | U.S. Pat. No. 7,456,014 (e.g. the sequence identified as number 24) |
| FAD2/ FATBamiRNA | Combined amiRNA comprising 396b-fad2-1b and 159-fatBF | U.S. patent application Publication No. 20150089689 |
| FAD3amiRNA | amiRNA comprising 159-fad3c | U.S. patent application Publication No. 20150089689 |
| GAS RNAI | RNAi construct containing fragments of soy galactinol synthases designed to silence them | U.S. Pat. No.7,476,778 (e.g. nucleotides encoding the sequences identified as numbers: 2, 4, 6) U.S. Pat. No. 7,456,014 (e.g. the sequence identified as number 29) |
| GM::HRA/ GM-ALS | Soy Acetolactate Synthase gene and gene encoding a mutant soy ALS enzyme insensitive to sulfonylurea herbicides | U.S. Pat. No. 7,456,014 (e.g. the sequence identified as number 35) U.S. Pat. No. 7,217,858 (e.g. the sequences identified as numbers 22 and 23) |
| GM-DGAT1-C9C10C11 | Modified Soy diacylglycerol acyltransferase 1 | U.S. Pat. No. 8, 101,819 |
| GM-ODP1 | Soy Ovule Development Protein 1 | U.S. patent application Publication No. 2015-0143583. |
| GM-SUT4 | Soy Sucrose Transporter 4 | U.S. Pat. No. 8,993,840 |
| GY1 | Soybean Glycinin 1 Promoter | U.S. Pat. No. 8,084,074 |
| KTI | Soy Kunitz Trypsin Inhibitor 3 Promoter | Jofuku et al., *Plant Cell* 1: 1079-1093 (1989) |
| LEA | Soy Late Embryogenesis Abundant gene promoter | U.S. Pat. No. 7,456,014 |
| PGM RNAi | RNAi construct containing fragments of soy PGM designed to silence them | U.S. Pat. No. 7,323,560 |

TABLE 1-continued

List of promoters and gene/amiRNA/RNAi cassettes and their abbreviations

| Feature Name | Description | Reference |
|---|---|---|
| SALB | Soy albumin 2S promoter | U.S. Pat. No. 6,177,613 |
| SAMS | Soy S-adenosylmethionine synthetase promoter | U.S. Pat. No. 7,217,858 |
| SUS | GM::SUS2 Promoter | U.S. patent application Publication No. 2015-0143583 |
| YLDGAT2 | Yarrowia lipolitica diacylglycerol acyltransferase 2 | U.S. Pat. No. 8,143,473 U.S. Pat. No. 8,143,476 |
| FLP-Recombinase | Yeast FLP-Recombinase | U.S. patent application Publication No. 20160186195 |

Soybeans generated by modifying expression of these sequences and having different amounts of stachyose, raffinose, or both stachyose and raffinose can be used iteratively in the methods described herein to generate calibrations which provide accurate measurements of stachyose or both stachyose and raffinose. In some embodiments verbascose can be measured. As used herein, sucrosyl-oligosaccharide means the sum of stachyose and raffinose.

In some embodiments, the soybean is modified to have suppressed galactinol synthase (GAS) activity with one or more sequences that suppress expression of galactinol synthase (e.g. one or more of GAS1, GAS2 and GAS3) or raffinose synthase (e.g. RS2, RS3) activity (or a combination of GAS and raffinose synthase suppression), alone or in combination with increased DGAT activity (for example, by transforming with a yeast or soy DGAT described in Table 1 or genetically modifying the native DGAT or its regulatory sequences to enhance expression) and optionally other sequences, such as those described in Table 1, to increase oil and/or protein. Such enhanced expression or suppression can be achieved by one or more of genetic modification, such as by gene editing, the use of transgenes, or by mutation. Such seeds may have an amount of stachyose of about 0.1%, 0.2%, 0.3%, 0.4%, or 0.5%, such as at least about 0.05%, or 0.1%, 0.2%, 0.3%, 0.4% or 0.5% and less than about 2%, 1.5%, 1%, 0.9%, 0.8%, 0.7%, 0.6% or 0.5% stachyose (percentage points by weight). Such seeds may have an amount of sucrosyl-oligosaccharide of about 0.3%, 0.4%, 0.5% or 0.6%, such as at least about 0.05%, 0.1%, 0.2%, 0.3%, 0.4% or 0.5% and less than about 2%, 1.5%, 1%, 0.9%, 0.8%, 0.7%, 0.6% or 0.5% sucrosyl-oligosaccharides (percentage points by weight). By contrast, the comparable unmodified, control, null or wild-type seed may have a stachyose content of about 4%, such as at least about 1%, 2%, 2.5%, 3% or 3.5% and less than about 6%, 5.5%, 5% or 4.5% (percentage points by weight). The comparable unmodified, control, null or wild-type seed may have a sucrosyl-oligosaccharide content of about 5%, such as at least about 2%, 2.5%, 3%, 3.5%, 4%, or 4.5% and less than about 6.5%, 6%, 5.5%, or 5% (percentage points by weight).

Such modified seeds may also have an increased oil, protein or combination thereof in addition to reduced sucrosyl-oligosaccharide or stachyose. For example, such modified seeds may have an amount of oil in percentage points by weight of about 23%, 24%, 25%, 26%, 27%, 28%, 29%, 30%, such as at least about 21%, 22%, 23%, 24%, 25%, 26%, 27%, 28%, 29%, 30% and less than about 40%, 35%, 34%, 33%, 32%, 31%, 30%, 29% or 28% oil by weight. In contrast, a comparable unmodified, control, null or wild-type seed may have an amount of oil in percentage points by weight of about 16%, 17%, 18%, 19%, 20%, 21% or 22%, such as at least about 15%, 16%, 17%, 18%, 19%, 20% or 21% and less than about 23%, 22%, 21%, 20%, 19%, or 18% oil by weight. Useful examples of percent point increases in oil or total fatty acid content in a seed, such as a modified soybean seed described herein compared with a comparable or control soybean include, but are not limited to, percentage point increases by weight of at least 1%, 2%, 3%, 4% or 5% and less than 10%, 9%, 8%, 7%, 6%, 5% or 4%. Useful examples of the percent increases in oil or total fatty acid content in a modified soybean seed described herein compared with a comparable unmodified, control, null or wild-type soybean include, but are not limited to, percent increases of at least 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% and less than 99%, 95%, 90%, 80%, 70%, 60%, 50%, 40%, 35%, 30% and 25%.

Such modified seeds may have an amount of protein in percentage points by weight of about 38%, 39%, 40%, 41%, 42%, 43%, 44%, 45%, 46%, 47%, 48%, 49%, 50%, 51%, 52%, 53% or 54% such as at least about 35%, 36%, 37%, 38%, 39%, 40%, 41%, 42%, 43%, 44%, 45%, 46%, 47%, 48%, 49%, or 50% and less than about 55%54%, 53%, 52%, 51%, 50%, 49%, 48%, 47%, 46%, 45%, 44%, 43%, 42%, 41%, 40% or 39% protein. In contrast a comparable unmodified, control, null or wild-type seed may have an amount of protein in percentage points by weight of about 30%, 31%, 32%, 33%, 34%, 35%, 36%, 37%, or 38% such as at least about 25%, 26%, 27%, 28%, 29%, 30%, 31%, 32%, 33%, 34%, or 35% and less than about 38%, 37%, 36%, 35%, 34%, 33%, 32% 31%, 30%, 29% or 28% protein. Useful examples of percent point increases in protein (by weight) in a seed, such as a modified soybean seed compared with a comparable or control soybean include, but are not limited to, percentage point increases by weight of at least 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 6%, 7%, 8%, 9%, and 10% and less than 20%, 19%, 18%, 17%, 16%, 15%, 14%, 13%, 12%, 11%, 10%, 9%, 8%, 7%, 6%, 5% or 4%. Useful examples of the percent increases in protein content in a seed such as a modified seed compared with an unmodified, control, null or wild-type soybean seed described herein include, but are not limited to, percent increases of at least 5%, 10%, 15%, 20%, 25%, 30%, 35%, 40%, 45%, 50%, 55%, or 60% by weight and less than about 70%, 65%, 60%, 55%, 50%, 45%, 40%, 35%, 30%, 25%, 20%, 15% or 10%.

The methods can be used to accurately distinguish between individual soybean seeds, or populations or lines of soybeans that differ in percentage points by about 1% stachyose or sucrosyl-oligosaccharide, such as less than 3%, 2.5%, 2%, 1.9%, 1.8%, 1.7%, 1.6%, 1.5%, 1.4%, 1.3%, 1.2%, 1.1%, 1%, 0.9%, 0.8%, 0.7%, 0.6% or 0.5% stachyose or sucrosyl-oligosaccharide by weight and at least 0.1%, 0.2%, 0.3%, 0.4%, 0.5%, 0.6%, 0.7%, 0.85 or 0.9% stachyose or sucrosyl-oligosaccharide by weight. Values are given by weight percent.

The difference in sucrosyl-oligosaccharide, such as stachyose, between seed types being measured, such as a modified and unmodified seed as described herein, can be detected, for example, when the difference is at least 0.5 percentage points, 1.0 percentage points, 1.5 percentage points, 2.0 percentage points, 2.5 percentage points, 3.0 percentage points, or 4.0 percentage points and less than 5.0 percentage points, 4.5 percentage points, 4.0 percentage points, 3.5 percentage points, 3.0 percentage points, 2.5 percentage points, 2.0 percentage points, 1.5 percentage points, or 1.0 percentage points. Values are given by weight percent.

Useful examples of the amount of sucrosyl-oligosaccharide content in a seed such as a modified or unmodified soybean seed include, but are not limited to in percentage points by weight at least or at least about 0.1%, 0.2%, 0.25%, 0.5%, 1%, 1.5%, 2%, 2.5%, 3.0%, 3.5%, 4.0%, 4.5%, 5.0%, 5.5%, 6.0% or 6.5% and less than or less than about 7%, 6.5%, 6.0%, 5.0%, 4.5%, 4.0%, 3.5%, 3.0%, 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3% or 0.2%.

The methods can be used to accurately distinguish between individual soybeans, or populations or lines of soybeans that differ by in percentage points by weight at or about 0.5%, 0.7%, 0.8%, 0.9%, 1.0%, 1.5%, 2.0%, 2.5%, 3%, 3.5%, 4%, 4.5% 5%, 5.5%, 6%, 7%, 8%, 9% or 10% oil, such as in percentage points at least 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 2%. 3%, 4%, or 5% oil and less than 15%, 10%, 5%, 4%, 3%, 2.5%, 2%, 1.9%, 1.8%, 1.7%, 1.6%, 1.5%, 1.4%, 1.3%, 1.2%, 1.1%, 1.0%, 0.9%, 0.8%, 0.7%, 0.6% or 0.5% oil.

The methods can be used to accurately distinguish between individual soybeans, or populations or lines of soybeans that differ in percentage points by weight at or about 1%, 1.5%, 2%, 2.5%, 3%, 3.5% 4%, 4.5%, 5%, 5.5%, 6%, 7%, 8%, 9%, 10%, 11%, 12%, 13%, 14%, 15%, 20% or 25% protein, such as at least 0.5%, 1%, 1.5%, 2%, 2.5%, 3%, 3.5%, 4%, 5%, 6%, 7%, 8%, 9%, and 10% protein and less than 30%, 25%, 20%, 15%, 10%, 9%, 8%, 7%, 6%, 5%, 4%, 3%, 2%, or 1% protein.

If a yeast DGAT, such as *Yarrowia lipolytica* diacylglycerol acyltransferase 2 or a soy DGAT, such as soy DGAT1, is expressed in a soybean seed, optionally with one or more sequences that results in GAS or raffinose synthase suppression, the seed may have an oleic acid content of about 30%, 31% or 32% such as at least about 22%, 23%, 24%, 25%, 26%, 27%, or 28% and less than about 40%, 35%, 34%, or 33%. Unless indicated to the contrary, all percent values for a particular fatty acid are expressed herein as a percentage of the total fatty acid content. The oleic acid can be measured in combination with measuring the amount of sucrosyl-oligosaccharide or stachyose or other components described herein. By contrast, the comparable unmodified, control, null or wild-type seed may have an oleic acid content of about 22% or 23%, such as at least about 19%, 20% or 21% and less than about 25%, 24.5% or 24%. For such modified beans, the threshold for oleic acid to distinguish between the modified and unmodified seed may be about 25% or 30% or 35%, such as at least about 21%, 22%, 23%, 23.5%, 24%, 24.5%, 25%, 25.5%, 26%, 26.5%, 27%, 28%, 29%, 30%, 31%, 32%, 33%, 34%, 35% or 36% and less than about 37%, 36%, 35%, 34%, 33%, 32%, 31%, 30%, 29%, 28%, 27% 27% or 26% oleic acid.

If a soy DGAT, such as the modified soy diacylglycerol acyltransferase 1 described in Table 1, or a yeast DGAT, such as *Yarrowia lipolytica* diacylglycerol acyltransferase 2 is expressed or over-expressed in a soybean seed, optionally with one or more sequences that results in GAS and/or raffinose synthase suppression, the seed may have a stearic acid content of about 5% (such as at least or at least about 4%, 4.5% or 5% and less than or less than about 10%, 9%, 8%, 7% or 6%) which can be measured in combination with measuring the amount of stachyose or sucrosyl-oligosaccharide or other components described herein. By contrast, the comparable unmodified seed may have a stearic acid content of about 3.5% (such as at least or at least about 3%, 3.1%, 3.2%, 3.3%, 3.4% or 3.5% and less than or less than about 3.7%, 3.8%, 3.9%, 4.0%, 4.1%, 4.2%, 4.3%, 4.4%, 4.5%, 4.6%, 4.7%, 4.8% or 4.9%, 5.0%, 5.5%).

If a DGAT, such as the modified soy diacylglycerol acyltransferase 1 described in Table 1, is expressed or over expressed in a soybean seed, optionally with one or more sequences that results in GAS suppression, the seed may have a palmitic acid content of about 12% or 13% (such as at least or at least about 11%, 11.1%, 11.2%, 11.3%, 11.4%, 11.5%, 11.6%, 11.7%, 11.8%, 11.9%, or 12% and less than or less than about 15%, 14.5%, 14%, 14.5%, 14%, 13.5%, 13.4%, 13.3%, 13.2%, 13.1%, 13%, 12.9%, 12.8%, 12.7%, 12.6% or 12.5%) which can be measured in combination with measuring the amount of sucrosyl-oligosaccharide or stachyose or other components described herein. By contrast, the comparable unmodified seed may have a palmitic acid content of about 10% or 11% (such as at least or at least about 9%, 9.1%, 9.2%, 9.3%, 9.4%, 9.5%, 9.6%, 9.7%, 9.8%, 9.9% or 10% and less than or less than about 12%, 11.9%, 11.8%, 11.7%, 11.6%, 11.5%, 11.4%, 11.3%, 11.2%, 11.1%, 11%, 10.9%, 10.8%, 10.7%, 10.6%, or 10.5%).

If a DGAT, such as the modified soy diacylglycerol acyltransferase 1 described in Table 1, or such as *Yarrowia lipolytica* diacylglycerol acyltransferase 2 is expressed or over-expressed in a soybean seed, optionally with one or more sequences that results in GAS suppression, the seed may have a linoleic acid content of about 45% (such as at least or at least about 25%, 30%, 35%, 40% or 45% and less than or less than about 55%, 54%, 53%, 52%, 51%, 50%, 49%, 48%, 47%, 46% or 45%) which can be measured in combination with measuring the amount of sucrosyl-oligosaccharide, such as stachyose or sucrosyl-oligosaccharide or other components described herein. By contrast, the comparable unmodified seed may have a linoleic acid content of about 55% (such as at least or at least about 50%, 51%, 52%, 53%, 54% or 55% and less than or less than about 65%, 64%, 63%, 62%, 61%, 60%, 59%, 58%, 57%, 56% or 55%).

A modified soybean seed such as a soybean seed with enhanced diacylglycerol acyltransferase (DGAT) activity, such as containing a modified soy DGAT1, for example described in Table 1, or a yeast DGAT, such as *Yarrowia lipolytica* diacylglycerol acyltransferase 2, optionally with one or more modified sequences that results in suppression of one or more GAS sequences, raffinose synthase sequences or both, may have a linolenic acid content of about 5% or 6% (such as at least or at least about 0.1%, 0.5%, 1%, 1.5%, 2%, 2.5%, 3%, 3.5%, 4% 4.5% or 5% and less than or less than about 10%, 9%, 8%, 7.5%, 7%, 6.9%, 6.8%, 6.7%, 6.6%, 6.5%, 6.4%, 6.3%, 6.2%, 6.1% or 6%) which can be measured in combination with measuring the amount of sucrosyl-oligosaccharide or stachyose or other components described herein. A modified soybean seed such as a soybean seed with one or more modified FAD3 genes, such as by mutation, genome editing or transgenes, alone or in combination with one or more of DGAT, GAS, raffinose synthase, and FAD sequences, may have a linolenic content of no more than about 0.5%, 1%, 1.5%, 2%, 2.5% or 3% (such as at least about or at least 0.1%, 0.2%, 0.3%, 0.4%, 0.5%, 0.6%, 0.7%, 0.8%, 0.9%, 1%, 1.5%, 2%, 2.5% or 3% and less than 6%, 5.5%, 5%, 4.5%, 4%, 3.5%, 3%, 2.5%, 2%, 1.5%, 1.4%, 1.3%, 1.2%, 1.1%, 1%, 0.9%, 0.8%, 0.7%, 0.6%, 0.5%, 0.4%, 0.3%, 0.2%, 0.1%, 0.05%). By contrast, the comparable unmodified seed may have a linolenic acid content of about 7% or 8% (such as at least or at least about 5%, 5.5%, 6%, 6.5%, or 7% and less than or less than about 12%, 11%, 10%, 9.5%, 9%, 8.5% or 8%. Linolenic acid may be further reduced in a modified soybean by modifying one or more of the FAD2 alleles such as described herein.

Fingerprints regarding the seed composition can be developed based on the modified light from the soybean seed, wherein a sorting decision is made based upon the measured amounts of sucrosyl-oligosaccharides, in any combination with one or more of the fatty acids (such as oleic acid content or saturated fatty acid content), oil content, or protein content in the soybean seed. The combined measurement can be used to increase accuracy as to whether a seed is modified or not. In some embodiments the soybean seed may contain low sucrosyl-oligosaccharide and, for example, high oil, high protein, one or more altered (increased or decreased) fatty acids, or a combination thereof. In some embodiments, the methods described herein for sorting a seed from a plurality of seeds further includes measuring the amount of oil, one or more fatty acids and/or protein in the seed based on the modified light from the soybean seed, wherein a decrease in the amount of sucrosyl-oligosaccharide correlates with an increase in the oil, protein, altered fatty acid content or combination thereof in the soybean seed.

Threshold values for one or more components can be useful for determining whether a soybean is modified or unmodified. The threshold value for a component measured in a soybean is a value selected to facilitate distinguishing, sorting or separating a soybean, such as a modified soybean, having an amount or concentration of the component that is different (for example, a significantly higher or lower amount or concentration of that component) from another soybean, such as an unmodified soybean.
The threshold value may vary depending on the moisture content of the soybean, and can be set or adjusted to 13% moisture. Values for sucrosyl-oligosaccharides, stachyose, raffinose, oil, protein, total soluble carbohydrate, sucrose and PROIL are provided as percentage points based on weight percent (wt. %). For the fatty acids, such as one or more of oleic acid, palmitic acid, stearic acid, linoleic acid, linolenic acid, values described are expressed as a percentage of that fatty acid relative to the total fatty acid pool.

For sucrosyl-oligosaccharide, (a combination of stachyose and raffinose) the threshold value include values at, about, at least, or at least about 0.1%, 0.2%, 0.25%, 0.5%, 1%, 1.25%, 1.5%, 2%, 2.5%, 3.0%, 3.5%, 4.0% sucrosyl-oligosaccharide and at, about, less than, or less than about 5.0%, 4.5%, 4.0%, 3.9%, 3.8%, 3.7%, 3.6%, 3.5%, 3.4%, 3.3%, 3.2%, 3.1%, 3.0%, 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3% or 0.2% sucrosyl-oligosaccharide.

The threshold for stachyose to distinguish between the modified and unmodified seed may be about 1%, 1.5%, 2%, or 2.5%, such as at least about 0.1%, 0.5%, 0.6%, 0.7%, 0.8%, 0.9%, 1.0%, 1.5%, 2%, 2.5%, 3%, 3.5%, 4%, 4.5% or 5% stachyose and less than about 6.0%, 5.5%, 5%, 4.5%, 4%, 3.5%, 3%, 2.5%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3% or 0.2% stachyose.

The threshold for raffinose to distinguish between the modified and unmodified seed may be about 0.7% raffinose such as at least about 0.1%, 0.2%, 0.3%, 0.4%, 0.5%, 0.6%, 0.7%, 0.8%, 0.9%, or 1% raffinose and less than about 1.5%, 1.4%, 1.3%, 1.2%, 1%, 0.9%, 0.8% or 0.7% raffinose.

The threshold value for oil to assist in distinguishing between modified and unmodified seed may be at or about 17%, 18%, 19%, 20%, 21%, 22%, 23%, 24% or 25%, with the modified soybean, such as described herein, containing at least or at least about 19%, 19.5%, 20%, 20.5%, 21%, 21.5%, 22%, 22.5%, 23%, 23.5%, 24%, 24.5%, 25%, 26%, 27%, 28% or 29% oil and less than or less than about 32%, 31%, 30%, 29%, 28%, 27%, 26%, 25%, 24.5%, 24%, 23.5%, 23%, 22.5%, 22%, 21.5%, 21%, 20.5% or 20% oil and the comparable unmodified or null soybean containing at least or at least about 15%, 15.5%, 16%, 16.5%, 17%, 17.5% or 18% oil and less than or less than about 23%, 22.5%, 22%, 21.5%, 21%, 20.5%, 20%, 19.5%, 19%, 18.5%, 18%, 17.5% or 17% oil. The threshold value for oil includes values of at least or at least about 16%, 16.5%, 17%, 17.5%, 18%, 18.5%, 19%, 19.5%, 20%, 20.5%, 21%, 21.5%, 22%, 22.5%, 23%, 23.5% or 24% oil and less than or less than about 26%, 25.5%, 25%, 24.5%, 24%, 23.5%, 23%, 22.5%, 22%, 21.5%, 21%, 20.5%, 20%, 19.5%, 19%, 18.5% or 18% oil.

The threshold value for total protein to distinguish between the modified and unmodified seed may be at or about 32%, 33%, 34%, 35%, 36%, 37%, or 38%, with the modified soybean, such as described herein, containing at least or at least about 37%, 38%, 39%, 40%, 41%, 42%, 43%, 44%, 45%, 46%, 47%, 48%, 49% or 50% protein and less than or less than about 55%, 54%, 53%, 52%, 51%, 49%, 48%, 47%, 46%, 45%, 44%, 43%, 42%, 41% or 40% protein and the comparable unmodified or null soybean containing at least or at least about 30%, 31%, 32%, 33%, 34%, 35%, 36% or 37% protein and less than or less than about 39%, 38%, 37%, 36%, 35%, 34%, 33% or 32% protein. The threshold value for protein includes values of at least 32%, 33%, 34%, 35%, 36%, 37%, 38%, 39%, 40%, 41%, 42%, 43%, 44%, 45%, 46%, 47% or 48% protein and less than or less than about 53%, 52%, 51%, 50%, 49%, 48%, 47%, 46%, 45%, 44%, 43%, 42%, 41%, 40%, 39%, 38%, 37%, 36%, 35%, 34% or 33% protein.

For palmitic acid, a suitable threshold value may be at or about 10.5% or 11%, with the modified soybean such as described herein containing at least or at least about 10.5%, 11%, 12%, or 13% and less than or less than about 20%, 15% 14% or 13% palmitic acid and the comparable unmodified or null soybean containing at least or at least about 5%, 7%, 8%, 9% or 10% and less than or less than about 11%, 10.5%, 10%, 9%, 8% or 7% palmitic acid. The threshold value for palmitic acid includes values at, about, at least or at least about 8%, 9%, 10%, 10.5%, 11% or 12% and at, about, less than or less than about 15%, 14%, 13%, 12%, 11% or 10.5%.

For stearic acid, a suitable threshold value may be at or about 4.5%, with the modified soybean such as described herein containing at least or at least about 4.5%, 5%, 5.5%, or 6% stearic acid and less than or less than about 10%, 9%, 8% or 7% stearic acid and the comparable unmodified or null soybean containing at least or at least about 2%, 2.5%, 3%, 3.5%, or 4% stearic acid and less than or less than about 4.5%, 4%, 3.5%, 3% or 2.5% stearic acid. The threshold value for stearic acid includes values at, about, at least or at least about 3%, 3.5%, 4%, 4.5%, or 5% and at, about, less than or less than about 6%, 5.5%, 5%, 4.5%, 4% or 3.5%.

For oleic acid, a suitable threshold value may be at or about 28%, with the modified soybean such as described herein containing at least or at least about 28%, 30%, 35%, 40%, 45%, 50%, 55%, 60%, 65%, 70%, 75%, 80% or 85% oleic acid and less than or less than about 95%, 90%, 85%, 80%, 75%, 70%, 65%, 60%, 55%, 50%, 45%, 40%, 35% or 30% oleic acid and the comparable unmodified or null soybean containing at least or at least about 10%, 15%, 20%, 25%, or 27% oleic acid and less than or less than about 28%, 25%, 20%, or 15% oleic acid. The threshold value for oleic acid includes values at, about, at least or at least about 18%, 19%, 20%, 21%, 22%, 23%, 24% or 25% and at, about, less than or less than about 75%, 50%, 45%, 40%, 35%, 30% or 28%.

For linoleic acid, a suitable threshold value may be at or about 50%, with the modified soybean such as described herein containing at least or at least about 30%, 35%, 40%, 45%, or 50% linoleic acid and less than or less than about 60%, 55%, 50%, 45%, 40%, or 35% linoleic acid and the comparable unmodified or null soybean containing at least or at least about 50%, 55%, or 60% linoleic acid and less than or less than about 65%, 60%, 55% or 50% linoleic acid. The threshold value for linoleic acid includes values at, about, at least or at least about 45%, 50%, or 55% and at, about, less than or less than about 60%, 55%, or 50%.

For linolenic acid, a suitable threshold value may be at or about 6.5%, with the modified soybean such as described herein containing at least or at least about 0.5%, 1%, 1.5%, 2%, 2.5%, 3%, 3.5%, 4%, 4.5%, 5%, 5.5% or 6% linolenic acid and less than or less than about 6.5%, 6%, 5.5%, 5%, 4.5%, 4%, 3.5%, 3%, 2.5%, 2%, 1.5% or 1% linolenic acid and the comparable unmodified or null soybean containing at least or at least about 6.5%, 7%, 7.5%, 8%, 8.5% or 9% linolenic acid and less than or less than about 10%, 9.5%, 9%, 8.5%, 8%, 7.5%, or 7% linolenic acid. The threshold value for linolenic acid includes values at, about, at least or at least about 1%, 1.5%, 2%, 2.5%, 3%, 3.5%, 4%, 4.5%, 5%, 5.5% or 6% and at, about, less than or less than about 10%, 9.5%, 9%, 8.5%, 8%, 7.5%, 7% or 6.5%.

For total saturated fatty acids (stearic acid plus palmitic acid), a suitable threshold value may be at or about 15.5%, with the modified soybean such as described herein containing at least or at least about 15.5%, 16%, 16.5%, 17%, 17.5%, 18%, 18.5%, 19% or 19.5% total saturated fatty acids and less than or less than about 30%, 25%, 20%, 19%, 18%, 17%, or 16% total saturated fatty acids and the comparable unmodified or null soybean containing at least or at least about 9%, 10%, 10.5%, 11%, 11.5%, 12%, 12.5%, 13%, 13.5%, 14%, 14.5% or 15% total saturated fatty acids and less than or less than about 15.5%, 15%, 14.5%, 14%, 13.5%, 13%, 12.5%, 12%, 11.5%, 11%, 10.5% or 10% total saturated fatty acids. The threshold value for total saturated fatty acids includes values at, about, at least or at least about 10.5%, 11%, 11.5%, 12%, 12.5%, 13%, 13.5%, 14%, 14.5%, or 15% and at, about, less than or less than about 10%, 9.5%, 9%, 8.5%, 8%, 7.5%, 7% or 6.5%.

In some embodiments, soybeans may be modified to have lower total saturated fatty acids (stearic acid plus palmitic acid) than unmodified soybeans, such as at least or at least about 4%, 5%, 6% or 7% total saturated fatty acids and less than about 15%, 12%, 10%, 9%, 8% or 7% with a threshold value of at, about, at least or at least about 5%, 6%, 6.5%, 7%, 7.5%, 8%, 8.5%, 9%, 9.5%, 10%, 10.5%, 11%, 11.5%, 12% or 12.5% and at, about, less than or less than about 18%, 17%, 16%, 15%, 14%, 13%, 12%, 11%, 10%, 9%, or 8%.

For total soluble carbohydrate, a suitable threshold value may be at or about 9%, with the modified soybean such as described herein containing at least or at least about 3%, 3.5%, 4%, 4.5%, 5%, 5.5%, 6%, 6.5%, 7%, 7.5%, 8% or 8.5% total soluble carbohydrate and less than or less than about 6.5%, 6%, 5.5%, 5%, 4.5%, 4%, 3.5%, 3%, 27.5%, 2%, 1.5% or 1% total soluble carbohydrate and the comparable unmodified or null soybean containing at least or at least about 9%, 9.5%, 10%, 10.5%, 11%, 11.5%, 12% or 12.5% total soluble carbohydrate and less than or less than about 15%, 14%, 13%, 12.5%, 12%, 11.5%, 11%, 10.5%, 10% or 9.5% total soluble carbohydrate. The threshold value for total soluble carbohydrate includes values at, about, at least or at least about 4%, 4.5%, 5%, 5.5%, 6%, 6.5%, 7%, 7.5%, 8%, 8.5%, or 9% and at, about, less than or less than about 9.5%, 10%, 10.5%, 11%, 11.5%, 12%, or 12.5%.

For sucrose, a suitable threshold value may be at or about 3.8%, with the modified soybean such as described herein containing at least or at least about 0.5%, 1%, 1.5%, 2%, 2.5%, 3%, or 3.5% sucrose and less than or less than about 3.8%, 3.5%, 3%, 2.5%, 2%, 1.5%, 1%, or 0.5% sucrose and the comparable unmodified or null soybean containing at least or at least about 3.8%, 4%, 4.5%, 5%, 5.5% or 6% sucrose and less than or less than about 7%, 6.5%, 6%, 5.5%, 5%, 4.5%, or 4% sucrose. The threshold value for sucrose includes values at, about, at least or at least about 1%, 1.5%, 2%, 2.5%, 3%, or 3.5% and at, about, less than or less than about 6%, 5.5%, 5%, 4.5%, 4%, 3.5%, 3% or 2.5%.

For the sum of oil and protein content, also referred to as the PROIL content, a suitable threshold value may be at or about 54%, with the modified soybean such as described herein containing at least or at least about 54%, 55%, 56%, 57%, 58%, 59%, 60%, 61%, 62% or 63% PROIL and less than or less than about 70%, 65%, 60%, 59%, 58%, 57%, 56%, or 55% PROIL and the comparable unmodified or null soybean containing at least or at least about 45%, 46%, 47%, 48%, 49%, 50%, 51%, 52% or 53% PROIL and less than or less than about 55%, 54%, 53%, 52%, 51%, 50%, or 49% PROIL. The threshold value for PROIL includes values at, about, at least or at least about 50%, 51%, 52%, 53%, 54%, or 55% and at, about, less than or less than about 64%, 63%, 62%, 61%, 60%, 59%, 58%, 57%, 56%, or 55%.

Useful examples of percent point increases in PROIL in a seed, such as a modified soybean seed compared with a comparable or control soybean include, but are not limited to, percentage point increases of at least or at least about 50%, 55%, 60%, 65%, 70%, 75%, 80%, 85%, 90%, or 95% and less than or less than about 98%, 97%, 96%, 95%, 90%, 85%, 80%, 75%, 70%, 65%, 60%, 65% 60%, 55%, 50%, 45% or 40%.

The methods may be used for seeds from plants with two, three, four, five or ten or more transgenes or genetic modifications, wherein accumulating or stacking of transgenic regions or genetic modifications into plants or lines is achieved by addition of transgenes by transformation, by genome editing, by crossing parent plants or lines containing different transgenic regions or modifications, or any combination thereof. Analyses can be conducted to select individual seeds on the basis of the presence of one or more characteristics associated with at least one transgene or modification. Such characteristics include, but are not limited to, a seed composition, a transgene per se, a genetic marker linked to a transgene or modification, mRNA expressed from a transgene or modification, and a protein product of a transgene or modified region or gene.

Methods and systems provided herein may include the step of confirming a phenotype, for example, by extracting or isolating nucleic acids, such as DNA, from a seed or population of seeds and using appropriate genetic techniques to analyze or detect the genotype. Such genetic techniques include, for example, contacting isolated or extracted nucleic acids with one or more genetic markers, the detection of single nucleotide polymorphisms, simple sequence repeats, restriction fragment length polymorphisms, haplotypes, tag SNPs, alleles of genetic markers, genes, DNA-derived sequences, RNA-derived sequences, promoters, 5' untranslated regions of genes, 3' untranslated regions of genes, microRNA, siRNA, quantitative trait loci (QTL), satellite markers, transgenes, mRNA, ds mRNA, transcriptional profiles, and methylation patterns. Examples of genetic analyses to identify or select seeds for trait integration include, without limitation, identification of high recurrent parent allele frequencies, tracking of transgenes of interest or screening for the absence of unwanted transgenes, selection of hybrid testing seed, selection of seed expressing a gene of interest, selection of seed expressing a heritable phenotype, identification of seed with selected genetic loci, and zygosity testing.

Assaying of soybean seeds according to the provided methods and systems can also be done rapidly, with an accurate measure of the composition, such as the amount of sucrosyl-oligosaccharides, of the single soybean or a batch of soybeans achieved in less than 5, 4, 3, 2, or 1 minutes or less than one second following commencement of the method. For example, using FT-NIR, up to 100 g (about 400 to 500) soybean seeds as a single batch can be measured in less than 3, 2 or 1 minutes, for example, in about 1 to 2 minutes or 1 to 3 minutes. For example, using NIT, up to 500 g (about 2,500) soybean seeds can have seed composition, including sucrosyl-oligosaccharides, be measured in less than 3, 2 or 1 minutes, for example, in about 0.5 to 1 minutes, 0.5 to 2 minutes, 0.5 to 3 minutes, or 0.5 to 5 minutes. For example, using SS-NIR, a single seed can be measured in about 1 or 2 minutes, such as 0.5 to 3 minutes, 0.5 to 4 minutes or 0.5 to 5 minutes. Using SS-NIR, a single seed can also be measured in less than a second, such as at least 5, 10, 20, 30, 40, 50, 60, 70, 80, 90 or 100 soybean seeds per second and less than about 1000, 500, 400, 300, 200, or 100 seeds per second.

The methods and systems provided herein can enhance efficiency and facilitate high throughput of sorting and selecting seed and plants grown from the seed with a desired trait.

In some embodiments, the methods described herein are used in transgenic, genome modification or research breeding programs where sample size may be limited, such as a single seed from a segregating plant, and when intact viable seed are required for propagation and advancement. In some embodiments, the methods are used for seed analysis where destructive analytical methods are not desirable because intact seeds are required for processing or when there is insufficient time to undertake destructive analysis.

The progeny seed can be selected, bulked and used to make further breeding crosses or in further research. The progeny seed can be made subject to the methods of non-destructive analysis provided herein.

Also provided herein is a method for producing a soybean plant with one or more desired traits, e.g. transgenes or modifications. Donor soybean plants for a parental line containing the desired trait are selected. Selected plant material may represent, among others, an inbred line, a hybrid line, a heterogeneous population of soybean plants, or an individual plant. According to techniques well known in the art of plant breeding, the donor parental line is crossed with a second parental line. In some embodiments, the second parental line is a high yielding line. This cross produces a segregating plant population composed of genetically heterogeneous plants. Seeds of plants of the segregating plant population are screened for the desired trait using the analytical methods as disclosed herein. Further breeding may include, among other techniques, additional crosses with other lines, hybrids, backcrossing, or self-crossing. The result is a line of soybean plants that has the desirable trait and optionally also has other desirable traits from one or more other soybean lines.

The methods and systems provided herein provide an increased capacity to evaluate a larger number of breeding populations per field unit, and increased capacity to analyze breeding populations for desired traits prior to planting. For example, the methods and systems allow a breeder to analyze at least 100, 250, 500, or 1,000 seeds and sort or select the 5, 10, 25 or 50 desired seeds from that population for planting without having to plant assess, tag and sample the original population of 100, 250, 500, or 1,000 seeds. Very large sample sizes can be processed quickly by either single seed or bulk analysis, such as at least about 1 kg, 5 kg, 10 kg, 100 kg, 500 kg, 1000 kg, 1500 kg, 2000 kg, 3000 kg, 4000 kg or 5000 kg of soybean seeds per hour and less than 25,000 kg, 20,000 kg, 15,000 kg, 10,000 kg, 7,500 kg, 5,000 kg, 2,000 kg, 1000 kg, 500 kg, 100 kg, 10 kg or 5 kg soybean seeds per hour.

The methods and systems provided herein further permit quality assurance (QA) and quality control (QC) by assuring that soybean seeds are free of regulated or unwanted transgenes, undesirable genetic traits, or undesirable inherited phenotypes by identifying such phenotypes and discarding such seed.

Soybean seeds which can be used may additionally contain desirable agronomic traits that enhance production and consistency of production of soybean grain, such as herbicide tolerance, disease resistance, insect resistance, increased grain yield, increased nutritional content, increased growth rates, enhanced stress tolerance, altered maturity, and combinations thereof. Quality traits such as higher oil, higher protein, modifications in essential amino acids and protein compositional changes, changes in oil composition, nutritional traits such as vitamins, and traits with industrial uses including biodiesel, biolubricants, and polymers can also be identified and selected.

The methods and systems can be used in a plant breeding program which selects plants or seeds having a desired genetic or phenotypic trait, wherein a desired genetic trait includes one or more of a genotype, a haplotype, an allele, a sequence, a transcript profile, and a methylation pattern. The methods and systems may be further used in combination with plant breeding methods where a single seed selected or sorted is crossed or backcrossed and a single generation or multiple generations of progeny plants are generated. Seed of the progeny plants may be processed according to the methods described herein. The crossing and backcrossing steps of the first and subsequent generation of progeny plants and seeds may be carried out in any combination. The choice of breeding method depends on the mode of plant reproduction, the heritability of the trait(s) being improved, and the type of cultivar used commercially (e.g., hybrid cultivar, pureline cultivar, etc.). Selected, non-limiting approaches for breeding the plants are set forth below. It is further understood that any soybean lines, varieties or cultivars can be utilized in a breeding program. Factors including, for example, without limitation, emergence vigor, vegetative vigor, stress tolerance, disease resistance, branching, flowering, seed set, seed size, seed density, standability, and threshability may be selected for use in the breeding program.

In some embodiments, the single seed identity of the seed is preserved. Several methods of preserving single seed identity can be used while transferring or transporting seed from the location of the seed, such as at or following harvest, to the location where analysis is conducted, to the field or greenhouse location where the selected plants are to be grown. Methods include, but are not limited to, transferring selected individuals to seed tape, a cassette tray, or indexing tray, transplanting with peat pots, and hand-planting from individual seed packets.

The apparatus, device, system or method for measuring and sorting seeds can comprise or use a transport system which supports at least one seed at a time and exposes the at least one seed to an optical interrogation device or an imaging system, such as NIT, NIR or FT-NIR, which captures at least one near-infrared image of the at least one seed. The imaging system can be configured to accurately measure the amount of one or more sucrosyl-oligosaccharides in the first seed compared with the standard reference analytical method provided herein. The apparatus, device, system or method can include an electronic controller which makes a sorting decision with at least two sorting outcomes regarding the seed based on the modified light, image or near infrared spectra obtained from the seed and a sorting system to alter the path of the seed based on the sorting decision, wherein the electronic controller associates a first sorting outcome with the first seed and the electronic controller associates a second sorting outcome with the second seed. Seed containing low amounts of sucrosyl-oligosaccharides below (or at) a threshold value can be separated from seed containing higher amounts of sucrosyl-oligosaccharides above (or at) the threshold value. For example, greater confidence in the sorting decisions may achieved by combining the sucrosyl-oligosaccharide threshold value with a threshold value for one or more fatty acid percentages, altered, such as increased oil or protein content, changes in the soluble sugar levels, or a combination thereof. Each of these parameters can be measured from the same near infrared spectra captured from a single seed, bulk seeds or protein meal.

In some embodiments, a method for determining the amount of a sucrosyl-oligosaccharide in a single soybean seed or a sample of intact soybean seeds, comprises directing light from a light source onto a soybean seed or seeds to form modified light from the soybean seed or seeds; receiving the modified light in an imaging device, such as capturing the near infrared absorption spectra, and measuring the amount of a sucrosyl-oligosaccharide in the seed or seeds based on the received modified light, the amount of sucrosyl-oligosaccharide being measured to an accuracy according to the standard reference analytical method provided herein.

The imaging device can be a commercially available infrared spectrometer, including for example, an infrared spectrometer, a Fourier transform infrared spectrometer, or a spectrophotometer with a diffuser and lens and filter array such as described in U.S. Pat. Nos. 9,500,523, 9,383,258, 9,377,396 and 9,291,504, or a seed sorting device such as described in U.S. Pat. No. 8,907,241 or a device useful for single seed analysis such as described in U.S. Pat. No. 8,965,060.

In some embodiments, a method for processing seeds or for determining the amount of a sucrosyl-oligosaccharide in a soybean seed comprises directing light from a light source onto an individual soybean seed to form modified light from the soybean seed; receiving the modified light in an imaging device; measuring the amount of a sucrosyl-oligosaccharide in the seed based on the received modified light, the amount of sucrosyl-oligosaccharide being measured to an accuracy that is within the parameters provided herein. The seed can be transported to a first location when the amount of sucrosyl-oligosaccharide measured is below a threshold value and transporting the seed to a different second location when the amount of sucrosyl-oligosaccharide measured is at or above the threshold value. The seed can be separated into modified and unmodified seed wherein the amount of sucrosyl-oligosaccharide, such as stachyose or a combination of stachyose and raffinose, differ between the modified and unmodified seed as described herein.

In some embodiments, the method or system includes an automated method or system, wherein a seed is separated from a plurality of seeds prior to directing light from a light source onto an individual soybean seed to form modified light from the soybean seed. The light source can be comprised in an optical interrogation device or system and comprises near infrared light such as a broad spectrum light source or a near infrared light source. The automated system may include a transport system for transporting separated seeds to the optical interrogation device and for transporting the seeds to one, two, three or more different locations based on the composition of the seed measured by the optical interrogation device. Individual seeds can be automatically transported to a first station for receiving light where light is directed from a light source on the individual soybean seed at a first station to form modified light, the modified light from the soybean seed is received in an imaging device, and the amount of one or more sucrosyl-oligosaccharides in the seed measured based on the modified light, to an accuracy as provided herein. The method may further comprise following the measurement of the amount of a sucrosyl-oligosaccharide, transporting the seed to a first location when the amount of sucrosyl-oligosaccharide measured is below a threshold value and transporting the seed to a different second location when the amount of sucrosyl-oligosaccharide measured is at or above the threshold value. All of the prior steps can be repeated for a second and subsequent individual seeds.

In some embodiments, a plurality of seeds to be measured either as single seeds or as a sample of intact seeds includes both modified and unmodified seeds as described herein, wherein the modified seeds are transported to the first location and the unmodified seeds are transported to the second location based on the compositional differences detected by the optical interrogation device. The steps of sorting a seed from a plurality of seeds and carrying out this method as disclosed herein can be repeated for at least a second, third or fourth seed. In some embodiments, seeds are selected or separated depending on the composition measured using the methods described herein.

The methods are suitable for measuring and processing small and large sample sizes. In some embodiments, a sample or population of at least 5, 10, 15, 20, 25, 30, 40, or 50 seeds and less than 250, 225, 200, 175, 150, 125, 100, 90, 80, 70, or 60 whole, intact and/or viable seeds are assayed together as a batch of seeds in the methods and systems provided. In some embodiments, a sample of at least 1 g, 5 g, 10 g, 100 g, 150 g, 200 g, 250 g, or 300 g seeds and less than 5000 g, 2000 g, 1000 g, 900 g, 800 g, 700 g, 600 g, or 500 g whole, intact and/or viable seeds are assayed together as a batch of seeds in the methods and systems provided. In some embodiments, at least 5, 10, 15, 20, 25, 30, 40, 50, 75, 100, 150, 200, 250, 500 or 1000 and less than 1,000,000, 500,000, 100,000, 75,000, 50,000, 25,000, 10,000, 5,000, 2,500, 1,000, 500, 250, 100, 75, 50 or 25 individual seeds, seed, meal or soybean flake batches, or seed populations are measured.

Methods and systems provided can be used to analyze individual seeds or seed batch samples within a population of seeds to measure one or more compositional differences in one or more components of the seed or seeds.

Following the measurement of the composition of the seeds, for example, the amount of sucrosyl-oligosaccharide, oil, protein, sugars, starch, carbohydrate, fiber or combination thereof, the soybean seeds can be processed. Processing steps can include one or more of dehulling of the soybeans, extraction of oil, for example by use of solvents, processing soy flakes to soy meal for animal feed, grinding soy flakes to produce soy flour, sizing soy flakes to produce soy grits or texturizing soy flakes to produce textured vegetable protein. Soy protein concentrates and isolated soy protein can be further refined and produced from soy flakes. The methods and systems provided may include the step of processing the soybeans into meal without the need for dehulling, based on the low non-digestible carbohydrate content, including one or more of stachyose and raffinose. The composition of the soy beans can be accurately measured in the field or at the grain elevator to facilitate processing decisions on a large scale. Protein meal can be accurately measured at the grain processing plants to determine meal quality and value.

Some embodiments include methods and systems for selecting a plant or plant seed, comprising directing light from a light source onto an individual soybean seed to form modified light from the soybean seed; receiving the modified light in an imaging device; measuring the amount of a sucrosyl-oligosaccharide in the seed based on the received modified light, the amount of sucrosyl-oligosaccharide being measured to an accuracy that is within an amount measured using the standard reference analytical methods as provided herein; transporting the seed to a first location when the amount of sucrosyl-oligosaccharide measured is below a threshold value and transporting the seed to a different second location when the amount of sucrosyl-oligosaccharide measured is at or above the threshold value. The seed from the first location and/or the second location can be grown to produce a plant which can be crossed with a different plant or selfed/allowed to self. The progeny seed produced from seed at the first location may contain a lower or reduced amount or concentration of sucrosyl-oligosaccharide, when compared to progeny seed produced from seed at the second location. The seed transported to either the first or second location and produced through crossing or selfing can be transgenic or non-transgenic and may comprise at least one recombinant construct in the genome, or may not comprise a recombinant construct in the genome. The seeds selected by the methods as disclosed herein may be further selected and used in breeding.

Some embodiments include methods for sorting seeds, the methods comprising directing light from a light source onto an individual soybean seed to form modified light from the soybean seed receiving the modified light in an imaging device measuring the amount of a sucrosyl-oligosaccharide in the seed based on the received modified light, the amount of sucrosyl-oligosaccharide being measured to an accuracy that is within 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2 percentage points of the amount measured using the standard reference analytical method; and transporting the seed to a first location when the amount of sucrosyl-oligosaccharide measured is below a threshold value and transporting the seed to a different second location when the amount of sucrosyl-oligosaccharide measured is at or above the threshold value. The method of sorting as disclosed herein may further comprise growing a plant from the sorted seed and crossing the plant with itself or a different plant and using the seed and plant in a breeding program as provided herein.

Any seed, including monocot and dicot seeds, may be adapted to be utilized in a method, systems or device provided herein. The seed may be, for example, alfalfa seed, apple seed, banana seed, barley seed, bean seed, broccoli seed, castor bean seed, citrus seed, clover seed, coconut seed, coffee seed, maize seed, cotton seed, cucumber seed, Douglas fir seed, Eucalyptus seed, Loblolly pine seed, linseed seed, melon seed, oat seed, olive seed, palm seed, pea seed, peanut seed, pepper seed, poplar seed, Radiata pine seed, rapeseed seed, rice seed, rye seed, sorghum seed, Southern pine seed, soybean seed, strawberry seed, sugar beet seed, sugarcane seed, sunflower seed, sweetgum seed, tea seed, tobacco seed, tomato seed, turf seed, wheat seed, and *Arabidopsis* seed.

Depending on the seed composition, the seed may be discarded prior to planting or planted such as when being used in a plant breeding program, or can be directed to an appropriate processing plant or process if the seed is harvested from a crop and intended for processing. Processing that may occur, depending on the seed composition, may include or exclude one or more of the steps of dehulling, extracting oil, processing meal and producing protein from the soybean. In general, soybean oil is produced from cleaned, tempered, dehulled, and flaked soybeans using solvent (hexane) extraction or a combination of physical pressure and/or solvent extraction.

The following examples are presented in order to more fully illustrate some embodiments of the invention. They should, in no way be construed, however, as limiting the broad scope of the invention. Those of ordinary skill in the art will readily adopt the underlying principles of this discovery to design various compounds without departing from the spirit of the current invention.

EXAMPLES

In the following Examples, parts and percentages are by weight and degrees are Celsius, unless otherwise stated. The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kB" means kilobase(s).

Example 1

Creation of Events Having Compositional Diversity

Soybean lines having a broad range of compositional diversity were created as described below.

RNAi was used to silence seed-specific gene expression of soy fatty acid desaturase 2 (fad2) to produce soybeans with a seed oil composition having increased oleic acid according to U.S. Pat. No. 7,456,014.

RNAi was used to silence seed-specific gene expression of soy phosphoglucomutase (PGM) to produce soybeans with a seed oil composition having increased oil and protein according to U.S. Pat. No. 7,323,560.

RNAi comprising polynucleotide fragments were prepared for galactinol synthase 1 (GAS1), according to U.S. Pat. No. 5,648,210, galactinol synthase 2 (GAS2) according to U.S. Pat. No. 6,967,262 and galactinol synthase 3 (GAS3) according to U.S. Pat. No. 7,294,756. The use of seed-specific silencing of gene expression of soy galactinol synthases (GAS) to produce soybeans with a decreased raffinose and stachyose carbohydrate content and increased sucrose content was carried out according to PCT/US14/48825.

Artificial microRNAs (am iRNAs) were used to silence seed-specific gene expression of soy fatty acid desaturase 3 (fad3) to produce soybeans with a seed oil composition having decreased alpha-linolenic acid according to PCT/US13/22654 and PCT/US14/48825.

Artificial microRNAs (amiRNAs) were used to silence seed-specific gene expression of soy fatty acid desaturase 2 (fad2) to produce soybeans with a seed oil composition having increased oleic acid according to PCT/US08/87082, PCT/US13/22654 and PCT/US14/48825.

Artificial microRNAs (amiRNAs) were used to silence seed-specific gene expression of soy fatty acid thioesterase 2 (fatB) to produce soybeans with a seed oil composition having decreased palmitic and stearic acids according to, for example, PCT/US13/22654 and PCT/US14/48825. Combining amiRNAs together to silence multiple genes such as fad2 and fatB was carried out according to, for example, PCT/US13/22654 and PCT/US14/48825.

A modified soy diacylglycerol acyltransferase 1 gene (GM-DGAT1-C9C10C11) under control of a seed-specific promoter was used to produce soybeans having higher oil and protein in the seed according to, for example, U.S. Pat. No. 8,101,819 and PCT/US14/48825.

A *Yarrowia lipolytica* diacylglycerol acyltransferase 2 gene (YL-DGAT2) under control of a seed-specific promoter was used to produce soybeans having higher oil and protein in the seed according to U.S. Pat. Nos. 8,143,473, 8,143,476 and in PCT/US14/48825.

YL-DGAT2, under control of a seed-specific promoter, was combined with a fad3 amiRNA under control of a seed-specific promoter, and with a GAS RNAi cassette under control of a seed-specific promoter according to PCT/US14/48825.

A soy sucrose transporter 4 (GM-SUT4) alone or in combination with YL-DGAT2 under control of a seed-specific promoter was used to produce soybeans having higher seed oil has according to U.S. Pat. No. 8,993,840.

A soy ovule development protein 1 (GM-ODP1) alone or in combination with YL-DGAT2 or GM-DGAT1-C9C10C11 under control of the soy sucrose synthase promoter was used to produce soybeans having higher oil and protein in the seed according to PCT/US12/70828.

Mutations in the sucrosyl-oligosaccharide pathway, such as low2 (mutant with reduced raffinose synthase expression leading to low stachyose and raffinose and elevated sucrose and galactinol and low4 (mutant with reduced myo-inositol-1P-synthase leading to low stachyose and raffinose) according to U.S. Pat. No. 6,653,451.

Wildtype commodity soybeans were also included in the test set along with transgenic null materials (i.e., lines that had undergone the typical transformation process but that were found, on subsequent analysis, to not be expressing the trait of interest). Varieties used included one or more of the following commercial or public varieties: 91M10, 92Y51, 92Y61, 93E367, 93E368, 93E386, 93M02, 93M11, 93M12, 93Y21, 93Y30, 93Y41, 93Y42, 93Y83, 93Y84, 94Y23, 95E334, 98Y11, ASGA232HS, EX82J07, JACK, P29T68PR, P32T80PR, SP6634911, YR25C09, YR37Y09.

A list of experiment names and the corresponding DNA constructs used to create soybean events having a range of compositions as described herein is shown in Table 2.

TABLE 2

Experiment names and corresponding DNA plasmids/DNA fragments used to create soybean events producing a diverse range of compositions.

| Experiment Name | Transformation Type | DNA Plasmid/ Fragment | SEQ ID NO: | Second DNA Plasmid/ Fragment | SEQ ID NO: |
|---|---|---|---|---|---|
| Soil2 | SSI | PHP48070 | 1 | n/a | n/a |
| Soil19 | SSI | PHP50573 | 2 | n/a | n/a |
| Soil91 | SSI | PHP64612 | 3 | n/a | n/a |
| Soil92 | SSI | PHP64613 | 4 | n/a | n/a |
| Meal 18 | Random Particle Bombardment | PHP25066A | 5 | n/a | n/a |
| Oil119 | Random Particle Bombardment | PHP64207A | 6 | n/a | n/a |
| HOGAS | Random Particle Co-Bombardment | PHP17522A | 7 | PHP17734A | 8 |
| Meal34 | Random Particle Co-Bombardment | PHP29252A | 9 | PHP19031A | 10 |
| Meal36 | Random Particle Co-Bombardment | PHP29882A | 11 | PHP29959A | 12 |

The Soil 2 PHP48070 plasmid contains the following noted sequences: GAS hairpin from position: 13833-17206 of SEQ ID NO: 1, FAD2-specific amiRNA precursor from position: 6980-8557 of SEQ ID NO: 1, and the FAD3-specific amiRNA precursor from position: 10514-11472 of SEQ ID NO: 1.

The Soil 19 PHP50573 plasm id contains the following noted sequences: GAS hairpin from position: 13809-17182 of SEQ ID NO: 2, FAD3-specific amiRNA precursor from position: 10490-11448 of SEQ ID NO: 2, and the YL-DGAT2 from position: 6996-8540 of SEQ ID NO: 2.

The Soil 91 PHP64612 plasm id contains the following noted sequences: GAS hairpin from position: 15112-18485 of SEQ ID NO: 3, Gm_SUT4 from position: 12428-13945 of SEQ ID NO: 3, Gm_DGAT1 from position: 9879-11390 of SEQ ID NO: 3, and Gm_ODP1: from position: 6823-8058 of SEQ ID NO: 3.

The Soil 92 PHP64613 plasm id contains the following noted sequences: GAS hairpin from position: 17136-18849 of SEQ ID NO: 4, Gm_SUT4 from position: 12961-14478 of SEQ ID NO: 4, Gm_DGAT1 from position: 9454-10998 of SEQ ID NO: 4, and Gm_ODP1: from position: 6823-8058 of SEQ ID NO: 4.

The Meal 18 PHP25066A plasmid contains the following noted sequences: GAS suppression fragments from position: 76-2194 of SEQ ID NO: 5.

The Oil 119 PHP64207A plasmid contains the following noted sequences: GAS hairpin from position: 10496-13869 of SEQ ID NO: 6, Gm_SUT4 from position: 7812-9329 of SEQ ID NO: 6, and Gm_DGAT1 from position: 5262-6773 of SEQ ID NO: 6.

The HOGAS PHP17734A plasmid contains the following noted sequences: GAS suppression fragments from position: 1132-1977 of SEQ ID NO: 8 and a FAD2 suppression fragment from position: 5376-5986 of SEQ ID NO: 8. The HOGAS plasmid PHP17522A (SEQ ID NO: 7) contains a selectable marker (herbicide resistance).

The Meal 34 PHP29252A plasm id contains the following noted sequence: GAS/PGM hairpin structure from position: 2117-6630 of SEQ ID NO: 9. The Meal 34 plasmid PHP19031A (SEQ ID NO: 10) contains a selectable marker (herbicide resistance).

The Meal 36 PHP29882A plasmid contains the following noted sequence: PGM hairpin from position: 634-1973 of SEQ ID NO: 11. The Meal 36 PHP29959A plasmid contains the following noted sequence: GAS hairpin from position: 321-3694 of SEQ ID NO: 12.

AscI fragments were prepared transformed into soy using particle gun bombardment, events were selected, plants grown and seed were harvested as described in U.S. Pat. No. 8,084,074 for random particle bombardment [Meal18 (PHP25066A) or Oil119 (PHP64207A)] and random particle co-bombardment [HOGAS (PHP17522A+PHP17734A), Meal34 (PHP29252A+PHP19031A) or Meal36 (PHP29882A+PHP29959A)] experiments.

Transgenic SSI target event "A", previously described in U.S. Pat. No. 8,293,533, was transformed with the donor constructs [Soil2 (PHP48070), Soil19 (PHP50573), Soil91 (PHP64612) or Soil92 (PHP64613)] and the FLP recombinase construct PHP44664 as previously described in PCT/US14/48825 and events were selected, plants grown and seed were harvested as described previously and in U.S. Pat. No. 8,084,074.

Example 2

Reference Chemistry for Development of Single Seed Compositional Models.

2.1. Sample Preparation for Single Seed Reference Chemistry.

A single soybean was placed in a Spex Certiprep ½×2" polycarbonate vial with cap (cat #3116PC). A ⅜" stainless steel ball bearing was added. Grinding was performed in a Spex Certiprep 2000 Geno/Grinder at 1500 strokes/min for three 30 second intervals with a 1-minute rest between each cycle.

2.2. Lipid and Non-Structural Carbohydrate Extraction; GC Fatty Acid Profile Determinations Quantitative oil determinations were performed (on both the whole and ground bean samples) by NMR (see below). The lipid extracts of the single soybean powders were used solely to determine the fatty acid profiles. Three replicate extractions were performed on each sample as follows:

2.2.1. Weigh sample (approximately 20-50 mg; to an accuracy of 0.1 mg) into 13×100 mm tube (with Teflon® lined cap; VWR (53283-800) and record weight. In later studies sample size was standardized at ~20.0 mg.

2.2.2. Add 2 mL Heptane, vortex and place into an ultrasonic bath (VWR Scientific Model 750D) at 60° C. for 15 min at full sonification-power (~360 W).

2.2.3. Centrifuge for 5 min at 1700×g at room temperature.

2.2.4. Decant the supernatant to a clean 13×100 mm glass tube.

2.3. Fatty Acid Profile Determination: GC Method:

2.3.1. Transfer 200 uL aliquot of the heptane extract into a clean screw top GC vial National Scientific (C4000-186 W)

2.3.2. To the 200 uL add 300 uL heptane and 50 uL trimethylsulfonium hydroxide in methanol (JenaChem)

2.3.3. Shake the vials on an orbital shaker at room temperature for 15 minutes.

2.3.4. The fatty acid methyl esters were analyzed by directly injecting 1 uL samples (at a 5:1 split ratio) onto an Agilent 6890 gas chromatography system fitted with a Supelco Omegawax 320 (30 m×0.320 mm×0.25 um film) capillary column. Hydrogen was used as the carrier gas (39 cm/sec average linear velocity). Inlet and FID detector temperatures were held at 260° C. and the oven column temperature was ramped from 180 to 240° C. at a rate of 12° C. per minute.

2.4. Non-structural Carbohydrate Extraction:

2.4.1. Add 1 mL acetone to the heptane extracted pellet from the fatty acid profile method above, vortex mix to disperse the material into the acetone and dry in a SpeedVac.

2.4.2. To the dry pellet add 2 mL of 80% ethanol. Vortex to break up pellet as much as possible. Extract on sonicator (see 2.2.2) for 15 min at 60° C.

2.4.3. Centrifuge for 5 min at 1700×g. Transfer supernatant to a clean 13×100 mm tube.

2.4.4. Repeat Steps 2.4.2 and 2.4.3 two more times, combining the supernatant with the above (3) each time.

2.4.5. Add 100 μL of phenyl-β-D glucopyranoside internal standard (β-phenyglucopyranoside stock 0.5000+/−0.0010 g in 100 ml water) to the combined supernatant. Dry the extract in a SpeedVac and analyze for non-structural carbohydrates as described below.

2.4.6. Add 1 ml acetone and dry the remaining pellet in the SpeedVac.

2.5. Starch Digestion and Extraction:
- 2.5.1. Perform starch digestion directly on the acetone dried pellets from non-structural carbohydrate extraction.
- 2.5.2. Add 100 units of α-Amylase (α-amylase; Heat Stable from *Bacillus licheniformis* e.g. Sigma-Aldrich A-4551) in 0.9 mL 50 mM MOPS (3-(N-Morpholino) propane sulfonic acid) buffer pH 7.0, containing 5 mM $CaCl_2$ and mix.
- 2.5.3. Place tubes into a heating block at 90° C. for 75 minutes. Mix several times during hydrolysis.
- 2.5.4. Allow tubes to cool to room temperature and add 5 units of Amyloglucosidase (commercially available from Roche 11 202 367 001) in 0.6 mL of 285 mM acetate buffer, pH 4.5 and incubate in a reciprocating water bath at 55° C. for 15-18 hours.
- 2.5.5. Remove rack of tubes and bring to room temperature.
- 2.5.6. Add 4.5 mL of absolute ethanol to each tube to attain a final ethanol concentration 80% and vortex. Extract on sonicator for 15 min at 60° C.
- 2.5.7. Centrifuge 5 min at 1700×g and decant supernatant to a 13×100 mm tube and immediately place tube in SpeedVac to reduce the volume. 2.5.8. Extract pellet a further 2 times with 2 mL 80% ethanol, combining supernatant with above each time. 2.5.9. Add 100 µL of phenyl-β-D glucopyranoside (see 2.4.5) to the combined supernatant before it is fully dry. Once the extract in the SpeedVac is dry analyze for non-structural sugars as described below. 2.5.10. Add 1 ml acetone and dry the remaining pellet in the SpeedVac and store (at −20° C.) for structural sugar analysis.

2.6. Total Soluble Carbohydrate Derivatization and Analysis.
- 2.6.1. The dried samples from the soluble and starch extractions described above along with sets of sugar standard (pinitol, sorbitol, fructose, glucose, β-phenyl glucopyranoside, sucrose, raffinose and stachyose; at 0, 0.05, 0.10, 0.50, 1.00, 2.00, 3.00, 4.00 and 5.00 mg/tube) mixtures were solubilized in anhydrous pyridine (Sigma-Aldrich P57506) containing 30 mg/ml of hydroxylamine HCl (Sigma-Aldrich 159417).
- 2.6.2. Samples were placed on an orbital shaker (300 rpm) overnight and were then heated for 1 hr (75° C.) with vigorous vortex mixing applied every 15 min.
- 2.6.3. After cooling to room temperature 1 ml hexamethyldisilazane (Sigma-Aldrich H-4875) and 100 µL trifluoroacetic acid (Sigma-Aldrich T-6508) were added. The samples were vortex mixed and the precipitates were allowed to settle prior to transferring the supernatants to GC sample vials.
- 2.6.4. Samples were analyzed on an Agilent 6890 gas chromatography system fitted with a DB-17MS capillary column (30 m×0.32 mm×0.25 um film). Inlet and detector temperatures were both 275° C. After injection (2 µL, 20:1 split) the initial column temperature (150° C.) was increased to 180° C. at a rate 3° C./min and then at 25° C./min to a final temperature of 320° C. The final temperature was maintained for 10 min. The carrier gas was $H_2$ at a linear velocity of 51 cm/sec. Detection was by flame ionization. A 1 m length of plain 0.320 mm capillary tube (Agilent; 160-2325-5) was inserted between the inlet and the analytical column to act as a guard column. The two column sections were connected using a push-fit connector. Prior to all analytical runs three injections of a standard mixture containing 5 mg of each sugar was made to passivate the chromatography system. This process was found to enable full recovery of stachyose from the analytical samples, especially as the column aged. Ultra-Inert Inlet Liners (Agilent; 5190-3164) were also used and were routinely changed based on indications of loss in chromatographic performance.
- 2.6.5. Data analysis was performed using Agilent ChemStation software. Each sugar was quantified relative to its own calibration curve, after dividing each individual peak by the area of the internal standard in each sample and standard. Final carbohydrate concentrations were expressed on a weight percent basis, corrected for moisture content as set forth herein. Residual sucrose, raffinose and stachyose recovered in the starch digestions were included in the total values reported for each sugar.

2.7. Supplemental Methods.
Moisture Content Determinations were Performed according to American Oil Chemists Society (AOCS Official Method Ba 2a-38, Modified for Small Samples) as follows:
- 2.7.1. Weigh powdered sample material (approximately 100 mg; to an accuracy of 0.1 mg) into a pre-weighed (and recorded) 13×100 mm glass tube VWR (53283-800) and weigh again.
- 2.7.2. Place samples into a forced air oven preheated to 130° C.
- 2.7.3. Allow material to dry for 2 h.
- 2.7.4. Remove tubes into a desiccator cabinet and allow to come to room temperature before weighing again.
- 2.7.5. Cap tube and save residual dried material for subsequent combustion analysis for protein (see below).
- 2.7.6. Store in a desiccator for further analysis.

2.8. Calculation of Moisture Content.

$$\text{Moisture} = \frac{(\text{wt. tube} + \text{tissue as is} - \text{wt. tube}) - (\text{wt. tube} + \text{tissue dry} - \text{wt. tube})}{(\text{wt. tube} + \text{tissue as is} - \text{wt. tube})} \times 100$$

2.9. Whole Seed Moisture Calibrations.

Whole seed moisture calibrations for the SS-NIR were developed according to the methods described below. Pods were harvested from Jack, 93686 and 93Y21 soybeans between the R7 and R8 stage of development (i.e., yellow to brown pod stage) when the soybeans had moisture contents of below 20%. Beans were removed from the pods and their weight was measured and recorded to 0.0001 g accuracy prior to spectral capture using the SS-NIR instrument. The beans were then subjected to controlled drying (@105° C. in a forced draft oven for short periods of time) to attain a broad range of moisture contents before repeat weighing and spectral capture. A final dry weight for each bean was obtained after drying in a forced draft oven at 105° C. for 18 h. Moisture content was calculated as follows:

$$\text{moisture content} = \frac{((\text{wt. tube} + \text{bean as is}^* - \text{wt. tube}) - (\text{wt. tube} + \text{oven dried bean} - \text{wt. tube}))}{(\text{wt. of bean as is} - \text{wt. tube})^*} \times 100$$

*at time of spectral capture.

Alternatively, mature soybeans were placed in 5×6" aluminum foil trays in 1 gallon ZipLock® plastic bags. The relative humidity of the atmosphere within the bags was controlled by adding a second foil pan in which either a layer of self-indicating DrieRite desiccant (W. A. Hammond Inc; Xenia OH) or a saturated aqueous solution of sodium chloride (200 g NaCl in ⅓rd pan depth of water). A third bag containing seed but without any atmospheric moisture control was also set up. The beans were exposed to the controlled moisture atmospheres for one month prior to weighing followed by immediate spectral capture on the SS-NIR. In order to maintain the individual identity of each bean after scanning they were placed into 16×125 mm Pyrex® glass tubes. The beans were then dried according to AOCS Official Method Ac 2-41 (modified for small samples) as follows:

2.9.1. Place bean into a pre-weighed (and recorded) 16×125 mm glass tube and weigh again; record weights to an accuracy of 0.1 mg.
2.9.2. Place samples into a forced air oven preheated to 130° C.
2.9.3. Allow material to dry for 3 h.
2.9.4. Remove tubes into a desiccator cabinet and allow to come to room temperature before weighing again.

$$\text{moisture content} = \frac{((\text{wt. tube} + \text{bean as is}^*) - \text{wt. tube}) - (\text{wt. tube} + \text{oven dried bean} - \text{wt. tube}))}{(\text{wt. tube bean as is}^* - \text{wt. tube})} \times 100$$

*at time of spectral capture.

Predictive spectral models for seed moisture content were developed by combining the spectral information with the measured moisture contents for each bean.

2.10. Protein Analysis.

Protein contents were estimated by combustion analysis of the oven dried powders described above. Analysis was performed on a Flash™ 1112 EA combustion analyzer (commercially available from Thermo Scientific) running in the Nitrogen, Carbon, Sulfur (NCS) mode. Samples of oven dried (according to AOCS Official Method Ba 2a-38 as described above) powdered samples, 4-8 mg (NCS Mode), weighed to an accuracy of 0.001 mg on a Mettler-Toledo MX5 microbalance were used for analysis. Protein contents were calculated by multiplying % N, determined by the analyzer, by 6.25. All samples were run in duplicate. If the difference between the protein contents of the replicate samples was >5% of the mean value, additional replicates were analyzed. Final protein contents were measured on a dry weight basis and adjusted to the desired moisture content.

Alternatively, the Thermo Scientific™ Flash™ 1112 EA combustion analyzer was run in N-protein mode, according to the Manufacturer's instructions, using aspartic acid as the standard. Samples of oven dried (according to AOCS Official Method Ba 2a-38 described above). The powdered samples, 30-40 mg, weighed to an accuracy of 0.001 mg on a Mettler-Toledo MX5 microbalance were used for analysis. Protein contents were calculated by multiplying % N, determined by the analyzer, by 6.25. All samples were run in duplicate. If the difference between the protein contents of the replicate samples was >5% of the mean value, additional replicates (if material was available) were analyzed. Final protein contents were measured on a dry weight basis and adjusted to the desired moisture content.

2.11. NMR Based Analysis of Seed Oil Content.

Whole seed and powdered sample oil contents were determined using a Maran Ultra NMR analyzer (Resonance Instruments Ltd, Whitney, Oxfordshire, UK). Samples (either individual intact soy seed or batches ~200 mg of ground soy powder) were placed into pre-weighed 2 ml polypropylene tubes (Corning Inc, Corning NY, USA; part #430917) previously labeled with unique bar code identifiers. Samples were placed into 96 place carriers and processed through the following series of steps by an Adept Cobra 600 SCARA robotic system.

2.11.1. Pick up tube using robotic arm fitted with a vacuum pickup device.
2.11.2. Read bar code.
2.11.3. Expose tube to antistatic device to ensure powdered samples do not adhere to the tube walls.
2.11.4. Weigh sample, to 0.1 mg accuracy.
2.11.5. NMR reading; measured as the intensity of the proton spin echo 1 msec after a 22.9 MHz signal was applied to the sample. Data was collected for 32 NMR scans per sample.
2.11.6. Return tube to rack.
2.11.7. Repeat process with next tube.

Bar codes, seed weights and NMR readings were recorded by a computer connected to the system.

Seed oil content was calculated as follows:

$$\% \text{ oil} (\% \text{ wt. basis}) = \frac{[(NMR \text{ signal/seed wt. } (g)) - 70.58]}{351.45}$$

Calibration parameters were determined by precisely weighing samples of soy oil (ranging from 0.0050 to 0.0700 g at approximately 0.0050 g intervals; weighed to an accuracy of 0.0001 g) into the polypropylene tubes (see above) and subjecting them to NMR analysis. A calibration curve of oil content (% seed wt. basis; assuming a standard seed weight of 0.1500 g) to NMR value was established.

Analytical Methods for Bulk Samples.

2.12. Moisture Determinations and Creation of Bulk Bean Moisture Calibrations.

Field or greenhouse-grown soybeans varieties 93686 (U.S. Pat. No. 6,610,910) and 93Y21 (commercially available from Pioneer Hybrid International) were harvested and the moisture calibrations for the FT-NIR were developed according to the methods described below. Pods were harvested from soybean plants between the R7 and R8 stage of development (i.e., yellow to brown pod stage) when the soybeans had moisture contents below 50 wt. %. Beans were removed from the pods and were separated into groups of approximately 25 g based on their state of maturity. The weight of the bean sample was measured and recorded to 0.0001 g accuracy, prior to FT-NIR spectral capture in a 54 mm spinning cup. The beans were then placed into 5"×6" foil trays and positioned in a laminar flow hood to dry at room temperature for varying times. After the seed had undergone measurable drying, the beans were weighed again and rescanned. This process was repeated until no further weight loss was observed. The samples were then taken to complete dryness using AOCS Official Method Ac 2-41, and were allowed to come to room temperature in a desiccator prior to weighing and rescanning on the FT-NIR. Moisture content was calculated as follows:

$$\text{Moisture Content} = \frac{(\text{wt. of beans as is}^* - \text{wt. of oven dried beans})}{\text{wt. of beans as is}^*} \times 100$$

*at time of spectral capture.

Alternatively, mature soybeans were placed in 5"×6" aluminum foil trays in 1 gallon ZipLock® brand plastic sealable bags. The relative humidity of the atmosphere within the bags was controlled by adding a second foil pan which contained either a layer of self-indicating DrieRite desiccant (W. A. Hammond Inc; Xenia OH), or a saturated aqueous solution of sodium chloride. A third bag containing the seed tray but without any atmospheric moisture control was also set up. The beans were exposed to the controlled moisture atmospheres for one month prior to weighing followed by immediate spectral capture on the FT-NIR. The beans were then dried according to AOCS Official Method Ac 2-41, as described above, and scanned again. Predictive spectral models for seed moisture content were developed by combining the spectral information with the measured moisture contents for each bean sample.

2.13. Sample Grinding and Preparation for Bulk Reference Chemistry.

Seventy-five gram batches of beans were ground to a powder in a Foss Knifetec 1095 grinder (commercially available from FOSS North America, Eden Prairie, MN). The grinding chamber was cooled prior to and during the process by a circulating chiller set to 14° C. Samples were ground for 2×10 second bursts using a standard rotor blade. The ground sample was transferred to a 6" diameter stainless steel sieve (1 mm mesh) and sifted (resulting in less than 2% loss of material) before being placed into an airtight sample cup. The sample chamber and blade were cleaned thoroughly with a soft brush and pneumatic air prior to introduction of the next sample. Sample cups were stored at room temperature in the dark prior to further analysis.

In later experiments the grinding method was modified to remove the need for sifting. Under these conditions the beans were ground for 6×10 second bursts under the conditions described above. The chamber was opened between each burst and material adhering to the chamber wall was scraped off with a plastic spatula and returned to the center of the chamber. This grinding protocol was found to create a powdered sample that would pass through a US No 20 mesh sieve with no loss and be more suitable for crude fat extraction.

2.14. Crude Protein Analysis.

Crude Protein contents were measured by combustion analysis of the oven dried powders described above in accordance to AOCS Official Method Ba 4e-93. Analyses were either performed by a contract research organization according to Industry Standard methods for soybean or otherwise as described herein. The protocols are essentially the same as those used for single seed (Example 2.10) but have been modified to accommodate a larger sample size. Analysis was performed on a Thermo Scientific™ Flash™ 1112 EA combustion analyzer running in the N-Protein mode, following the manufacturer's recommendations. Samples of the dried powders, 30-40 mg, weighed to an accuracy of 0.001 mg on a Mettler-Toledo MX5 microbalance, were used for analysis. Protein contents were calculated by multiplying % N, determined by the analyzer, by 6.25. Final protein contents were expressed on a 13% moisture corrected basis. All samples were run in duplicate and further replication was performed if the difference between the replicate samples was >5% of the mean value.

2.15. Crude Fat/Oil Analysis

Crude Fat/Oil determinations were performed according to AOCS Official Method Ba 3-38. Analyses were either performed a commercial service laboratory (Eurofins Scientific Inc., Des Moines, IA 50321) or done using a Foss SoxTec 8000 Extraction Unit (commercially available from Foss Analytical AB Höganäs, Sweden), according to the manufacturers recommendations (Application Note_AN 3487), with slight modification. Powder samples taken at the time of analysis were subjected to moisture determinations using AOCS Official Method Ba 2a-38, as described above. Final crude oil contents were expressed on a 13% moisture corrected basis. All samples were run in duplicate.

Example 3

Single Seed Spectral Analysis of Soybeans and Development of Accurate Measurements Seed with a high degree of compositional diversity selected from the materials described in Example 1 were analyzed on a proprietary Single Seed Near Infrared (SS-NIR) spectrometer (U.S. Pat. No. 7,274,456 B2, issued Sep. 25, 2007; U.S. Pat. No. 7,508,517B2, issued Mar. 24, 2009). Briefly, in the SS-NIR system an individual bean was introduced into the analytical cell where it was illuminated from all points in three dimensions. The seed was tumbled with an air stream, within an approximated integrating sphere constructed from a 16-mm-diameter quartz cup coated with 6080 white reflectance coating (Labsphere, North Hutton, NH). Illumination was provided through 12 optical fibers, connected to four 20 Watt 8211-002 light bulbs (Welch Allyn, Skaneateles Falls, NY), the ends of which were incorporated into the cell cover. The reflected spectral region from 904 to 1686 nm was collected through the apex of the cover of the sampling cell by an NIR512 spectrometer (Control Development, South Bend, IN). Each seed was scanned for 6 seconds to collect spectra that were optimized for maximal signal to noise ratio. Spectral quality was monitored during each sample scan by regularly checking the Root Mean Square (RMS) noise of the 100% lines. The 100% lines were computed by the ratio between every two spectra of the triplicate measurement for each sample. Under ideal, noise-free conditions, the 100% lines would be straight horizontal lines at zero absorbance units (AU) since all replicate spectra come from the same sample providing the same spectral features. To minimize instrumental drift, system noise, seed condition and other environmental changes, noise and off-sets were observed in the actual 100% lines. After scanning, the seed was ejected from the sample cup and transferred to an indexed sample tray. The individual identity of each seed was therefore preserved, facilitating instrument calibration.

Separate calibration models were generated for every constituent of interest using Partial Least Square (PLS) analysis coupled with an optimized number of latent variables, spectral range and spectral preprocessing, before being applied to online/offline compositional analysis of the individual seed components, such as the sucrosyl-oligosaccharides. The optimized number of latent variables, spectral range and spectral preprocessing were determined by analyzing the training and monitoring subset from the calibration data where the calibration performance reached an optimum level, in terms of Root Mean Square Error of Calibration (RMSEC) and Root Mean Square Error of Cross Validation (RMSECV). Taking stachyose as an example, the optimized number of latent variables was determined by the co-constituents with the least distinct spectral features. The calibration model used two components: the fewest latent variables and the most stachyose-related information. The balance of compromising these two components is dependent on the distinctness of the pure component spectrum for stachyose within the spectral matrix. For those co-constituents with distinct spectra, such as oil, a few PLS latent variables were used to capture enough information. More PLS latent variables were needed to separate stachyose from the co-constituents such as sucrose and raffinose which are chemically related and therefore give a high degree of spectral overlap. The optimized spectral range for stachyose was in the vicinity of 1000, 1200, 1380 and 1460 nm. These wavelengths enabled stachyose to be measured distinctly from the other constituents of the soybean seed. After the spectra were preprocessed for multiplicative scatter corrections, Savitsky-Golay derivatives and polynomial smoothing were applied in the spectral region between 904-1540 nm. The number of latent variables was determined as the fewest number of latent variables that resulted in an optimal calibration/cross validation accuracy as determined by the RMSEC (Root Mean Square Error of Calibration) and RMSECV (Root Mean Square Error of Cross Validation), respectively. The optimum calibration model was selected based on the $R^2$ (statistical measure of how close the predicted and reference chemistry data are fitted by the regression line), RMSEC (Root Mean Square Error of Calibration) and RMSECV (Root Mean Square Error of Cross Validation) statistics.

TABLE 3

Statistics for various seed component SS-NIR calibrations. The number of reference chemistry measurements used to develop the calibrations for each constituent are shown in column n. The dynamic range in composition underpinning each constituent calibration is shown in the range column. Under these conditions, stachyose could be detected as low as 0.05 wt. %.

| Constituent | n | Range (wt. %-wt. %) | $R^2$ | RMSEC | RMSECV |
|---|---|---|---|---|---|
| weight | 3096 | 0.09-0.30 | 0.99 | 4.2 mg | 4.4 mg |
| moisture | 618 | 5.4-15.7 | 0.94 | 0.51% | 0.54% |
| protein | 563 | 32.9-49.6 | 0.92 | 0.89% | 1.04% |
| oil | 1608 | 15.2-26.4 | 0.98 | 0.32% | 0.33% |
| oleic | 2725 | 12.8-90.1 | 0.99 | 2.80% | 2.83% |
| linoleic | 2725 | 1.1-61.8 | 0.98 | 2.67% | 2.72% |
| linolenic | 2725 | 1.1-12.7 | 0.92 | 0.81% | 0.86% |
| stearic | 2725 | 2.1-7.3 | 0.78 | 0.45% | 0.47% |
| palmitic | 2725 | 2.2-13.4 | 0.91 | 0.60% | 0.65% |
| stachyose | 730 | 0.05-5.5 | 0.91 | 0.52% | 0.56% |
| sucrose | 952 | 2.51-9.88 | 0.81 | 0.58% | 0.67% |
| total carbohydrate | 670 | 5.6-14.1 | 0.87 | 0.55% | 0.65% |

Stachyose measurements by SS-NIR and reference chemistry methods are shown in Table 4

TABLE 4

Stachyose contents of 20 individual T1 seed from Soil 2-7879-1-2-1 event. Each seed was analyzed by SS-NIR and was then ground and the stachyose content was measured using reference chemistry. Null segregants were identified (bold values underlined) based on the reference chemistry stachyose values. The mean and standard deviation (SD) values for the null and transgenic positive seed are also presented.

| Seed ID | Event ID | Stachyose by Reference Chemistry | Single Seed Stachyose by NIR |
|---|---|---|---|
| 1 s | Soil 2 AFS 7879-1-2-1 T1 seed | 4.09 | 4.53 |
| 2 s | Soil 2 AFS 7879-1-2-1 T1 seed | 0.22 | 0.83 |
| 3 s | Soil 2 AFS 7879-1-2-1 T1 seed | 0.31 | 0.44 |
| 4 s | Soil 2 AFS 7879-1-2-1 T1 seed | 0.22 | 0.56 |
| 5 s | Soil 2 AFS 7879-1-2-1 T1 seed | 0.19 | 0.24 |
| 6 s | Soil 2 AFS 7879-1-2-1 T1 seed | 0.29 | 0.82 |
| 7 s | Soil 2 AFS 7879-1-2-1 T1 seed | 0.18 | 0.46 |
| 8 s | Soil 2 AFS 7879-1-2-1 T1 seed | 0.42 | 0.33 |
| 9 s | Soil 2 AFS 7879-1-2-1 T1 seed | 3.91 | 4.55 |
| 10 s | Soil 2 AFS 7879-1-2-1 T1 seed | 0.09 | 0.37 |
| 11 s | Soil 2 AFS 7879-1-2-1 T1 seed | 3.61 | 3.83 |
| 12 s | Soil 2 AFS 7879-1-2-1 T1 seed | 0.08 | −0.01 |
| 13 s | Soil 2 AFS 7879-1-2-1 T1 seed | 0.24 | 0.49 |
| 14 s | Soil 2 AFS 7879-1-2-1 T1 seed | 0.14 | 0.31 |
| 15 s | Soil 2 AFS 7879-1-2-1 T1 seed | 0.18 | 0.20 |
| 16 s | Soil 2 AFS 7879-1-2-1 T1 seed | 0.22 | 0.97 |
| 17 s | Soil 2 AFS 7879-1-2-1 T1 seed | 3.82 | 3.80 |
| 18 s | Soil 2 AFS 7879-1-2-1 T1 seed | 0.28 | 0.65 |
| 19 s | Soil 2 AFS 7879-1-2-1 T1 seed | 3.67 | 4.09 |
| 20 s | Soil 2 AFS 7879-1-2-1 T1 seed | 0.41 | 0.70 |
| | Mean Soil 2 AFS 7879-1-2-1 Null | 3.82 | 4.16 |
| | SD | 0.19 | 0.37 |
| | Mean Soil 2 AFS 7879-1-2-1 Pos | 0.23 | 0.49 |
| | SD | 0.10 | 0.27 |

The construct used to create the Soil 92-2499.1.1.1 event contained transgenic components a Yarrowia lipolytica, Diacyl glycerol transferase-2 (DGAT-2) under the control of the strong seed specific β-Conglycinin promoter, the soy transcription factor ODP1, a sucrose transporter SUT4 and a GAS suppression component under the seed-specific kTi promoter. Seed from Soil 92 events have elevated oil, protein, oleic and stearic acids in conjunction with decreased linoleic and linolenic acids, sucrose and total soluble sugars. Lower stachyose contents would be expected and were measured using SS-NIR. The compositions of 36 T1 seed from the Soil 92-2499.1.1.1 event measured by NIR are given in Table 5A and 5B.

TABLE 5A

Single seed compositions for 36 T1 seed from Soil 92-2499.1.1.1 event. The composition of the seeds provided a distinct finger print that was used to discriminate between transgenic positive and null-segregant seed. Seed identified as null segregants are indicated in bold type and underlined.

| Seed ID | Event ID | Stach-yose | Oil | Pro-tein | Su-crose | Total soluble CBH |
|---|---|---|---|---|---|---|
| 14SN30-829 | Soil 92 SOY 2499.1.1.1 | 3.2 | 28.1 | 36.2 | 4.4 | 8.5 |
| 14SN30-830 | Soil 92 SOY 2499.1.1.1 | 3 | 25 | 43.6 | 4.2 | 7.8 |
| 14SN30-831 | Soil 92 SOY 2499.1.1.1 | 3.1 | 25.2 | 42.7 | 3.3 | 7.4 |
| 14SN30-832 | Soil 92 SOY 2499.1.1.1 | 4.4 | 19 | 40.1 | 6.1 | 11.5 |

TABLE 5A-continued

Single seed compositions for 36 T1 seed from Soil 92-2499.1.1.1 event. The composition of the seeds provided a distinct finger print that was used to discriminate between transgenic positive and null-segregant seed. Seed identified as null segregants are indicated in bold type and underlined.

| Seed ID | Event ID | Stachyose | Oil | Protein | Sucrose | Total soluble CBH |
|---|---|---|---|---|---|---|
| 14SN30-833 | Soil 92 SOY 2499.1.1.1 | 4.2 | 15.6 | 42.8 | 6.8 | 12.1 |
| 14SN30-834 | Soil 92 SOY 2499.1.1.1 | 3.3 | 28.2 | 46 | 3 | 7.4 |
| 14SN30-835 | Soil 92 SOY 2499.1.1.1 | 4.3 | 18.9 | 40.1 | 6.2 | 11.9 |
| 14SN30-836 | Soil 92 SOY 2499.1.1.1 | 3.1 | 27.1 | 42.3 | 2.9 | 6.6 |
| 14SN30-837 | Soil 92 SOY 2499.1.1.1 | 3.9 | 19.4 | 37.1 | 6.8 | 12.3 |
| 14SN30-838 | Soil 92 SOY 2499.1.1.1 | 2.4 | 25.5 | 43.4 | 4.3 | 7.3 |
| 14SN30-839 | Soil 92 SOY 2499.1.1.1 | 4.1 | 18 | 41.7 | 7 | 11.9 |
| 14SN30-840 | Soil 92 SOY 2499.1.1.1 | 3.2 | 27.1 | 40.9 | 3.4 | 7.2 |
| 14SN30-841 | Soil 92 SOY 2499.1.1.1 | 3.2 | 26.2 | 42.8 | 3.4 | 7.2 |
| 14SN30-842 | Soil 92 SOY 2499.1.1.1 | 4.2 | 19.9 | 38.9 | 6.4 | 12 |
| 14SN30-843 | Soil 92 SOY 2499.1.1.1 | 2.7 | 25.7 | 45.5 | 2.9 | 6.1 |
| 14SN30-844 | Soil 92 SOY 2499.1.1.1 | 3.4 | 26.6 | 40.7 | 2.7 | 6.6 |
| 14SN30-845 | Soil 92 SOY 2499.1.1.1 | 3.4 | 25 | 40.3 | 3 | 7.1 |
| 14SN30-846 | Soil 92 SOY 2499.1.1.1 | 3.8 | 27.5 | 41.8 | 3.5 | 8.1 |
| 14SN30-847 | Soil 92 SOY 2499.1.1.1 | 4 | 17.3 | 41.9 | 6.4 | 11.7 |
| 14SN30-848 | Soil 92 SOY 2499.1.1.1 | 4.1 | 20.2 | 37.8 | 6.7 | 12.1 |
| 14SN30-849 | Soil 92 SOY 2499.1.1.1 | 2.7 | 25.6 | 43.9 | 4.2 | 7 |
| 14SN30-850 | Soil 92 SOY 2499.1.1.1 | 2.5 | 28.8 | 41.4 | 3.6 | 6.6 |
| 14SN30-851 | Soil 92 SOY 2499.1.1.1 | 2.9 | 27.7 | 42.6 | 3.8 | 7.2 |
| 14SN30-852 | Soil 92 SOY 2499.1.1.1 | 2.7 | 25 | 44.3 | 4 | 7.2 |
| 14SN30-853 | Soil 92 SOY 2499.1.1.1 | 3.3 | 25.2 | 44.7 | 3.3 | 6.7 |
| 14SN30-854 | Soil 92 SOY 2499.1.1.1 | 4.3 | 19.6 | 37.4 | 7.1 | 13 |
| 14SN30-855 | Soil 92 SOY 2499.1.1.1 | 3.5 | 23.4 | 43 | 4.4 | 8.1 |
| 14SN30-856 | Soil 92 SOY 2499.1.1.1 | 4.7 | 19.8 | 38.5 | 7.3 | 12.7 |
| 14SN30-857 | Soil 92 SOY 2499.1.1.1 | 3 | 25.3 | 43.4 | 3.7 | 7.2 |
| 14SN30-858 | Soil 92 SOY 2499.1.1.1 | 3.4 | 25.8 | 40.6 | 4 | 7.6 |
| 14SN30-859 | Soil 92 SOY 2499.1.1.1 | 2.9 | 28.6 | 40.8 | 3.9 | 7.2 |
| 14SN30-860 | Soil 92 SOY 2499.1.1.1 | 3.3 | 26.6 | 39.5 | 4.1 | 8.1 |
| 14SN30-861 | Soil 92 SOY 2499.1.1.1 | 2.7 | 28.4 | 40 | 4.1 | 7.3 |
| 14SN30-862 | Soil 92 SOY 2499.1.1.1 | 2.9 | 25.1 | 43.7 | 3.9 | 7.4 |
| 14SN30-863 | Soil 92 SOY 2499.1.1.1 | 3.5 | 24 | 42 | 4 | 7.8 |
| 14SN30-864 | Soil 92 SOY 2499.1.1.1 | 3.8 | 19.9 | 41.8 | 4.5 | 8.9 |
| Mean Soil 92 2499.1.1.1 T1 Null | | 4.18 | 18.87 | 39.83 | 6.48 | 11.83 |
| SD | | 0.25 | 1.40 | 2.02 | 0.76 | 1.06 |
| Mean 92 2499.1.1.1 T1 Pos | | 3.08 | 26.27 | 42.24 | 3.68 | 7.31 |
| SD | | 0.34 | 1.49 | 2.13 | 0.51 | 0.56 |
| Delta | | −1.10 | 7.40 | 2.42 | −2.80 | −4.52 |

TABLE 5B

Single seed compositions (fatty acid methyl esters as a percent of the sum of all of the fatty acid methyl esters) for 36 T1 seed from Soil 92-2499.1.1.1 events (as in Table 5A). The composition of the seeds provided a distinct finger print that was used to discriminate between transgenic positive and null-segregant seed. Seed identified as null segregants are indicated in bold type and underlined.

| Seed ID | Event ID | Oleic | Linolenic | Palmitic | Stearic | Linoleic | Weight | Moisture |
|---|---|---|---|---|---|---|---|---|
| 14SN30-829 | Soil 92 SOY 2499.1.1.1 | 29.1 | 5.5 | 12.7 | 6.3 | 46.3 | 0.2 | 8.3 |
| 14SN30-830 | Soil 92 SOY 2499.1.1.1 | 28.6 | 5.3 | 12.8 | 6.1 | 48.2 | 0.3 | 8.1 |
| 14SN30-831 | Soil 92 SOY 2499.1.1.1 | 30.2 | 5.2 | 12.2 | 6.2 | 45.9 | 0.2 | 8.1 |
| 14SN30-832 | Soil 92 SOY 2499.1.1.1 | 20.4 | 9.9 | 11.3 | 4 | 54.9 | 0.3 | 8.9 |
| 14SN30-833 | Soil 92 SOY 2499.1.1.1 | 17.4 | 12 | 12 | 4.4 | 54.4 | 0.2 | 8.9 |
| 14SN30-834 | Soil 92 SOY 2499.1.1.1 | 38.2 | 7.4 | 12.9 | 9.3 | 34.7 | 0.2 | 7.2 |
| 14SN30-835 | Soil 92 SOY 2499.1.1.1 | 17.4 | 10.9 | 11.7 | 4.2 | 57.2 | 0.2 | 8.8 |
| 14SN30-836 | Soil 92 SOY 2499.1.1.1 | 35.1 | 4.8 | 12.2 | 7.4 | 40.8 | 0.2 | 8.1 |
| 14SN30-837 | Soil 92 SOY 2499.1.1.1 | 16.8 | 11 | 10.9 | 4.2 | 58.6 | 0.2 | 8.7 |

TABLE 5B-continued

Single seed compositions (fatty acid methyl esters as a percent of the sum of all of the fatty acid methyl esters) for 36 T1 seed from Soil 92-2499.1.1.1 events (as in Table 5A). The composition of the seeds provided a distinct finger print that was used to discriminate between transgenic positive and null-segregant seed. Seed identified as null segregants are indicated in bold type and underlined.

| Seed ID | Event ID | Oleic | Linolenic | Palmitic | Stearic | Linoleic | Weight | Moisture |
|---|---|---|---|---|---|---|---|---|
| 14SN30-838 | Soil 92 SOY 2499.1.1.1 | 29.6 | 4.2 | 12.2 | 6 | 48.6 | 0.3 | 8.1 |
| 14SN30-839 | Soil 92 SOY 2499.1.1.1 | 15.7 | 11 | 12 | 4.2 | 57.4 | 0.2 | 9.4 |
| 14SN30-840 | Soil 92 SOY 2499.1.1.1 | 32.9 | 4.4 | 12.4 | 6.8 | 42.7 | 0.2 | 7.9 |
| 14SN30-841 | Soil 92 SOY 2499.1.1.1 | 34 | 3.9 | 12.1 | 7 | 43.6 | 0.2 | 8.2 |
| 14SN30-842 | Soil 92 SOY 2499.1.1.1 | 18.2 | 9.8 | 11.6 | 4.3 | 56.8 | 0.2 | 9 |
| 14SN30-843 | Soil 92 SOY 2499.1.1.1 | 34 | 3.7 | 11.7 | 6.7 | 44.3 | 0.3 | 7.7 |
| 14SN30-844 | Soil 92 SOY 2499.1.1.1 | 33.3 | 5 | 13 | 7.5 | 40.8 | 0.2 | 8.2 |
| 14SN30-845 | Soil 92 SOY 2499.1.1.1 | 29.8 | 7.2 | 11.6 | 6.2 | 45.4 | 0.2 | 8.8 |
| 14SN30-846 | Soil 92 SOY 2499.1.1.1 | 32.1 | 7.6 | 12.1 | 7.5 | 42.3 | 0.2 | 7.5 |
| 14SN30-847 | Soil 92 SOY 2499.1.1.1 | 17.9 | 11.5 | 11 | 4.1 | 56.1 | 0.3 | 8.7 |
| 14SN30-848 | Soil 92 SOY 2499.1.1.1 | 16.7 | 10.4 | 11.8 | 4.3 | 57.8 | 0.2 | 8.9 |
| 14SN30-849 | Soil 92 SOY 2499.1.1.1 | 30.5 | 4.4 | 11.8 | 5.5 | 46.6 | 0.3 | 8.4 |
| 14SN30-850 | Soil 92 SOY 2499.1.1.1 | 36 | 3 | 11.4 | 6.3 | 40.9 | 0.2 | 7.6 |
| 14SN30-851 | Soil 92 SOY 2499.1.1.1 | 32.3 | 5.9 | 11.1 | 6.5 | 43.5 | 0.2 | 7.2 |
| 14SN30-852 | Soil 92 SOY 2499.1.1.1 | 32.1 | 4.6 | 11.2 | 6 | 44.6 | 0.2 | 8.3 |
| 14SN30-853 | Soil 92 SOY 2499.1.1.1 | 37.7 | 5.3 | 11.7 | 6.3 | 37.6 | 0.2 | 8.1 |
| 14SN30-854 | Soil 92 SOY 2499.1.1.1 | 18.5 | 10.4 | 10.4 | 4 | 56 | 0.2 | 8.9 |
| 14SN30-855 | Soil 92 SOY 2499.1.1.1 | 31.7 | 5 | 11.2 | 5.9 | 43.6 | 0.2 | 8.8 |
| 14SN30-856 | Soil 92 SOY 2499.1.1.1 | 20.2 | 9.2 | 11 | 4.2 | 53.6 | 0.2 | 9.2 |
| 14SN30-857 | Soil 92 SOY 2499.1.1.1 | 32.1 | 4.7 | 11.7 | 5.9 | 44 | 0.2 | 8.5 |
| 14SN30-858 | Soil 92 SOY 2499.1.1.1 | 32.2 | 6.1 | 11.3 | 5.6 | 42.7 | 0.2 | 8.1 |
| 14SN30-859 | Soil 92 SOY 2499.1.1.1 | 35.5 | 3.9 | 11.8 | 6.9 | 40.5 | 0.2 | 8 |
| 14SN30-860 | Soil 92 SOY 2499.1.1.1 | 31.7 | 5.2 | 11.5 | 5.7 | 44 | 0.2 | 8.6 |
| 14SN30-861 | Soil 92 SOY 2499.1.1.1 | 34.8 | 3.7 | 12.2 | 6.7 | 39.8 | 0.2 | 8.1 |
| 14SN30-862 | Soil 92 SOY 2499.1.1.1 | 32 | 4.9 | 11.6 | 6.1 | 44.2 | 0.2 | 8.5 |
| 14SN30-863 | Soil 92 SOY 2499.1.1.1 | 32.6 | 5.4 | 11.8 | 6 | 42.6 | 0.2 | 9.1 |
| 14SN30-864 | Soil 92 SOY 2499.1.1.1 | 20.9 | 10.1 | 9.9 | 3.5 | 54.5 | 0.2 | 9 |
| Mean Null | | 18.19 | 10.56 | 11.24 | 4.13 | 56.12 | 0.22 | 8.95 |
| SD | | 1.67 | 0.81 | 0.67 | 0.24 | 1.60 | 0.04 | 0.21 |
| Mean Pos | | 32.72 | 5.05 | 11.93 | 6.50 | 43.13 | 0.22 | 8.14 |
| SD | | 2.51 | 1.14 | 0.54 | 0.81 | 3.12 | 0.04 | 0.46 |
| Delta | | 14.53 | −5.51 | 0.69 | 2.37 | −12.99 | 0.00 | −0.81 |

From the results presented in Tables 5A and 5B, all components except for stachyose were measured at the expected values. Stachyose contents were lowered by an average of 1.1% (percentage points), instead of the expected at least 3% (percentage points) indicating that the construct did not produce the expected composition. Additional components were used to assist in distinguishing transgenic positive from null-segregant seeds where transgenic changes are subtle. For example, seeds 14SN30-846 and 14SN30-864 each had a stachyose content of 3.8%, which was the threshold used for discriminating between transgenic positive and null-segregant seed. By inspecting the other components (27.5% oil, 41.8% protein, 32.1% oleic, 3.5% sucrose, 8.1% soluble carbohydrates, 7.5% linolenic acid) it was apparent that 14SN30-846 was a transgenic positive seed and that 14SN30-864 (19.9% oil, 41.8% protein, 20.9% oleic, 4.5% sucrose, 8.9% soluble carbohydrates, 10.1% linolenic acid) was a null segregant.

The methods are also suitable for screening material generated in crossing experiments designed to introgress the low sucrosyl-oligosaccharide/high oil transgenes into elite soybean backgrounds. In this example pollen from heterozygous BC1F1 plants from the Oil 119 event (segregating for the transgenes for the low sucrosyl-oligosaccharide/high oil traits) was used to fertilize the emasculated receptive flowers of three elite soybean varieties. The cross fertilized plants were grown to maturity and the resulting BC2F1 seed harvested from the cross-pollinated flowers were analyzed by SS-NIR. This SS-NIR analysis allowed the non-destructive identification of seed carrying the desired transgenic phenotype (i.e., those displaying a low stachyose and high oil phenotype). These positively identified seed were grown and pollen from these plants was again used to pollinate the emasculated receptive flowers of the same three elite soybean varieties. The results in Table 6 show the composition of mature seed harvested after three rounds of backcrossing onto the recurrent female elite parent. In most cases a threshold value for stachyose content of 2.0% was used to differentiate between the wild type seeds (>2.0% stachyose; indicated with bold type and underlined) and those (<<2.0%) that resulted from successful transgene introgressions (Transgenic pos). Further confirmation of successful transgene introgressions was provided by the other constituents influenced by the transgenic traits i.e., elevated oil, protein and oleic acid, reduced levels of sucrose, total soluble carbohydrates and linolenic acid. Transgenic hybrid seed could be identified using SS-NIR by combining the low stachyose phenotype (of ≤0.32%) with a combination of high oil, high protein, high oleic acid, low sucrose, low total soluble carbohydrates and low linolenic acid phenotypes (dependent on the background) that result from the expression of the high oil components of the transgenic cassette. Soybeans seeds of varied genetic backgrounds outside of those used to generate the calibration curves could be successfully identified as containing introgressed transgenes.

TABLE 6A

SS-NIR compositions (oil/protein/carbohydrate (CBH)) for segregating seed resulting from backcrosses of an Oil 119 event. The construct used to create the Oil119 event contained the following transgenic components, a modified Glycine max diacyl glycerol transferase-1 (DGAT-1) under the control of the seed specific S-albumen promoter, a sucrose transporter SUT4 and a GAS 1, 2, 3 suppression component under the control of the strong seed specific β-conglycinin promoter. This construct conferred a low stachyose/high oil phenotype in three elite female soybean lines.

| Female/Male | Plant ID | SSNIR zyg call | Stach-yose | Oil | Pro-tein | Su-crose | Total soluble CBH |
|---|---|---|---|---|---|---|---|
| 92Y51/ BC75638705 | 4 | Wild type | 2.50 | 19.32 | 45.47 | 7.42 | 11.55 |
| 92Y51/ BC75638705 | 3 | Wild type | 2.61 | 19.08 | 45.93 | 7.32 | 11.65 |
| 92Y51/ BC75638705 | 2 | TG POS | 0.17 | 24.32 | 46.98 | 6.31 | 8.33 |
| 92Y51/ BC75638705 | 5 | TG POS | 0.25 | 24.61 | 46.60 | 7.54 | 7.97 |
| 92Y51/ BC75638705 | 1 | TG POS | 0.28 | 24.01 | 46.63 | 7.40 | 8.46 |
| | Wild type | Mean SD | 2.55 0.08 | 19.20 0.17 | 45.70 0.32 | 7.37 0.07 | 11.60 0.07 |
| | TG POS | Mean SD | 0.23 0.06 | 24.31 0.30 | 46.74 0.21 | 7.08 0.67 | 8.25 0.26 |
| 95Y40/ BC75638779 | 2 | Wild type | 2.80 | 20.93 | 45.80 | 6.00 | 10.83 |
| 95Y40/ BC75638779 | 8 | Wild type | 2.97 | 20.95 | 45.59 | 6.23 | 11.15 |
| 95Y40/ BC75638779 | 3 | Wild type | 3.26 | 20.53 | 41.63 | 7.77 | 12.43 |
| 95Y40/ BC75638779 | 26 | Wild type | 3.33 | 20.61 | 41.29 | 7.11 | 12.73 |
| 95Y40/ BC75638779 | 9 | Wild type | 3.35 | 21.03 | 42.59 | 6.73 | 12.67 |
| 95Y40/ BC75638779 | 1 | Wild type | 3.35 | 19.70 | 44.88 | 7.39 | 12.05 |
| 95Y40/ BC75638779 | 4 | Wild type | 3.36 | 19.76 | 44.11 | 6.48 | 12.19 |
| 95Y40/ BC75638779 | 19 | Wild type | 3.45 | 20.82 | 40.56 | 7.08 | 12.88 |
| 95Y40/ BC75638779 | 16 | Wild type | 3.62 | 20.73 | 41.74 | 6.97 | 12.22 |
| 95Y40/ BC75638779 | 12 | Wild type | 3.64 | 20.42 | 41.73 | 7.47 | 13.13 |
| 95Y40/ BC75638779 | 18 | Wild type | 3.68 | 20.45 | 43.42 | 6.48 | 12.15 |
| 95Y40/ BC75638779 | 11 | Wild type | 3.89 | 22.17 | 39.33 | 7.14 | 13.14 |
| 95Y40/ BC75638779 | 27 | TG POS | −0.23 | 23.67 | 46.40 | 7.84 | 8.83 |
| 95Y40/ BC75638779 | 5 | TG POS | 0.00 | 24.35 | 43.52 | 8.29 | 9.40 |
| 95Y40/ BC75638779 | 6 | TG POS | 0.20 | 24.43 | 46.23 | 6.58 | 7.84 |
| 95Y40/ BC75638779 | 14 | TG POS | 0.27 | 26.64 | 42.45 | 6.87 | 8.92 |
| 95Y40/ BC75638779 | 7 | TG POS | 0.32 | 25.39 | 43.93 | 6.64 | 8.78 |
| 95Y40/ BC75638779 | 17 | TG POS | 0.32 | 24.97 | 45.10 | 7.00 | 8.76 |
| 95Y40/ BC756387790 | 22 | TG POS | 0.36 | 26.48 | 43.02 | 7.06 | 9.01 |
| 95Y40/ BC75638779 | 13 | TG POS | 0.47 | 27.24 | 39.30 | 7.48 | 9.87 |
| 95Y40/ BC75638779 | 15 | TG POS | 0.51 | 25.11 | 44.13 | 7.30 | 8.46 |
| 95Y40/ BC75638779 | 23 | TG POS | 0.57 | 24.12 | 47.16 | 6.50 | 8.36 |
| 95Y40/ BC75638779 | 10 | TG POS | 0.59 | 26.18 | 41.61 | 7.17 | 9.74 |
| 95Y40/ BC75638779 | 20 | TG POS | 0.68 | 24.58 | 45.89 | 6.26 | 8.60 |
| 95Y40/ BC75638779 | 21 | TG POS | 0.73 | 25.71 | 44.06 | 6.13 | 8.47 |
| 95Y40/ BC75638779 | 24 | TG POS | 0.84 | 25.25 | 44.37 | 6.73 | 9.01 |
| 95Y40/ BC75638779 | 25 | TG POS | 0.73 | 26.18 | 39.21 | 7.48 | 10.19 |
| | Wild type | Mean SD | 3.39 0.30 | 20.67 0.64 | 42.72 2.05 | 6.90 0.53 | 12.30 0.72 |
| | TG POS | Mean SD | 0.42 0.29 | 25.35 1.03 | 43.76 2.38 | 7.02 0.59 | 8.95 0.63 |

TABLE 6A-continued

SS-NIR compositions (oil/protein/carbohydrate (CBH)) for segregating seed resulting from backcrosses of an Oil 119 event. The construct used to create the Oil119 event contained the following transgenic components, a modified Glycine max diacyl glycerol transferase-1 (DGAT-1) under the control of the seed specific S-albumen promoter, a sucrose transporter SUT4 and a GAS 1, 2, 3 suppression component under the control of the strong seed specific β-conglycinin promoter. This construct conferred a low stachyose/high oil phenotype in three elite female soybean lines.

| Female/Male | Plant ID | SSNIR zyg call | Stachyose | Oil | Protein | Sucrose | Total soluble CBH |
|---|---|---|---|---|---|---|---|
| 98Y11/BC75638838 | 16 | Wild type | 0.37 | 21.42 | 40.03 | 8.65 | 11.11 |
| 98Y11/BC75638838 | 5 | Wild type | 0.55 | 16.05 | 45.20 | 7.69 | 11.80 |
| 98Y11/BC75638838 | 13 | Wild type | 1.45 | 19.68 | 40.29 | 8.60 | 12.75 |
| 98Y11/BC75638838 | 12 | Wild type | 1.71 | 19.42 | 43.92 | 8.18 | 12.13 |
| 98Y11/BC75638838 | 6 | Wild type | 1.83 | 19.81 | 39.92 | 8.73 | 13.17 |
| 98Y11/BC75638838 | 11 | Wild type | 2.15 | 17.52 | 38.76 | 8.27 | 13.18 |
| 98Y11/BC75638838 | 10 | Wild type | 2.63 | 18.03 | 47.73 | 6.66 | 11.19 |
| 98Y11/BC75638838 | 7 | Wild type | 3.13 | 17.11 | 44.58 | 7.43 | 12.64 |
| 98Y11/BC75638838 | 4 | TG POS | −0.66 | 22.72 | 46.17 | 7.93 | 8.96 |
| 98Y11/BC75638838 | 14 | TG POS | −0.59 | 23.01 | 46.62 | 7.74 | 8.64 |
| 98Y11/BC75638838 | 15 | TG POS | −0.36 | 21.30 | 49.38 | 7.01 | 8.05 |
| 98Y11/BC75638838 | 2 | TG POS | −0.34 | 21.81 | 48.48 | 7.65 | 8.40 |
| 98Y11/BC75638838 | 1 | TG POS | −0.13 | 20.70 | 47.63 | 7.55 | 8.83 |
| 98Y11/BC75638838 | 8 | TG POS | 0.32 | 20.93 | 48.73 | 7.61 | 9.35 |
| 98Y11/BC75638838 | 3 | TG POS | −0.23 | 18.19 | 44.31 | 7.84 | 9.31 |
| Wild type | | Mean | 1.72 | 18.63 | 42.55 | 8.03 | 12.25 |
| | | SD | 0.95 | 1.75 | 3.22 | 0.72 | 0.82 |
| TG POS | | Mean | −0.28 | 21.24 | 47.33 | 7.62 | 8.79 |
| | | SD | 0.3 | 1.6 | 1.8 | 0.3 | 0.5 |

TABLE 6B

SS-NIR compositions (fatty acid profile/weight/moisture) for segregating seed resulting from backcrosses of an Oil 119 event as described in Table 6A. This construct conferred a low stachyose/high oil phenotype in three elite female soybean lines. conferring a low stachyose/high oil phenotype into three elite female soybean lines (as in Table 6A).

| Female/Male | Plant ID | SSNIR zyg call | Oleic | Linolenic | Palmitic | Stearic | Linoleic | Weight | Moisture |
|---|---|---|---|---|---|---|---|---|---|
| 92Y51/BC75638705 | 4 | Wild type | 22.17 | 8.02 | 11.60 | 4.25 | 53.31 | 0.19 | 6.0 |
| 92Y51/BC75638705 | 3 | Wild type | 21.71 | 8.48 | 11.34 | 4.07 | 51.09 | 0.20 | 5.9 |
| 92Y51/BC75638705 | 2 | TG POS | 33.05 | 2.85 | 10.66 | 5.45 | 44.21 | 0.20 | 6.9 |
| 92Y51/BC75638705 | 5 | TG POS | 34.75 | 3.48 | 10.60 | 4.92 | 43.52 | 0.21 | 6.9 |
| 92Y51/BC75638705 | 1 | TG POS | 36.47 | 2.73 | 9.83 | 4.56 | 42.74 | 0.21 | 5.4 |
| Wild type | | Mean | 21.94 | 8.25 | 11.47 | 4.16 | 52.20 | 0.20 | 6.0 |
| | | SD | 0.32 | 0.33 | 0.18 | 0.13 | 1.57 | 0.01 | 0.1 |
| TG pos | | Mean | 34.76 | 3.02 | 10.37 | 4.98 | 43.49 | 0.21 | 6.4 |
| | | SD | 1.71 | 0.40 | 0.46 | 0.45 | 0.74 | 0.01 | 0.8 |
| 95Y40/BC75638779 | 2 | Wild type | 32.90 | 6.41 | 11.24 | 4.36 | 42.02 | 0.19 | 6.8 |
| 95Y40/BC75638779 | 8 | Wild type | 34.64 | 6.11 | 11.09 | 4.43 | 41.30 | 0.18 | 6.6 |
| 95Y40/BC75638779 | 3 | Wild type | 22.58 | 8.03 | 11.44 | 4.25 | 50.17 | 0.21 | 6.6 |
| 95Y40/BC75638779 | 26 | Wild type | 23.73 | 7.98 | 11.58 | 4.72 | 49.01 | 0.17 | 6.7 |
| 95Y40/BC75638779 | 9 | Wild type | 24.03 | 7.19 | 12.02 | 4.42 | 50.14 | 0.21 | 6.6 |
| 95Y40/BC75638779 | 1 | Wild type | 23.89 | 7.62 | 11.73 | 4.28 | 49.41 | 0.21 | 7.1 |
| 95Y40/BC75638779 | 4 | Wild type | 26.36 | 7.61 | 11.45 | 3.94 | 47.83 | 0.22 | 6.8 |
| 95Y40/BC75638779 | 19 | Wild type | 24.70 | 7.41 | 11.70 | 4.20 | 49.63 | 0.19 | 6.6 |
| 95Y40/BC75638779 | 16 | Wild type | 22.89 | 7.70 | 11.66 | 4.34 | 50.73 | 0.19 | 6.4 |
| 95Y40/BC75638779 | 12 | Wild type | 22.76 | 7.96 | 11.65 | 4.35 | 50.26 | 0.18 | 6.4 |

TABLE 6B-continued

SS-NIR compositions (fatty acid profile/weight/moisture) for segregating seed resulting
from backcrosses of an Oil 119 event as described in Table 6A. This construct conferred
a low stachyose/high oil phenotype in three elite female soybean lines. conferring a low
stachyose/high oil phenotype into three elite female soybean lines (as in Table 6A).

| Female/Male | Plant ID | SSNIR zyg call | Oleic | Linolenic | Palmitic | Stearic | Linoleic | Weight | Moisture |
|---|---|---|---|---|---|---|---|---|---|
| 95Y40/ BC75638779 | 18 | Wild type | 24.39 | 7.36 | 11.54 | 4.00 | 50.68 | 0.20 | 6.7 |
| 95Y40/ BC75638779 | 11 | Wild type | 23.46 | 6.83 | 11.87 | 4.24 | 50.41 | 0.19 | 6.7 |
| 95Y40/ BC75638779 | 27 | TG POS | 41.24 | 4.01 | 10.05 | 4.75 | 36.17 | 0.22 | 6.4 |
| 95Y40/ BC75638779 | 5 | TG POS | 36.44 | 4.97 | 10.78 | 4.67 | 39.94 | 0.19 | 6.4 |
| 95Y40/ BC75638779 | 6 | TG POS | 35.61 | 4.92 | 10.92 | 5.37 | 39.35 | 0.19 | 5.8 |
| 95Y40/ BC75638779 | 14 | TG POS | 33.49 | 4.33 | 10.96 | 5.54 | 41.65 | 0.16 | 6.3 |
| 95Y40/ BC75638779 | 7 | TG POS | 32.12 | 3.92 | 11.06 | 5.46 | 43.11 | 0.16 | 5.9 |
| 95Y40/ BC75638779 | 17 | TG POS | 36.50 | 4.33 | 11.11 | 5.41 | 38.70 | 0.18 | 6.0 |
| 95Y40/ BC75638779O | 22 | TG POS | 32.24 | 4.36 | 11.59 | 5.37 | 42.55 | 0.18 | 5.7 |
| 95Y40/ BC75638779 | 13 | TG POS | 30.25 | 4.54 | 11.72 | 5.86 | 43.04 | 0.14 | 5.5 |
| 95Y40/ BC75638779 | 15 | TG POS | 34.64 | 4.11 | 10.62 | 4.51 | 42.88 | 0.19 | 5.4 |
| 95Y40/ BC75638779 | 23 | TG POS | 29.91 | 4.07 | 11.71 | 5.24 | 45.28 | 0.17 | 5.7 |
| 95Y40/ BC75638779 | 10 | TG POS | 32.52 | 5.77 | 10.92 | 5.63 | 41.43 | 0.15 | 6.0 |
| 95Y40/ BC75638779 | 20 | TG POS | 32.67 | 4.84 | 11.11 | 4.96 | 43.33 | 0.17 | 5.5 |
| 95Y40/ BC75638779 | 21 | TG POS | 30.50 | 4.41 | 11.54 | 5.02 | 44.76 | 0.17 | 5.6 |
| 95Y40/ BC75638779 | 24 | TG POS | 31.37 | 3.93 | 11.86 | 5.19 | 44.08 | 0.17 | 5.8 |
| 95Y40/ BC75638779 | 25 | TG POS | 29.02 | 5.59 | 12.42 | 5.90 | 43.35 | 0.14 | 6.2 |
|  | Wild type | Mean SD | 25.53 4.00 | 7.35 0.62 | 11.58 0.25 | 4.29 0.20 | 48.47 3.28 | 0.20 0.02 | 6.7 0.2 |
|  | TG POS | Mean SD | 33.24 3.21 | 4.54 0.57 | 11.22 0.59 | 5.26 0.41 | 41.98 2.48 | 0.17 0.02 | 5.9 0.3 |
| 98Y11/ BC75638838 | 16 | Wild type | 25.52 | 9.80 | 12.67 | 6.89 | 42.40 | 0.06 | 7.1 |
| 98Y11/ BC75638838 | 5 | Wild type | 18.07 | 12.28 | 11.70 | 5.24 | 50.34 | 0.15 | 7.2 |
| 98Y11/ BC75638838 | 13 | Wild type | 17.59 | 9.86 | 11.52 | 4.78 | 53.22 | 0.18 | 7.2 |
| 98Y11/ BC75638838 | 12 | Wild type | 25.24 | 8.35 | 11.07 | 4.31 | 49.12 | 0.24 | 6.4 |
| 98Y11/ BC75638838 | 6 | Wild type | 17.72 | 10.47 | 11.76 | 5.20 | 52.48 | 0.17 | 7.1 |
| 98Y11/ BC75638838 | 11 | Wild type | 16.44 | 12.58 | 12.16 | 5.28 | 51.37 | 0.08 | 7.5 |
| 98Y11/ BC75638838 | 10 | Wild type | 26.66 | 7.93 | 11.17 | 4.63 | 47.42 | 0.20 | 6.3 |
| 98Y11/ BC75638838 | 7 | Wild type | 16.02 | 11.66 | 12.24 | 4.67 | 54.64 | 0.17 | 6.4 |
| 98Y11/ BC75638838 | 4 | TG POS | 37.51 | 5.42 | 10.93 | 5.44 | 37.70 | 0.20 | 6.2 |
| 98Y11/ BC75638838 | 14 | TG POS | 32.13 | 6.46 | 11.23 | 5.66 | 40.99 | 0.19 | 6.1 |
| 98Y11/ BC75638838 | 15 | TG POS | 33.22 | 6.10 | 10.82 | 5.36 | 40.96 | 0.17 | 5.9 |
| 98Y11/ BC75638838 | 2 | TG POS | 36.06 | 5.05 | 10.69 | 5.28 | 40.20 | 0.17 | 5.6 |
| 98Y11/ BC75638838 | 1 | TG POS | 40.73 | 6.50 | 10.04 | 5.46 | 35.31 | 0.22 | 6.4 |

TABLE 6B-continued

SS-NIR compositions (fatty acid profile/weight/moisture) for segregating seed resulting from backcrosses of an Oil 119 event as described in Table 6A. This construct conferred a low stachyose/high oil phenotype in three elite female soybean lines. conferring a low stachyose/high oil phenotype into three elite female soybean lines (as in Table 6A).

| Female/Male | Plant ID | SSNIR zyg call | Oleic | Linolenic | Palmitic | Stearic | Linoleic | Weight | Moisture |
|---|---|---|---|---|---|---|---|---|---|
| 98Y11/ BC75638838 | 8 | TG POS | 35.43 | 5.14 | 10.84 | 5.21 | 40.02 | 0.21 | 5.8 |
| 98Y11/ BC75638838 | 3 | TG POS | 47.17 | 8.22 | 10.52 | 4.96 | 25.80 | 0.19 | 6.1 |
| | Wild type | Mean | 20.41 | 10.37 | 11.79 | 5.12 | 50.13 | 0.16 | 6.9 |
| | | SD | 4.54 | 1.72 | 0.55 | 0.79 | 3.88 | 0.06 | 0.5 |
| | TG POS | Mean | 37.46 | 6.13 | 10.72 | 5.34 | 37.29 | 0.19 | 6.00 |
| | | SD | 5.1 | 1.1 | 0.4 | 0.2 | 5.5 | 0.0 | 0.3 |

Example 4

In the following example FT-NIR is used to analyze seed of sample sizes of about 50 seeds to 250 seeds.

Development of NIR Models for FT-NIR

Spectral analyses and capture were performed on a Bruker Multi-Purpose Analyzer (MPA) Fourier Transformed Near Infrared (FT-NIR) spectrometer fitted with a 54 mm diameter rotating cup assembly. Sample sizes of as few as 50 seeds (approximately 10 g of seed) to a full cup load (approximately 53 g of seed) were used, with a sample size of approximately 100 seed (20 g) used where possible. The weight of each sample (to an accuracy of 0.01 g) was recorded prior to scanning. The reflected spectra were captured for each sample to a resolution of 8 cm$^{-1}$ in the wave length range between 833 and 2778 nm with the instrument in Macro-Reflectance mode. The cup was rotated over the source and detector while sixty-four full spectral scans were collected. The rotation of the cup was stopped and the beans were poured into a foil pan and then returned to the cup prior to scanning for a second time. Three full scan cycles (with complete mixing of the sample between each scan) was found to provide good data quality and sample throughput. Captured spectra were analyzed and models were developed using the Bruker OPUS 7.0 software package. Spectral regions utilized for the prediction of stachyose with the Bruker MPA after model optimization were 1157-1283 nm and 1437-2254 nm.

TABLE 7

Statistics of FT-NIR calibration curves. The number of reference chemistry measurements are shown in column n. Range (wt. %) shows the minimum and maximum reference method measured value in the samples for each constituent.

| Constituent | n | Range | R$^2$ | RMSEC | RMSECV |
|---|---|---|---|---|---|
| moisture | 811 | 0-47.2 | 0.99 | 0.40 | 0.44 |
| protein | 102 | 32.1-40.1 | 0.91 | 0.56 | 0.67 |
| oil | 114 | 15.7-23.0 | 0.96 | 0.28 | 0.39 |
| oleic | 1080 | 20.3-89.6 | 0.98 | 2.74 | 3.01 |
| linoleic | 1080 | 1.2-55.6 | 0.98 | 2.51 | 2.67 |
| linolenic | 1080 | 0.9-9.4 | 0.87 | 0.82 | 0.98 |
| stearic | 1080 | 3.1-7.1 | 0.77 | 0.35 | 0.39 |
| palmitic | 1080 | 1.9-12.4 | 0.83 | 0.84 | 0.91 |
| stachyose | 1080 | 0.1-4.9 | 0.78 | 0.66 | 0.73 |
| sucrose | 1080 | 2.15-9.57 | 0.82 | 0.61 | 0.70 |
| total soluble carbohydrates | 1080 | 5.8-12.1 | 0.85 | 0.53 | 0.58 |

TABLE 8

FT-NIR measured compositions for ~20 g batches of homozygous positive and null events of Soil 91 (Soil 91-1, Soil 91-2 and Soil 92-1) soybeans. Values presented are means and standard deviations for two positive (pos) and two null (null) replicates for each event. The delta values indicate the difference between the transgenic positive and null means for each component.

| Sample | Method | | | Stachyose | Oil | Protein | Oleic acid | Linolenic acid | Sucrose | Total soluble carbohydrate |
|---|---|---|---|---|---|---|---|---|---|---|
| Soil 91-1 | FT-NIR | Pos | Mean | 1.9 | 21.3 | 36.8 | 38.2 | 5.8 | 3.4 | 7.2 |
| | | | SD | 0.0 | 0.1 | 0.4 | 0.8 | 0.3 | 0.0 | 0.0 |
| | | Null | Mean | 4.5 | 17.5 | 33.7 | 25.1 | 8.1 | 4.9 | 11.0 |
| | | | SD | 0.3 | 0.2 | 1.6 | 0.4 | 0.2 | 0.9 | 0.5 |
| | | | Delta | -2.6 | 3.9 | 3.1 | 13.1 | -2.2 | -1.5 | -3.8 |
| | Ref Chem | Pos | Mean | 0.3 | 21.3 | 38.0 | 24.3 | 5.4 | 4.8 | 6.2 |
| | | | SD | 0.3 | 1.2 | 0.9 | 3.6 | 0.6 | 0.3 | 0.6 |
| | | Null | Mean | 3.5 | 14.9 | 34.5 | 19.1 | 9.3 | 5.4 | 10.2 |
| | | | SD | 0.1 | 1.7 | 1.6 | 0.7 | 0.0 | 1.0 | 1.2 |
| | | | Delta | -3.2 | 6.4 | 3.4 | 5.2 | -3.9 | -0.6 | -4.0 |
| Soil 91-2 | FT-NIR | Pos | Mean | 1.6 | 20.9 | 37.2 | 39.0 | 5.2 | 3.6 | 7.0 |
| | | | SD | 0.4 | 0.9 | 0.6 | 0.1 | 0.6 | 0.4 | 1.1 |
| | | Null | Mean | 4.7 | 17.1 | 32.6 | 26.1 | 7.8 | 4.9 | 11.5 |
| | | | SD | 0.2 | 0.7 | 0.6 | 0.1 | 0.4 | 0.4 | 0.6 |
| | | | Delta | -3.1 | 3.8 | 4.6 | 12.8 | -2.6 | -1.3 | -4.5 |
| | Ref Chem | Pos | Mean | 0.1 | 18.8 | 38.2 | 24.6 | 5.2 | 4.9 | 6.1 |
| | | | SD | 0 | 1.5 | 0.3 | 3.9 | 0.7 | 0.2 | 0.2 |
| | | Null | Mean | 3.4 | 15.7 | 34.2 | 17.9 | 9.5 | 5.2 | 9.9 |
| | | | SD | 0.1 | 2.1 | 0.5 | 0.3 | 0 | 0.1 | 0.4 |
| | | | Delta | -3.3 | 3.1 | 4.1 | 6.7 | -4.3 | -0.3 | -3.8 |

TABLE 8-continued

FT-NIR measured compositions for ~20 g batches of homozygous positive and null events of Soil 91 (Soil 91-1, Soil 91-2 and Soil 92-1) soybeans. Values presented are means and standard deviations for two positive (pos) and two null (null) replicates for each event. The delta values indicate the difference between the transgenic positive and null means for each component.

| Sample | Method | | | Stachyose | Oil | Protein | Oleic acid | Linolenic acid | Sucrose | Total soluble carbohydrate |
|---|---|---|---|---|---|---|---|---|---|---|
| Soil 92-1 | FT-NIR | Pos | Mean | 1.84 | 23.60 | 36.39 | 43.64 | 2.47 | 3.40 | 7.64 |
| | | | SD | 0.40 | 0.58 | 2.68 | 4.07 | 1.00 | 0.12 | 0.34 |
| | | Null | Mean | 4.54 | 17.39 | 31.89 | 26.78 | 7.82 | 5.23 | 12.09 |
| | | | SD | 0.62 | 0.18 | 1.22 | 2.82 | 0.10 | 0.26 | 0.62 |
| | | | Delta | −2.7 | 6.2 | 4.5 | 16.9 | −5.3 | −1.8 | −4.5 |
| | Ref Chem | Pos | Mean | 2.78 | 20.70 | 39.28 | 30.22 | 3.78 | 1.89 | 5.70 |
| | | | SD | 0.56 | 0.73 | 2.72 | 6.96 | 0.52 | 0.85 | 0.44 |
| | | Null | Mean | 3.53 | 15.98 | 33.16 | 20.07 | 8.56 | 5.82 | 11.00 |
| | | | SD | 0.07 | 0.97 | 1.30 | 1.44 | 0.79 | 0.41 | 0.68 |
| | | | Delta | −0.8 | 4.7 | 6.1 | 10.2 | −4.8 | −3.9 | −5.3 |

The FT-NIR methods used in this example enable detection of transgenic positive material despite discrepancies between the predicted and reference chemistry measured compositions.

Further NIR Models for FT-NIR

FT-NIR measurements for stachyose and other components were taken from 13,881 field grown samples which were screened using NIT to access the compositional diversity of the sample set. Samples that represented the extreme concentrations (both high and low) were selected along with material that was evenly distributed across the intermediate concentrations for each component. Further selections were made to maximize genetic diversity in the samples, along with samples that were clear outliers (i.e., those having measured compositions that were outside the expected ranges). A final set of approximately 400 samples resulted. Spectra were captured on the FT-NIR, as described above. The samples will be analyzed by reference chemistry to determine the concentrations of each constituent and the data will be used to refine the calibrations to facilitate accurate determinations of the sucrosyl-oligosaccharides and other constituents.

Example 5

Development of NIR Models for Near Infrared Transmittance (NIT).

NIR Spectra, from 850-1050 nm (2-nm step; 30-mm path length), for 400-500 g bulk samples of intact soybeans were acquired in transmission mode using a Foss Tecator AB model 1241 grain analyzer (commercially available from Foss Tecator AB, Höganäs, Sweden) fitted with a standard instrument hopper and sample transport mechanism. The average NIR absorption spectrum for a given sample was arrived at by duplicate analyses each using 10 subsample scans.

All data analysis was performed using InfraSoft International (ISI) chemometrics software WinISI II v. 1.50e (commercially available from NIRSystems Inc., Silver Spring, MD, USA), MATLAB 7.10.0 R2010a with Neural Network Toolbox (Mathworks, 2010) and ANN Trainer v1.0a12 (Foss Tecatur AB, 2002) software. Pre-treatment of the raw NIR (log 1/Transmittance) spectral data (850-1050 nm) included multiplicative scatter correction, mean centering and unit vector scaling. Oil and protein content (corrected to a 13% moisture basis) were measured according to techniques developed by USDA-FGIS\GIPSA. Models for palmitic acid, stearic acid, oleic acid, linoleic acid, linolenic acid, sucrose, stachyose and total soluble sugars were developed using Artificial Neural Network (ANN) techniques utilizing the transformed spectrum captured from material presenting a wide compositional diversity for these components. The reference chemistry used for the calibrations was obtained, following spectral capture, using the bulk methods described in Example 2. All calibration development work was performed using standard ANN algorithms available in the software. A Levenberg-Marquardt training function was used with log-sigmoid input and pure-linear output transfer functions. Between four and nine neurons were used in one hidden node layer.

The optimum number of iterations (epochs) was chosen when the randomly selected test set error was minimized. The coefficient of determination ($R^2$) was used to describe the correlation between reference (observed) and NIR-predicted values for the calibration set. The Ratio of Performance to Deviation (RPD), defined as the ratio of the SD of the reference values to the SECV (or test set Standard Error of Prediction (SEP)), was used as a normalized indicator for comparing NIR models.

NIT wavelengths useful in the prediction of stachyose concentration in whole soybeans were 850, 866, 880, 890, 902, 910, 920, 930, 944, 952, 964, 978, 990, 1004, 1016, 1032, and 1042 nm. Measurements were taken using the spectra and reference chemistry collected from three years of field grown soybeans from multiple sites within the United States, Argentina, and Puerto Rico. The statistics for the accuracy of the non-destructive NIR methods compared with the standard methods disclosed herein are shown in Table 9.

TABLE 9

Statistics of accuracy of NIT measurements. n = number of reference chemistry measurements used for each constituent comparison between the NIR methods compared with the standard methods disclosed herein.

| Constituent | n | Range | $R^2$ | RMSEC | RMSECV |
|---|---|---|---|---|---|
| moisture (approx.) | 379 | | 0.99 | 0.30 | 0.30 |
| protein | 266 | 31.9-51.0 | 0.97 | 0.54 | 0.54 |
| oil | 103 | 16.9-25.0 | 0.96 | 0.35 | 0.35 |
| oleic | 2277 | 19.2-91.9 | 0.995 | 1.59 | 1.56 |
| linoleic | 2190 | 0.2-58.4 | 0.98 | 2.19 | 2.20 |
| linolenic | 2277 | 0.9-10.3 | 0.96 | 0.46 | 0.31 |
| stearic | 2276 | 2.6-9.5 | 0.86 | 0.41 | 0.33 |
| palmitic | 2277 | 1.79-12.5 | 0.96 | 0.52 | 0.51 |
| stachyose | 354 | 0.05-4.9 | 0.89 | 0.49 | 0.57 |

TABLE 9-continued

Statistics of accuracy of NIT measurements. n = number of reference chemistry measurements used for each constituent comparison between the NIR methods compared with the standard methods disclosed herein.

| Constituent | n | Range | $R^2$ | RMSEC | RMSECV |
|---|---|---|---|---|---|
| sucrose | 354 | 2.2-9.9 | 0.90 | 0.48 | 0.39 |
| total soluble carbohydrates | 354 | 5.7-12.1 | 0.88 | 0.48 | 0.42 |

Values for stachyose measured using NIT and reference chemistry for bulk samples of transgenic positive and negative events of Soil 19 are given in Table 10.

TABLE 10

NIT predicted stachyose content of bulk samples of transgenic positive and negative events of Soil 19. The beans were harvested from plants grown at 9 independent mid-Western sites. The samples were subjected to reference chemistry after the NIT spectra had been captured.

| Event | Trait Call | 2013 EUid | Ref Chem Stachyose (wt. %) | NIT Stachyose (wt. %) |
|---|---|---|---|---|
| Soil19 1.2.1 | Pos | 242479091 | 0.45 | 0.25 |
| Soil19 1.2.1 | Neg | 242479093 | 3.62 | 3.40 |
| | | Δ between mean NIT measurement and the reference chem value | | 0.20 |
| Soil19 2.2.1 | Neg | 219154850 | 3.59 | 3.61 |
| Soil19 2.2.1 | Neg | 219154734 | 3.76 | 3.54 |
| Soil19 2.2.1 | Neg | 219154901 | 4.53 | 4.26 |
| Soil19 2.2.1 | Neg | 219154925 | 4.23 | 4.37 |
| Soil19 2.2.1 | Neg | 219154941 | 4.01 | 3.43 |
| Soil19 2.2.1 | Neg | 219154949 | 4.47 | 3.93 |
| Soil19 2.2.1 | Neg | 219154957 | 3.49 | 3.74 |
| Soil19 2.2.1 | Neg | 219154981 | 4.34 | 3.57 |
| | | Mean | 4.05 | 3.81 |
| | | SD | 0.40 | 0.35 |
| | | Δ between mean NIT measurement and the reference chem value | | 0.25 |
| Soil19 2.2.1 | Pos | 219154736 | 1.03 | 1.38 |
| Soil19 2.2.1 | Pos | 219154769 | 0.51 | 0.20 |
| Soil19 2.2.1 | Pos | 219154781 | 1.00 | 1.02 |
| Soil19 2.2.1 | Pos | 219154832 | 0.88 | 1.01 |
| Soil19 2.2.1 | Pos | 219154842 | 1.01 | 0.94 |
| Soil19 2.2.1 | Pos | 219154886 | 1.03 | 0.85 |
| Soil19 2.2.1 | Pos | 219154918 | 0.46 | 0.27 |
| Soil19 2.2.1 | Pos | 244113717 | 1.01 | 1.02 |
| | | Mean | 0.87 | 0.84 |
| | | SD | 0.24 | 0.40 |
| | | Δ between mean NIT measurement and the reference chem value | | 0.03 |
| Soil19 5.3.3 | Neg | 219154682 | 3.73 | 3.43 |
| Soil19 5.3.3 | Neg | 219154848 | 3.52 | 3.62 |
| Soil19 5.3.3 | Neg | 219154923 | 4.10 | 4.06 |
| Soil19 5.3.3 | Neg | 219154939 | 4.23 | 3.41 |
| Soil19 5.3.3 | Neg | 219154947 | 4.66 | 3.41 |
| Soil19 5.3.3 | Neg | 219154955 | 3.53 | 3.89 |
| Soil19 5.3.3 | Neg | 219154979 | 4.33 | 3.33 |
| Soil19 5.3.3 | Neg | 244113714 | 3.68 | 3.76 |
| | | Mean | 3.97 | 3.61 |
| | | SD | 0.42 | 0.27 |
| | | Δ between mean NIT measurement and the reference chem value | | 0.36 |
| Soil19 5.3.3 | Pos | 242479108 | 0.84 | 0.92 |
| Soil19 5.3.3 | Pos | 242479110 | 0.57 | 0.50 |
| Soil19 5.3.3 | Pos | 219154766 | 0.30 | 0.21 |
| Soil19 5.3.3 | Pos | 219154778 | 0.74 | 0.59 |
| Soil19 5.3.3 | Pos | 219154830 | 0.51 | 0.22 |
| Soil19 5.3.3 | Pos | 219154838 | 0.72 | 0.93 |
| Soil19 5.3.3 | Pos | 219154884 | 0.74 | 0.64 |
| Soil19 5.3.3 | Pos | 219154900 | 0.80 | 1.59 |
| Soil19 5.3.3 | Pos | 219154916 | 0.41 | 0.25 |
| Soil19 5.3.3 | Pos | 219154940 | 0.44 | 0.55 |
| Soil19 5.3.3 | Pos | 244113715 | 0.83 | 0.35 |
| | | Mean | 0.61 | 0.59 |
| | | SD | 0.19 | 0.44 |
| | | Δ between mean NIT measurement and the reference chem value | | 0.02 |

The data show that the NIT measurements of stachyose in the transgenic positive events was <1.6% whereas the minimal measured value for the transgenic negative (null) events was 3.3%, allowing distinctions between the transgenic positive and negative events to be made, based on the stachyose measurements alone. The average stachyose NIT measurements for both the transgenic positive and negative events were within 0.4% of those measured by reference chemistry (Table 10) showing a high degree of precision (ability to differentiate between transgenic positive and negative events) and accuracy (closeness to the reference chemistry determined value).

Example 6

The use of Near Infrared Transmittance (NIT) Spectroscopy to Identify Material for Improved Accuracy of Measurements made with NIR or NIT The development of robust spectroscopic models for the identification of transgenic materials that have been altered in their composition is dependent on several factors:

The sample sizes used for NIT analysis in this example were large enough to be subjected to industry standard reference chemistry methods (which typically require more than 60 g of seed). Measurements taken using NIT were scalable and were transferred between NIR and NIT instruments. The sample size used for NIT (400-500 g) was compatible with growing transgenic and breeding lines in short (2 to 3 meter) field plots. Field culture allowed for the introduction of environmental variation to be accounted for i.e., representatives of the same events (such as transgenes or genetic modifications) grown in different states and under different field conditions. The sample size was sufficient to provide material to calibrate instruments with smaller sample size requirements i.e., the FT-NIR and SS-NIR, single seed reference chemistry used for SS-NIR.

NIT spectroscopy was used to analyze 3692 samples containing 400-500 g of seed grown in field plots Johnston, Iowa during the 2014 season. Compositional data for each of the 11 constituents listed in Table 11 were collected. The data was analyzed by plotting the entire ranges of composition for each component. Samples that represented the extreme concentrations (both high and low) were selected along with material that was evenly distributed across the intermediate concentrations for each component. Further selections were made to maximize genetic diversity in the samples, along with samples that were clear outliers (i.e., those having measured compositions that were outside the expected ranges). This process resulted in the selection of 183 samples for further analysis; i.e., approximately 5% of the initial set. The subset was then analyzed by SS-NIR, FT-NIR (on both a Bruker MPA and Tango FT=NIR spectrometers) prior to being ground and subjected to reference chemistry.

Another set of 2020 soybean samples containing 400-500 g of seed grown in Argentina field plots during the 2015-2016 growing season were scanned on a Foss 1241 NIT spectrometer. Compositional data for the 11 constituents in Table 11 was generated using the collected absorption spectra. A selection of 139 calibration expansion samples was made based on uniform predicted composition, and individual sample spectra compared to the model spectral database. This procedure utilized principal component analysis of the model database, and the relative similarity of the Argentina set to identify samples not currently represented in the model population. Another set of 40 samples intended to validate the model performance was selected based on wide ranging, uniform estimated concentration and the presence of similar samples in the model or currently being selected for calibration expansion.

Each sample was scanned on a Bruker MPA and then on a Bruker Tango (Fourier Transform Near Infra-Red (FT-NIR) spectrometers) each fitted with 54 mm diameter rotating cup assemblies. Twenty grams (approximately 100 seed) samples were removed from the bulk packages, after thorough mixing, and were used for analysis on one of the FT-NIR instruments. The seed samples were then returned to the bulk bags and a second sample was used for spectral capture on the second instrument. The weight of each sample (to an accuracy of 0.01 g) was recorded prior to scanning. The conditions for spectral capture on the Tango instrument were similar to those described for the Bruker MPA (Example 4) except that the wave length range was slightly narrower (867 and 2530 nm on the Tango vs 833 and 2778 nm on the MPA). Captured spectra from both instruments were analyzed and prediction models were developed using the Bruker OPUS 7.0 software package.

Twelve seeds from each sample were selected randomly from the bulk packages and were analyzed by SS-NIR. Individual seed identities were maintained during the spectral capture process. Each bean was then placed into 2 ml polypropylene tubes (Corning Inc, Corning NY, USA; part #430917) previously labeled with unique bar code identifiers, in preparation for single seed reference chemistry analysis (Example 2) and subsequent SS-NIR model refinement.

Seventy-five gram samples were then removed from each of the bulk samples and after grinding the samples were subjected to bulk reference chemistry analysis (see Examples 2). The mean, SD, minimum and maximum values for each component from each analytical platform are given in Table 11.

TABLE 11

Mean, SD, minimum and maximum values soybean compositional components.

| Data Source | | OIL wt. % | PROT wt. % | Palmitic acid | Stearic acid | Oleic acid | Linoleic acid | Linolenic acid | Sucrose wt. % | Raffinose wt. % | Stachyose wt. % | Total soluble carbohydrates wt. % |
|---|---|---|---|---|---|---|---|---|---|---|---|---|
| NIT 3692 | Mean | 19.5 | 36.1 | 11.0 | 4.0 | 24.0 | NA | 5.5 | 5.2 | 0.6 | 2.4 | 8.8 |
| | SD | 1.7 | 0.9 | 1.0 | 0.7 | 9.5 | NA | 2.6 | 0.6 | 0.1 | 1.0 | 0.9 |
| | Min | 16.0 | 33.1 | 4.1 | 0.8 | 12.1 | NA | 1.0 | 2.7 | 0.1 | 0.2 | 5.6 |
| | Max | 24.2 | 40.6 | 14.1 | 9.5 | 88.3 | NA | 16.5 | 7.6 | 1.2 | 4.2 | 11.3 |
| Select | Mean | 19.5 | 36.3 | 10.8 | 4.1 | 28.9 | NA | 5.5 | 5.3 | 0.6 | 2.3 | 8.8 |
| 183 NIT | SD | 1.8 | 1.1 | 1.6 | 0.9 | 18.2 | NA | 2.6 | 0.7 | 0.1 | 1.1 | 1.0 |
| | Min | 16.2 | 33.8 | 4.1 | 2.5 | 13.0 | NA | 1.1 | 2.7 | 0.1 | 0.2 | 5.7 |
| | Max | 24.2 | 40.6 | 14.1 | 9.5 | 88.3 | NA | 16.5 | 7.4 | 1.2 | 4.1 | 11.0 |
| Reference | Mean | NA | 36.8 | 10.6 | 4.3 | 31.2 | 47.0 | 6.0 | 5.8 | 0.6 | 2.6 | 9.5 |
| Chemistry | SD | NA | 1.2 | 2.7 | 0.8 | 17.4 | 14.6 | 3.0 | 1.1 | 0.2 | 1.6 | 1.3 |
| | Min | NA | 33.9 | 2.5 | 2.7 | 16.2 | 1.1 | 1.2 | 2.6 | 0.1 | 0.1 | 6.3 |
| | Max | NA | 39.7 | 19.2 | 6.8 | 86.9 | 57.4 | 9.4 | 9.7 | 1.2 | 5.2 | 13.3 |
| SS-NIR | Mean | 21.5 | 42.2 | 10.0 | 3.9 | 31.0 | 49.0 | 5.5 | 6.3 | NA | 2.5 | 10.1 |
| Means Only | SD | 2.1 | 1.7 | 1.4 | 0.9 | 16.7 | 13.9 | 2.4 | 1.0 | NA | 1.2 | 1.4 |
| | Min | 17.5 | 37.8 | 4.3 | 2.6 | 14.9 | 2.4 | 0.6 | 4.0 | NA | −0.5 | 6.8 |
| | Max | 26.1 | 46.9 | 11.9 | 6.8 | 88.4 | 62.2 | 9.8 | 9.8 | NA | 4.3 | 13.4 |
| FT-NIR | Mean | 19.5 | 36.3 | 8.9 | 4.5 | 31.8 | 44.5 | 5.6 | 6.0 | NA | 2.2 | 9.5 |
| MPA | SD | 1.9 | 1.3 | 1.7 | 0.9 | 16.2 | 13.5 | 2.2 | 0.8 | NA | 1.4 | 1.3 |
| | Min | 16.4 | 33.1 | 3.3 | 3.3 | 17.6 | −0.7 | −1.4 | 3.5 | NA | −1.1 | 5.7 |
| | Max | 23.0 | 40.1 | 11.6 | 6.5 | 86.2 | 55.8 | 8.7 | 9.2 | NA | 4.7 | 11.5 |
| FT-NIR | Mean | 19.1 | 36.6 | 9.0 | 5.2 | 30.6 | 49.2 | 4.4 | 6.1 | NA | 0.8 | 8.3 |
| Tango | SD | 1.6 | 1.4 | 1.6 | 0.9 | 16.7 | 14.2 | 2.1 | 0.7 | NA | 1.4 | 1.2 |
| | Min | 16.6 | 33.0 | 3.2 | 3.6 | 17.1 | 0.1 | −2.0 | 4.1 | NA | −2.4 | 5.1 |
| | Max | 22.4 | 40.2 | 10.5 | 7.6 | 87.2 | 60.4 | 7.3 | 9.0 | NA | 3.0 | 10.5 |

Comparison of the means, minimum and maximum values for the whole sample set (represented by the "Original NIT Values" which were developed for 3692 samples) and those for the selected set of 183 samples shows that the latter set covered the available dynamic range for each of the predicted components (Table 11). Further, the close agreement between the mean, minimum and maximum NIT predicted values for the selected set of 183 samples and the actual compositional contents measured for these samples by reference chemistry indicates the high degree of precision and accuracy of the measurements for most of the components. For example, the predicted mean, minimum and maximum stachyose contents for the 183 sample subset differed from the reference chemistry measured values by −0.3wt %, 0.1wt % and −1.1wt %, respectively. In contrast the predicted mean, minimum and maximum palmitic acid contents for the 183 sample subset differed from the reference chemistry measured values by 0.2 relative %, 1.6 relative % and −5.0 relative %, respectively. Inclusion of the reference chemistry values into the NIT models will lead to improvements in the precision of the measurements (i.e., the ability to differentiate between unknown samples differing in their composition) and the accuracy (the ability to predict compositions that are indistinguishable from those measured using standard reference chemistry methods).

Example 7

As an illustration of the precision of the reference chemistry assay for sucrose, raffinose and stachyose, bulk samples of beans from three different commodity soybean samples were subjected to analysis as blind duplicates. Six replicates for each duplicated sample were analyzed using the standard analytical methods for total soluble carbohydrate derivatization and analysis according to the methods set forth in Example 2.

Each sugar was quantified relative to its own calibration curve, after dividing each individual peak by the area of the internal standard in each sample and standard. Final carbohydrate concentrations were expressed corrected for moisture content as set forth herein. Residual sucrose, raffinose and stachyose recovered in the starch digestions were included in the total values reported for each sugar.

The average coefficient of variation (mean/standard deviation of the mean, expressed as a percentage) for sucrose, raffinose and stachyose were, 1.43%, 1.34% and 2.11%, respectively. As an illustration of the accuracy of the reference chemistry assay for sucrose, raffinose and stachyose, bulk samples of beans from three different commodity soybean samples were subjected to analysis as blind duplicates using the methods described here and at two contract research organizations. The mean values for sucrose of 4.31+/−0.22 (internal), 4.26+/−0.11, 4.26+/−0.21 were not significantly different at the 95% confidence interval. The mean values for stachyose were 3.45+/−0.13 (internal), 3.16+/−0.14 and 3.36+/−0.27 were not significantly different at the 95% confidence interval. Significant differences were observed in the raffinose values of 0.93+/−0.02 (internal), 0.73+/−0.10 and 0.47+/−0.03.

Example 8

Analysis of Soybean Meal

Rapid compositional analyses of soybean meals, including analyses reporting on the concentration of anti-nutritional factors such as the sucrosyl oligosaccharide, raffinose and stachyose and nutritionally desirable components such as protein, amino acids and sucrose can be carried out.

Defatted powders remaining after the bulk oil extraction process (Example 2.15) from soybeans are used to capture NIR reflection absorption spectra, either on a Bruker MPA or on a Foss 6500 full spectrum instrument. The integrating sphere channel of the MPA operating in macro reflectance mode is utilized to scan the powders contained within a 15×45 mm borosilicate vial (Qorpak p/n GLC-00982) in triplicate at a resolution of 8 cm-1 from 833-2778 nm. Alternately a Foss/NIRSystems 6500 near infrared reflectance instrument equipped with an autosampler attachment will be utilized to scan the powders contained within a 51 mm ring cup in duplicate at a resolution of 2 nm from 400-2500 nm. The samples are analyzed for the concentration of protein, moisture, sucrose, raffinose, stachyose and total soluble carbohydrates using reference chemistry methods described in Example 2. The resulting spectral and chemical data will enable accurate determination of each constituent's concentration.

Example 9

A diverse set of soybeans grown in the field in North America and Argentina in 2015 and North America in 2016 were selected for their compositional diversity using the methodology described in Example 6. After spectral capture on both the FT-NIR (Example 4) and the NIT (Example 5) platforms the samples were subjected to reference chemistry using the bulk sample methodologies described in Example 2. The statistical characteristics of the models obtained are described in Table 12. In generating the models raffinose and total saturated fatty acids were added as analytes. The moisture models were not updated.

TABLE 12

Statistics of accuracy of NIT measurements. n = number of reference chemistry measurements used for each constituent comparison between the NIR methods compared with the standard methods disclosed herein. Oil, protein and carbohydrate ranges are presented on a 13% moisture basis. Fatty acids are presented on a relative % basis.

| Constituent | n | Range | $R^2$ | RMSEC | RMSECV |
|---|---|---|---|---|---|
| moisture | 379 | | 0.99 | 0.3 | 0.3 |
| protein | 1101 | 28.3-41.0 | 0.94 | 0.40 | 0.40 |
| oil | 1105 | 15.3-28.4 | 0.98 | 0.30 | 0.31 |
| oleic | 1141 | 14.6-87.3 | 1.00 | 1.40 | 1.51 |
| linoleic | 1141 | 0.8-59.2 | 1.00 | 1.24 | 1.28 |
| linolenic | 1141 | 0.8-10.2 | 0.96 | 0.49 | 0.51 |
| stearic | 1141 | 2.7-16.1 | 0.89 | 0.24 | 0.34 |
| palmitic | 1141 | 2.0-23.1 | 0.96 | 0.63 | 0.52 |
| total sats | 1141 | 4.7-28.0 | 0.98 | 0.51 | 0.52 |
| raffinose | 1200 | 0.1-1.5 | 0.56 | 0.19 | 0.26 |
| stachyose | 1200 | 0.02-5.2 | 0.95 | 0.37 | 0.44 |
| sucrose | 1200 | 1.7-9.9 | 0.72 | 0.62 | 0.67 |
| total soluble carbohydrates | 1200 | 3.7-13.3 | 0.86 | 0.62 | 0.78 |

The performance of the stachyose model improved with the addition of the new data; $R^2$ 0.95 vs 0.89 (compare Tables 9 and 12); RMSEC 0.37 vs 0.49 (the lower value indicates an improved resolution between samples in the model); RMSECV 0.44 vs 0.57 (a lower value indicates an improved resolution between samples not in the model, i.e., unknowns). The model statistics for sucrose and total soluble carbohydrates did not improve.

Example 10

Analysis of soybean meals; Defatted Powder Model Derivation

Rapid compositional analyses of soybean meals, including analyses of the concentration of anti-nutritional factors such as the sucrosyl oligosaccharide, raffinose and stachyose and nutritionally desirable components such as sucrose was carried out. Defatted powder was used; defatted soybean flakes could also be used.

Defatted powders remaining after the bulk oil extraction process (Example 2.15) from soybeans were used to capture NIR reflection absorption spectra on a Bruker MPA. The integrating sphere channel of the MPA operating in macro reflectance mode was utilized to scan the powders contained within a 15×45 mm borosilicate vial (Qorpak p/n GLC-00982) in triplicate, at a resolution of 8 cm-1 from 800-2778 nm. It is expected that a Foss/NIRSystems 6500 near infrared reflectance instrument equipped with an autosampler attachment could also be utilized to scan the powders contained, for example, within a 51 mm ring cup in duplicate at a resolution of 2 nm from 400-2500 nm.

After spectral capture samples were analyzed for the concentration of protein, moisture, sucrose, raffinose, stachyose and total soluble carbohydrates using reference chemistry methods described in Example 2. The resulting spectral and chemical data were used to generate calibrations for the prediction of the meal compositions.

Captured spectra and accompanying reference chemistry were used to derive Partial Least Squares predictive models utilizing Bruker's Opus 7.0 software package. Individual triplicate spectra were averaged into a single observation prior to the model regression. Spectral regions and absorption data pre-treatment were selected for each analyte using the OPUS optimization algorithm. Raffinose, stachyose, and total soluble carbohydrates employed first derivative and standard normal variate pre-treatment while using regions 1333-2355 nm, 1464-2355 nm, and 1063-1125 nm plus 1465-2355 nm respectively. Sucrose modeling entailed using first derivative and multiplicative scatter correction to pre-treat spectra and incorporated 1639-2355 nm wavelength regions. The resulting model statistics are displayed in Table 13.

TABLE 13

Statistics of FT-NIR calibration curves for Defatted Powders. The number of reference chemistry measurements are shown in column n. Range (wt. % corrected to 13% Moisture) shows the minimum and maximum reference method measured value in the samples for each constituent.

| Constituent | n | Range | $R^2$ | RMSEC | RMSECV |
|---|---|---|---|---|---|
| Raffinose | 231 | 0.15-1.76 | 0.73 | 0.20 | 0.22 |
| Stachyose | 238 | 0.05-5.81 | 0.97 | 0.34 | 0.39 |
| Sucrose | 230 | 3.75-8.34 | 0.85 | 0.34 | 0.38 |
| Total Carbs | 232 | 6.26-13.75 | 0.96 | 0.33 | 0.40 |

The data indicate that stachyose in soybean meals were measured to a similar degree of precision and accuracy as those achieved for whole beans using the methods described here, i.e., $R^2$ 0.97 and 0.95, RMSEC 0.34 and 0.37 for the meal and whole bean NIT models (Table 12), respectively.

All publications, patents, and patent applications mentioned in the specification are incorporated by reference herein for the purpose cited to the same extent as if each was specifically and individually indicated to be incorporated by reference herein.

The foregoing invention has been described in detail by way of illustration and example for purposes of clarity and understanding. As is readily apparent to one skilled in the art, the foregoing description represents only some of the methods and compositions that illustrate the embodiments of the foregoing invention. It will be apparent to those of ordinary skill in the art that variations, changes, modifications, and alterations may be applied to the compositions and/or methods described herein without departing from the true spirit, concept, and scope of the invention.

As used herein, the terms "comprises," "comprising," "includes," "including," "has," "having," "contains", "containing," "characterized by" or any other variation thereof, are intended to cover a non-exclusive inclusion.

Unless expressly stated to the contrary, "or" is used as an inclusive term. For example, a condition A or B is satisfied by any one of the following: A is true (or present) and B is false (or not present), A is false (or not present) and B is true (or present), and both A and B are true (or present). The indefinite articles "a" and "an" preceding an element or component are nonrestrictive regarding the number of instances (i.e., occurrences) of the element or component. Therefore "a" or "an" should be read to include one or at least one, and the singular word form of the element or component also includes the plural unless the number is obviously meant to be singular.

arated and further used in soybean processing or breeding.

What is claimed is:

1. A method for measuring the amount of stachyose in soybean powder, soybean meal or soybean flakes, the method comprising:
   (a) directing near infrared light from a light source onto a soybean powder, soybean meal, or soybean flake sample to form modified light from the soybean powder, soybean meal, or soybean flake sample;
   (b) receiving the modified light in an imaging device;
   (c) measuring the amount of stachyose in the soybean powder, soybean meal, or soybean flake sample based on the received modified light, the amount of the stachyose being measured to an accuracy that is within 1 wt. % of the amount measured using a standard reference analytical method.

2. The method of claim 1, further comprising transporting the soybean meal, soybean powder or soybean flakes to a first location when the amount of stachyose measured is below a threshold value and transporting the soybean powder, soybean meal or soybean flakes to a different second location when the amount of stachyose measured is at or above the threshold value.

3. The method of claim 2, wherein threshold value is between 2 wt. % and 0.1 wt. %.

4. The method of claim 2, wherein threshold value is between 1.5 wt. % and 0.1 wt %.

5. The method of claim 2, wherein threshold value is between 1 wt. % and 0.1 wt. %.

6. The method of claim 2, wherein the soybean meal, soybean powder or soybean flakes above the threshold value differ by a least 1 wt. % stachyose from the soybean meal, soybean powder or soybean flakes below the threshold value.

7. The method of claim 2, wherein the threshold value is about 1 percentage point.

8. The method of claim 2, wherein the modified light comprises reflected light.

9. The method of claim 2, wherein the amount of stachyose is measured in soybean powder.

10. The method of claim 2, wherein the amount of stachyose is measured in soybean meal.

11. The method of claim 2, wherein the amount of stachyose is measured in soybean flakes.

12. The method of claim 2, wherein the amount of stachyose measured in step (c) is an average amount for the soybean powder, soybean meal or soybean flakes.

13. The method of claim 1, wherein the modified light comprises transmitted light.

14. The method of claim 1, wherein the modified light comprises reflected light.

15. The method of claim 1, wherein the amount of stachyose is measured in soybean powder.

16. The method of claim 1, wherein the amount of stachyose is measured in soybean meal.

17. The method of claim 1, wherein the amount of stachyose is measured in soybean flakes.

18. The method of claim 1, wherein the soybean powder, soybean meal or soybean flakes are processed to produce a soy protein concentrate when the amount of sucrosyl-oligosaccharide measured is below a threshold value between 2 wt. % and 0.1 wt. % and wherein the soybean powder, soybean meal or soybean flakes are processed without producing a soy protein concentrate when the amount of sucrosyl-oligosaccharide measured is at or above the threshold value.

19. The method of claim 18, wherein the threshold value between 1.5 wt. % and 0.1 wt. %.

20. The method of claim 18, wherein the threshold value between 1 wt. % and 0.1 wt. %.

* * * * *

SEQUENCE LISTING

```
Sequence total quantity: 12
SEQ ID NO: 1                moltype = DNA  length = 17719
FEATURE                     Location/Qualifiers
misc_feature                1..17719
                            note = synthesized DNA of PHP48070
source                      1..17719
                            mol_type = other DNA
                            organism = synthetic construct
SEQUENCE: 1
cgcgccggaa ttaattaggt aatttcacgc gccggatcct taattaagtc tagagtcgac   60
tgtttaattc tagtggccgg cccagctgat gatcccggtg aagttcctat tccgaagttc  120
ctattctcca gaaagtatag gaacttcact agagcttgcg gccgctcgag ttctatagtg  180
tcacctaaat cgtatgtgta tgatacataa ggttatgtat taattgtagc cgcgttctaa  240
cgacaatatg tccatatggt gcactctcag tacaatctgc tctgatgccg catagttaag  300
ccagcccga cacccgccaa cacccgctga cgcgcccctga cgggcttgtc tgctcccggc  360
atccgcttac agacaagctg tgaccgtctc cgggagctgc atgtgtcaga ggttttcacc  420
gtcatcaccg aaacgcgcga gacgaaaggg cctcgtgata cgcctatttt tataggttaa  480
tgtcatgacc aaaatccctt aacgtgagtt ttcgttccac tgagcgtcag accccgtaga  540
aaagatcaaa ggatcttctt gagatccttt ttttctgcgc gtaatctgct gcttgcaaac  600
aaaaaaacca ccgctaccag cggtggtttg tttgccggat caagagctac caactctttt  660
tccgaaggta actggcttca gcagagcgca gataccaaat actgtccttc tagtgtagcc  720
gtagttaggc caccacttca agaactctgt agcaccgcct acatacctcg ctctgctaat  780
cctgttacca gtggctgctg ccagtggcga taagtcgtgt cttaccgggt tggactcaag  840
acgatagtta ccggataagg cgcagcggtc gggctgaacg gggggttcgt gcacacagcc  900
cagcttggag cgaacgacct acaccgaact gagataccta cagcgtgagc attgagaaag  960
cgccacgctt cccgaaggga gaaaggcgga caggtatccg gtaagcggca gggtcggaac 1020
aggagagcgc acgagggagc ttccaggggg aaacgcctgg tatctttata gtcctgtcgg 1080
gtttcgccac ctctgacttg agcgtcgatt tttgtgatgc tcgtcagggg ggcggagcct 1140
atggaaaaac gccagcaacg cggccttttt acggttcctg gccttttgct ggccttttgc 1200
tcacatgttc tttcctgcgt tatccctga ttctgtggat aaccgtatta ccgcctttga 1260
gtgagctgat accgctcgcc gcagccgaac gaccgagcgc agcgagtcag tgagcgagga 1320
agcggaagag cgcccaatac gcaaaccgcc tctcccgcg cgttggccga ttcattaatg 1380
caggttgatc agatctcgat cccgcgaaat taatacgact cactataggg agaccacaac 1440
ggtttccctc tagaaataat tttgtttaac tttaagaagg agatataccc atggaaaagc 1500
ctgaactcac cgcgacgtct gtcgagaagt ttctgatcga aaagttcgac agcgtctccg 1560
acctgatgca gctctcggag ggcgaagaat ctcgtgcttt cagcttcgat gtaggagggc 1620
```

```
gtggatatgt cctgcgggta aatagctgcg ccgatggttt ctacaaagat cgttatgttt   1680
atcggcactt tgcatcggcc gcgctcccga ttccggaagt gcttgacatt ggggaattca   1740
gcgagagcct gacctattgc atctcccgcc gtgcacaggg tgtcacgttg caagacctgc   1800
ctgaaaccga actgcccgct gttctgcagc cggtcgcgga ggctatggat gcgatcgctg   1860
cggccgatct tagccagacg agcgggttcg gcccattcgg accgcaagga atcggtcaat   1920
acactacatg gcgtgatttc atatgcgcga ttgctgatcc ccatgtgtat cactggcaaa   1980
ctgtgatgga cgacaccgtc agtgcgtccg tcgcgcaggc tctcgatgag ctgatgcttt   2040
gggccgagga ctgccccgaa gtccggcacc tcgtgcacgc ggatttcggc tccaacaatg   2100
tcctgacgga caatggccgc ataacagcgg tcattgactg gagcgaggcg atgttcgggg   2160
attcccaata cgaggtcgcc aacatcttct tctggaggcc gtggttggct tgtatggagc   2220
agcagacgcg ctactcgagc ggaggcatcc ggagcttgc aggatcgccg cggctccggg   2280
cgtatatgct ccgcattggt cttgaccaac tctatcagag cttggttgac ggcaatttcg   2340
atgatgcagc ttgggcgcag ggtcgatgcg acgcaatcgt ccgatccgga gccgggactg   2400
tcgggcgtac acaaatcgcc cgcagaagcg cggccgtccg gaccgatgcg tgtgtagaag   2460
tactcgccga tagtggaaac cgacgcccca gcactcgtcc gagggcaaag gaatagtgag   2520
gtacagcttg gatcgatccg gctgctaaca aagcccgaaa ggaagctgag ttggctgctg   2580
ccaccgctga gcaataacta gcataacccc ttggggcctc taaacgggtc ttgaggggtt   2640
ttttgctgaa aggaggaact atatccggat gatcgtcgag gcctcacgtg ttaacaagct   2700
tgcatgccgg tttaaacagt cgaggtcgac ggtatcgata agcttgttaa cagaagttcc   2760
tattccgaag ttcctattct ctagaaagta taggaacttc caccacacaa cacaatggcg   2820
gccaccgctt ccagaaccac ccgattctct tcttcctctt cacaccccac cttccccaaa   2880
cgcattacta gatccaccct ccctctctct catcaaaccc caaccacgct   2940
ctcaaaatca aatgttccat ctccaaaccc cccacggcgg cgcccttcac caaggaagcg   3000
ccgaccacgg agcccttcgt gtcacggttc gcctccggcg aacctcgcaa gggcgcggac   3060
atccttgtgg aggcgctgga gaggcagggc gtgacgacgg tgttcgcgta ccccggcggt   3120
gcgtcgatgg agatccacca ggcgctcacg cgctcccgca ccatccgcaa cgtgctcccg   3180
cgccacgagc agggcggcgt cttcgccgcc gaaggctacg cgcgttcctc cggcctcccc   3240
ggcgtctgca ttgccacctc cggccccggc gccaccaacc tcgtgagcgg cctcgccgac   3300
gctttaatgg acagcgtccc agtcgtcgcc atcaccggcc aggtcgcccg ccggatgatc   3360
ggcaccgacg ccttccaaga aaccccgacg gtggaggtga gcagatccat cacgaagcac   3420
aactacctca tcctcgacgt cgacgacatc ccccgcgtcg tcgccgaggc tttcttcgtc   3480
gccacctccg gccgcccgg tccggtcctc atcgacattc ccaaagacgt tcagcagcaa   3540
ctcgccgtgc ctaattggga cgagcccgtt aacctcccg gttacctcgc caggctgccc   3600
aggccccccg ccgaggccca attggaacac atttgtcagc tcatcatgga ggcccaaaag   3660
cccgttctct acgtcggcgg tggcagtttg aattccagtg ctgaattgag gcgctttgtt   3720
gaactcactg gtattcccgt tgctagcact ttaatgggtc ttggaacttt tcctattggt   3780
gatgaatatt cccttcagat gctgggtatg catggtactg tttatgctaa ctatgctgtt   3840
gacaatagtg atttgttgct tgcctttggg gtaaggtttg atgaccgtgt tactgggaag   3900
cttgaggctt ttgctagtag ggctaagatt gttcacattg atattgattc tgccgagatt   3960
gggaagaaca agcaggcgca cgtgtcggtt tgcgcggatt tgaagttggc cttgaaggga   4020
attaatatga ttttggagga aaaggagtg gagggtaagt ttgatcttgg aggttggaga   4080
gaagagatta atgtgcagaa acacaagttt ccatggggtt acaagacatt ccaggacgcg   4140
attttctccgc agcatgctat cgaggttctt gatgagttga ctaatgaaga tgctattgtt   4200
agtactgggg ttgggcagca tcaaatgtgg gctcgcagt tttacaagta caagagaccg   4260
aggcagtggt tgacctcagg gggtcttgga gccatgggt ttggattgcc tgcggctatt   4320
ggtgctgctg ttgctaaccc tgggctgtt gtggttgaca ttgatgggga tggtagtttc   4380
atcatgaatg ttcaggagtt ggccactata agagtggaga atctcccagt taagatattg   4440
ttgttgaaca atcagcattt gggtatggtg gttcagtggg aggataggg ctacaagtcc   4500
aatagagctc acacctatct tggagatccg tctagcgaga gcgagatatt cccaaacatg   4560
ctcaagtttg ctgatgcttg tgggataccg gcagcgcgag tgacgaagaa ggaagagctt   4620
agagcggcaa ttcagagaat gttggacacc cctggcccct accttcttga tgtcattgtg   4680
ccccatcagg agcatgtgtt gccgatgatt cccagtaatg gatccttcaa ggatgtgata   4740
actgagggtg atggtagaac gaggtactga ctagctagtc agttaaccta gacttgtcca   4800
tcttctggat tggccaactt aattaatgta tgaaataaaa ggatgcacac atagtgacat   4860
gctaatcact ataatgtggg catcaaagtt gtgtgttatg tgtaattact agttatctga   4920
ataaaagaga aagagatcat ccatatttct tatcctaaat gaatgtcacg tgtctttata   4980
attctttgat gaaccagatg catttcatta accaaatcca tatacatata aatattaatc   5040
atatataatt aatatcaatt gggttagcaa acaaatcta gtctaggtgt gttttgcccc   5100
caagcttatc gataccgtcg gcgcgggta cgttagctga ttaagtcagc atgcgcggat   5160
ggcgtatgaa ctaaaatgca tgtaggtgta agagctcatg gagagcatgg aatattgtat   5220
ccgaccatgt aacagtataa taactgagct ccatctcact tcttctatga ataaacaaag   5280
gatgttatga tatattaaca ctctatctat gcacttatt gttctatgat aaatttcctc   5340
ttattattat aaatcatctg aatcgtgacg gcttatggaa tgcttcaaat agtacaaaaa   5400
caaatgtgta ctataagact ttctaaacaa ttctaacctt agcattgtga acgagacata   5460
agtgttaaga agacataaca attataatgg aagaagtttg tctccattta tatattat    5520
attacccact tatgtattat attaggatgt taaggagaca taacaattat aaagagagaa   5580
gtttgtatcc atttatatat tatatactac ccatttatat attatactta tccacttatt   5640
taatgtcttt ataaggtttg atccatgata tttctaatat tttagttgat atgtatatga   5700
aaaggtacta tttgaactct cttactctgt ataaaggttg gatcatcctt aaagtgggtc   5760
tatttaattt tattgcttct tacagataaa aaaaaaatta tgagttggtt tgataaaata   5820
ttgaaggatt taaataaata ataaataaca tataatatat gtataaat ttattataat   5880
ataacattta tctataaaaa agtaaatatt gtcataaatc tatacaatcg tttagccttg   5940
ctggaacgaa tctcaattat ttaaacgaga gtaaacatat ttgactttt ggttatttaa   6000
caaattatta tttaacacta tatgaaattt tttttttaat cagcaaagaa taaattaaa   6060
ttaagaagga caatggtgtc ccaatccttaa tacaaccaac ttccacaaga aagtcaagtc   6120
agagacaaca aaaaaacaag caaaggaaat tttttaattt gagttgtctt gtttgctgca   6180
taatttatgc agtaaaacac tacacataac ccttttagca gtagagcaat ggttgaccgt   6240
gtgcttagct tcttttattt tatttttta tcagcaaaga ataaataaaa taaaatgaga   6300
cacttcaggg atgtttcaac aggtacccat cacttaagtg gcgcgccgtc gacggatccg   6360
```

```
tacgatccat gcccttcatt tgccgcttat taattaattt ggtaacagtc cgtactaatc    6420
agttacttat ccttcccca tcataattaa tcttggtagt ctcgaatgcc acaacactga    6480
ctagtctctt ggatcataag aaaaagccaa ggaacaaaag aagacaaaac acaatgagag    6540
tatccttgc atagcaatgt ctaagttcat aaaattcaaa caaaaacgca atcacacaca    6600
gtggacatca cttatccact agctgatcag gatcgccgcg tcaagaaaaa aaaactggac    6660
cccaaaagcc atgcacaaca acacgtactc acaaaggtgt caatcgagca gcccaaaaca    6720
ttcaccaact caacccatca tgagccctca catttgttgt ttctaaccca acctcaaact    6780
cgtattctct tccgccacct cattttgtt tatttcaaca cccgtcaaac tgcatgccac    6840
cccgtggcca aatgtccatg catgttaaca agacctatga ctataaatag ctgcaatcat    6900
ggcccaggtt ttcatcatca agaaccagtt caatatccta gtacaccgta ttaaagaatt    6960
taagatatac tgcggccgcg cgagaaactt tgtatgggca tggttatttc tcacttctca    7020
ccctccttta ctttcttatg ctaaatcctc cttccctat atctccaccc tcaacccctt    7080
tttctcatta taactttgg tgcctagatg gtgtgtgtgt gtgcgcgcga gagatctgag    7140
ctcaattttc ctctctcaag tcctggtcat gcttgaggg aaaagggttg aggaacttat    7200
gcatcttata tctctccacc tccaggattt taagccctag ttactcaacc cttttccctc    7260
agaatatggc aattcaggct tttaattgct ttcatttggt accatcactt gcaagatttc    7320
agagtacaag gtgaacacac acatcttcct cttcatcaat tctctagttt catccttatc    7380
ttttcattca cggtaactct cactacccct tttcatctta taagttatac cggggggtgtg    7440
atgttgatga gtgtaaatta aatatatgtg atctctttct ctggaaaaat tttcagtgtg    7500
atatacataa taatctctta atctagagat tttatggctt tgttatatat aagcggcgca    7560
agggcgaatt ctgcagatat ccatcacact tgggccgctt ctagctagct agggtttggg    7620
tagtgagtgt aataaagttg caaagttttt ggttaggtta cgttttgacc ttattattat    7680
agttcaaagg gaaacattaa ttaaggggga ttatgaaggt ggatgatgcc tgattggatt    7740
gaggatctta ctgggtgaat tgagctgctt agctatggat cccacagttc tacccatcaa    7800
taagtgcttt tgtggtagtc ttgtggcttc catatctggg gagcttcatt tgcctttata    7860
gtattaacct tcttccaatc cagcatcatc caccacccct ctcttctttt ctctcataat    7920
aatttaaatt tgttatagac tctaaactttt aaatgttttt tttgaagttt ttccgttttt    7980
ctcttttgcc atgatcccgt tcttgctgtg gagtaacctt gtccgaggta tgtgcatgat    8040
tagatccata cttaatttgt gtgcatcacg aaggtgaggt tgaaatgaac tttgcttttt    8100
tgaccttta ggaaagttct tttgttgcag taatcaattt taattagttt taattgacac    8160
tattactttt attgtcatct tgttagttt tattgttgaa ttgagtgcat atttcctagg    8220
aaattctctt acctaacatt ttttatacag atctatgctc ttggctcttg cccttactct    8280
tggccttgtg ttggttattt gtctacatat ttattgactg gtcgatgaga catgtcacaa    8340
ttcttgggct tatttgttgg tctaataaaa ggagtgctta ttgaaagatc aagacggaga    8400
ttcggtttta tataaataaa ctaaagatga catattagtg tgttgatgtc tcttcaggat    8460
aattttgtt tgaaataata tggtaatgtc ttgtctaaat ttgtgtacat aattcttact    8520
gattttgga ttgttggatt tttataaaca aatctgggc ccaagcggcc gcaagtgatga    8580
actaaaatgc atgtaggtgt aagagctcat ggagagcatg gaatattgta tccgaccatg    8640
taacagtata ataactgagc tccatctcac ttcttctatg aataaacaaa ggatgttatg    8700
atatattaac actctatcta tgcacccttat tgttctatga taaaatttcct cttattatta    8760
taaatcatct gaatcgtgac ggcttatgga atgcttcaaa tagtacaaaa acaaatgtgt    8820
actataagac tttctaaaca attctaacct tagcattgtg aacgagacat aagtgttaag    8880
aagacataac aattataatg gaagaagttt gtctccatt atattatta tattacccac    8940
ttatgtatta tattaggatg ttaaggagac ataacaatta taaagagaga gtttgtatc    9000
catttatata ttatatacta cccatttata tattatactt atccacttat ttaatgtctt    9060
tataaggttt gatccatgat atttctaata ttttagttga tatgtatatg aaaaggtact    9120
atttgaactc tcttactctg tataaaggtt ggatcatcct taaagtggtt ctatttaatt    9180
ttattgcttc ttacagataa aaaaaaatt atgagttggt ttgataaaat attgaaggat    9240
ttaaaataat aataaataac ataataata tgtatataaa tttattataa taacattt    9300
atctataaaa aagtaaatat tgtcataaat ctatacaatc gtttagcctt gctgaacga    9360
atctcaatca tttaaacgag agtaaacata tttgactttt tggttattta acaaattatt    9420
atttaacact atatgaaatt ttttttttta tcagcaaaga ataaaattaa attaagaagg    9480
acaatggtgt cccaatcctt atacaaccaa cttccacaag aaagtcaagt cagagacaac    9540
aaaaaaacaa gcaaaggaaa ttttttaatt tgagttgtct tgtttgctgc ataatttatg    9600
cagtaaaaca ctacacataa cccttttagc agtagagcaa tggttgaccg tgtgcttagc    9660
ttcttttatt ttattttttt atcagcaaag aataaataaa ataaatgag cacttcagg    9720
gatgtttcaa cgtacgtctt tccacaatac ataactatta attaatctta aataaataaa    9780
ggataaaata ttttttttc ttcataaagt taaaatatgt tattttttgt ttagatgtat    9840
attcgaataa atctaaatat atgataatga tattttttata tgattaaaca tataatcaat    9900
attaaatatg atatttttt ataggttg tacacataat tttataaagga taaaaaatat    9960
gataaaaata aattttaaat attttttat ttacgagaaa aaaaaatatt ttagccataa    10020
ataaatgacc agcatatttt acaaccttag taattcataa attcctatat gtatatttga    10080
aattaaaaac agataatcgt taaggaaagg aatcctacgt catctcttgc catttgtttt    10140
tcatgcaaac agaaagggac gaaaaaccac ctcaccatga atcactcttc acacccatttt    10200
tactagcaaa caagtctcaa caactgaagc cagctctctt tccgtttctt tttacaacac    10260
tttctttgaa atagtagtat tttttttcac atgatttatt aacgtgccaa aagatgctta    10320
ttgaatagag tgcacatttg taatgtacta ctaattagaa catgaaaaag cattgttcta    10380
acacgataat cctgtgaagg cgttaactcc aaagatccaa tttcactata taaattgtga    10440
cgaaagcaaa atgaattcac atagctgaga gagaaaggaa aggttaacta agaagcaata    10500
cttcagcggc cgcttctagc tagctagggt ttgggtagtg agtgtaataa agttgcaaag    10560
ttttggtta ggttacgttt tgaccttatt attatagttc aaaggaaac attaattaaa    10620
ggggattatg aagtgggctc tcttgattct tggatgagga tcttactggg tgaattgagc    10680
tgcttagcta tggatccac agtctaccc atcaataagt gcttttgtgg tagtcttgtg    10740
gcttccatat ctggggagct tcatttgcct ttatagtact aaccttctcc aagaacaaag    10800
agagcccaca cccttctctt cttttctctc ataataattt aaatttgtta tagactctaa    10860
actttaaatg tttttttga gtttttccg tttttctctt tgccatgat cccgttcttg    10920
ctgtggagta accttgtccg aggtatgtgc atgattagat ccatacttaa tttgtgtgca    10980
tcacgaaggt gaggttgaaa tgaacttgc tttttgacc tttttaggaaa gttcttttgt    11040
tgcagtaatc aattttaatt agttttaatt gacactatta cttttattgt catctttgtt    11100
```

```
agttttattg ttgaattgag tgcatatttc ctaggaaatt ctcttaccta acatttttta    11160
tacagatcta tgctcttggc tcttgccctt actcttggcc ttgtgttggt tatttgtcta    11220
catatttatt gactggtcga tgagacatgt cacaattctt gggcttattt gttggtctaa    11280
taaaaggagt gcttattgaa agatcaagac ggagattcgg ttttatataa ataaactaaa    11340
gatgacatat tagtgtgttg atgtctcttc aggataattt ttgtttgaaa taatatggta    11400
atgtcttgtc taaatttgtg tacataattc ttactgattt tttggattgt tggatttta     11460
taaacaaatc tgcggccgca tgagccgtaa aggttcaata caacgagtgc ttgttttctt    11520
agggacaagc attgtactta tgtatgattc tgtgtaacca tgagtcttcc acgttgtact    11580
aatgtgaagg gcaaaaataa aacacagaac aagttcgttt ttctcaaata atgtgaaggt    11640
agaaaatgga accatgcctc ctctcttgca tgtgatttaa aatattagca gatggtacgt    11700
cgagtcgacc tgcaggtcga ctcgacgtac gtcctcgaag agaagggtta ataacacatt    11760
ttttaacatt tttaacacaa attttagtta tttaaaaatt tattaaaaaa tttaaaataa    11820
gaagaggaac tctttaaata aatctaactt acaaaattta tgatttttaa taagttttca    11880
ccaataaaaa atgtcataaa aatatgttaa aaagtatatt atcaatattc tctttatgat    11940
aaataaaaag aaaaaaaaaa taaagttaa gtgaaaatga gattgaagtg actttaggtg     12000
tgtataaata tatcaacccc gccaacaatt tatttaatcc aaatatattg aagtatatta    12060
ttccatagcc tttatttatt tatatattta ttatataaaa gctttatttg ttctaggttg    12120
ttcatgaaat attttttttgg ttttatctcc gttgtaagaa aatcatgtgc tttgtgtcgc   12180
cactcactat tgcagctttt tcatgcattg gtcagattga cggttgattg tattttttgtt  12240
ttttatggtt ttgtgttatg acttaagtct tcatctcttt atctcttcat caggtttgat   12300
ggttacctaa tatggtccat gggtacatgc atggttaaat taggtggcca actttgttgt   12360
gaacgataga atttttttta tattaagtaa actatttta tattatgaaa taataataa     12420
aaaaatattt tatcattatt aacaaaatca tattagttaa tttgttaact ctataataaa   12480
agaaatactg taacattcac attacatggt aacatctttc cacccttttca tttgttttttt 12540
gtttgatgac ttttttttctt gtttaaattt atttcccttc tttaaattt ggaatacatt   12600
atcatcatat ataaactaaa atactaaaaa caggattaca caaatgataa ataataacac   12660
aaatatttat aaatctagct gcaatatatt taaactagct atatcgatat tgtaaaataa   12720
aactagctgc attgatactg ataaaaaaat atcatgtgct ttctggactg atgatgcagt   12780
atactttga cattgccttt attttatttt tcagaaaagc tttcttagtt ctgggttctt     12840
cattatttgt ttcccatctc cattgtgaat tgaatcattt gcttcgtgtc acaaatacaa   12900
tttagntagg tacatgcatt ggtcagattc acggttatt atgtcatgac ttaagttcat    12960
ggtagtacat tacctgccac gcatgcatta tattggttag atttgatagg caaatttggt   13020
tgtcaacaat ataaatataa ataatgtttt tatattcga ataacagtg atcaaaacaa      13080
acagttttat cttttattaac aagattttgt ttttgtttg tgacgtttt taatgtttac    13140
gctttccccc ttcttttgaa tttagaacac tttatcatca taaaatcaaa tactaaaaaa   13200
attacatatt tcataaataa taacacaaat attttaaaaa aatctgaaat aataatgaac   13260
aatattcat attatcacga aaattcatta ataaaaatat tatataaata aaatgtaata    13320
gtagttatat gtaggaaaaa agtactgcac gcataatata tacaaaaaga ttaaaataaa   13380
ctattataaa taataacact aaattaatgg tgaatcatat caaaataatg aaaaagtaaa   13440
taaaatttgt aattaacttc tatatgtatt acacacacaa ataataaata atagtaaaaa    13500
aaattatgat aaatatttac catctcataa gatatttaaa aataatgataa aaatatagat  13560
tatttttttat gcaactagct agccaaaaag agaacacggg tatatataaa aagagtacct   13620
ttaaattcca ctgtacttcc tttattcctg acgttttat atcaagtgga catcgtgaa     13680
gattttaatt atcagtctaa atatttcatt agcacttaat acttttctgt tttattccta   13740
tcctataagt agtcccgatt ctccaacat tgcttattca cacaactaac taagaaagtc    13800
ttccatagcc ccccaagcgg ccgctagtcg actaagtcat caactattcc aagctacgta   13860
tttgggagtt tgtggagtac agcaagatga tacctaga cggtgatatc caagtttttg     13920
acaacattga ccacttgttt gacttgcctg ataactactt ctatgcggtg atggactgtt   13980
tctgtgagcc aacttgggc cacactaaac aatatcgat cggttactgc cagcagtgcc     14040
cccataaggt tcagtggccc actcactttg ggccaaaacc tcctctctat ttcaatgctg   14100
gcatgtttgt gtatgagccc aatttggcta cttaccgtga cctccttcaa acagtccaag   14160
tcacccagcc cacttccttt gctgaacagg attttttgaa catgtacttc aaggacaaat   14220
ataggccaat tcctaatgtc tacaatcttg tgctggccat gctgtggcgt caccctgaga   14280
acgttgagct tgacaaagtt aaagtggttc actactgtgc tgctgggtct aagccttgga   14340
ggtacactgg gaagtgactc gaggtcatca attactccaa gctacgtatt tgggagttcg   14400
tggagtacaa gaagacgata tacctagacg gtgacatcca agtatttgga aacatagacc   14460
acttgtttga tctgcctgat aattatttct atgcggtgat ggattgttc tgcgagaaga    14520
cttggagcca caccctcag ttccagattg gtactgccca acagtgccct gataaggttc    14580
aatggccctc tcactttggt tccaaacctc ctctatattt caatgctgac atgttttgtt   14640
atgagcctaa tctcgacacc taccgtgatc ttctccaaac tgtccaactc accaagccca   14700
cttcttttgc tgagcaggac tttctcaaca tgtacttcaa ggacaagtac aagcaaatac   14760
cgaacatgta caacctgtg ctggccatgt gtggcgtca ccctgaaaat gttgaacttg     14820
ataaagttca agtggttcat tactgtgctg ctgggtctaa gccttggagg ttcactggga   14880
agtaactgca ggtcatcaac tactccaagc tccgtatatg gagtttgtg gagtacagca   14940
agatgatata cttggacgga gacattgagg tatatgagaa catagaccac ctatttgacc   15000
tacctgatgg taactttac gctgtgatgg attgtttctg cgagaagaca tggagtcaca   15060
cccctcagta caaggtgggt tactgccagc aatgcccgga gaaggtgcgg tggcccaccg   15120
aattgggtca gcccccttct cttacttca acgctggcat gttcgtgttc gaaccaaaca   15180
tcgccaccta tcatgaccta ttgaaaacgg tgcaagtcac cactcccacc tcgttcgctg   15240
aacaagattt cttgaacatg tacttcaagg acatttacaa gccaatccct ttaaattaca   15300
atcttgtcct cgccatgctg tggcgccacc cggaaaacgt taaattagac caagtcaagg   15360
ttgttcacta ttgcgcagcg gggtccaagc catgagata tacggggaag tagcctaggc   15420
gtacgcaggt aagtttctgc ttctaccttt gatatatata taataattat cattaattag   15480
tagtaatata atattttcaaa tattttttc aaaataaata atgtagtat atagcaattg    15540
cttttctgta gttataaagt gtgtatattt taatttataa cttttctaat atatgaccaa   15600
aacatggtga tgtgcaggtc ctaggctact tccccgtata tctccatggc ttggaccccg   15660
ctgcgcaata gtgaacaacc ttgacttggt ctaatttaac gttttccggg tggcgccaca   15720
gcatggcgag acaagattg taatttaaag ggattggctt gtaaatgtcc ttgaagtaca    15780
tgttcaagaa atcttgttca gcgaacgagg tgggagtggt gacttgcacc gttttcaata   15840
```

```
ggtcatgata ggtggcgatg ttgggttcga acacgaacat gccagcgttg aagtaaagag    15900
aaggggctg  acccaattcg gtgggccacc gcaccttctc cgggcattgc tggcagtaac    15960
ccaccttgta ctgaggggtg tgactccatg tcttctcgca gaaacaatcc atcacagcgt    16020
aaaagttacc atcaggtagg tcaaataggt ggtctatgtt ctcatatacc tcaatgtctc    16080
cgtccaagta tatcatcttg ctgtactcca caaactccca tatacgagc  ttggagtagt    16140
tgatgacctg cagttacttc ccagtgaacc tccaaggctt agaccagca  gcacagtaat    16200
gaaccacttg aactttatca agttcaacat tttcagggtg acgccacaac atggccagca    16260
caaggttgta catgttcggt attggcttgt acttgtcctt gaagtacatg ttgagaaagt    16320
cctgctcagc aaaagaagtg ggcttggtga gttggacagt ttggagaaga tcacggtagg    16380
tgtcgagatt aggctcataa acaaacatgc cagcattgaa atatagagga ggtttggaac    16440
caaagtgaga gggccattga accttatcag ggcactgttg gcagtaccca atctggaact    16500
gaggggtgtg gctccaagtc ttctcgcaga aacaatccat caccgcatag aaataattat    16560
caggcagatc aaaagtgg  tctatgtttc caaatacttg gatgtcaccg tctaggtata    16620
tcgtcttctt gtactccacg aactcccaaa tacgtagctt ggagtaattg atgacctcga    16680
gtcacttccc agtgtacctc caaggcttag acccagcagc acagtagtga accactttaa    16740
ctttgtcaag ctcaacgttc tcagggtgac gccacagcat ggccagcaca agattgtaga    16800
cattaggaat tggcctatat ttgtccttga agtacatgtt caaaaaatcc tgttcagcaa    16860
aggaagtggg ctgggtgact tggactgttt gaaggaggtc acggtaagta gccaaattgg    16920
gctcatacac aaacatgcca gcattgaaat agagaggagg tttgggccca agtgagtgg    16980
gccactgaac cttatggggg cactgctggc agtaaccgat ctgatattgt ttagtgtggc    17040
cccaagttgg ctcacagaaa cagtccatca ccgcatagaa gtagttatca ggcaagtcaa    17100
acaagtggtc aatgttgtca aaaacttgga tatcaccgtc taggtatatc atcttgctgt    17160
actccacaaa ctcccaaata cgtagctgg  aatagttgat gacttagtcg actagcggcc    17220
gcgacacaag tgtgagagta ctaaataaat gctttggttg tacgaaatca ttacactaaa    17280
taaaataatc aaagcttata tatgccttcc gctaaggccg aatgcaaaga aattggttct    17340
ttctcgttat cttttgccac tttttactagt acgtattaat tactacttaa tcatctttct    17400
ttacggctca ttatatccgg tctaggccaa ggccgcgaag ttaaaagcaa tgttgtcact    17460
tgtacgtact aacacatgat gtgatagttt atgctagcta gctataacat aagctgtctc    17520
tgagtgtgtt gtatattaat aaagatcatc actggtgaat ggtgatcgtg tacgtaccct    17580
acttagtagg caatggaagc acttagagtg tgctttgtgc atggccttgc ctctgttttg    17640
agacttttgt aatgttttcg agtttaaatc tttgcctttg cgtacgtggg cggatcccct    17700
gcaggagatc caagcttgg                                                17719
```

SEQ ID NO: 2         moltype = DNA  length = 17679
FEATURE              Location/Qualifiers
misc_feature       1..17679
                     note = synthesized DNA of PHP50573
source              1..17679
                     mol_type = other DNA
                     organism = synthetic construct
SEQUENCE: 2

```
ggagatccaa gcttggcgcg ccggaattaa ttaggtaatt tcacgcgccg gatccttaat     60
taagtctaga gtcgactgtt taattctagt ggccggccca gctgatgatc ccggtgaagt    120
tcctattccg aagttcctat tctccagaaa gtataggaac ttcactagag cttgcggccg    180
ctcgagttct atagtgtcac ctaaatcgta tgtgtatgat acataaggtt atgtattaat    240
tgtagccgcg ttctaacgac aatatgtcca tatggtgcac tctcagtaca atctgctctg    300
atgccgcata gttaagccag ccccgacacc cgccaacacc gcctgacgcg ccctgacggg    360
cttgtctgct cccggcatcc gcttacagac aagctgtgac cgtctccggg agctgcatgt    420
gtcagaggtt ttcaccgtca tcaccgaaac gcgcgagacg aaagggcctc gtgatacgcc    480
tatttttata ggttaatgtc atgaccaaaa tcccttaacg tgagttttcg ttccactgag    540
cgtcagaccc cgtagaaaag atcaaaggat cttcttgaga tccttttttt ctgcgcgtaa    600
tctgctgctt gcaaacaaaa aaaccaccgc taccagcggt ggtttgtttg ccggatcaag    660
agctaccaac tctttttccg aaggtaactg gcttcagcag agcgcagata ccaaatactg    720
tccttctagt gtagccgtag ttaggccacc acttcaagaa ctctgtagca ccgcctacat    780
acctcgctct gctaatcctg ttaccagtgg ctgctgccag tggcgataag tcgtgtctta    840
ccgggttgga ctcaagacga tagttaccgg ataaggcgca gcggtcgggc tgaacggggg    900
gttcgtgcac acagcccagc ttggagcgaa cgacctacac cgaactgaga tacctacagc    960
gtgagcattg agaaagcgcc acgcttcccg aaggagaaa ggcggacagg tatccggtaa   1020
gcggcagggt cggaacagga gagcgcacga ggagcttcc aggggggaaac gcctggtatc   1080
tttatagtcc tgtcgggttt cgccacctct gacttgagcg tcgatttttg tgatgctcgt   1140
caggggggcg gagcctatgg aaaaacgcca gcaacgcggc ctttttacgg ttcctggcct   1200
tttgctggcc ttttgctcac atgttctttc ctgcgttatc ccctgattct gtggataacc   1260
gtattaccgc ctttgagtga gctgataccg ctcgccgcag ccgaacgacc gagcgcagcg   1320
agtcagtgag cgaggaagcg gaagagcgcc caatacgcaa accgcctctc cccgcgcgtt   1380
ggccgattca ttaatgcagg ttgatcagat ctcgatcccg cgaaattaat acgactcact   1440
atagggagac cacaacggtt tccctctaga aataattttg tttaacttta agaaggagat   1500
atacccatga aaagcctga  actcaccgcg acgtctgtcg agaagtttct gatcgaaaag   1560
ttcgacagcg tctccgacct gatgcagctc tcggagggcg aagaatctcg tgcttttcagc   1620
ttcgatgtag gagggcgtgg atatgtcctg cgggtaaata gctgcgccga tggtttctac   1680
aaagatcgtt atgtttatcg gcactttgca tcggccgcgc tcccgattcc ggaagtgctt   1740
gacattgggg aattcagcga gagcctgacc tattgcatct cccgccgtgc acagggtgtc   1800
acgttgcaag acctgcctga aaccgaactg cccgctgttc tgcagccggt cgcggaggct   1860
atggatgcga tcgctgcggc cgatcttagc cagacgagcg gttcggccc  attcggaccg   1920
caaggaatcg gtcaatacac tacatggcgt gatttcatat gcgcgattgc tgatccccat   1980
gtgtatcact ggcaaactgt gatggacgac accgtcagtg cgtccgtcgc gcaggctctc   2040
gatgagctga tgctttgggc cgaggactgc cccgaagtcc ggcaccgtg  gcacgcgcat   2100
tcggctccaa caatgtcct  gacggacaat ggccgcataa cagcggtcat tgactggagc   2160
gaggcgatgt tcgggattcc caatacgag  gtcgccaaca tcttcttctg gaggccgtgg   2220
ttggcttgta tggagcagca gacgcgctac ttcgagcgga ggcatccgga gcttgcagga   2280
```

```
tcgccgcggc tccgggcgta tatgctccgc attggtcttg accaactcta tcagagcttg   2340
gttgacggca atttcgatga tgcagcttgg gcgcagggtc gatgcgacgc aatcgtccga   2400
tccggagccg ggactgtcgg gcgtacacaa atcgcccgca gaagcgcggc cgtctggacc   2460
gatggctgtg tagaagtact cgccgatagt ggaaaccgac gccccagcac tcgtccgagg   2520
gcaaaggaat agtgaggtac agcttggatc gatccggctg ctaacaaagc ccgaaaggaa   2580
gctgagttgg ctgctgccac cgctgagcaa taactagcat aaccccttgg ggcctctaaa   2640
cgggtcttga ggggtttttt gctgaaagga ggaactatat ccggatgatc gtcgaggcct   2700
cacgtgttaa caagcttgca tgccggttta acagtcgag gtcgacggta tcgataagct   2760
tgttaacaga agttcctatt ccgaagttcc tattctctag aaagtatagg aacttccacc   2820
acacaacaca atggcggcca ccgcttccag aaccacccga ttctcttctt cctcttcaca   2880
ccccaccttc cccaaacgca ttactagatc caccctccct ctctctcatc aaaccctcac   2940
caaacccaac cacgctctca aaatcaaatg ttccatctcc aaaccccca cggcggcgcc   3000
cttcaccaag gaagcgccga ccacggagcc cttcgtgtca cggttcgcct ccggcgaacc   3060
tcgcaagggc gcggacatcc ttgtggaggc gctggagagg cagggcgtga cgacggtcgt   3120
cgcgtacccc ggcggtgcgt cgatggagat ccaccaggcg ctcacgcgct ccgccgccat   3180
ccgcaacgtg ctcccgcgcc acgagcaggg cggcgtcttc gccgccgaag gctacgcgcg   3240
ttcctccggc ctccccggcg tctgcattgc cacctccggc cccggcgcca ccaacctcgt   3300
gagcggcctc gccgacgctt taatggacag cgtcccagtc gtcgccatca ccggccaggt   3360
cgcccgccgg atgatcggca ccgacgcctt ccaagaaacc ccgatcgtgg aggtgagcag   3420
atccatcacg aagcacaact acctcatcct cgacgtcgac gacatccccc gcgtcgtcgc   3480
cgaggctttc ttcgtcgcca cctccggccg ccccggtccg gtcctcatcg acattcccaa   3540
agacgttcag cagcaactcg ccgtgcctaa ttgggacgag cccgttaacc tcccggtta   3600
cctcgccagg ctgcccaggc ccccgccga ggcccaattg gaacacattg tcagactcat   3660
catggaggcc caaaagcccg ttctctacgt cggcggtggc agtttgaatt ccagtgctga   3720
attgaggcgc tttgttgaac tcactggtat tcccgttgct agcactttaa tgggtcttgg   3780
aacttttcct attggtgatg aatattccct tcagatgctg ggtatgcatg gtactgttta   3840
tgctaactat gctgttgaca atagtgattt gttgcttgcc tttggggtaa ggtttgatga   3900
ccgtgttact gggaagcttg aggcttttgc tagtagggct aagattgttc acattgatat   3960
tgattctgcc gagattggga agaacaagca ggcgcacgtg tcggtttgcg cggatttgaa   4020
gttggccttg aagggaatta atatgatttt ggaggagaaa ggagtgggag gtaagtttga   4080
tcttggaggt tggagagaag agattaatgt gcagaaacac aagtttccat tgggttacaa   4140
gacattccag gacgcgattt ctccgcagca tgctatcgag gttcttgatg agttgactaa   4200
tggagatgct attgttagta ctggggttgg gcagcatcaa atgtgggctg cgcagttta   4260
caagtacaag agaccgaggc agtggttgac ctcaggggg cttggagcca tgggttttgg   4320
attgcctgcg gctattggtg ctgctgttgc taaccctggg gctgttgtgg ttgacattga   4380
tggggatggt agtttcatca tgaatgttca ggagttggcc actataagag tggagaatct   4440
cccagttaag atattgttgt tgaacaatca gcatttgggt atggtggttc agtgggagga   4500
taggttctac aagtccaata gagctcacac ctatcttgga gatccgtcta gcgagagcga   4560
gatattccca aacatgctca agtttgctga tgcttgtgga ataccggcag cgcgagtgac   4620
gaagaaggaa gagcttagag cggcaattca gagaatgttg gacacccctg cccctacct   4680
tcttgatgtc attgtgcccc atcaggagca tgtgttgccg atgattccca gtaatggatc   4740
cttcaaggat gtgataactg agggtgatgg tagaacgagg tactgactag ctagtcagtt   4800
aacctagact tgtccatctt ctggattggc caacttaatt aatgtatgaa ataaaaggat   4860
gcacacatag tgacatgcta atcactataa tgtgggcatc aaagttgtgt gttatgtgta   4920
attactagtt atctgaataa aagagaaaga gatcatccat atttcttatc ctaaatgaat   4980
gtcacgtgtc tttataattc tttgatgaac cagatgcatt tcattaacca aatccatata   5040
catataaata ttaatcatat ataattaata tcaattgggt tagcaaaaca aatctagtct   5100
aggtgtgttt tgccccaag cttatccgata ccgtcggcgc ggggtacgtt agctgattaa   5160
gtcagcatgc gcggccggcg tatgaactaa aatgcatgta ggtgtaagag ctcatggaga   5220
gcatggaata ttgtatccga ccatgtaaca gtataataac tgagctccat ctcacttctt   5280
ctatgaataa acaaaggatg ttatgtatata ttaacactct atctatgcac cttattgttc   5340
tatgataaat ttcctcttat tattataaat catctgaatc gtgacggctt atggaatgct   5400
tcaaatagta caaaaacaaa tgtgtactat aagactttct aaacaattct aaccttagca   5460
ttgtgaacga gacataagtg ttaagaagac ataacaatta taatgaaga agtttgtctc   5520
catttatata ttatatatta cccacttatg tattatatta ggatgttaag gagacataac   5580
aattataaag agagaagttt gtatccattt atatatatta tactacccat ttatatatta   5640
tacttatcca cttatttaat gtctttataa ggtttgatcc atgatatttc taatattta   5700
gttgatatgt atatgaaaag gtactatttg aactctctta ctctgtataa aggttggatc   5760
atccttaaag tgggtctatt taattttatt gcttcttaca gataaaaaaa aaattatgag   5820
ttggtttgat aaaatattga aggatttaaa ataataataa ataacatata atatatgtat   5880
ataaattat tataatataa catttatcta taaaaagta aatattgtca taatctata     5940
caatcgttta gccttgctgg aacgaatctc aattatttaa acgagagtaa acatatttga   6000
cttttggtt atttaacaaa ttattattta acactatatg aaattttttt tttatcagc    6060
aaagaataaa attaaattaa gaaggacaat ggtgtcccaa tccttataca accaacttcc   6120
acaagaaagt caagtcagag acaacaaaaa aacaagcaaa ggaattttt taatttgagt   6180
tgtcttgttt gctgcataat ttatgcagta aaacactaca cataaccctt ttagcagtag   6240
agcaatggtt gaccgtgtgc ttagcttctt ttattttatt ttttatcag caaagaataa    6300
ataaaataaa atgagacact tcagggatgt ttcaacaggt acccatcact taagtggcgc   6360
gccgtcgacg gatccgtacg ttcatttgcc gcttattaat taatttggta   6420
acagtccgta ctaatcagtt acttatcctt ccccccatcat aattaatctt ggtagtctcg   6480
aatgccacaa cactgactag tctcttggat cataagaaaa agccaaggaa caaagaaga    6540
caaaacacaa tgagagtatc ctttgcatag caatgtctaa gttcataaaa ttcaaacaaa   6600
aacgcaatca cacacagtgg acatcactta tccactagct gatcaggatc gccgcgtcaa   6660
gaaaaaaaaa ctggacccca aaagccatgc acaacaacac gtactcacaa aggtgtcaat   6720
cgagcagccc aaaacattca ccaactcaac ccatcatgag ccctcacatt tgttgtttct   6780
aacccaacct caaactcgta ttctcttccg ccacctcatt tttgtttatt tcaacacccg   6840
tcaaactgca tgccacccg tggccaaatg tccatgcatg ttaacaagac ctatgactat    6900
aaatagctgc aatctcggcc caggttttca tcatcaagaa ccagttcaat atcctagtac   6960
accgtattaa agaatttaag atatactgcg gccgcatgac tatcgactca caatactaca   7020
```

```
agtcgcgaga caaaaacgac acggcaccca aaatcgcggg aatccgatat gccccgctat   7080
cgacaccatt actcaaccga tgtgagacct tctctctggt ctggcacatt ttcagcattc   7140
ccactttcct cacaatttc atgctatgct gcgcaattcc actgctctgg ccatttgtga    7200
ttgcgtatgt agtgtacgct gttaaagacg actcccgtc caacgagga gtggtcaagc     7260
gatactcgcc tatttcaaga aacttcttca tctggaagct cttttggccg tacttcccca   7320
taactctgca caagacggtg gatctggagc ccacgcacac atactaccct ctggacgtcc   7380
aggagtatca cctgattgct gagagatact ggccgcagaa caagtacctc cgagcaatca   7440
tctccaccat cgagtacttt ctgcccgcct tcatgaaacg gtctctttct atcaacgagc   7500
aggagcagcc tgccgagcga gatcctctcc tgtctcccgt ttctcccagc tctccgggtt   7560
ctcaacctga caagtggatt aaccacgaca gcagatatag ccgtggagaa tcatctggct   7620
ccaacggcca cgcctcgggc tccgaactta acggcaacgg caacaatggc accactaacc   7680
gacgacctt tgtcgtccgcc tctgctggct ccactgcatc tgattccacg cttcttaacg    7740
ggtccctcaa ctcctacgcc aaccagatca ttggcgaaca cgacccacag ctgtcgccca    7800
caaaactcaa gcccactggc agaaaataca tcttcggcta ccacccccac ggcattatcg    7860
gcatgggagc ctttggtgga attgccaccg agggagctgg atggtccaag ctctttccgg    7920
gcatccctgt ttctcttatg actctcacca acaacttccg agtgcctctc tacagagagt    7980
acctcatgag tctgggagtc gcttctgtct ccaagaagtc ctgcaaggcc ctcctcaagc    8040
gaaaccagtc tatctgcatt gtcgttggtg gagcacagga aagtcttctg gccagacccg    8100
gtgtcatgga cctggtgcta ctcaagcgaa agggtttgt tcgacttggt atggaggtcg     8160
gaaatgtcgc ccttgttccc atcatggcct ttggtgagaa cgacctctat gaccaggtta    8220
gcaacgacaa gtcgtccaag ctgtaccgat tccagcagtt tgtcaagaac ttccttggat    8280
tcacccttcc tttgatgcat gcccgaggcg tcttcaacta cgatgtcggt cttgtcccct    8340
acaggcgacc cgtcaacatt gtggttggt ccccccattga cttgccttat ctcccacacc    8400
ccaccgacga agaagtgtcc gaataccacg accgatacat cgccgagctg cagcgaatct    8460
acaacgagca caaggatgaa tatttcatcg attggaccga ggagggcaaa ggagcccag    8520
agttccgaat gattgagtaa gcggccgcaa gtatgaacta aaatgcatgt aggtgtaaga    8580
gctcatggag agcatggaat attgtatccg accatgtaac agtataataa ctgagctcca    8640
tctcacttct tctatgaata aacaaaggat gttatgatat attaacactc tatctatgca    8700
ccttattgtt ctatgataaa tttcctctta ttattataa tcatctgaat cgtgacggct     8760
tatggaatgc ttcaaatagt acaaaaacaa atgtgtacta taagacttc taaacaattc     8820
taaccttagc attgtgaacg agacataagt gttaagaaga cataacaatt ataatgaag     8880
aagtttgtct ccatttatat attatatatt acccacttat gtattatatt aggatgttaa    8940
ggagacataa caattataaa gagagaagtt tgtatccatt tatatattat atactaccca    9000
tttatatatt atacttatcc acttatttaa tgtctttata aggttgatc catgatattt     9060
ctaatatttt agttgatatg tatatgaaaa ggtactattt gaactctctt actctgtata    9120
aaggttggat catccttaaa gtgggtctat ttaattttat tgcttcttac agataaaaaa    9180
aaaattatga gttggtttga taaaatattg aaggatttaa ataataata aataacatat    9240
aatatatgta tataaattta ttataatata acatttatct ataaaaaagt aaatattgtc    9300
ataaatctat acaatcgttt agccttgctg gaacagatct caattattta aacgagagta    9360
aacatatttg acttttggt tatttaacaa attattattt aacactatat gaaattttt     9420
tttttatcag caaagaataa aattaaatta agaaggacaa tggtgtccca atccttatac    9480
aaccaacttc cacaagaaag tcaagtcaga gacaacaaaa aaacaagcaa aggaaatttt    9540
ttaatttgag ttgtcttgtt tgctgcataa ttatgcagt aaaacactac acataaccct     9600
tttagcagta gagcaatggt tgaccgtgtg cttagcttct tttattttat tttttttatca    9660
gcaaagaata aataaaataa aatgagacac ttcagggatg tttcaacgta cgtctttcca    9720
caatacataa ctattaatta atcttaaata aataaaggat aaaatatttt ttttttcttca    9780
taaagttaaa atatgttatt ttttgtttag atgtatatca gaataaatct aaatatatga    9840
taatgatttt ttatattgat taaacatata atcaatatta aatatgatat tttttatat    9900
aggttgtaca cataattta taaggataaa aaatatgata aaaatataatt ttaaatattt    9960
ttatatttac gagaaaaaaa aatatttag ccataaataa atgaccagca tattttacaa    10020
ccttagtaat tcataaattc ctatatgtat atttgaaatt aaaaacagat aatcgttaag   10080
ggaaggaatc ctacgtcatc tcttgccatt tgtttttcat gcaaacgaaa agggacgaaa   10140
aaccacctca ccatgaatca ctcttcacac catttttact agcaaacaag tctcaacaac   10200
tgaagccagc tctctttccg tttctttta caacactttc tttgaaatag tagtattttt    10260
tttcacatga tttattaacg tgccaaaaga tgcttattga atagagtga catttgtaat     10320
gtactactaa ttagaacatg aaaaagcatt gttctaacac gataatcctg tgaaggcgtt   10380
aactccaaag atccaatttc actatataaa ttgtgacgaa agcaaatga attcacatag    10440
ctgagagaga aaggaaaggt taactaagaa gcaatacttc agcggccgct tctagctagc   10500
taggggttgg gtagtgagtg taataaagtt gcaaagtttt tggttaggtt acgttttgac   10560
cttattatta tagttcaaag ggaaacatta attaaagggg attatgaagt gggctctctt    10620
gattcttgga tgaggatctt actgggtgaa ttgagctgct tagctatgga tcccacagtt    10680
ctacccatca ataagtgctt ttgtggtagt cttgtggctt ccatatctgg ggagcttcat    10740
ttgcctttat agtattaacc ttctccaaga acaaagagag cccacaccct tctcttcttt     10800
tctctcataa taatttaaat ttgttataga ctctaaactt taatgttttt ttttgaagtt    10860
tttccgtttt tctcttttgc catgatcccg ttcttgctgt ggagtaacct tgtccgaggt    10920
atgtgcatga ttagatccat acttaatttg tgtgcatcac gaaggtgagg ttgaaatgaa    10980
ctttgctttt ttgaccttttt aggaaagttc tttttgttgca gtaatcaatt ttaattagtt   11040
ttaattgaca ctattacttt tattgtcatc tttgttagtt ttattgttga attgagtgta     11100
tattcctag gaaattctct tacctaacat tttttataca gatctatgct cttgctctt      11160
gcccttactc ttggccttgt gttggttatt tgtctacata tttattgact ggtcgatgag     11220
acatgtcaca attcttgggc ttatttgttg gtctaataaa aggagtgctt attgaaagat    11280
caagacggag attcggtttt atataaataa actaaagatg acatattagt gtgttgatgt    11340
ctcttcagga taattttgt tgaaataat atggtaatgt cttgtctaaa tttgtgtaca     11400
taattcttac tgtattttg gattgttgga ttttataaa caatctgcg gccgcatgag       11460
ccgtaaaggt tcaatacaac gagtgcttgt tttcttaggg acaagcattg tacttatgta     11520
tgattctgtg taaccatgag tcttccacgt tgtactaatg tgaagggcaa aaataaaaca    11580
cagaacaagt tcgtttttct caaataatgt gaaggtagaa aatggaacca tgcctcctct    11640
cttgcatgtg atttaaaata ttagcagatg gtacgtcgag tcgacctgca ggtcgactcg    11700
acgtacgtcc tcgaagagaa gggttaataa cacatttttt aacattttta acacaaattt    11760
```

```
tagttattta aaaatttatt aaaaaattta aaataagaag aggaactctt taaataaatc    11820
taacttacaa aatttatgat ttttaataag ttttcaccaa taaaaaatgt cataaaaata    11880
tgttaaaaag tatattatca atattctctt tatgataaat aaaaagaaaa aaaaaataaa    11940
agttaagtga aaatgagatt gaagtgactt taggtgtgta taaatatatc aaccccgcca    12000
acaatttatt taatccaaat atattgaagt atattattcc atagcctttta tttatttata    12060
tatttattat ataaaagctt tatttgttcc aggttgttca tgaaatattt ttttggtttt    12120
atctccgttg taagaaaatc atgtgctttg tgtcgccact cactattgca gcttttcat     12180
gcattggtca gattgacggt tgattgtatt tttgttttt atggttttgt gttatgactt     12240
aagtcttcat ctctttatct cttcatcagg tttgatggtt acctaatatg gtccatgggt    12300
acatgcatgg ttaaattagg tggccaactt tgttgtgaac gatagaattt tttttatatt    12360
aagtaaaacta ttttttatatt atgaaataat aataaaaaaa atatttttatc attattaaca   12420
aaatcatatt agttaatttg ttaactctat aataaaagaa atactgtaac attcacatta    12480
catggtaaca tctttccacc cttttcatttg tttttttgttt gatgacttttt tttcttgttt   12540
aaatttattt cccttctttt aaatttggaa tacattatca tcatatataa actaaaatac    12600
taaaaacagg attacacaaa tgataaataa taacacaaat atttataaat ctagctgcaa    12660
tatatttaaa ctagctatat cgatattgta aaataaaact agctgcattg atactgataa    12720
aaaaaatatca tgtgctttct ggactgatga tgcagtatac ttttgacatt gcctttattt   12780
tattttttcag aaaagctttc ttagttctgg gttcttcatt atttgttttcc catctccatt  12840
gtgaattgaa tcatttgctt cgtgtcacaa atacaattta gntaggtaca tgcattggtc    12900
agattcacgg tttattatgt catgacttaa gttcatggta gtacattacc tgccacgcat    12960
gcattatatt ggttagattt gataggcaaa tttggttgtc aacaatataa atataaataa    13020
tgtttttata ttacgaaata acagtgatca aaacaaacag tttatctttt attaacaaga    13080
ttttgttttt gtttgatgac gtttttaat gtttacgctt tccccctttct tttgaatta    13140
gaacacttta tcatcataaa atcaaatact aaaaaaatta catatttcat aaataataac    13200
acaaatattt ttaaaaaatc tgaaaataa atgaacaata ttacatatta tcacgaaaat    13260
tcattaataa aaatattata taaataaaat gtaatagtag ttatatgtag gaaaaaagta    13320
ctgcacgcat aatatataca aaaagattaa aatgaactat tataaataat aacactaaat    13380
taatggtgaa tcatatcaaa ataatgaaaa agtaaataaa atttgtaatt aacttctata    13440
tgtattacac acacaaataa taaataatag taaaaaaaat tatgataaat atttaccatc    13500
tcataagata tttaaaataa tgataaaaat atagattatt ttttatgcaa ctagctagcc    13560
aaaaagagaa cacgggtata tataaaaaga gtacctttaa attctactgt acttcctta    13620
ttcctgacgt ttttatatca agtggacata cgtgaagatt taattatca gtctaaatat    13680
ttcattagca cttaatactt ttctgttta ttcctatcct ataagtagtc ccgattctcc    13740
caacattgct tattcacaca actaactaag aaagtcttcc atagccccccc aagcggccgc   13800
tagtcgacta agtcatcaac tattccaagc tacgtatttg ggagtttgtg gagtacagca   13860
agatgatata cctagacggt gatatccaag tttttgacaa cattgaccac ttgtttgact   13920
tgcctgataa ctacttctat gcggtgatgg actgttctg tgagccaact tggggccaca    13980
ctaaacaata tcagatcggt tactgccagc agtgccccca taaggttcag tggcccactc   14040
actttgggcc caaacctcct ctctatttca atgctggcat gtttgtgtat gagcccaatt   14100
tggctactta ccgtgacctc cttcaaacag tccaagtcac ccagcccact tcctttgctg   14160
aacaggattt tttgaacatg tacttcaagg acaaatatag gccaattcct aatgtctaca   14220
atcttgtgct ggccatgctg tggcgtcacc ctgagaacgt tgagcttgac aaagttaaag   14280
tggttcacta ctgtgctgct gggtctaagc cttggaggta cactgggaag tgactcgagg    14340
tcatcaatta ctccaagcta cgtatttggg agttcgtgga gtacaagaag acgatatacc   14400
tagacggtga catccaagta tttggaaaca tagaccactt gtttgatctg cctgataatt    14460
atttctatgc ggtgatggat tgtttctgcg agaagacttg gagccacacc cctcagttcc   14520
agattggata ctgccaacag tgccctgata aggttcagtg gccctctcac tttggttcca   14580
aacctcctct atatttcaat gctggcatgt ttgtttatga gcctaatctc gacacctacc   14640
gtgatcttct ccaaactgtc caactcacca agcccacttc ttttgctgag caggactttc   14700
tcaacatgta cttcaaggac aagtacaagc caataccgaa catgtacaac cttgtgctgg   14760
ccatgttgtg gcgtcaccct gaaaatgttg aacttgataa agttcaagtg gttcattact    14820
gtgctgctgg gtctaagcct tggaggttca ctgggaagta actgcaggtc atcaactact   14880
ccaagctccg tatatgggag tttgtggagt acagcaagat gatatacttg gacggagaca   14940
ttgaggtata tgagaacata gaccaccact ttgacctacc tgatggtaac ttttacgctg    15000
tgatggattg tttctgcgag aagacatgga gtcacacccc tcagtacagg tgggttact    15060
gccagcaatg cccggagaag gtgcggtggc ccaccgaatt gggtcagccc ccttctcttt   15120
acttcaacgc tggcatgttc gtgttcgaac ccaacatcgc cacctatcat gacctattga   15180
aaacggtgca agtcaccact cccacctcgt tcgctgaaca agatttcttg aacatgtact   15240
tcaaggacat ttacaagcca atcccctttaa attacaatct tgtcctcgcc atgctgtggc   15300
gccaccgga aaacgttaaa ttagaccaag tcaaggttgt tcactattgc gcagcgggt    15360
ccaagccatg gagatatacg gggaagtagc ctaggcgtac gcaggtaagt ttctgcttct    15420
acctttgata tatataat aattatcatt aattagtagt aatataatat ttcaaatatt    15480
ttttccaaaa taaagaatg tagtatatag caattgcttt tctgtagttt ataagtgtgt    15540
atattttaat ttataacttt tctaatatat gaccaaaaca ttgtgatgtg caggtcctag    15600
gctacttccc cgtatatctc catgcttgg accccgctgc gcaatagtga acaacccttga   15660
cttggtctaa tttaacgttt tccgggtggc gccacagcat ggcgaggaca agattgtaat    15720
ttaaagggat tggcttgtaa atgtccttga agtacatgtt caagaaatct tgttcagcga    15780
acgaggtggg agtggtgact tgcaccgttt caataggctc atgataggtg gcgatgttgg    15840
gttcgaacac gaacatgcca gcgttgaagt aaagagaagg gggctgaccc aattcggtgg    15900
gccaccgcac cttctccggg cattgctggc agtaacccac cttgtactga ggggtgtgac    15960
tccatgtctt ctcgcagaaa caatccatca cagcgtaaaa gttaccatca ggtaggtcaa    16020
ataggtggtc tatgttctca tataccctcaa tgtctccgtc caagtatatc atcttgctgt    16080
actccacaaa ctcccatata cggagcttgg agtagttgat gacctgcagt tacttcccag   16140
tgaacctcca aggcttagac ccagcagcac agtaatgaac cacttgaact ttatcaagtt    16200
caacattttc agggtgacgc cacaacatgg ccagcacaag gttacatgt tcggtattg     16260
gcttgtactt gtccttgaag tacatgttga gaaagtcctg ctcagcaaaa gaagtgggct    16320
tggtgagttg gacagtttgg agaagatcac ggtaggtgtc gagattaggc tcataaacaa    16380
acatgccagc attgaaatat agaggaggtt tggaaccaaa gtgagaggc cattgaacct     16440
tatcagggca ctgttggcag tacccaatct ggaactgagg ggtgtggctc caagtcttct   16500
```

```
cgcagaaaca atccatcacc gcatagaaat aattatcagg cagatcaaac aagtggtcta   16560
tgtttccaaa tacttggatg tcaccgtcta ggtatatcgt cttcttgtac tccacgaact   16620
cccaaatacg tagcttggag taattgatga cctcgagtca cttcccagtg tacctccaag   16680
gcttagaccc agcagcacag tagtgaacca ctttaacttt gtcaagctca acgttctcag   16740
ggtgacgcca cagcatggcc agcacaagat tgtagacatt aggaattggc ctatatttgt   16800
ccttgaagta catgttcaaa aaatcctgtt cagcaaagga agtgggctgg gtgacttgga   16860
ctgtttgaag gaggtcacgg taagtagcca aattgggctc atacacaaac atgccagcat   16920
tgaaatagag aggaggtttg ggcccaaagt gagtgggcca ctgaaccttta tgggggcact   16980
gctggcagta accgatctga tattgtttag tgtggcccca agttggctca cagaaacagt   17040
ccatcaccgc atagaagtag ttatcaggca agtcaaacaa gtggtcaatg ttgtcaaaaa   17100
cttggatatc accgtctagg tatatcatct tgctgtactc cacaaactcc caaatacgta   17160
gcttggaata gttgatgact tagtcgacta gcggccgcga cacaagtgtg agagtactaa   17220
ataaatgctt tggttgtacg aaatcattac actaaataaa ataatcaaag cttatatatg   17280
ccttccgcta aggccgaatg caaagaaatt ggttctttct cgttatcttt tgccacttt    17340
actagtacgt attaattact acttaatcat ctttgtttac ggctcattat atccggtcta   17400
ggccaaggcc gcgaagttaa aagcaatgtt gtcacttgta cgtactaaca catgatgtga   17460
tagtttatgc tagctagcta taacataagc tgtctctgag tgtgttgtat attaataaag   17520
atcatcactg gtgaatggtg atcgtgtacg tacccctactt agtaggcaat ggaagcactt   17580
agagtgtgct ttgtgcatgg ccttgcctct gttttgagac ttttgtaatg ttttcgagtt   17640
taaatctttg cctttgcgta cgtgggcgga tccctgca                           17679
```

SEQ ID NO: 3          moltype = DNA   length = 22374
FEATURE               Location/Qualifiers
misc_feature          1..22374
                      note = synthesized DNA of PHP64612
source                1..22374
                      mol_type = other DNA
                      organism = synthetic construct
SEQUENCE: 3

```
cctcacgtgt taacagaagt tcctattccg aagttcctat tctctagaaa gtataggaac    60
ttccaccaca caacacaatg gcggccaccg cttccagaac cacccgattc tcttcttcct   120
cttcacaccc caccttcccc aaacgcatta ctagatccac cctcccctc  tctcatcaaa   180
ccctcaccaa acccaaccac gctctcaaaa tcaaatgttc catctccaaa cccccacgg    240
cggcgcccctt caccaaggaa gcgccgacca cggagcgcct cgtgtcacgg ttcgcctccg   300
gcgaacctcg caagggcgcg gacatccttg tggaggcag ggcgtgacga                360
cggtgttcgc gtaccccggc ggtgcgtcga tggagatcca ccaggcgctc acgcgctccg   420
ccgccatccg caacgtgctc ccgcgccacg agcagggcgg cgtcttcgcc gccgaaggct   480
acgcgcgttc ctccggcctc cccggcgtct gcattgccac ctccggcccc ggcgccacca   540
acctcgtgag cggcctcgcc gacgctttaa tggacagcgt cccagtcgtc gccatcaccg   600
gccaggtcag ccgccggatg atcggcaccg acgccttcca agaaaccccg atcgtggagg   660
tgagcagatc catcacgaag cacaactacc tcatcctcga cgtcgacgac atcccccgcg   720
tcgtcgccga ggctttcttc gtcgccacct ccggccgccc cggtccggtc ctcatcgaca   780
ttcccaaaga cgttcagcag caactcgccg tgcctaattg ggacgagccc gttaacctcc   840
ccggttacct cgccaggctg cccaggcccc ccgccgaggc caattggaa cacattgtca     900
gactcatcat ggaggcccaa aagcccgttc tctacgtcgg cggtggcagt ttgaattcca   960
gtgctgaatt gaggcgcttt gttgaactca ctggtattcc cgttgctagc actttaatgg  1020
gtcttggaac ttttcctatt ggtgatgaat attcccttca gatgctgggt atgcatggta  1080
ctgtttatgc taactatgct gttgacaata gtgatttgtt gcttgccttt ggggtaaggt  1140
ttgatgaccg tgttactggg aagcttgagg cttttgctag tagggctaag attgttcaca  1200
ttgatattga ttctgccgag attgggaaga acaagcaggc gcacgtgtcg gtttgcgcgg  1260
attttgaagtt ggccttgaag ggaattaata tgattttgga ggagaaagga gttggagggta 1320
agtttgatct tggaggttgg agagaagaga ttaatgtgca gaaacacaag tttccattgg  1380
gttacaagac attccaggac gcgatttctc cgcagcatgc tatcgaggtt cttgatgagt  1440
tgactaatgc agatgctatt gttagtactg gggttgggca gcatcaaatg tgggctgcgc  1500
agtttacaa gtacaagaga ccgaggcagt ggttgacctc aggggtcttgg gagccatgg   1560
gtttttggatt gcctgcgcgt attggtgctg ctgttgctaa ccctggggct gttgtggttg  1620
acattggtga tggatggagt ttcatcatga atgttcagga gttggccact ataagagtgg  1680
agaatctccc agttaagata ttgttgttga acaatcagca tttgggtatg gtggttcagt  1740
gggaggatag gttctacaag tccaatagag ctcacaccta tcttggagat ccgtctagcg  1800
agagcgagat attcccaaac atgctcaagt ttgctgatgc ttgtgggata ccggcagcgc  1860
gagtgacgaa gaaggaagag cttagagcgg caattcagag aatgttggac accctggcc   1920
cctaccttct tgatgtcatt gtgccccatc aggagcatgt gttgccgatg attcccagta  1980
atggatcctt caaggatgtg ataactgagg gtgatggtag aacgaggtac tgactagcta  2040
gtcagttaac ctagacttgt ccatcttctg gattggccaa cttaattaat gtatgaaata  2100
aaaggatgca cacatagtga catgctaatc actataatgt gggcatcaaa gttgtgtgtt  2160
atgtgtaatt actagttatc tgaataaaag agaagagat catccatatt tcttatccta  2220
aatgaatgtc acgtgtcttt ataattcttt gatgaaccag atgcatttca ttaaccaaat  2280
ccatatacat ataaatatta atcatatata attaatatca attgggttaa caaaacaaat  2340
ctagtctagg tgtgttttgc ccccaagctt atcgataccg tcgcgcgggg gtacgttagc  2400
tgattaagtc agcatgcgcg gccggcgtat gaactaaaat gcatgtaggt gtaagagctc  2460
atggagagca tggaatattg tatccgacca tgtaacagta taataactga gctccatctc  2520
acttcttcta tgaataaaca aaggatgtta tgatatatta acactctatc tatgcaccctt 2580
attgttctat gataaaattc tcttattat tataaatcat ctgaatcgtg acggcttatg   2640
gaatgcttca aatagtacaa aaacaaatgt gtactaaagt actttctaaa caattctaac  2700
cttagcattg tgaacgagac ataagtgtta agaagacata acaattataa tggaagaagt  2760
ttgtctccat ttatatatta tatattaccc acttatgtat tatattagga tgttaaggag  2820
acataacaat tataaagaga gaagtttgta tccatttata tattatatac tacccattta  2880
tatattatac ttatccactt atttaatgtc tttataaggt tgatccatg atatttctaa   2940
tattttagtt gatatgtata tgaaaaggta ctatttgaac tctcttactc tgtataaagg  3000
```

```
ttggatcatc cttaaagtgg gtctatttaa ttttattgct tcttacagat aaaaaaaaaa  3060
ttatgagttg gtttgataaa atattgaagg atttaaaata ataataaata acatataata  3120
tatgtatata aatttattat aatataacat ttatctataa aaaagtaaat attgtcataa  3180
atctatacaa tcgtttagcc ttgctggaac gaatctcaat tatttaaacg agagtaaaca  3240
tatttgactt tttggttatt taacaaatta ttatttaaca ctatatgaaa ttttttttt   3300
tatcagcaaa gaataaaatt aaattaagaa ggacaatggt gtcccaatcc ttatacaacc  3360
aacttccaca agaaagtcaa gtcagagaca acaaaaaaac aagcaaagga aattttttaa  3420
tttgagttgt cttgtttgct gcataattta tgcagtaaaa cactcacat aacccttta    3480
gcagtagagc aatggttgac cgtgtgctta gcttcttta ttttatttt ttatcagcaa     3540
agaataaata aaataaaatg agacacttca gggatgtttc aacaggtacc catcacttaa  3600
gtggcgcgcc gtcgacggat ccgtaccat ctgcaggtaa aattgcagctg aaggacagtg   3660
aagggtgaat ttatccattt aaaccatttt ctttttaaca catttcttat ggtaatctct  3720
tctcactaca ctataaaaat ggcttctcaa tcccattttc tacatcatcc cattctattg  3780
agttttgttt atttgctttc acttttttt ttatctgcct cttcccttaa tttgcttgac    3840
ttcttcttca cattttgctt tgttttctcc tccggcttcc ggtatttcaa attcaagatg  3900
agcaagttga aatttataaa tagaaataca gatattatt acaacgtcaa atctttggta   3960
ttttcaatat ttgaatgggg taaatttgtc atatagtcat catcactgac tacttatcta  4020
acctatttaa tttggagcat attctttata aggtccctct cacggccaat gtctaattat  4080
tgatatacag ctcttgtttt ctagtgctgc ttataatatt atctacacat atatatggta  4140
ctgcacacta ctactatata gtagtaagta aactagcaac agccggggcc aaactccaat  4200
aactaggcat tggggtttag ttggtaatat aaatataaca tcaaaagtc tttgcttgtg   4260
acgaacatca caatgcaccc accattgatg ccacgacaga cattgttaat ttttttta    4320
atttttaaaa aagaagcaat tccaatagtt ctatattaca atctcacgtg atccaagcac  4380
aacgtttcat ttttttgtaca tgctcgatat ataaataata tttcatttta tagtaaaata  4440
taatgacatt ttcgaatata attttgaaa tttcatttc caaatgaaat actaatatta    4500
atattaatga gattaccaca aatcatgtta tgaatgaaat aaagagtttt ggcattctaa  4560
cttctcttga atagaacaaa atgtatacaa cactctccat atatacacga tttattcagg  4620
gatcatatac atttctctcat gattaacata gtctgctttc ttcacgtcta agcagataat  4680
ttttggtcca caagataaaa ttatcattag tcgttttaat taattcctg agcatcaagc   4740
actaaaataa ttaaacttct ccattaccaa aaaaaaaga taggattgc agtaacatgt    4800
agtactagta ctactgattt tttttcttt ttgattttaa tgaatggttc gtatcgagca    4860
tcgagaaatc catttattag gtgtgtaatg taatagtagt atttccttga ttttcagtaa  4920
taagatggat tcttacattt atatctgttt gacagaaaat gttgtcaatg catttcttgg  4980
gcacaaagtt ttttgaaaca tgaattaatt tttcaaatt atttatgaca tcaaattgac   5040
cctaaaataa gtgataaagc tttaacgtgg aatgacatta attttccat gataaaataaa  5100
acacttaaaa catttaata ttaatattat aatcagttac aactatgttc aattaatgca   5160
ataacttta aataaatatt aaaatatttt ttttctgttc tccaataaag agatcttgtt   5220
gcacggaaaa agtcacattc ttatttagta aaaaattata attattgttt gaaaaaatatc 5280
attttcactg cagaaaattt gatccagctc tacagatcat acttttattg tacaataata  5340
caataaaaat attcatctgc aggaaatatc attttcattg tacaataata taagataaa   5400
tatataccag aaaagaaaaa gaaactgatg tggcacaatg tattcactga agaatgcat   5460
attgtatttc acctttcaag cagcactaag aatatacttc ttttattata cttgtgcatt  5520
tactcaacca ccctcggtgg agtaagaaag aagtagata aaagtttttt ttgacatttg   5580
gtgaatctct taattaaaaa aataaataaa tccatttcct ttatttaatt tctttttcc    5640
catctgtgaa attccaattc tgcttcgcgc tcctgtctat aaattgactt agccaccacc  5700
tcagtttcca ttcattcact tcttctcttt ataccccccc tctctttttt gcgttcattc  5760
tgttttcgta agtactgttg tttttctctt ctatttcttt tttgtttgt gttgtttttt   5820
tttcttcctt atcgttgttc tgcctctcct ctgtttcggt gctctgttca ccacttccac  5880
gtgagaatga tcttccttct ttgcatgttc attctctcgt gaccactgga tcagactcca  5940
tgttctgatc cagggtctct ctctaacgcc tgtactttca tccatgacca ccttaaaaac  6000
aacatgggg tggtgctgtt acactaactc tgtttctggg gtgctgtctt tgttcaattt   6060
tactcagaaa atatcttttc ttggattcta ttcggtgtgt gggaacatga tcctgtcggt  6120
cggttgtttt taggttaatc cttaactggt tacaaggatc taacgcttga atgcatgtcc  6180
tgagttaaag aaacaaaaga agaacacacc tagtacagcc tggcctcgaa ccaagaactt  6240
ctttgttggt ttctcattat tactaaaata aaataaagta tacgttttct ttttctttg   6300
ggatgaacgg ttcagactta tgagaagttt aagctaatcc tgtagtggag tgttcaattt  6360
attttaaact ttaaagcaat agctcaagca ctaaacttct ttttcaagtt caaccacttt  6420
ggtagcttgc taattgctgc tattgttcta attaattaat gtaattattg tttaaaaaag  6480
aaaagttggt gacactggaa taaaaaagtg tactatctgg caattattct tctgcagcaa  6540
tgtttgaggt tgaaatctta gtagaacaaa gtagaagatc tggtatttat atttttgta   6600
gacagatggt ggggtgggt ggtaggcctt gaaatccaat atagtttgt agaataattt    6660
tattattttt ttttttgct cacttgtttg tggtattgat tttgtgatga ctcaagatta   6720
atgatttacc ttcattttt tcatggtgac atattatgta tattcttgat ctgtttctta   6780
cacttctttt tcgttgttgt agctgttgaa gtctcgcgcc gcatgaagag gtctccgaag  6840
tcttcttgtt catcatctac ttcctctgtt gggtttgaag ctcccattga aaaagaagg   6900
cctaagcatc caaggaggaa taatttgaag tcacaaaaat gcaagcagaa ccaaaccacc  6960
actggtggca gaagaagctc tatctataga ggagttacaa gcataggtg acagggagg    7020
tttgaagctc acctatggga taagagctct tggaacaaca ttcagagcaa gaagggtcga  7080
caagtttatt tgggggcata tgatactgaa gaatctgcag cccgtaccta tgacccttga  7140
gcccttaaat actggggaaa agatgcaacc ctgaatttcc cgatagaaac ttataccaag  7200
gagctcgagg aaatggacaa ggtttcaaga gaagaatatt tggcttcttt gcggcgccaa  7260
agcagtggct tttctagagg cctgtctaag taccgtgggg ttgctaggca tcatcataat  7320
ggtcgctggg aagcacgaat tggaagagta tgcggaaaca agtacctcta cttggggaca  7380
tataaaactc aagaggaggc agcagtggca tatgacaga gtaccgtgga  7440
gtcaatgcag tgaccaattt tgacataagc aactacatgg acaaatataaa gaagaaaat   7500
gaccaaaccc aacaacaaca aacagaagca caaacggaaa cagttcctaa ctcctctgac  7560
tctgaagaag tagaagtaga acaacagaca acaacaataa ccacaccacc cccatctgaa  7620
aatctgcaca tgccaccaca gcagcaccaa gttcaataca cccccccatgt ctctccaagg  7680
gaagaagaat catcatcact gatcacaatt atggaccatg tgcttgagca ggatctgcca  7740
```

```
tggagcttca tgtacactgg cttgtctcag tttcaagatc caaacttggc tttctgcaaa    7800
ggtgatgatg acttggtggg catgtttgat agtgcagggt ttgaggaaga cattgatttt    7860
ctgttcagca ctcaacctgg tgatgagact gagagtgatg tcaacaatat gagcgcagtt    7920
ttggatagtg ttgagtgtgg agacacaaat ggggctggtg gaagcatgat gcatgtggat    7980
aacaagcaga agatagtatc atttgcttct tcaccatcat ctacaactac agtttcttgt    8040
gactatgctc tagatctatg agcggccgca tttcgcacca aatcaatgaa agtaataatg    8100
aaaagtctga ataagaatac ttaggcttag atgcctttgt tacttgtgta aaataacttg    8160
agtcatgtac ctttggcgga aacagaataa ataaaaggtg aaattccaat gctctatgta    8220
taagttagta atacttaatg tgttctacgg ttgtttcaat atcatcaaac tctaattgaa    8280
actttagaac cacaaatctc aatcttttct taatgaaatg aaaaatctta attgtaccat    8340
gtttatgtta aacaccttac aattaattgg ttggagagga ggaccaaccg atgggacaac    8400
attgggagaa agagattcaa tggagatttg gataggagaa caacattctt tttcacttca    8460
atacaagatg agtgcaacac taaggatatg tatgagactt tcagaagcta cgacaacata    8520
gatgagtgag gtggtgattc ctagcaagaa agacattaga ggaagccaaa atcgaacaag    8580
gaagacatca agggcaagag acaggaccat ccatctcagg aaaaggagct ttgggatagt    8640
ccgagaagtt gtacaagaaa ttttttggag ggtgagtgat gcattgctgg tgactttaac    8700
tcaatcaaaa ttgagaaaga aagaaaaggg aggggggctca catgtgaata gaagggaaac    8760
gggagaattt tacagttttg atctaatggg catcccagct agtggtaaca tattcaccat    8820
gtttaacctt cacgtacgaa accaactgcg tttggggctc cagattaaac gacgccgttt    8880
cgttcctttc gcttcacggc ttaacgatgt cgtttctgtc tgtgcccaaa aaataaaggc    8940
atttgttatt tgcaccagat atttactaag tgcaccctag tttgacaagt aggcgataat    9000
tacaaataga tgcggtgcaa ataataaatt ttgaaggaaa taattacaaa agaacagaac    9060
ttatatttac tttatttaa aaaactaaaa tgaagaaca aaaaaagtaa aaaatacaaa    9120
aaatgtgctt taaccacttt cattatttgt tacagaaagt atgattctac tcaaattgat    9180
ctgttgtatc tggtgctgcc ttgtcacact ggcgatttca atccctaaa gatatggtgc    9240
aaactgcgaa gtgatcaata tctgctcggt taatttagt taattaataa tattcaacgt    9300
gatgtaccaa aaaaagacaa ttttttgctc cattgacaaa ttaaacctca tcaaggtaat    9360
ttccaaacct ataagcaaaa aaatttcaca ttaattggcc cgcaatccta ttagtcttat    9420
tatactagag taggaaaaaa aacaattaca caacttgtct tattattctc tatgctaatg    9480
aatattttc ccttttgtta gaaatcagtg tttcctaatt tattgagtat taattccact    9540
caccgcatat atttaccgtt gaataagaaa attttacaca taattctttt taagataaat    9600
aattttttta tactagatct tatatgatta cgtgaagcca agtgggttat actaatgata    9660
tataatgttt gatagtaatc agtttataaa ccaaatgcat ggaaatgtta cgtggaagca    9720
cgtaaattaa caagcattga agcaaatgca gccaccgcac caaaaccacc ccacttcact    9780
tccacgtacc atattccatg caactacaac accctaaaac ttcaataaat gccccacct    9840
tcacttcact tcacccatca atagcaagcg gccgcaccat ggcgatttcc gatgagcctg    9900
aaagtgtagc cactgctctc aaccactctt ccctgcgccg ccgtccctcc gccacctcca    9960
ccgccggcct cttcaattcg cctgagacaa ccaccgacag ttccggtgat gacttggcca   10020
aggattctgg ttccgacgac tccatcaaca acgacgaccg tcccgcccaat tcccaacagc   10080
aaaacgaaaa acaagacact gatttctccg tcctcaaatt cgcctaccgt ccttccgtcc   10140
ccgctcaccg caaagtgaag gaaagtccgc tcagctccga cactattttc cgtcagagtc   10200
acgcgggcct cttcaacctt tgtatagtag tccttgttgc tgtgaatagc cgactcatca   10260
ttgagaattt aatgaagtat ggttggttga tcaaatctgg cttttggttt agtgcaaagt   10320
cattgagaga ctggcccctt tcatgtgtt gtcttctct tgtggtattt cctttcgctg   10380
cctttatggt ggagaagttg gcacaacgga agtgtatacc cgaaccagtt gttgttgtac   10440
ttcatataat cattacctca acttcgcttt tctatccagt tttagttatt ctcaagtgtg   10500
attctgcttt tgtatcaggt gtcacgttaa tgctgttttc ttgtgttgta tggttaaaat   10560
tggtgtcttt tgcacataca aactatgata tgagagcact taccaaatta gttgaaaagg   10620
gagaagcact gctcgatact ctgaacatgg agtatcctta caacgtaacc ttcaagagct   10680
tggcatattt cctgcttgcc cctacattat gttaccagcc aagctatcct cgcacacctt   10740
atattcgaaa gggttggttg tttcgccaac ttgtcaagct gatagtattt acaggagtta   10800
tgggatttat aatagaacaa tatattaatc ccatagtaca aaattcacag catcctctca   10860
agggaaacct tctttacgcc accgagagag ttctgaagct ttctgttcca aatttatatg   10920
tgtggctctg catgttctat tgcttttttcc acctttggtt aaatatcgtg gcagagcttc   10980
ttcgatttgg tgatcgtgaa ttctacaagg atttggtggaa tgccaaaact gtcgaagatt   11040
attggaggat gtggaatatg cctgttcaca aatggatgat ccgccaccta tattttccat   11100
gtttaaggca cggtctacca aaggctgctc tcttttaat ttccttcctg gtttctgctt   11160
tattccatga gctgtgcatt gctgttcctt gccacatgtt caagttgtgg gctttcggtg   11220
gaattatgtt tcaggttcct ttggtcttga tcactaatta tctgcaaaat aaattcaaaa   11280
actcaatggt tggaaatatg atttttggt tcatattcag tatcgttggt caacctatgt   11340
gtgtactgct atactaccat gacttgtgat ataggaaagg caaacttgac tgagcggccg   11400
cgaagttaaa agcaatgttg tcacttgtcg tactaacaca tgatgtgata gtttatgcta   11460
gctagctata acataagctg tctctgagtg tgttgtatat taataaagat catcactggt   11520
gaatggtgat cgtgtacgta ccctacttag taggcaatgg aagcacttag agtgtgcttc   11580
gtgcatggcc ttgcctctgt tttgagactt ttgtaatgtt ttcgagttta aatctttgcc   11640
tttgcgtacg tctttccaca atacataact attaattaat cttaaataaa taaggataa   11700
aatattttt tttcttcata aagttaaaat atgttatttt ttgtttagat gtatattcga   11760
ataaatctaa atattattga atgattttt atattgatta aacatataat caatattaaa   11820
tatgatattt ttttatatag gttgtacaca taattttata aggataaaaa atatgataaa   11880
aataaatttt aaatatttt atatttacga gaaaaaaaaa tattttagcc ataaataaat   11940
gaccagcata ttttacaacc ttagtaattc ataaattcct atatgtatat ttgaaattaa   12000
aaacagataa tcgttaaggg aaggaatcct acgtcatctc ttgccatttg tttttcatgc   12060
aaacagaaag ggacgaaaaa ccacctcacc atgaatcact cttcacacca tttttactag   12120
tcaacaagtc tcaacaactg aagccagctc tcttttccgt tcttttttaca acactttctt   12180
tgaaatagta gtattttttt tcacatgatt tattaacgtg ccaaaagatg cttattgaat   12240
agagtgcaca tttgtaatgt actactaatt agaacatgaa aaagcattgt tctaacacga   12300
taatcctgtg aaggcgttaa ctccaaagat ccaatttcac tatataaatt gtgacgaaag   12360
caaaatgaat tcacatagct gagagagaaa ggaaggttaa ctaagaagc aatacttcag   12420
cggccgcatg ccgaatcccg aggctcacca ccccctcccgg tcccgggccc ggccctccac   12480
```

```
gtcagccgcg gcccgccccc cggcccggcc ccgcgtctcc ctccgccagc ttctgcgcgt   12540
ggcatcagtc gcgagcggca tccagttcgg gtgggcctta cagctctctc tgctgacgcc   12600
ctacgttcag cagctgggga tcccccacca atgggccagc atcatctggc tctgcggccc   12660
agtctccggc ctcttcgtgc agcccctcgt cggccacatg agcgaccgct gcaccagccg   12720
ctacggccgc cgcaggcccct tcatcctcgt cggcgccgtc gccatcgtcg ccgctgttct   12780
cgtcatcgct tacgccgccg acatcggctg gctcctcggc gacaccgcgg actaccgccc   12840
tgccgccatc accgtcttca tcgtcggctt ctggatcctc gacgtcgcta caacgtcac    12900
gcaaggtccc tgccgtgcct tgctcggtga tctcactagc aaggatcctc gaaggacacg   12960
tgttgcaaat gcttattact cactgtttat ggccattggt aacattcttg gctatgcaat   13020
tggatcatat agtggttggt acaagatttt tacttttgcc cttttcccctg cttgcacaat   13080
tagttgtgca aatctcaagt ctgctttctt tcttgacatt gctttcattg cggtcacaac   13140
atatatcagc atcatggcag ctcatgaagt gcctctaaat tcaagtgagg cggcccatgc   13200
tgaagcaggg gcagggagt caggtagtgc agaagaagct ttcatgtggg aattatttgg   13260
gacattcaaa tattttacaa cccctgtatg gataattcct tctgttactg ctctgacatg   13320
gattgggtgg ttcccattta ctctctttga tactgattgg atgggtcgag agatttatg   13380
tggtgatcca aatcaaggcc ttgtttatga tactggagtt agaatgggag cacttggttt   13440
gttgcttaat tcagttgttc ttgcattaac atcattgttc atggagaggc tatgcaggaa   13500
gagggagct ggttttggtt ggggaatctc aaatatcatg atgaccgttt gcttttcttgc   13560
aatgctagta gtaacctatg tggcaaataa catgggctat ataggcaaag atttaccacc   13620
aactggcatt gtgatagctg cgttgattat ctttaccatt cttgggtttc cactggcaat   13680
cacttatagt gttccatatg ccttaatttc cacacatatt gagtcattgg gactcggcca   13740
agggttatca atgggtgtcc taaatctggc aatagtgctc ccacagataa tagtgtcact   13800
gggaagtgga ccatgggatc agctatttgg tggaggaaac tccccagcct tgctgtgtg    13860
agctgtttca gcccttatca gtggactcat agctgtgttg gctattcctc gatctggtgc   13920
tcaaaaggct cgaagccatg tatgagcggc cgcctgaacg ggaattaaac ctataaacat   13980
aaatataaat aatatatata aacctaagtg tctaagttca aaataattag ctgtagtctc   14040
tggcttaaaa catgttaggt ttgtttatac aagtagttgg atgtttggag tacttcggtc   14100
ttttgcgtac catcaatatt taagaactaa gttagttatg ttccgtaact tatgggctct   14160
taattaaact atatctgcac aaaattatat atatatcaaa tgtgatggta tgtggactat   14220
aaaaagatat ggttgagaac cacaaacttt gaaacttcga atatatatt gccagtgaca   14280
gtcttgttga tttgttatag caagtcctat tttcttaatc attgctttgt tttaacgtac   14340
ctagatttca taactttttgt ctttgtctca agctgaacct aatgatgata gtaatattaa   14400
cttattgtat agggggtattt cataggataa aaaatgatgt gcaattacgt gtagaccaaa   14460
tattacttga tgacagatgg cctgcaggat ccatgccctt catttgccgc ttattaatta   14520
atttggtaac agtccgtact aatcgattac ttatccttcc cccatcataa ttaatcttgg   14580
tagtctcgaa tgccacaaca ctgactagtc tcttggatca taagaaaaag ccaaggaaca   14640
aaagaagaca aaacacaatg agagtatcct ttgcatagca atgtctaagt tcataaaatt   14700
caaacaaaaa cgcaatcaca cacagtggac atcacttatc cactagctga tcaggatcgc   14760
cgcgtcaaga aaaaaaaact ggaccccaaa agcatgcac aacaacacgt actcacaaga    14820
gtgtcaatcg agcagcccaa aacattcacc aactcaaccc atcatgagcc ctcacatttg   14880
ttgtttctaa cccaacctca aactcgtatt ctcttccgcc acctcatttt tgtttatttc   14940
aacacccgtc aaactgcatg ccaccccgtg gccaaatgtc catgcatgtt aacaagacct   15000
atgactataa atgactcgaa tctcggccca ggttttcata tcaagaacc agttcaatat    15060
cctagtacac cgtattaaag aatttaagat atactgcggc cgctagtcga ctaagtcatc   15120
aactattcca agctacgtat ttgggagttt gtggagtaca gcaagatgat atacctagac   15180
ggtgatatcc aagttttga caacattgac cacttgtttg acttgcctga taactacttc   15240
tatgcggtga tggactgttt ctgtgagcca acttggggcc acactaaaca atatcagatc   15300
ggttactgcc agcagtgccc ccataaggtt cagtggccca ctcactttgg gcccaaacct   15360
cctctctatt tcaatgctgg catgtttgtg tatgagccca atttggctac ttaccgtgac   15420
ctccttcaaa cagtccaagt cacccagccc acttcctttg ctgaacagga ttttttgaac   15480
atgtacttca aggacaaata taggccaatt cctaatgtct acaatcttgt gctggccatg   15540
ctgtggcgtc accctgagaa cgttgagctt gacaaagtta aagtggttca ctactgtgct   15600
gctgggtcta agccttggag gtacactggg aagtgactcg aggtcatcaa ttactccaag   15660
ctacgtattt gggagttcgt ggagtacaag aagacgatat acctagacgg tgacatccaa   15720
gtatttggaa acatagacca cttgtttgat ctgcctgata attatttctca tgcggtgatg   15780
gattgtttct gcgagaagac ttggagccac accctcagt tccagattgg gtactgccaa    15840
cagtgccctg ataaggttca atggccctct cactttggtt ccaaacctcc tctatatttc   15900
aatgctggca tgtttgttta tgagcctaat ctcgacacct accgtgatct tctccaaact   15960
gtccaactca ccaagcccac ttcttttgct gagcaggact ttctcaacat gtacttcaag   16020
gacaagtaca agccaatacc gaacatgtac aaccttgtgc tggcatgtt gtggcgtcac   16080
cctgaaaatg ttgaacttga taaagttcaa gtggttcatt actgtgctgc tgggtctaag   16140
ccttggaggt tcactgggaa gtaactcag gtcatcaact actccaagct ccgtatatgg    16200
gagtttgtgg agtacagcaa gatgatatac ttggacggag acattgaggt atatgagaac   16260
atagaccacc tattttgacct acctgatggt aacttttcac ctgtgatgga ttgtttctgc   16320
gagaagacat ggagtcacac ccctcagtac aaggtgggtt actgccagca atgcccggaa   16380
aaggtgcggg gcccaccga attgggtcag ccccttctc tttacttcaa cgctggcatg    16440
ttcgtgttcg aacccaacat cgccacctat catgacctat gaaaacggt gcaagtcacc    16500
actcccacct cgttcgctga acaagatttc ttgaacatgt acttcaagga catttacaag   16560
ccaatccctt taaattcaa tcttgtcctc gccatgctgt ggcgccaccc ggaaaacgtt    16620
aaattagacc aagtcaaggt tgttcactat tgcgcagcgg ggtccaagcc atggagatat   16680
acggggaagt agcctaggcg tacgcaggta agtttctgct tctacctttg atatatatat   16740
aataattatc attaattagt agtaatataa tatttcaaat attttttca aaataaaga    16800
atgtagtata tagcaattgc ttttctgtag tttataagtg tgtatatttt aatttataac   16860
ttttctaata tatgaccaaa acatggtgat gtgcaggtcc taggctactt cccgtatat    16920
ctccatggct tggaccccgc tgcgcaatag tgaacaacct tgacttgtc taatttaacg    16980
ttttccgggt ggcgccacag catggcgagg acaagattgt aatttaaagg gattggcttg   17040
taaatgtcct tgaagtacat gttcaagaaa tcttgttcag cgaacgaggt gggagtggtg   17100
acttgcaccg tttcaatag gtcatgatag gtggcgatgt tgggttcgaa cacgaacatg    17160
ccagcgttga agtaaagaga agggggctga cccaattcgg tgggccaccg caccttctcc   17220
```

```
gggcattgct ggcagtaacc caccttgtac tgaggggtgt gactccatgt cttctcgcag   17280
aaacaatcca tcacagcgta aaagttacca tcaggtaggt caaataggtg gtctatgttc   17340
tcatatacct caatgtctcc gtccaagtat atcatcttgc tgtactccac aaactcccat   17400
atacggagct tggagtagtt gatgacctgc agttacttcc cagtgaacct ccaaggctta   17460
gacccagcag cacagtaatg aaccacttga actttatcaa gttcaacatt ttcagggtga   17520
cgccacaaca tggccagcac aaggttgtac atgttcggta ttggcttgta cttgtccttg   17580
aagtacatgt tgagaaagtc ctgctcagca aaagaagtgg gctggtgag ttggacagtt    17640
tggagaagat cacggtaggt gtcgagatta ggctcataaa caaacatgcc agcattgaaa   17700
tatagaggag gtttggaacc aaagtgagag ggccattgaa ccttatcagg gcactgtttg   17760
cagtacccaa tctggaactg aggggtgtgg ctccaagtct tctcgcagaa acaatccatc   17820
accgcataga aataattatc aggcagatca aacaagtggt ctatgtttcc aaatacttgg   17880
atgtcaccgt ctaggtatat cgtcttcttg tactccacga actcccaaat acgtagcttg   17940
gagtaattga tgacctcgag tcacttccca gtgtacctcc aaggcttaga cccagcagca   18000
cagtagtgaa ccactttaac tttgtcaagc tcaacgttct caggggtgacg ccacagcatg   18060
gccagcacaa gattgtagac attaggaatt ggcctatatt tgtccttgaa gtacatgttc   18120
aaaaaatcct gttcagcaaa ggaagtgggc tgggtgactt ggactgtttg aaggaggtca   18180
cggtaagtag ccaaattggg ctcatacaca aacatgccag cattgaaata gagaggaggt   18240
ttgggcccaa agtgagtggg ccactgaacc ttatgggggc actgctggca gtaaccgatc   18300
tgatattgtt tagtgtggcc ccaagttggc tcacagaaac agtccatcac cgcatagaag   18360
tagttatcag gcaagtcaaa caagtggtca atgttgtcaa aaacttggat atcaccgtct   18420
aggtatatca tcttgctgta ctccacaaac tcccaaatac gtagcttgga atagttgatg   18480
acttagtcga ctagcggccg caagtatgaa ctaaaatgca tgtaggtgta agagctcatg   18540
gagagcatgg aatattgtat ccgaccatgt aacagtataa taactgagct ccatctcact   18600
tcttctatga ataaacaaag gatgttatga tatattaaca ctctatctat gcaccttatt   18660
gttctatgat aaatttcctc ttattattat aaatcatctg aatcgtgacg gcttatgaa    18720
tgcttcaaat agtacaaaaa caaatgtgta ctataagact ttctaaacaa ttctaacctt   18780
agcattgtga acgagacata agtgttaaga agacataaca attataatgg aagaagtttg   18840
tctccattta tatattatat attcccacact tatgtattat attaggatgt taaggagaca   18900
taacaattat aaagagagaa gtttgtatcc atttatatat tatatactac ccatttatat   18960
attatactta tccacttatt taatgtcttt ataaggtttg atccatgata tttctaaatt   19020
tttagttgat atgtatatga aaaggtacta tttgaactct cttactctgt ataaaggttg   19080
gatcatcctt aaagtgggtc tatttaattt tattgcttct tacagataaa aaaaaaatta   19140
tgagttggtt tgataaaaata ttgaaggatt taaaataata ataataaca tataatatat    19200
gtatataaat ttattataat ataacattta tctataaaaa agtaaatatt gtcataaatc   19260
tatacaatcg tttagccttg ctggaacgaa tctcaattat ttaaacgaga gtaaacatat   19320
ttgactttt ggttattaa caaattatta tttaacacta tatgaaattt tttttttttat   19380
cagcaaagaa taaattaaa ttaagaagga caatggtgtc ccaatcctta tacaaccaac    19440
ttccacaaga aagtcaagtc agagacaaca aaaaaacaag caaaggaaat tttttaattt   19500
gagttgtctt gtttgctgca taatttatgc agtaaaacac tacacataac ccttttagca   19560
gtagagcaat ggttgaccgt gtgcttagct tcttttattt tatttttttta tcagcaaaga   19620
ataaataaaa taaaatgaga cacttcaggg atgtttcaac ctgcagggca tgcaagcttg   19680
gcgcgccgga attaattagg taatttcacg cgccggatcc ttaattaagt ctagagtcga   19740
ctgtttaatt ctagtggccg gcctctgcct gcgttctgct gtggaagttc ctattccgaa   19800
gttcctattc tccagaaagt ataggaactt cacatgctgc ctcgtgcaag tcacgatctc   19860
gagttctata gtgtcaccta aatcgtatgt gtatgataca taaggttatg tattaattgt   19920
agccgcgttc taacgacaat atgtccatat ggtgcactct cagtacaatc tgctctgatg   19980
ccgcatagtt aagccagccc cgacaccegc caacacccgc tgacgcgccc tgacgggctt   20040
gtctgctccc ggcatccgct tacagacaag ctgtgaccgt ctccgggagc tgcatgtgtc   20100
agaggttttc accgtcatca ccgaaacgcg cgagacgaaa gggcctcgtg atacgcctat   20160
ttttataggt taatgtcatg accaaaatcc cttaacgtga gttttcgttc cactgagcgt   20220
cagaccccgt agaaaagatc aaaggatctt cttgagatcc tttttttctg cgcgtaatct   20280
gctgcttgca aacaaaaaaa ccaccgctac cagcggtggt ttgtttgccg gatcaagagc   20340
taccaactct ttttccgaag gtaactggct tcagcagagc gcagatacca aatactgtcc   20400
ttctagtgta gccgtagtta ggccaccact tcaagaactc tgtagcaccg cctacatacc   20460
tcgctctgct aatcctgtta ccagtggctg ctgccagtgg cgataagtcg tgtcttaccg   20520
ggttggactc aagacgatag ttaccggata aggcgcagcg gtcgggctga acggggggtt   20580
cgtgcacaca gcccagcttg gagcgaacga cctacaccga actgagatac ctacagcgtg   20640
agcattgaga aagcgccacg cttcccgaag ggagaaaggc ggacaggtat ccggtaagcg   20700
gcagggtcgg aacaggagag cgcacgaggg agcttccagg gggaaacgcc tggtatcttt   20760
atagtcctgt cgggtttcgc cacctctgac ttgagcgtcg atttttgtga tgctcgtcag   20820
gggggcggag cctatggaaa aacgccagca acgcggcctt tttacggttc ctggcctttt   20880
gctgcctttt tgctcacatg ttctttcctg cgttatcccc tgattctgtg gataaccgta   20940
ttaccgcctt tgagtgagct gataccgctc gccgcagccg aacgaccgag cgcagcgagt   21000
cagtgagcga ggaagcggaa gagcgcccaa tacgcaaacc gcctctcccc gcgcgttggc   21060
cgattcatta atgcagttg atcagatctc gatcccgcga aattaatacg actcactata    21120
gggagaccac aacggtttcc ctctagaaat aattttgttt aactttaaga aggagatata   21180
cccatgaaa agcctgaact caccgcgacg tctgtcgaga agtttctgat cgaaaagttc   21240
gacacgtct ccgacctggat gcagctctcg gagggcgaag aatctcgtgc tttcagcttc   21300
gatgtaggag ggcgtggata tgtcctgcgg gtaaatagct gcgccgatgg tttctacaaa   21360
gatcgttatg tttatcggca ctttgcatcg gccgcgctcc cgattccgga agtgcttgac   21420
attgggggaat tcagcgagag cctgacctat tgcatctccc gccgtgcaca gggtgtcacg   21480
ttgcaagacc tgcctgaaac cgaactgccc gctgttctgc agccggtcgc ggaggctatg   21540
gatgcgatcg ctgcggccga tcttagccag acgagcgggt tcggcccatt cggaccgcaa   21600
ggaatcggtc aatacactac atggcgtgat ttcatatgcg cgattgctga tccccatgtg   21660
tatcactggc aaactgtgat ggacgacacc gtcagtgcgt ccgtcgcgca ggctctcgat   21720
gagctgatgc tttgggccga ggactgcccc gaagtccggc acctcgtgca cgcggatttc   21780
ggctccaaca atgtcctgac ggacaatggc cgcataacag cggtcattga ctggagcgag   21840
gcgatgttcg gggattccca atacgaggtc gccaacatct tcttctggag gccgtggttg   21900
gcttgtatgg agcagcagac gcgctacttc gagcggaggc atccggagct tgcaggatcg   21960
```

```
ccgcggctcc gggcgtatat gctccgcatt ggtcttgacc aactctatca gagcttggtt   22020
gacggcaatt tcgatgatgc agcttgggcg cagggtcgat gcgacgcaat cgtccgatcc   22080
ggagccggga ctgtcgggcg tacacaaatc gcccgcagaa gcgcggccgt ctggaccgat   22140
ggctgtgtag aagtactcgc cgatagtgga aaccgacgcc ccagcactcg tccgagggca   22200
aaggaatagt gaggtacagc ttggatcgat ccggctgcta acaaagcccg aaaggaagct   22260
gagttggctg ctgccaccgc tgagcaataa ctagcataac cccttgggc ctctaaacgg    22320
gtcttgaggg gttttttgct gaaaggagga actatatccg gatgatcgtc gagg          22374
```

| SEQ ID NO: 4 | moltype = DNA  length = 22047 |
|---|---|
| FEATURE | Location/Qualifiers |
| misc_feature | 1..22047 |
| | note = synthesized DNA of PHP64613 |
| source | 1..22047 |
| | mol_type = other DNA |
| | organism = synthetic construct |

SEQUENCE: 4
```
cctcacgtgt taacagaagt tcctattccg aagttcctat tctctagaaa gtataggaac     60
ttccaccaca caacacaatg gcggccaccg cttccagaac caccegattc tcttcttcct    120
cttcacaccc caccttcccc aaacgcatta ctagatccac cctccctctc tctcatcaaa    180
ccctcaccaa acccaaccac gctctcaaaa tcaaatgttc catctccaaa cccccacgg    240
cggcgccctt caccaaggaa gcgccgacca cggagccctt cgtgtcacgg ttcgcctccg   300
gcgaacctcg caagggcgcg gacatccttg tggaggcgct ggagaggcag gcgtgacga    360
cggtgttcgc gtaccccggc ggtgcgtcga tggagatcca ccaggcgctc acgcgctccg   420
ccgccatccg caacgtgctc ccgcgccacg agcagggcgg cgtcttcgcc gccgaaggct   480
acgcgcgttc ctccggcctc cccggcgtct gcattgccac ctccgccccc ggcgccacca   540
acctcgtgag cggcctcgcc gacgctttaa tggacagcgt cccagtcgtc gccatcaccg   600
gccaggtcag ccgccggatg atcggcaccg acgccttcca agaaacccg atcgtggagg    660
tgagcagatc catcacgaag cacaaactac catcctcga cgtcgacgac atcccccgcg   720
tcgtcgccga ggctttcttc gtcgccacct ccggccgccc cggtccggtc ctcatcgaca   780
ttcccaaaga cgttcagcag caactcgccg tgcctaattg gacgagcccc gttaacctcc   840
ccggttacct cgccaggctg cccaggcccc ccgccgaggc ccaattggaa cacattgtca   900
gactcatcat ggaggcccaa aagcccgttc tctacgtcgg cggtgccagt ttgaattcca   960
gtgctgaatt gaggcgcttt gttgaactca ctggtattcc cgttgctagc actttaatgg  1020
gtcttggaac ttttcctatt ggtgatgaat attcccttca gatgctgggt atgcatggta  1080
ctgtttatgc taactatgct gttgacaata gtgatttgtt gcttgccttt ggggtaaggt  1140
ttgatgaccg tgttactggg aagcttgagg cttttgctag tagggctaag attgttcaca  1200
ttgatattga ttctgccgag attgggaaga acaagcaggc gcacgtgtcg gtttgcgcgg  1260
atttgaagtt ggccttgaag ggaattaata tgattttgga ggagaaagga gtggaggtta  1320
agtttgatct tggaggttgg agagaagaga ttaatgtgca gaaacacaag tttccattgg  1380
gttacaagac attccaggac gcgatttctc cgcagcatgc tatcgaggtt cttgatgagt  1440
tgactaatgg agatgctatt gttagtactg gggttgggca gcatcaaatg tgggctgcgc  1500
agttttacaa gtacaagaga ccgaggcagt ggttgacctc agggggtctt ggagccatgg  1560
gttttggatt gcctgcgggct attggtgctg ctgttgctaa ccctggggct gttgtggttg  1620
acattgatgg ggatggtagt ttcatcatga atgttcagga gttggccact ataagagtgg  1680
agaatctccc agttaagata ttgttgttga caatcagca tttgggtatg gtggttcagt   1740
gggaggatag gttctacaag tccaatagag ctcacaccta tcttggagat ccgtctagcg   1800
agagcgagat attcccaaac atgctcaagt tgctgatgc ttgtgggaca ccggcagcgc   1860
gagtgacgaa gaaggaagag cttagagcgg caattcagag aatgttggac accctggcc   1920
cctaccttct tgatgtcatt gtgccccatc aggagcatgt gttgccgatg attcccagta   1980
atggatcctt caaggatgtg ataactgagg gtgatggtag aacgaggtac tgactagcta   2040
gtcagttaac ctagacttgt ccatcttctg gattggccaa cttaattaat gtatgaaata  2100
aaaggatgca cacatagtga catgctaatc actataatgt gggcatcaaa gttgtgtgtt   2160
atgtgtaatt actagttatc tgaataaaag agaagagat catccatatt tcttatccta   2220
aatgaatgtc acgtgtcttt ataattcttt gatgaaccag atgcatttca ttaaccaaat   2280
ccatatacat ataaatatta atcatatata attaatatca attgggttag caaaacaaat   2340
ctagtctagg tgtgttttgc ccccaagctt atcgataccg tcggcgcggg gtacgttagc   2400
tgattaagtc agcatgcgcg gccggcgtat gaactaaaat gcatgtaggt gtaagagctc   2460
atggagagca tggaatattg tatccgacca tgtaacagta taataactga gctccatctc   2520
acttcttcta tgaataaaca aaggatgtta tgatatatta acactctatc tatgcacctt   2580
attgttctat gataaatttc ctcttattat tataaatcat ctgaatcgtg acggcttatg   2640
gaatgcttca aatagtacaa aaacaaatgt gtactataag actttctaaa caattctaac   2700
cttagcattg tgaacgagac ataagtgtta agaagacata acaattataa tggaagaagt   2760
ttgtctccat ttatatatta tatattaccc acttatgtat tatattagga tgttaaggag   2820
actaacaat ataaagaga gaagtttgta tccatttata tattatatac taccccattta   2880
tatattatac ttatccactt atttaatgtc tttataaggt ttgatccatg atatttctaa   2940
tatttagtt gatatgtata tgaaaggta ctatttgaac tctcttactc tgtataaagg    3000
ttggatcatc cttaaagtgg gtctatttaa ttttattgct tcttacagat aaaaaaaaaa   3060
ttatgagttg gtttgataaa atattgaagg atttaaaata ataataata acatataata   3120
tatgtatata aatttattat aatataacat ttatctataa aaaagtaaat attgtcataa   3180
atctatacaa tcgtttagcc ttgctggaac gaatctcaat tatttaaacg agagtaaaca   3240
tatttgactt tttggttatt taacaaatta ttatttaaca ctatatgaaa ttttttttt    3300
tatcagcaaa gaataaaatt aaattaagaa ggacaatggt gtcccaatcc ttatacaacc  3360
aacttccaca agaaagtcaa gtcagagaca acaaaaaaac aagcaaagga aattttttaa   3420
tttgttgt cttgtttgct gcataattta cagaatacac cactacacat aaccctttta    3480
gcagtgagc aatggttgac cgtgtgctta gcttctttta ttttattttt ttatcagcaa   3540
agaataaata aaataaaatg agacacttca gggatgtttc aacaggtacc catcacttaa   3600
gtggcgcgcc gtcgacggat ccgtacccat ctgcaggtaa attgcagctg aaggacagtg   3660
aagggtgaat ttatccattt aaaccatttt ctttttaaca catttcttat ggtaatctct   3720
tctcactaca ctataaaaat ggcttctcaa tcccattttc tacatcatcc cattctattg   3780
```

```
agttttgttt atttgctttc acttttttt  ttatctgcct cttcccttaa tttgcttgac  3840
ttcttcttca cattttgctt tgttttctcc tccggcttcc ggtatttcaa attcaagatg  3900
agcaagttga aatttataaa tagaaataca gatattattt acaacgtcaa atctttggta  3960
ttttcaatat ttgaatgggg taaatttgtc atatagtcat catcactgac tacttatcta  4020
acctatttaa tttggagcat attctttata aggtccctct cacggccaat gtctaattat  4080
tgatatacag ctcttgtttt ctagtgctgc ttataatatt atctacacat atatatggta  4140
ctgcacacta ctactatata gtagtaagta aactagcaac agccggggcc aaactccaat  4200
aactaggcat tggggtttag ttggtaatat aaatataaca tcaaaagtc tttgcttgtg  4260
acgaacatca caatgcaccc accattgatg ccacgacaga cattgttaat tttttttta  4320
attttaaaa aagaagcaat tccaatagtt ctatattaca atctcacgtg atccaagcac  4380
aacgtttcat ttttgtaca tgctcgatat ataataata tttcatttta tagtaaaata  4440
taatgacatt ttcgaatata attttgaaa tttcattttc caaatgaaat actaatatta  4500
atattaatga attaccaca aatcatgtta tgaatgaaat aaagagttt ggcattctaa  4560
ctttctttga atagaacaaa atgtatacaa cactctccat atatacacga tttattcagg  4620
gatcatatac attctctcat gattaacata gtctgctttc ttcacgtcta agcagataat  4680
ttttggtcca caagataaaa ttatcattag tcgttttaat taattcctg agcatcaagc  4740
actaaaataa ttaaacttct ccattaccaa aaaaaaaga taggtgattc agtaacatgt  4800
agtactagta ctactgattt tttttttctt ttgattttaa tgaatggttc gtatcgagca  4860
tcgagaaatc catttattag gtgtgtaatg taatagtagt atttccttga ttttcagtaa  4920
taagatggat tcttacattt atatctgttt gacagaaaat gttgtcaatg catttcttgg  4980
gcacaaagtt ttttgaaaca tgaattaatt ttttcaaaat atttatgaca tcaaattgac  5040
cctaaaataa gtgataaagc tttaacgtgg aatgacatta attttccat gataaataaa  5100
acacttaaaa cattttaata ttaatattat aatcagttac aactatgttc aattaatgca  5160
ataacttta aataaatatt aaaatatttt ttttctgttc tccaataaag agatcttgtt  5220
gcacggaaaa agtcacattc ttatttagta aaaaattata attattgttt gaaaaatatc  5280
attttcactg cagaaaattt gatccagctc tacagatcat actttattg tacaataata  5340
caataaaaat attcatctgc aggaaatatc attttcattg tacaataata taagataaa  5400
tataccag aaaagaaaaa gaaactgatg tggcacaatg tattcactga aagaatgcat  5460
attgtatttc acctttcaag cagcactaag aatatacttc ttttattata cttgtgcatt  5520
tactcaacca ccctcggtgg agtaagaaag aagtagata aaagttttt ttgacatttg  5580
gtgaatctct taattaaaa aataaaataa tccatttcct ttatttaatt tcttttttcc  5640
catctgtgaa attccaattc tgctcgcgc tcctgtctat aaattgactt agccaccacc  5700
tcagtttcca ttcattcact tcttctcttt atacccccc tctctttttt gcgttcattc  5760
tgttttcgta agtactgttg ttttttctt ctattttttt tttgtttgt gttgttttt  5820
tttcttcctt atcgttgttc tgcctctcct ctgtttcggt gctctgttca ccacttccac  5880
gtgagaatga tcttccttct ttgcatgttc attctctcgt gaccactgga tcagactcca  5940
tgttctgatc cagggtctct ctctaacgcc tgtactttca tccatgacca ccttaaaaac  6000
aacatggggg tggtgctgtt acactaactc tgtttctggg gtgctgtctt tgttcaattt  6060
tactcagaaa atatctttc ttggattcta ttcggtgtgt gggaacatga tcctgtcggt  6120
cggttgtttt taggttaatc cttaactggt tacaaggatc taacgcttga atgcatgtcc  6180
tgagttaaag aaacaaaaga agaacacacc tagtacagcc tggcctcgaa ccaagaactt  6240
ctttgttggt ttctcattat tactaaaata aaataaagta tacgttttct ttttctttg  6300
ggatgaacgg ttcagactta tgagaagttt aagctaatcc tgtagtggag tgttcaattt  6360
attttaaact ttaaagcaat agctcaagca ctaaacttct ttttcaagtt caaccacttt  6420
ggtagcttgc taattgctgc tattgttcta attaattaat gtaattattg tttaaaaaag  6480
aaaagttggt gacactggaa taaaaagtg tactatctgg caattattct tctgcagcaa  6540
tgtttgaggt tgaaatctta gtagaacaaa gtagaagatc tggtatttat attttttgta  6600
gacagatggt ggggggtggt ggtaggcctt gaaatccaat atagtttgt agaataattt  6660
tattatttt ttttttgct cacttgtttg tggtattgat tttgtgatga ctcaagatta  6720
atgatttacc ttcatttttt tcatggtgac atattatgta tattcttgat ctgtttctta  6780
cacttctttt tcgttgttgt agctgttgaa gtctgcggcc gcatgaagag gtctccagca  6840
tcttcttgtt catcatctac ttcctctgtt gggtttgaag ctcccattga aaaagaagg  6900
cctaagcatc caaggaggaa taatttgaag tcacaaaaat gcaagcagaa ccaaaccacc  6960
actggtggca gaagaagctc tatctataga ggagttacaa ggcataggtg gacagggagg  7020
tttgaagctc acctatggga taagagctct tggaacaaca ttcagagcaa gaagggtcgg  7080
caagtttatt tggggggcata tgatactgaa gaatctgcag cccgtaccta tgaccttgca  7140
gcccttaaat actggggaaa agatgcaacc ctgaatttcc cgatagaaac ttataccaag  7200
gagctcgagg aaatggacaa ggtttcaaga gaagaatatt tggcttcttt gcggcgccaa  7260
agcagtggct tttctagagg cctgtctaag taccgtgggg ttgctaggca tcatcataat  7320
ggtcgctggg aagcacgaat tggaagagta tgcggaaaca agtaccctca cttggggaca  7380
tataaaactc aagaggaggc agcagtggca tatgacatgg cagcaataga gtaccgtgga  7440
gtcaatgcag tgaccaattt tgacataagc aactacatgg acaaaataaa gaagaaaat  7500
gaccaaaccc aacaacaaca aacagaagca caaacgaaa cagttcctaa ctcctctgac  7560
tctgaagaag tagaagtaga taaagtaga acaacagaca acaacaccacc cccatctgaa  7620
aatctgcaca tgccaccaca gcagcaccaa gttcaataca ccccccatgt ctctccaagg  7680
gaagaagaat catcatcact gatcacaatt atggaccatg tgcttgagca ggatctgcca  7740
tggagcttca tgtacactgg cttgtctcag tttcaagatc caaacttggc tttctgcaaa  7800
ggtgatgatg acttggtggg catgtttgat agtgcagggt ttgaggaaga cattgattt  7860
ctgttcagca ctcaacctgg tgatgagact gagagtgata ttcaacaatat gacgcagtt  7920
ttggatagtg ttgagtgtgg agacacaaat ggggctggtg gaagcatgat gcatgtggat  7980
aacaagcaga gatagtatc atttgcttct tcaccatcat ctacaactac agtttcttgt  8040
gactatgctc tagatctatg agcggccgca tttcgcacca aatcaatgaa agtaataatg  8100
aaaagtctga ataagaatac ttaggcttag atgcctttgt tacttgtgta aaataacttg  8160
agtcatgtac ctttggcgga aacagaataa ataaatccaat gctctatgta  8220
taagttagta atacttaatg tgttctacgg ttgtttcaat atcatcaaac tctaattgaa  8280
acttagaac cacaaatctc aatctttct taatgaaatg aaaaatctta attgtaccat  8340
gtttatgtta aacccttac aattaattgg ttggagagga ggaccaaccg atgggacaac  8400
attgggagaa agagattcaa tggagatttg gataggagaa caacattctt tttcacttca  8460
atacaagatg agtgcaacac taaggatatg tatgagactt tcagaagcta cgacaacata  8520
```

```
gatgagtgag gtggtgattc ctagcaagaa agacattaga ggaagccaaa atcgaacaag   8580
gaagacatca agggcaagag acaggaccat ccatctcagg aaaaggagct ttgggatagt   8640
ccgagaagtt gtacaagaaa ttttttggag ggtgagtgat gcattgctgg tgactttaac   8700
tcaatcaaaa ttgagaaaga aagaaaaggg aggggggctca catgtgaata gaagggaaac   8760
gggagaattt tacagttttg atctaatggg catcccagct agtggtaaca tattcaccat   8820
gtttaacctt cacgtacgat ccatgccctt catttgccgc ttattaatta atttggtaac   8880
agtccgtact aatcagttac ttatccttcc cccatcataa ttaatcttgg tagtctcgaa   8940
tgccacaaca ctgactagtc tcttggatca taagaaaaag ccaaggaaca aaagaagaca   9000
aaacacaatg agagtatcct ttgcatagca atgtctaagt tcataaaatt caaacaaaaa   9060
cgcaatcaca cacagtggac atcacttatc cactagctga tcaggatcgc cgcgtcaaga   9120
aaaaaaaact ggaccccaaa agccatgcac aacaacacgt actcacaaag gtgtcaatcg   9180
agcagcccaa aacattcacc aactcaaccc atcatgagcc ctcacatttg ttgtttctaa   9240
cccaacctca aactcgtatt ctcttccgcc acctcatttt tgtttattc aacacccgtc   9300
aaactgcatg ccaccccgtg gccaaatgtc catgcatgtt aacaagacct atgactataa   9360
atagctgcaa tctcggccca ggttttcatc atcaagaacc agttcaatat cctagtacac   9420
cgtattaaag aatttaagat atactgcggc cgcatgacta tcgactcaca atactacaag   9480
tcgcgagaca aaaacgacac ggcacccaaa atcgcgggaa tccgatatgc cccgctatcg   9540
acaccattac tcaaccgatg tgagaccttc tctctggtct ggcacatttt cagcattccc   9600
actttcctca caattttcat gctatgctgc gcaattccac tgctctggcc atttgtgatt   9660
gcgtatgtag tgtacgctgt taaagacgac tcccgtcca acggaggagt ggtcaagcga   9720
tactcgccta tttcaagaaa cttcttcatc tggaagctct ttggccgcta cttcccccata   9780
actctgcaca agacggtgga tctgagccc acgcacacat actaccctct ggacgtccag   9840
gagtatcacc tgattgctga gagatactgg ccgcagaaca agtacctccg agcaatcatc   9900
accaccatcg agtactttct gcccgccttc atgaaacggt ctctttctat caacgagcag   9960
gagcagcctc ccgagcgaga tcctctcctg tctcccgttt ctcccagctc tccgggttct  10020
caacctgaca agtggattaa ccacgacagc agatatagcc gtggagaatc atctggctcc  10080
aacggccacg cctcgggctc cgaacttaac ggcaacggca acaacggcac cactaaccga  10140
cgacctttgt cgtccgcctc tgctggctcc actgcatctg attccacgct tcttaacggg  10200
tccctcaact cctacgccaa ccagatcatt ggcgaaaacg acccacagct gtcgcccaca  10260
aaactcaagc ccactggcag aaaatacatc ttcggctcac acccccacgg cattatccgc  10320
atgggagcct ttggtggaat tgccaccgag ggagctggat ggtccaagct ctttccgggc  10380
atccctgttt ctcttatgac tctcaccaac aacttccgag tgcctctcta cagagagtac  10440
ctcatgagtc tgggagtcgc ttctgtctcc aagaagtcct gcaaggccct cctcaagcga  10500
aaccagtcta tctgcattgt cgttggtgga gcacaggaaa gtcttctggc cagacccggt  10560
gtcatggacc tggtgctact caagcgaaag ggttttgttc gacttggtat ggaggtcgga  10620
aatgtcgccc ttgttcccat catggccttt ggtgagaacg acctctatga ccaggttagc  10680
aacgacaagt cgtccaagct gtaccgattc cagcagtttg tcaagaactt ccttggattc  10740
accccttcctt tgatgcatgc ccgaggcgtc ttcaactacg atgtcggtct tgtcccctac  10800
aggcgaaccg tcaacattgt ggttggttcc cccattgact tgccttatct ccacaccccc  10860
accgacgaag aagtgtccga ataccacgac cgatacatcg ccgagctgca gcgaatctac  10920
aacgagcaca aggatgaata tttcatcgat tggaccgagg agggcaaagg agccccagag  10980
ttccgaatga ttgagtaagc ggccgcaagt atgaactaaa atgcatgtag gtgtaagagc  11040
tcatggagag catggaatat tgtatccgac catgtaacga tataatact gagctccatc  11100
tcacttcttc tatgaataaa caaggatgt tatgatatat taacactcta tctatgcacc  11160
ttattgttct atgataaatt tcctcttatt attataaatc atctgaatcg tgacggctta  11220
tggaatgctt caaatagtac aaaaacaaat gtgtactata agactttcta aacaattcta  11280
accttagcat tgtgaacgag acataagtgt taagaagaca tcaaattat aatggaagaa  11340
gtttgtctcc atttatatat tatatattac ccactatgt attatattag gatgttaagg  11400
agacataaca attataaga gagaagtttg tatccattta tatattatat actacccatt  11460
tatatattat acttatccac ttatttaatg tctttataag gttgatcca tgatatttct  11520
aatattttag ttgatatgta tatgaaaagg tactatttga actctcttac tctgtataaa  11580
ggttggatca tccttaaagt gggtctattt aattttattg cttcttacag ataaaaaaaa  11640
aattatgagt tggtttgata aaatattgaa ggatttaaaa taataataaa taacatataa  11700
tatatgtata taaatttatt ataatataac atttatctat aaaaaagtaa atattgtcat  11760
aaatctatac aatcgtttag ccttgctgga acgaatctca attattttaaa cgagagtaaa  11820
catatttgac ttttttggtta tttaacaaat tattttttaa cactatatga aatttttttt  11880
tttatcagca aagaataaaa ttaaattaag aaggacaatg gtgtcccaat ccttatacaa  11940
ccaacttcca caagaaagtc aagtcagaga caacaaaaaa acaagcaaag gaatttttt  12000
aatttgagtt gtcttgtttg ctgcataatt tatgcagtaa aacactacac ataacccttt  12060
tagcagtaga gcaatggttg accgtgtgct tagcttcttt tatttattt ttttatcagc  12120
aaagaataaa taaaataaaa tgagacactt caggggatgtt tcaacgtact ttctagacgt  12180
acgtctttcc acaatacata actattaatt aatcttaaat aaaataaagga taaaatattt  12240
tttttcttc ataagttaa aatatgttat ttttgttta gatgtatatt cgaataaatc  12300
taaatatatg ataatgattt tttatattga ttaaacatat aatcaatatt aaatatgata  12360
ttttttata taggttgtac acataatttt ataaggataa aaaatatgat aaaatataat  12420
tttaaatatt tttatattta cgagaaaaaaa aaatatttta gccataaata aatgaccagc  12480
atattttaca accttagtaa ttcataaatt cctatatgta tatttgaaat taaaaacaga  12540
taatcgttaa gggaaggaat cctacgtcat ctcttgccat ttgttttca tgcaaacaga  12600
aagggacgaa aaaccacctc accatgaatc actcttcaca ccattttac tagcaaacaa  12660
gtctcaacaa ctgaagccag ctctcttcca gtttctttt acaacactt ctttgaaata  12720
gtagtatttt ttttcacatg atttattaac gtgccaaaag atgcttattg aatagagtgc  12780
acatttgtaa tgtactacta attagaacat gaaaagcat tgttctaaca cgataatcct  12840
gtgaaggcgt taactccaaa gatccaattt cactatataa attgtgacga aagcaaaatg  12900
aattcacata gctgagagag aaaggaaagg ttaactaaga aaatactt cagcggcccgc  12960
atgccgaatc ccgaggctca ccacccctcc cggtccgggg cccggccctc cacgtcagcc  13020
gcggcccgcc ccccggcccg ggcccgcgtc tccctccgcc agcttctgcg cgtggcatca  13080
gtcgcgagcg gcatccagtt cgggtgggcc ttacagctct ctctgctgac gccctacgtt  13140
cagcagctgg ggatcccca ccaatgggcc agcatcatct ggctctgcgg cccagtctcc  13200
ggcctcttcg tgcagcccct cgtcggccac atgagcgacc gctgcaccag ccgctacggc  13260
```

```
cgccgcaggc ccttcatcct cgtcggcgcc gtcgccatcg tcgccgctgt tctcgtcatc   13320
gcttacgccg ccgacatcgg ctggctcctc ggcgacaccg cggactaccg ccctgccgcc   13380
atcaccgtct tcatcgtcgg cttctggatc ctcgacgtcg ctaacaacgt cacgcaaggt   13440
ccctgccgtg ccttgctcgg tgatctcact agcaaggatc ctcgaggac acgtgttgca   13500
aatgcttatt actcactgtt tatggccatt ggtaacattc ttggctatgc aactggatca   13560
tatagtggtt ggtacaagat ttttactttt gcccttccc ctgcttgcac aattagttgt    13620
gcaaatctca agtctgcttt cttcttgac attgctttca ttgcggtcac aacatatatc    13680
agcatcatgg cagctcatga agtgcctcta aattcaagtg aggcggccca tgctgaagca   13740
ggggcagggg agtcaggtag tgcagaagaa gctttcatgt gggaattatt tgggacattc   13800
aaatattta caaccctgt atggataatt ctgtctgtta ctgctctgac atggattggg     13860
tggttcccat ttactctctt tgatactgat tggatgggtc gagagattta tggtggtgat   13920
ccaaatcaag gccttgttta tgatactgga gttagaatgg gagcacttgg tttgttgctt   13980
aattcagttg ttcttgcatt aacatcattg ttcatggaga ggctatgcag gaagagggga   14040
gctggttttg tgtggggaat ctcaaatatc atgatgaccg tttgcttct tgcaatgcta    14100
gtagtaacct atgtgcaaaa taacatgggc tatataggca aagatttacc accaactggc   14160
attgtgatag ctgcgttgat tatctttacc attcttgggt ttccactggc aatcacttat   14220
agtgttccat atgccttaat ttccacacat attgagtcat tgggactcgg ccaagggtta   14280
tcaatgggtg tcctaaatct ggcaatagtg gtcccacaga taatagtgtc actgggaagt   14340
ggaccatggg atcagctatt tggtggagga aactccccag cctttgctgt ggcagctgtt   14400
tcagcccta tcagtggact catagctgtg ttggctattc ctcgatctgg tgctcaaaag    14460
gctcgaagcc atgtatgagc ggccgcctga acgggaatta aacctataaa cataaatata   14520
aataaatat ataaacctaa gtgtctaagt tccataaatt aagctgtagt ctctggctta    14580
aaacatgtta ggtttgttta tacaagtagt tggatgtttg gagtacttcg gtcttttgcg   14640
taccatcaat atttaagaac taagttagtt atgttccgta acttatgggc tcttaattaa   14700
actatatctg cacaaaatta tatatatatc aaatgtgatg gtatgtggac tataaaaaga   14760
tatggttgag aaccacaaac tttgaaactt cgaataatat attgccagtg acagtcttgt   14820
tgatttgtta tagcaagtcc tattttctta atcattgctt tgttttaacg tacctagatt   14880
tcataacttt tgtctttgtc tcaagctgaa cctaatgatg atagtaatat taacttattg   14940
tataggggta tttcatagga taaaaaatga tgtgcaatta cgtgtagacc aaatattact   15000
tgatgacaga tggcctgcag gtcgactcga cgtacgtcct cgaagagagg ggttaataac   15060
acattttta acatttttaa cacaaatttt agttatttaa aaatttatta aaaatttaa     15120
aataagaaga ggaactctt aaatatctc aacttacaaa atttatgatt tttaataagt      15180
tttcaccaat aaaaaatgtc ataaaatat gttaaaaagt atattatcaa tattctcttt     15240
atgataaata aaaagaaaaa aaaataaaa gttaagtgaa aatgagattg aagtgacttt     15300
aggtgtgtat aaaatatca accccgccaa caattttattt aatccaaata tattgaagta    15360
tattattcca tagcctttat ttatttatat atttattata taaaagcttt atttgttcta    15420
ggttgttcat gaaatatttt tttggtttta tctccgttgt aagaaaatca tgtgctttgt    15480
gtcgccactc actattgcag cttttttcatg cattggtcag attgacggtt gattgtattt   15540
ttgttttta tggttttgtg ttatgactta agtcttcatc tctttatctc ttcatcaggt     15600
ttgatggtta cctaatatgg tccatgggta catgcatggt taaattaggt ggccaacttt    15660
gttgtgaacg atagaatttt ttttatatta agtaaactat ttttatatta tgaaataata   15720
ataaaaaaaa tatttttatca ttattaacaa aatcatatta gttaatttgt taactctata   15780
ataaaagaaa tactgtaaca cttcacattac atggtaacat ctttccaccc tttcatttgt   15840
ttttttgtttg atgactttt ttcttgttta aatttatttc ccttctttta aatttggaat    15900
acattatcat catatataaa ctaaaatact aaaaacagga ttacacaaat gataaataat    15960
aacacaaata tttataaatc tagctgcaat atatttaaac tagctatatc gatattgtaa    16020
aataaaacta gctcattga tactgataaa aaaatatact gtgcttttctg gactgatgat   16080
gcagtatact tttgacattg cctttatttt attttttcaga aaagctttct tagttctggg   16140
ttcttcatta tttgttccc atctccattg tgaattgaat catttgcttc gtgtcacaaa    16200
tacaatttag ntaggtacat gcattggtca gattcacggt ttattatgtc atgacttaag   16260
ttcatggtag tacattacct gccacgcatg cattatattg gttagatttg ataggcaaat   16320
ttggttgtca acaatataaa tataaataat gtttttatat tacgaaataa cagtgatcaa   16380
aacaaacagt tttatcttta ttaacaagat ttttgttttg tttgatgacg ttttttaatg   16440
tttacgcttt cccccttctt ttgaatttag aacactttat catcataaaa tcaaatacta   16500
aaaaaattac atattcata aataataaca caaatttttt taaaaaatct gaaataataa    16560
tgaacaatat tacatattat cacgaaaatt cattaataaa aatattatat aaataaaatg   16620
taatagtagt tatatgtagg aaaaaagtac tgcacgcata atatatcaa aaagattaaa    16680
atgaactatt ataaataata acactaaatt aatggtgaat catatcaaaa taatgaaaaa   16740
gtaaataaaa tttgtaatta acttctatat gtattacaca cacaaataat aaataatagt   16800
aaaaaaatt atgataaata tttaccatct cataagatat ttaaaataat gataaaaata   16860
tagattattt tttatgcaac tagctagcca aaaagagaac acgggtatat ataaaaagag    16920
taccttaaa ttctactgta cttcctttat tcctgacgtt tttatatcaa gtggacatac    16980
gtgaagattt taattatcag tctaaatatt tcattagcac ttaatacttt tctgttttat    17040
tcctatccta taagtagtcc cgattctccc aacattgctt attcacacaa ctaactaaga   17100
aagtcttcca tagccccca agcggccgct ctagaccacc taacatcacc accgttgttg    17160
ccaatgtcac caccgagcaa ttacccaagg ctcgtgaggg aagtgggcgt gccttcgtga   17220
cctttcttgc tggaaacggt gattatgtaa agggtgttgt gggtttggcc aaaggactga   17280
gaaaggccaa aagcatgtac ccttggtgg ttgctgtgtt accagatgtt cctgaagaac     17340
atcgtgcgat tctcaaatcc caaggttgca ttgtcaggga gattgaacct gtgtaccctc   17400
ctgagaacca gacccagttc gggatcccata ttacgtcatc aactattcca agctacgtat   17460
ttgggagttt gtggagttca gcaagatgat ataccctagac ggtgatatac aagtgtttga   17520
caatattgac cacttgtttg acttgcctga taactacttt tatgcggtga tggactgttt   17580
ttgtgagccc acttggggcc acactctgca gtcatgacct attgaaaacg tgcaagtcaa   17640
ccactcccac ctcgttcgct gaacaagatt tcttgaacat gtacttcaag gacattttca   17700
ggccaatccc tttaaattac aatccttgtcc tcgccatgct gtggcgccac ccggaaaacg   17760
ttaaattaga ccaagtcaag gttgttcact attgcgcagc ggggtccaag ccatggagat   17820
atacggggaa ggaagagaat atgcagaggg aggacataaa gatgctggtg aagaaatggt   17880
gggatatcta caatgatgct tcgcttgact acaagccatt gatgaatgca agtgaagctc   17940
cagcagcgga tggtgttgac attgaacaat tcgtgcaggc tctatcagag gttggtcatg   18000
```

```
ttcaatatgt caccgaattc tatgtcctcc ctctgcatat tctcttcctt ccccgtatat  18060
ctccatggct tggaccccgc tgcgcaatag tgaacaacct tgacttggtc taatttaacg  18120
tttccgggt ggcgccacag catggcgagg acaagattgt aatttaaagg gattggcttg   18180
taaatgtcct tgaagtacat gttcaagaaa tcttgttcag cgaacgaggt gggagtggtg  18240
acttgcaccg ttttcaatag gtcatgaaag cttacacaaa catgccagca ttgaaataga  18300
gaggaggctt gggcccaaag tgagtgggcc actgaacctt atgagggcac tgctggcagt  18360
atccgatttg atactgcaga gtgtggcccc aagtgggctc acaaaaacag tccatcaccg  18420
cataaaagta gttatcaggc aagtcaaaca agtggtcaat attgtcaaac acttgtatat  18480
caccgtctag gtatatcatc ttgctgaact ccacaaactc ccaaatacgt agcttggaat  18540
agttgatgac gtaatatgtc gaccgaactg ggtctggttc tcaggaggqt acacaggttc  18600
aatctccctg acaatgcaac cttgggattt gagaatctca cgatgttctt caggaacatc  18660
tggtaacaca gcaaccacca aagggtacat gcttttggcc tttctcagtc ctttggccaa  18720
acccacgaca cccttacgt aatcaccgtt cccagcaaga aagtcacga aggcacgccc   18780
acttcctcca cgagcctgg gtaattgctc ggtggtgaca ttggcaacaa cggtggtgat  18840
gttaggtggg cggccgcgac acaagtgtga gagtactaaa taaatgcttt ggttgtacga  18900
aatcattaca ctaaataaaa taatcaaagc ttatatatgc cttccgctaa ggccgaatgc  18960
aaagaaattg gttcttttctc gttatctttt gccacttttta ctagtacgta ttaattacta  19020
cttaatcatc tttgtttacg gctcattata tccggtctag gccaaggccg cgaagttaaa  19080
agcaatgttg tcacttgtac gtactaacac atgatgtgat agtttatgct agctagctat  19140
aacataagct gtctctgagt gtgttgtata ttaataaaga tcatcactgg tgaatggtga  19200
tcgtgtacgt accctactta gtaggcaatg gaagcactta gagtgtgctt tgtgcatggc  19260
cttgcctctg ttttgagact tttgtaatgt tttcgagttt aaatcttttgc ctttgcgtac  19320
gtgggcggat cccctgcagg gcatgcaagc ttggcgcgcc ggaattaatt aggtaatttc  19380
acgcgccgga tccttaatta agtctagagt cgactgttta attctagtgg ccggcctctg  19440
cctgcgttct gctgtggaag ttcctattcc gaagttccta ttctccagaa agtataggaa  19500
cttcacatgc tgcctcgtgc aagtcacgat cgagttct atagtgtcac ctaaatcgta   19560
tgtgtatgat acataaggtt atgtattaat tgtagccgcg ttctaacgac aatatgtcca  19620
tatggtgcac tctcagtaca atctgctctg atgccgcata gttaagccag ccccgacacc  19680
cgccaacacc cgctgacgcg ccctgacggg cttgtctgct cccggcatcc gcttacagac  19740
aagctgtgac cgtctccggg agctgcatgt gtcagaggtt ttcaccgtca tcaccgaaac  19800
gcgcgagacg aaagggcctc gtgatacgcc tattttttata ggttaatgtc atgaccaaaa  19860
tcccttaacg tgagttttcg ttccactgag cgtcagaccc cgtagaaaag atcaaaggat  19920
cttcttgaga tccttttttt ctgcgcgtaa tctgctgctt gcaaacaaaa aaaccaccgc  19980
taccagcggt ggttttgttg ccggatcaag agctaccaac tctttttccg aaggtaactg  20040
gcttcagcag agcgcagata ccaaatactg tccttctagt gtagccgtag ttaggccacc  20100
acttcaagaa ctctgtagca ccgcctacat acctcgctct gctaatcctg ttaccagtgg  20160
ctgctgccaa tggcgataag tcgtgtctta ccgggttgga ctcaagacga tagttaccgg  20220
ataaggcgca gcggtcgggc tgaacgggg gttcgtgcac acagcccagc ttggagcgaa   20280
cgacctacac cgaactgaga tacctacagc gtgagcattg agaaagcgcc acgcttcccg  20340
aagggagaaa ggcggacagg tatccggtaa gcggcagggt cggaacagga gagcgcacga  20400
gggagcttcc aggggaaac gcctggtatc tttatagtcc tgtcgggttt cgccacctct   20460
gacttgagcg tcgatttttg tgatgctcgt caggggggcg gagcctatgg aaaaacgcca  20520
gcaacgcggc ctttttacgg ttcctggcct tttgctgacc ttttgctcac atgttcttc   20580
ctgcgttatc ccctgattct gtggataacc gtattaccgc ctttgagtga gctgataccg  20640
ctcgccgcag ccgaacgacc gagcgcagcg agtcagtgag cgaggaagcg gaagagcgcc  20700
caatacgcaa accgcctctc cccgcgcgtt ggccgattca ttaatgcagg ttgatcagat  20760
ctcgatcccg cgaaattaat acgactcact atagggagac cacaacggtt tccctctaga  20820
aataattttg tttaacttta agaaggagat atacccatgg aaaagcctga actcaccgcg  20880
acgtctgtcg agaagtttct gatcgaaaag ttcgacagcg tctccgacct gatgcagctc  20940
tcggagggcg aagaatctcg tgctttcagc ttcgatgtag gagggcgtgg atatgtcctg  21000
cgggtaaata gctgcgccga tggtttctac aaagatcgtt atgtttatcg gcactttgca  21060
tcggccgcgc tcccgattcc ggaagtgctt gacattgggg aattcagcga gagcctgacc  21120
tattgcatct cccgccgtgc acagggtgtc acgttgcaag acctgcctga aaccgaactg  21180
cccgctgttc tgcagccggt cgcggaggct atggatgcga tcgctgcggc cgatcttagc  21240
cagacgagcg gttcggccc attcggaccg caaggaatcg gtcaatacac tacatggcgt  21300
gatttcatat gcgcgattgc tgatccccat gtgtatcact ggcaaactgt gatggacgac  21360
accgtcagtg cgtccgtcgc gcaggctctc gatgagctga tgctttggc cgaggactgc  21420
cccgaagtcc ggcacctcgt gcacgcggat ttcggctcca acaatgtcct gacggacaat  21480
ggccgcataa cagcggtcat tgactggagc gaggcgatgt tcggggattc ccaatacgag  21540
gtcgccaaca tcttcttctg gaggccgtgg ttggcttgta tggagcagca gacgcgctac  21600
ttcgagcgga ggcatccgga gcttgcagga tcgccgcggc tccgggcgta tatgctccgc  21660
attggtcttg accaactcta tcagagcttg gttgacggca atttcgatga tgcagcttgg  21720
gcgcagggtc gatgcgacgc aatcgtccga tcccggagccg gactgtcgg gcgtacacaa  21780
atcgcccgca gaagcgcggc cgtctggacc gatggctgtg tagaagtact cgccgatagt  21840
ggaaaccgac gccccagcac tcgtccgagg gcaaaggaat agtgaggtac agcttggatc  21900
gatccggctg ctaacaaagc ccgaaaggaa gctgagttgg ctgctgccac cgctgagcaa  21960
taactagcat aaccccttgg ggcctctaaa cgggtcttga ggggtttttt gctgaaagga  22020
ggaactatat ccgatgatc gtcgagg                                       22047
```

SEQ ID NO: 5         moltype = DNA  length = 4376
FEATURE              Location/Qualifiers
misc_feature         1..4376
                     note = synthesized DNA of PHP25066A
source               1..4376
                     mol_type = other DNA
                     organism = synthetic construct
SEQUENCE: 5
```
cgcgccaagc ttggatctcc tgcaggatct ggccggccgg atctcgtacg gatccgtcga  60
ctctagaggc cggccgatcc atgcccttca tttgccgctt attaattaat ttggtaacag  120
```

```
tccgtactaa tcagttactt atccttcccc catcataatt aatcttggta gtctcgaatg    180
ccacaacact gactagtctc ttggatcata agaaaaagcc aaggaacaaa agaagacaaa    240
acacaatgag agtatccttt gcatagcaat gtctaagttc ataaaattca aacaaaaacg    300
caatcacaca cagtggacat cacttatcca ctagctgatc aggatcgccg cgtcaagaaa    360
aaaaaactgg accccaaaag ccatgcacaa caacacgtac tcacaaaggt gtcaatcgag    420
cagcccaaaa cattcaccaa ctcaacccat catgagccct cacatttgtt gtttctaacc    480
caacctcaaa ctcgtattct cttccgccac ctcattttg tttatttcaa cacccgtcaa     540
actgcatgcc accccgtggc caaatgtcca tgcatgttaa caagacctat gactataaat    600
agctgcaatc tcggcccagg ttttcatcat caagaaccag ttcaatatcc tagtacaccg    660
tattaaagaa tttaagatat actgcggccg cgtcatcaac tattccaagc tacgtatttg    720
ggagtttgtg gagtacagca agatgatata cctagacggt gatatccaag tttttgacaa    780
cattgaccac ttgtttgact tgcctgataa ctacttctat gcggtgatgg actgtttctg    840
tgagccaact tggggccaca ctaaacaata tcagatcggt tactgccagc agtgccccca    900
taaggttcag tggcccactc actttgggcc caaacctcct ctctatttca atgctggcat    960
gtttgtgtat gagcccaatt tggctactta ccgtgacctc cttcaaacag tccaagtcac   1020
ccagcccact tcctttgctg aacaggattt tttgaacatg tacttcaagg acaaatatag   1080
gccaattcct aatgtctaca atcttgtgct ggccatgctg tggcgtcacc ctgagaacgt   1140
tgagcttgac aaagttaaag tggttcacta ctgtgctgct gggtctaagc cttggaggta   1200
cactgggaag tgactcgagg tcatcaatta ctccaagcta cgtatttggg agttcgtgga   1260
gtacaagaag acgatatacc tagacggtga catccaagta tttggaaaca tagaccactt   1320
gtttgatctg cctgataatt atttctatgc ggtgatggat tgtttctgcg agaagacttg   1380
gagccacacc cctcagttcc agattgggta ctgccaacag tgccctgata aggttcaatg   1440
gccctctcac tttggttcca aacctcctct atatttcaat gctggcatgt ttgtttatga   1500
gcctaatctc gacacctacc gtgatcttct ccaaactgtc caactcacca gcccacttc    1560
ttttgctgag caggactttc tcaacatgta cttcaaggac aagtacaagc caataccgaa   1620
catgtacaac cttgtgctgg ccatgttgtg gcgtcaccct gaaaatgttg aacttgataa   1680
agttcaagtg gttcattact gtgctgctgg gtctaagcct tggaggttca ctgggaagta   1740
actgcaggtc atcaactact ccaagctccg tatatgggag tttgtggagt acagcaagat   1800
gatatacttg gacggagaca ttgaggtata tgagaacata gaccacctat ttgacctacc   1860
tgatggtaac ttttacgctg tgatgggattg tttctgcgag aagacatgga gtcacacccc   1920
tcagtacaag gtgggttact gccagcaatg cccggagaag gtgcggtggc ccaccgaatt   1980
gggtcagccc ccttctcttt acttcaacgc tggcatgttc gtgttcgaac ccaacatcgc   2040
cacctatcat gacctattga aaacggtgca agtcaccact cccacctcgt tcgctgaaca   2100
agattccttg aacatgtact tcaaggacat ttacaagcca atcccttaa attacaatct    2160
tgtcctcgcc atgctgtggc gccaccggga aaacgttaaa ttagaccaag tcaaggttgt   2220
tcactattgc gcagcggggt ccaagccatg gagatatacg gggaagtagc ggccgcttgg   2280
ggggctatgg aagactttct tagttagttg tgtgaataag caatgttggg agaatcggga   2340
ctacttatag gataggaata aaacagaaaa gtattaagtg ctaatgaaat atttagactg   2400
ataattaaaa tcttcacgta tgtccacttg atataaaaac gtcaggaata aaggaagtac   2460
agtagaattt aaaggtactc tttttatata tacccgtgtt ctctttttgg ctagctagtt   2520
gcataaaaaa taatctatat ttttatcatt attttaaata tcttatgaga tggtaaatat   2580
ttatcataat ttttttttact attatttatt atttgtgtgt gtaatacata tagaagttaa   2640
ttacaattt tatttacttt ttcattattt tgatatgatt caccattaat ttagtgttaa    2700
tatttataat agttcatttt aatctttttg tatatattat gcgtgcagta cttttttcct   2760
acatataact actattacat tttatttata taatatttt attaatgaat tttcgtgata    2820
atatgtaata ttgttcatta ttatttcaga tttttttaaa atatttgtgt tattatttat   2880
gaaatatgta atttttttag tatttgattt tatgatgata aagtgttcta aattcaaaag   2940
aagggggaaa gcgtaaacat taaaaaacgt catcaaacaa aaacaaaatc ttgttaataa   3000
agataaaact gtttgtttg atcactgtta tttcgtaata taaaaacatt atttatattt    3060
atattgttga caaccaaatt tgcctatcaa atctaaccaa tataatgcat gcgtggcagg   3120
taatgtacta ccatgaactt aagtcatgac ataataaacc gtgaatctga ccaatgcatg   3180
tacctancta aattgtattt gtgacacgaa gcaaatgatt caattcacaa tggagatggg   3240
aaacaaataa tgaagaaccc agaactaaga aagcttttct gaaaaataaa ataaaggcaa   3300
tgtcaaaagt atactgcatc atcagtccag aaagcacatg atattttttt atcagtatca   3360
atgcagctag ttttattta caatatcgat atagctagtt taaatatatt gcagctagat    3420
ttataaatat ttgtgttatt atttatcatt tgtgtaatcc tgttttagt attttagttt    3480
atatatgatg ataatgtatt ccaaatttaa aagaagggaa ataaatttaa acaagaaaaa   3540
aagtcatcaa acaaaaaaca aatgaaaggg tggaagatg ttaccatgta atgtgaatgt     3600
tacagtatttt cttttattat agagttaaca aattaactaa tatgattttg ttaataatga   3660
taaaatattt tttttattat tatttcataa tataaaaata gtttacttaa tataaaaaaa   3720
attctatcgt tcacaacaaa gttggccacc taatttaacc atgcatgtac ccatggacca   3780
tattaggtaa ccatcaaacc tgatgaagag ataaagagat gaagacttaa gtcataacac   3840
aaaaccataa aaaacaaaaa tacaatcaac cgtcaatctg accaatgcat gaaaaagctg   3900
caatagtgag tggcgacaca aagcacatga tttttcttaca acggagataa aaccaaaaaa   3960
atatttcatg aacaacctag aacaaataaa gcttttatat aataaatata taataaata    4020
aaggctatgg aataatatac ttcaatatat ttggattaaa taaattgttg gcggggttga   4080
tatatttata cacacctaaa gtcacttcaa tctcattttc acttacttt tatttttttt    4140
ttcttttat ttatcataaa gagaatattg ataatatact tttaacata ttttatgac     4200
atttttatt ggtgaaaact tattaaaaat cataaatttt gtaagttaga tttatttaaa    4260
gagttcctct tcttatttta aatttttaa taaatttta aataactaaa atttgttta      4320
aaaatgttaa aaaatgtgtt attaacccttt ctcttcgagg acctgcaggt cgacgg       4376
```

SEQ ID NO: 6    moltype = DNA  length = 15128
FEATURE            Location/Qualifiers
misc_feature      1..15128
                    note = synthesized DNA of PHP64207A
source             1..15128
                    mol_type = other DNA
                    organism = synthetic construct

SEQUENCE: 6

```
cgcgccggta ccgggccccc cctcgagtgg cgttagctga ttaagtcagc atgcgcggcc    60
ggccgcaagc tctagtgaag ttcctatact ttctggagaa taggaacttc ggaataggaa   120
cttcaccggg atcatcagct gggccggccg gtacctcagc tgatgggtct agaactagaa   180
acgtgatgcc acttgttatt gaagtcgatt acagcatcta ttctgtttta ctatttataa   240
ctttgccatt tctgactttt gaaaactatc tctggatttc ggtatcgctt tgtgaagatc   300
gagcaaaaga gactttttgt ggacgcaatg gtccaaatcc gttctacatg aacaaattgg   360
tcacaatttc cactaaaagt aaataaatgg caagttaaaa aaggaatatg cattttactg   420
attgcctagg tgagctccaa gagaagttga atctcacacg ctaccaaccg ctaaaaaaag   480
aaaaacattg aatatgtaac ctgattccat tagcttttga cttcttcaac agattctcta   540
cttagatttc taacagaaat attattacta gcacatcatt ttcagtctca ctacagcaaa   600
aaatccaacg gcacaataca gacaacagga gatatcagac tacagagata gatagatgct   660
actgcatgta gtaagttaaa taaaaggaaa ataaaatgtc ttgctaccaa aactactaca   720
gactatgatg ctcaccacag gccaaatcct gcaactacga cagcattatc ttatatatat   780
tgtacaaaac aagcatcaag gaacatttgg tctaggcaat cagtacctcg ttctaccatc   840
accctcagtt atcacatcct tgaaggatcc attactggga atcatcggca acacatgctc   900
ctgatggggc acaatgacat caagaaggta ggggccaggg gtgtccaaca ttctctgaat   960
tgccgctcta agctcttcct tcttcgtcac tcgcgctgcc ggtatcccac aagcatcagc  1020
aaacttgagc atgtttggga atatctcgct ctcgctagac ggatctccaa gataggtgtg  1080
agctctattg gacttgtaga acctatcctc ccactgaacc accataccca aatgctgatt  1140
gttcaacaac aatatcttaa ctgggagatt ctccactctt atagtggcca actcctgaac  1200
attcatgatg aaactaccat ccccatcaat gtcaaccaca acagcccag ggttagcaac  1260
agcagcacca atagccgcag gcaatccaaa acccatggct ccaagacccc ctgaggtcaa  1320
ccactgcctc ggtctcttgt acttgtaaaa ctgcgcagcc cacatttgat gctgcccaac  1380
cccagtacta acaatagcat ctccattagt caactcatca agaacctcga tagcatgctg  1440
cggagaaatc gcgtcctgga atgtcttgta acccaatgga aacttgtgtt tctgcacatt  1500
aatctcttct ctccaacctc caagatcaaa cttaccctcc actccttcct cctccaaaat  1560
catattaatt cccttcaagg ccaacttcaa atccgcgcaa accgacacgt gcgcctgctt  1620
gttcttccca atctcggcag aatcaatatc aatgtgaaca atcttagccc tactagcaaa  1680
agcctcaagc ttcccagtaa cacggtcatc aaaccttacc ccaaaggcaa gcaacaaatc  1740
actattgtca acagcatagt tagcataaac agtaccatgc ataccagca tctgaaggga  1800
atattcatca ccaataggaa aagttccaag acccattaaa gtgctagcaa cgggaatacc  1860
agtgagttca acaaagcgcc tcaattcagc actggaattc aaactgccac cgccgacgta  1920
gagaacgggc ttttgggcct ccatgatgag tctgacaatg tgttccaatt gggcctcggc  1980
ggggggcctg ggcagcctgg cgaggtaacc gggagggtta acgggccgt cccaattagg  2040
cacggcgagt tgctgctgaa cgtctttggg aatgtcgatg aggaccggac cggggcggcc  2100
ggaggtggcg acgaagaaag cctcggcgac gacgcggggg atgtcgtcga cgtcgaggat  2160
gaggtagttg tgcttcgtga tggatctgct cacctccacg atcggggttt cttggaaggc  2220
gtcggtgcga atcatccggc ggctgacctg gccggtgatg gccgacgactg ggacgctgtc  2280
cattaaagcg tcggcgaggc cgctcacgag gttggtggcg ccggggccgg aggtggcaat  2340
gcagacgccg ggaggccgg aggaacgcgc gtagccttcg gcggcgaaga cgccgccctg  2400
ctcgtggcgc gggagcacgt tgcggatggc ggcggagcgc gtgagcgcct ggtggatctc  2460
catcgacgca ccgccggggt acgcgaacac cgtcgtcacg ccctgcctct ccagcgcctc  2520
cacaaggatg tccgcgccct tgcgaggttc gccggaggcg aaccgtgaca cgaagggctc  2580
cgtggtcggc gcttccttgg tgaagggcgc cgccgtgggg ggtttggaga tggaacattt  2640
gattttgaga gcgtggttgg gtttggtgag ggtttgatga gagagaggga gggtggatct  2700
agtaatgcgt ttggggaagg tgggtgtga agaggaagaa gagaatcggg tggttctgga  2760
agcggtggcc gccattgtgt tgtgtggtgg aagttcctat actttctaga gaataggaac  2820
ttcggaatag gaacttctgt tgttatactt caaaaactgc acaacaagcc tagagttagt  2880
acctaaacag taaatttaca acagagagca aagacacatg caaaaatttc agccataaaa  2940
aaagttataa tagaatttaa agcaaaagtt tcatttttta aacatatata caaacaaact  3000
ggatttgaag gaagggatta attcccctgc tcaaagtttg aattcctatt gtgacctata  3060
ctcgaataaa attgaagcct aaggaatgta tgagaaacaa gaaaacaaaa caaaactaca  3120
gacaaacaag tacaattaca aaattcgcta aaattctgta atcaccaaac ccatctcag   3180
tcagcacaag gcccaaggtt tattttgaaa taaaaaaaaa gtgattttat ttctcataag  3240
ctaaaagaaa gaaaggcaat tatgaaatga tttcgactag atctgaaagt caaacgcgta  3300
ttccgcagat attaaagaaa gagtagagtt tcacatggat cctagatgga cccagttgag  3360
gaaaagcaa ggcaaagcaa accagaagtg caagatccga aattgaacca cggaatctag   3420
gatttggtag agggagaaga aaagtacctt gagaggtaga agagaagaga agagcagaga  3480
gatatatgaa cgagtgtgtc ttggtctcaa ctctgaagcg atacagtttt agaggggagc  3540
attgagttcc aatttatagg gaacccgggt ggcaggggtg agtaatgac ggaaaagccc   3600
ctaagtaacg agattggatt gtgggttaga ttcaaccgtt tgcatccgcg gcttagattg  3660
gggaagtcag agtgaatctc aaccgttgac tgagttgaaa attgaatgta gcaaccaatt  3720
gagccaaccc cagccttttgc cctttgattt tgatttgttt gttgcatact tttttatttgt 3780
cttctggttc tgactctctt tctctcgttt caatgccagg ttgcctactc ccacaccact  3840
cacaagaaga ttctactgtt agtattaaat attttttaat gtattaaatg atgaatgctt  3900
ttgtaaacag aacaagacta tgtctaataa gtgtcttgca acattttta agaaattaaa   3960
aaaatatat ttattatcaa aatcaaatgt atgaaaaatc atgaataata taattttata   4020
catttttttta aaaatctttt taatttctta attaatatct taaaatataa gattaatatt  4080
taacccaaaa taattagtat gattggtaag gaagatatcc atgttatgtt tggatgtgag  4140
tttgatctag agcaaagctt gggaagggcg aattccagca cactggcggc cgttactagt  4200
gtttgatccc ctagacgtac gaaaccaact gcgtttgggg ctccagatta aacgacgccg  4260
tttcgttcct ttcgcttcac ggcttaacga tgtcgtttct gtctgtgccc aaaaaatata  4320
ggcatttgtt attgcacca gatatttact aagtgcccc atgtaggcgat taggcgat    4380
aattacaaat agatgcggtg caaataataa attttgaagg aataattac aaaagaacag   4440
aacttatatt tactttattt taaaaaacta aaatgaaaga acaaaaaaag taaaaaatac   4500
aaaaatgtg ctttaaccac tttcattatt tgttacagaa agtatgattc tactcaaatt    4560
gatctgttgt atctggtgct gccttgtcac actggcgatt tcaatcccct aaagatatgg  4620
tgcaaactgc gaagtgatca atatctgctc ggttaattta gattaattaa taatattcaa  4680
```

```
cgtgatgtac caaaaaaaga caattttttg ctccattgtc aaatttaaacc tcatcaaggt   4740
aatttccaaa cctataagca aaaaaatttc acattaattg gcccgcaatc ctattagtct   4800
tattatacta gagtaggaaa aaaaacaatt acacaacttg tcttattatt ctctatgcta   4860
atgaatattt ttcccttttg ttagaaatca gtgtttccta atttattgag tattaattcc   4920
actcaccgca tatatttacc gttgaataag aaaattttac acataattct ttttaagata   4980
aataattttt ttatactaga tcttatatga ttacgtgaag ccaagtgggt tatactaatg   5040
atatataatg tttgatagta atcagtttat aaaccaaatg catggaaatg ttacgtggaa   5100
gcacgtaaat taacaagcat tgaagcaaat gcagccaccg caccaaaacc accccacttc   5160
acttccacgt accatattcc atgcaactac aacaccctaa aacttcaata aatgccccca   5220
ccttcacttc acttcaccca tcaatagcaa gcggccgcac catggcgatt tccgatgagc   5280
ctgaaagtgt agccactgct ctcaaccact cttccctgcg ccgccgtccc tccgccacct   5340
ccaccgccgg cctcttcaat tcgcctgaga caaccaccga cagttccggt gatgacttgg   5400
ccaaggattc tggttccgac gactccatca acaacgacga cgccgccgtc aattcccaac   5460
agcaaaacga aaacaagac actgatttct ccgtcctcaa attcgcctac cgtccttccg   5520
tccccgctca ccgcaaagtg aaggaaagtc cgctcagctc cgacactatt ttccgtcaga   5580
gtcacgcggg cctcttcaac ctttgtatag tagtccttgt tgctgtgaat agccgactca   5640
tcattgagaa tttaatgaag tatggttggt tgatcaaatc tggcttttgg tttagtgcaa   5700
agtcattgag agactggccc cttttcatgt gttgtctttc tcttgtggta tttccttccg   5760
ctgcctttat ggtggagaag ttggcacaac ggaagtgtat acccgaacca gttgttgttg   5820
tacttcatat aatcattacc tcaacttcgc ttttctatcc agttttagtt attctcaagt   5880
gtgattctgc ttttgtatca ggtgtcacgt taatgctgtt tcttgtgtt gtatggttaa   5940
aattggtgtc ttttgcacat acaaactatg atatgagagc acttaccaaa ttagttgaaa   6000
agggagaagc actgctcgat actctgaaca tggagtatcc ttacaacgta accttcaaga   6060
gcttggcata tttcctgctt gcccctacat tatgttacca gccaagctat cctcgcacac   6120
cttatattcg aaagggttgg ttgtttcgcc aacttgtcaa gctgatagta tttacaggag   6180
ttatgggatt tataatagaa caatatatta atcccatagt acaaaattca cagcatcctc   6240
tcaagggaaa ccttctttac gccaccgaga gagttctgaa gctttctgtt ccaaatttat   6300
atgtgtggct ctgcatgttc tattgctttt tccacctttg gttaaaatatc gtggcagagc   6360
ttcttcgatt tggtgatcgt gaattctaca aggattggtg gaatgccaaa actgtcgaag   6420
attattggag gatgtggaat atgcctgttc acaaatggat gatccgccac ctatatttcg   6480
catgtttaag gcacggtcta ccaaaggctg ctgctctttt aatttccttc ctggtttctg   6540
ctttattcca tgagctgtgc attgctgttc cttgccacat gttcaagttg gggctttcg   6600
gtggaattat gtttcaggtt cctttggtct tgatcactaa ttatctgcaa aataaattca   6660
aaaactcaat ggttggaaat atgattttt ggttcatatt cagtatcgtt ggtcaaccta   6720
tgtgtgtact gctatactac catgacttga tgaataggaa aggcaaactt gactgagcgg   6780
ccgcgaagtt aaaagcaatg ttgtcacttg tacgtactaa cacatgatgt gatagtttat   6840
gctagctagc tataacataa gctgtctctg agtgtgttgt atattaataa agatcatcac   6900
tggtgaatgg tgatcgtgta cgtacccttac ttaggtaggca atggaagcac ttagagtgtg   6960
ctttgtgcat ggccttgcct ctgttttgag acttttgtaa tgttttcgag tttaaatctt   7020
tgcctttgcg tacgtctttc cacaatacat aactattaat taatcttaaa taaatatagg   7080
ataaaatatt tttttttctt cataaagtta aaatatgtta ttttttgttt agatgtatat   7140
tcgaataaat ctaaatatat gataatgatt ttttatattg attaaacata taatcaatat   7200
taaatatgat atttttttat ataggttgta cacatatttt ataaggata aaaaatatga   7260
taaaataaaa ttttaaatat ttttatattt acgagaaaaa aaaatatttt agccataaat   7320
aaatgaccag catatttac aaccttagta attcataaat tcctatatgt atatttgaaa   7380
ttaaaaacag ataatcgtta agggaaggaa tcctacgtca tctcttgcca tttgttttc   7440
atgcaaacag aaagggacga aaaaccacct caccatgaat cactcttcac accattttta   7500
ctagcaaaca agtctcaaca actgaagcca gctctcttc cgtttctttt tacaacactt   7560
tctttgaaat agtagtattt ttttttcacat gatttattaa cgtgccaaaa gatgcttatt   7620
gaatagagtg cacatttgta atgtactact aattagaaca tgaaaaagca ttgttctaac   7680
acgataatcc tgtgaaggcg ttaactccaa agatccaatt tcactatata aattgtgacg   7740
aaagcaaaat gaattcacat agctgagaga gaaaggaaag gttaactaag aagcaatact   7800
tcagcggccg catgccgaat cccgaggctc accaccccctc ccggtcccgg gcccggccct   7860
ccacgtcagc cgcggcccgc ccccccggcc gggcccgcgt ctccctccgc cagcttctgc   7920
gcgtggcagc agtcgcgagc ggcatccagt tcgggtgggc cttacagctc tctctgctga   7980
cgccctacgt tcagcagctg gggatccccc accaatgggc cagcatcatc tggctctgga   8040
gcccagtctc cggcctcttc gtgcagcccc tcgtcggcca catgagcgac cgctgcacca   8100
gccgctacgg ccgccgcagg cccttcatcc tcgtcggcgc cgtcgccatc gtcgcgctg   8160
ttctcgtcat cgcttacgcc gccgacatcg gctggctcct cggcgacaac gcggactacg   8220
gccctgccgc catcaccgtc ttcatcgtcg gcttctggat cctcgacgtc gctaacaacg   8280
tcacgcaagg tccctgccgt gccttgctcg gtgatctcac tagcaaggat cctcgaagga   8340
cacgtgttgc aaatgcttat tactcactgt ttatggccat tggtaacatt cttggctatg   8400
caactggatc atatagtggt tggtacaaga ttttactttt gccctttcc cctgcttgca   8460
caattagttg tgcaaatctc aagtctgctt tcttctgga cattgctttc attgcgtca   8520
caacatatat cagcatcatg gcagctcatg aagtgcctct aaattcaagt gaggcggccc   8580
atgctgaagc aggggcaggg gagtcaggta gtgcagaaga gctttcatg tgggaattat   8640
ttgggacatt caaatatttt acaaccctg tatggataat tctgtctgtt actgctctga   8700
catggattgg gtggttccca tttactctct ttgatactga ttggatgggt cgagagattt   8760
atggtggtga tccaaatcaa ggccttgttt atgatactgg agttagaatg ggagcacttg   8820
gtttgttgct taattcagtt gttcttgcat taacatcatt gttcatggag aggctatgca   8880
ggaagagggg agctggtttt tgtgtgggaa tctcaaatat catgatgacc gtttgctttc   8940
ttgcaatgct agtagtaacc tatgtggcaa ataacatggg ctatataggc aaagatttac   9000
caccaactgg cattgtgata gctgcgttga ttatcttac cattcttggg tttccactgg   9060
caatcactta gtgttcca tatgccttaa tttccacaca tattgagtca tgggactcg   9120
gccaaggggtt atcaatgggt gtcctaaatc tggcaatagt ggtcccacag ataatagtgt   9180
cactgggaag tggaccatgg gatcagctat tggtgaggg aaactcccca gcctttgctg   9240
tggcagctgt tcagcccctt atcagtgac tcatagctgt gttggctatt cctcgatctg   9300
gtgctcaaaa ggctcgaagc catgtatgag cggccgcctg aacgggaatt aaacctataa   9360
acataaatat aaataatata tataaaccta agtgtctaag ttccataaat taagctgtag   9420
```

```
tctctggctt aaaacatgtt aggtttgttt atacaagtag ttggatgttt ggagtacttc   9480
ggtcttttgc gtaccatcaa tatttaagaa ctaagttagt tatgttccgt aacttatggg   9540
ctcttaatta aactatatct gcacaaaatt atatatatat caaatgtgat ggtatgtgga   9600
ctataaaaag atatggttga gaaccacaaa ctttgaaact tcgaataata tattgccagt   9660
gacagtcttg ttgatttgtt atagcaagtc ctattttcct aatcattgct ttgttttaac   9720
gtacctagat ttcataactt ttgtctttgt ctcaagctga acctaatgat gatagtaata   9780
ttaacttatt gtataggggt attttcatag ataaaaaatg atgtgcaatt acgtgtagac   9840
caaatattac ttgatgacag atggcctgca ggatccatgc ccttcatttg ccgcttatta   9900
attaatttgg taacagtccg tactaatcag ttacttatcc ttcccccatc ataattaatc   9960
ttggtagtct cgaatgccac aacactgact agtctcttgg atcataagaa aaagccaagg  10020
aacaaaagaa gacaaaacac aatgagagta tcctttgcat agcaatgtct aagttcataa  10080
aattcaaaca aaaacgcaat cacacacagt ggacatcact tatccactag ctgatcagga  10140
tcgccgcgtc aagaaaaaaa aactggaccc caaaagccat gcacaacaac acgtactcac  10200
aaaggtgtca atcgagcagc ccaaaacatt caccaactca acccatcatg agccctcaca  10260
tttgttgttt ctaacccaac ctcaaactcg tattctcttc cgccacctca tttttgttta  10320
tttcaacacc cgtcaaactg catgccaccc cgtggccaaa tgtccatgca tgttaacaag  10380
acctatgact ataaatagct gcaatctcgg cccaggtttt catcatcaag aaccagttca  10440
atatcctagt acaccgtatt aaagaattta agatatactg agccgctag tcgactaagt  10500
catcaactat tccaagctac gtatttggga gtttgtggag tacagcaaga tgatatacct  10560
agacggtgat atccaagttt ttgacaacat tgaccacttg tttgacttgc ctgataacta  10620
cttctatgcg gtgatggact gttctgtga gccaacttgg ggccacacta aacaatatca  10680
gatcggttac tgccagcagt gcccccataa ggttcagtgg cccactcact ttgggcccaa  10740
acctcctctc tatttcaatg ctggcatgtt tgtgtatgag cccaatttgg ctacttaccg  10800
tgacctcctt caaacagtcc aagtcaccca gcccacttcc tttgctgaac aggattttt  10860
gaacatgtac ttcaaggaca aatataggcc aattcctaat gtctacaatc ttgtgctggc  10920
catgctgtgg cgtcaccctg agaacgttga gcttgacaaa gttaaagtgg ttcactactg  10980
tgctgctggg tctaagcctt ggaggtacac tgggaagtga ctcgaggtca tcaattactc  11040
caagctacgt atttgggagt tcgtggagta caagaagacg atatacctag acggtgacat  11100
ccaagtattt ggaaacatag accacttgtt tgatctgcct gataattatt tctatgcggt  11160
gatggattgt ttctgcgaga agacttggag ccacacccct cagttccaga ttgggtactg  11220
ccaacagtgc cctgataagg ttcaatggcc ctctcacttt ggttccaaac ctcctctata  11280
tttcaatgct ggcatgtttg tttatgagcc taatctcgac acctaccgtg atcttctcca  11340
aactgtccaa ctcaccaagc ccacttcttt tgctgagcag gactttctca acatgtactt  11400
caaggacaag tacaagccaa taccgaacat gtacaacctt gtgctggcca tgttgtgacg  11460
tcacctgaa aatgttgaac ttgataaagt tcaagtggtt cattactgtg ctgctgggtc  11520
taagccttgg aggttcactg ggaagtaact gcaggtcatc aactactcca agctccgtat  11580
atgggagttt gtggagtaca gcaagatgat atacttggac ggagacattg aggtatatga  11640
gaacatagac cacctatttg acctacctga tggtaacttt tacgctgtga tggattgttt  11700
ctgcgagaag acatggagtc acacccctca gtacaaggtg ggttactgcc agcaatgccc  11760
ggagaaggtg cggtggccca ccgaattggg tcagcccct tctctttact tcaacgctgg  11820
catgttcgtg ttcgaaccca acatcgccac ctatcatgac ctattgaaaa cggtgcaagt  11880
caccactccc acctcgttcg ctgaacaaga tttcttgaac atgtacttca aggacattta  11940
caagccaatc cctttaaatt acaatcttgt cctcgccatg ctgtggcgcc accggaaaa  12000
cgttaaatta gaccaagtca aggttgttca ctattgcgca gcggggtcca agccatggag  12060
atatacgggg aagtagccta ggcgtacgca ggtaagtttc tgcttctacc tttgatatat  12120
atataataat tatcattaat tagtagtaat ataatttttc aaatattttt ttcaaaataa  12180
aagaatgtag tatatagcaa ttgcttttct gtagtttata agtgtgtata ttttaattta  12240
taacttttct aatatatgac caaaacatgg tgatgtgcag gtcctaggct acttcccgt  12300
atatctccat ggcttggacc ccgctgcgca atagtgaaca accttgactt ggtctaatt  12360
aacgttttcc gggtggcgcc acagcatggc gaggacaaga ttgtaattta aagggattgg  12420
cttgtaaatg tccttgaagt acatgttcaa gaaatcttgt tcagcgaacg aggtgggagt  12480
ggtgacttgc accgttttca ataggtcatg ataggtggcg atgttgggtt cgaacacgaa  12540
catgccagcg ttgaagtaaa gagaaggggg ctgacccaat tcggtgggcc accgcacctt  12600
ctccgggcat tgctggcagt aacccacctt gtactgaggg gtgtgactcc atgtcttctc  12660
gcagaaacaa tccatcacag cgtaaaagtt accatcaggt aggtcaaata ggtggtctat  12720
gttctcatat acctcaatgt ctccgtccaa gtatatcatc ttgctgtact ccacaaactc  12780
ccatatacgg agcttggagt agttgatgac ctgcagttac ttcccagtga acctccaagg  12840
cttagaccca gcagcacagt aatgaaccac ttgaacttta tcaagttcaa catttcagg  12900
gtgacgccac aacatggcca gcacaaggtt gtacatgttc ggtattggct tgtacttgtc  12960
cttgaagtac atgttgagaa gtcctgctc agcaaaagaa ggggcttgg tgagttggac  13020
agtttggaga agatcacggt aggtgtcgag attaggctca taaacaaaca tgccagcatt  13080
gaaatataga ggaggtttgg aaccaaagtg agagggccat tgaaccttat cagggcactg  13140
ttggcagtac ccaatctgga actgagggt gtggctccaa gtcttctcgc agaaacaatc  13200
catcaccgca tagaaataat tatcaggcag atcaaacaag tgctctatgt ttccaaatac  13260
ttggatgtca ccgtctaggt atatcgtctt cttgtactcc acgaactccc aaatacgtag  13320
cttggagtaa ttgatgacct cgagtcactt cccagtgtac ctccaaggct tagacccagc  13380
agcacagtag tgaaccactt taactttgtc aagctcaacg ttctcagggt gacgccacag  13440
catggccagc acaagattgt agacattagg aattggccta tatttgtcct tgaagtacat  13500
gttcaaaaaa tcctgttcag caaaggaagt gggctgggtg acttggactg tttgaaggag  13560
gtcacggtaa gtagccaaat tgggctcata cacaaacatg ccagcattga aatagagagg  13620
aggtttgggc ccaaagtgag tgggccactg aaccttatgg gggcactgct ggcagtaacc  13680
gatctgtatt tgtttagtgt ggccccaagt tggctcacag aaacagtcca tcaccgcata  13740
gaagtagtta tcaggcaagt caaacaagtg gtcaatgttg tcaaaaactt ggatatcacc  13800
gtctaggtat atcatcttgc tgtactccac aaactcccaa atacgtagtt tggaatagtt  13860
gatgacttag tcgactagcg gccgcaagta tgaactaaaa tgcatgtagg tgtaagagct  13920
catggagagc atgaaatatt gtatccgacc atgtaacagt ataataactg agctccatct  13980
cacttcttct atgaataaac aaaggatgtt atgatatatt aacactctat ctatgcacct  14040
tattgttcta tgataaattt cctcttatta ttataaatca tctgaatcgt gacggcttat  14100
ggaatgcttc aaatagtaca aaaacaaatg tgtactataa gactttctaa acaattctaa  14160
```

```
ccttagcatt gtgaacgaga cataagtgtt aagaagacat aacaattata atggaagaag   14220
tttgtctcca tttatatatt atatattacc cacttatgta ttatattagg atgttaagga   14280
gacataacaa ttataaagag agaagtttgt atccatttat atattatata ctacccattt   14340
atatattata cttatccact tatttaatgt ctttataagg tttgatccat gatatttcta   14400
atattttagt tgatatgtat atgaaaaggt actatttgaa ctctccttact ctgtataaag  14460
gttggatcat ccttaaagtg ggtctcattta attttattgc ttcttacaga taaaaaaaaa  14520
attatgagtt ggtttgataa aatattgaag gatttaaaat aataataaat aacatataat   14580
atatgtatat aaatttatta taatataaca tttatctata aaaagtaaa tattgtcata    14640
aatctataca atcgtttagc cttgctggaa cgaatcctaca ttatttaaac gagagtaaac  14700
atatttgact ttttggttat ttaacaaatt attatttaac actatatgaa atttttttt    14760
ttatcagcaa agaataaaat taaattaaga aggacaatgg tgtcccaatc cttatacaac   14820
caacttccac aagaaagtca agtcagagac aacaaaaaaa caagcaaagg aaattttta    14880
atttgagttg tcttgtttgc tgcataattt atgcagtaaa acactacaca taaccctttt   14940
agcagtagag caatggttga ccgtgtgctt agcttctttt attttatttt tttatcagca   15000
aagaataaat aaaataaaat gagacacttc agggatgttt caacctgcag gtcgactcta   15060
gtaagctaaa caccggtgtt aattaggtaa tttcaccgcg tctagtgagc tcggtacccg   15120
ggtaccgg                                                            15128

SEQ ID NO: 7                moltype = DNA  length = 3965
FEATURE                     Location/Qualifiers
misc_feature                1..3965
                            note = synthesized DNA of PHP17522A
source                      1..3965
                            mol_type = other DNA
                            organism = synthetic construct
SEQUENCE: 7
ggtcgactct agtaagcttt gctctagatc aaactcacat ccaaacataa catggatatc    60
ttccttacca atcatactaa ttattttggg ttaaatatta atcattattt ttaagatatt   120
aattaagaaa ttaaaagatt ttttaaaaaa atgtataaaa ttatattatt catgattttt   180
catacattta attttgataa taaatatatt ttttttaatt tcttaaaaaa tgttgcaaga   240
cacttattag acatagtctt gttctgttta caaaagcatt catcatttaa tacattaaaa   300
aatatttaat actaacagta gaatcttctt gtgagtggtg tgggagtagg caacctggca   360
ttgaaacgag agaagagag tcagaaccag aagacaaata aaaagtatgc aacaaacaaa    420
tcaaaatcaa agggcaaagg ctgggggttgg ctcaattggt tgctacattc aatttttcaac  480
tcagtcaacg gttgagattc actctgactt ccccaatcta agccgcggat gcaaacggtt   540
gaatctaacc cacaatccaa tctcgttact taggggcttt tccgtcatta actcacccct   600
gccaccggt ttccctataa attggaactc aatgctcccc tctaaactcg tatcgcttca    660
gagttgagac caagacacac tcgttcatat atctctctgc tcttctcttc tcttctacct   720
ctcaaggtac ttttcttctc cctctaccaa atcctagatt ccgtggttca atttcggatc    780
ttgcacttct ggtttgcttt gccttgcttt ttcctcaact gggtccatct aggatccatg    840
tgaaactcta ctctttcttt aatatctgcg gaatacgcgt ttgactttca gatctagtcg   900
aaatcatttc ataattgcct ttcttctctt tagcttatga gaaataaaat cacttttttt   960
ttatttcaaa ataaaccttg ggccttgtgc tgactgagta ggggtttggt gattacagaa  1020
ttttagcgaa ttttgtaatt gtacttgttt gtctgtagtt ttgttttgtt ttcttgtttc   1080
tcatacattc cttaggcttc aattttattc gagtataggt cacaatagga attcaaactt   1140
tgagcagggg aattaatccc ttccttcaaa tccagttttgt ttgtatatat gtttaaaaaa  1200
tgaaactttt gcttttaaatt ctattataac ttttttttatg gctgaaattt ttgcatgtgt  1260
ctttgctctc tgttgtaaat ttactgtttta ggtactaact ctaggcttgt tgtgcagttt   1320
ttgaagtata accatgccac acaacacaat ggcggccacc gcttcagaa ccacccgatt    1380
ctcttcttcc tcttcacacc ccaccttccc caaacgcatt actagatcca cctcccctct   1440
ctctcatcaa accctcacca aacccaacca cgctctcaaa atcaaatgtt ccatctccaa   1500
accccccacg gcggcgccct tcaccaagga agcgccgacc acggagccct tcgtgtcacg   1560
gttcgcctcc ggcgaacctc gcaagggcgc ggacatcctt gtggaggcgc tggagaggca   1620
gggcgtgacg acggtgttcg cgtacccccgg cggtgcgtcg atggagatcc accaggcgct   1680
cacgcgctcc gcgcgccatc gcaacgtgct cccgcgccac gagcagggcg gcgtcttcgc   1740
cgccgaaggc tacgcgcgtt cctccggcct cccggcgtc tgcattgcca cctccggccc    1800
cggcgccacc aacctcgtga gcggcctcgc cgacgcttta atggacagcg tcccagtcgt   1860
cgccatcacc ggccaggtcg cccgccggat gatcggcacc gacgccttcc aagaaacccc   1920
gatcgtggag gtgagcagat ccatcacgaa gcacaactac ctcatcctcg acgtcgacga   1980
catccccgc gtcgtcgccg aggctttctt cgtcgccacc tccggccgcc ccggtccggt   2040
cctcatcgac attcccaaag acgttcagca gcaactcgcc gtgccctaatt gggacgagcc   2100
cgttaaccttc cccggttacc tcgccaggct gccaggccc ccgccgagg cccaattgga    2160
acacattgtc agactcatca tggagcccca aaagcccgtt ctctacgtcg gcggtggcag   2220
tttgaattcc agtgctgaat tgaggcgctt tgttgaactc atcggtattc ccgttgctgaa  2280
cactttaatg gtcttggaa cttttcctat tggtgatgaa tattcccttc agatgctggg   2340
tatgcatggt actgtttatg ctaactatgc tgttgacaat agtgatttgt tgcttgcctt   2400
tggggtaagg tttgatgacc gtgttactgg gaagcttgag gcttttgcta gtagggctaa   2460
gattgttcac attgatattg attctgccga gattgggaag aacaagcagg cgcacgtgtc  2520
ggtttgcgcg gatttgaagt tggccttgaa gggaaattaat atgatttttgg aggagaaagg  2580
agtggagggt aagtttgatc ttggaggttg gagagaagga attaatgtgc agaaacacaa  2640
gtttccattg ggttacaaga cattccagga gcgcatttct cccgcagcatg ctatcgaggt   2700
tcttgatgag ttgactaatg gagatgctat tgttagtact gggggttggggc agcatcaaat   2760
gtgggctgcg cagttttaca agtacaagag accgaggcag tggttgacct caggggtcct   2820
tggagcggt ggttttggat tgcctgcggc tattggtgct gttgctgcta accctgggc    2880
tgttgtggtt gacattgatg gggatggtag tttcatcatg aatgttcagg agttggccac   2940
tataagagtg gagaatctcc cagttaagat attgttgttg aacaatcagc atttgggtat    3000
ggtggttcag ttggaggata ggttctacaa gtccaataga gctcacacct atcttggaga  3060
tccgtctagc gagagcgaga tattcccaaa catgctcaag tttgctgatg cttgtgggat   3120
accggcagcg cgagtgacga agaaggaaga gcttagagcg gcaattcaga gaatgttgga   3180
```

```
cacccctggc ccctaccttc ttgatgtcat tgtgccccat caggagcatg tgttgccgat 3240
gattccagt aatggatcct tcaaggatgt gataactgag ggtgatggta gaacgaggta 3300
ctgattgcct agaccaaatg ttccttgatg cttgttttgt acaatatata taagataatg 3360
ctgtcctagt tgcaggattt ggcctgtggt gagcatcata gtctgtagta gttttggtag 3420
caagacattt tattttcctt ttatttaact tactacatgc agtagcatct atctatctct 3480
gtagtctgat atctcctgtt gtctgtattg tgccgttgga ttttttgctg tagtgagact 3540
gaaaatgatg tgctagtaat aatatttctg ttagaaatct aagtagagaa tctgttgaag 3600
aagtcaaaag ctaatggaat caggttacat attcaatgtt tttctttttt tagcggttgg 3660
tagacgtgta gattcaactt ctcttggagc tcacctaggc aatcagtaaa atgcatattc 3720
ctttttaac ttgccattta tttactttta gtggaaattg tgaccaattt gttcatgtag 3780
aacggatttg gaccattgcg tccacaaaac gtctcttttg ctcgatcttc acaaagcgat 3840
accgaaatcc agagatagtt ttcaaaagtc agaaatggca aagttataaa tagtaaaaca 3900
gaatagatgc tgtaatcgac ttcaataaca agtggcatca cgtttctagt tctagacccg 3960
ggtac                                                             3965

SEQ ID NO: 8           moltype = DNA   length = 6270
FEATURE                Location/Qualifiers
misc_feature           1..6270
                       note = synthesized DNA of PHP17734A
source                 1..6270
                       mol_type = other DNA
                       organism = synthetic construct
SEQUENCE: 8
cgcgccaagc ttggatccgc ccgatccctc aattcttcta agataaaaaa tttaacagca 60
atacttttta aacaaattca ttcaaaattg ttttgcaaat tgcatttgat aaataattta 120
atcaagtact tacgccacac caacttacaa caatgtcata cataaatcat agtgtgacat 180
tattgcgatt tttgtactga aaataatat ttttaaata tatgtacgaa ggcaaagagc 240
taaactttgt tgttctatct ctatttcaaa ttcttccttt ccatctctct tttttctttt 300
caattcaccc ttcacattct ctttcaattg aggaatggtt caacactacg tgcgataggc 360
taaatgtcac ttccacttta atataaataa aggatcatat tcttgtatca attgataaag 420
aaagtttttt tttcttcat gttttttatct gcctctaact actagtaagt gctattaatt 480
agagcttaag ttgcatagaa ttaaagagaa acatttgaga gttgagagat gattagcaat 540
aatttttaatc aataacttta atcaataact tttagtatat ttcgcatttg atttaactt 600
ttattatcct ttttcaaatt attctttcaa aatgatatca ttttaaatat taatacaaat 660
cttaacatca tttggaaggg ataacggaga dcaatttgg aagggataag agaagtcaat 720
ttcatcccca attagattaa tcgaccgttt atgtaagccc ctattgcacg agtggttgat 780
tgccacgtgt ccctaacact gtgttgaagc tcgttgcaaa cagacacgcg gcaattacg 840
gtaagacgat tagtccaata atcctcagaa acttgccacg cgtactgcac tgacacgtgt 900
gcaaaagata gcgccgcacc taaatctatt tatttgtag catgcggtgt gctgttgaaa 960
gaagaaagaa cctaagtgag aaacaaagaa aggaataat tgatctttga aaatgcaggg 1020
aggaaagaaa gctggaggcg gccgggctag agcggccgga gctggtcatc tcgctcatcg 1080
tcgagtcggc ggccggagct ggtcatctcg ctcatcgtcg agtcggcggc cgctgagctg 1140
atttaaatca ccactgtcaa aaccaccatc accgacgctc aagccaaggt cgccaccgat 1200
catggtcgtg cctacgtcac cttcctcgcc ggaaacggtg actatgtgaa aggtgtcgtt 1260
ggcttggcaa aaggtctgag aaaagtgaag agcatgtacc ctctggtggt tgcagtgcta 1320
cccgatgttc cccaagatca ccgcaacatt ctccctcccc aaggttgcat tgttagagag 1380
attgagcccg tgtacccccc agagaatcaa acccagtttg ccatgacata ttacgtcatc 1440
aactattcca agctacgtat ttgggagttt gtggagtaca gcaagatgat atacctagac 1500
ggtgatatcc aagtttttga caacattgac cacttgggat cgatcctgag ctgatttaaa 1560
ccaccgttgt tgccaatgtc accaccgagc aattacccaa ggctcgtgga ggaagtgggc 1620
gtgccttcgt gacctttctt gctgggaacg gtgattacgt aaagggtgtc gtgggtttga 1680
ccaaaggact gagaaaggcc aaagcatgt accctttgt ggttgctgtg ttaccagatg 1740
ttcctgaaga acatcgtgag attctcaaat cccaagggtt cattgtcagg gagattgaac 1800
ctgtgtaccc tcctgagaac cagacccagt tcgtcatggc ctattatgtc atcaattact 1860
ccaagctacg tatttgggag ttcgtggagt acaagaagac gatatccta gacggtgaca 1920
tccaagtatt tggaaacata gaccacttgt ttgatctgtg agctgattta gcggccgcc 1980
gactcgacga tgagcgagat gaccagctcc ggcgccgac tcgacgatga gcagatgac 2040
cagctccggc gcaagtatg aactaaaatg cacgtaggtg taagagctca tggagagcat 2100
ggaatattgt atccgaccat gtaacagtat aataactgag ctccatctca cttcttctat 2160
gaataaacaa aggatgttat gatatatta cactctatct atgcacctta tgttcatg 2220
ataaatttcc tcttattatt ataaatcatc tgaatcgtga cggcttatgg aatgcttcaa 2280
atagtacaaa aacaaatgtg tactataaga ctttctaaac aattctaact ttagcattgt 2340
gaacgagaca taagtgttaa gaagacataa caattataat ggaagaagtt tgtctccatt 2400
tatatattat atattaccca cttatgtatt attataggt gttaaggaga cataacaatt 2460
ataaagagag aagtttgtat ccatttatat attatatact acccatttat atattatact 2520
tatccactta tttaatgtct ttataaggtt tgatccatga tatttctaat attttagttg 2580
atatgtatat gaaagggtac tatttgaact ctcttactct gtataaaggt tggatcatcc 2640
ttaaagtggg tctattaat tttattgctt ttcacagata aaaaaaaat tatgagttgg 2700
tttgataaaa tattgaagga tttaaaataa taataata catataatat atgtatataa 2760
atttattata ataaacatt tatctataaa aaagtaaata ttgtcataaa tctatacaat 2820
cgtttagcct tgctgaccga atctcaatta tttaaacgag agtaaacata tttgactttt 2880
tggttattta acaaattatt atttaacact atatgaaatt tttttttta tcagcaaaga 2940
ataaaattaa attaaggagg acaatggtgt cccaatcctt ataccaaccaa cttccacaag 3000
aaagtcaagt cagagacaac aaaaaaacaa gcaaaggaaa tttttttaatt tgagttgtct 3060
tgtttgctgc ataatttatg cagtaaaaca ctacacataa ccctttagc agtaaagcaa 3120
tggttgaccg tgtgcttagc ttcttttatt ttatttttt atcagcaaag aataaataaa 3180
ataaaatgag acacttcagg gatgtttcaa cggatcctcg aagagaaggg ttaataacac 3240
atttttaac attttaaaca caaatttag ttatttaaa atttattaaa aaattttaaa 3300
taagaagagg aactctttaa ataaatctaa cttacaaaat ttatgatttt taataagttt 3360
```

```
tcaccaataa aaaatgtcat aaaaatatgt taaaaagtat attatcaata ttctctttat    3420
gataaataaa aagaaaaaaa aaataaaagt taagtgaaaa tgagattgaa gtgacttttag   3480
gtgtgtataa atatatcaac cccgccaaca atttatttaa tccaaatata ttgaagtata    3540
ttattccata gcctttattt atttatatat ttattatata aaagctttat ttgttctagg    3600
ttgttcatga aatattttt tggttttatc tccgttgtaa gaaaatcagt tgctttgtgt    3660
cgccactcac tattgcagct ttttcatgca ttggtcagat tgacggttga ttgtattttt    3720
gtttttatg gttttgtgtt atgacttaag tcttcatctc tttatctctt catcaggttt    3780
gatggttacc taatatggtc catgggtaca tgcatggtta aattaggtgg ccaactttgt    3840
tgtgaacgat agaattttt ttatattaag taaactattt ttatattatg aaataaataa    3900
aaaaaaaata ttttatcatt attaacaaaa tcatattagt taatttgtta actctataat    3960
aaaagaaata ctgtaacatt cacattacat ggtaacatct ttccaccctt tcatttgttt    4020
tttgtttgat gactttttt cttgtttaaa tttatttccc ttcttttaaa tttggaatac    4080
attatcatca tatataaact aaaatactaa aaacaggatt acacaaatga taaataataa    4140
cacaaatatt tataaatcta gctgcaatat atttaaacta gctatatcga tattgtaaaa    4200
taaaactagc tgcattgata ctgataaaaa aatatcatgt gctttctgga ctgatgatgc    4260
agtatacttt tgacattgcc tttatttat ttttcagaaa agctttctta gttctgggtt    4320
cttcattatt tgtttcccat ctccattgtg aattgaatca tttgcttcgt gtcacaaata    4380
caatttagnt aggtacatgc attggtcaga ttcacggttt attatgtcat gacttaagtt    4440
catggtagta cattacctgc cacgcatgca ttatattggt tagatttgat aggcaaattt    4500
ggttgtcaac aatataaata taaataatgt ttttatatta cgaaataaca gtgatcaaaa    4560
caaacagttt tatcttatt aacaagattt tgttttgtt tgatgacgtt ttttaatgtt    4620
tacgctttcc cccttctttt gaatttagaa cacttttaca tcataaaatc aaatactaaa    4680
aaaattacat atttcataaa taataacaca aatattttta aaaaatctga aataataatg    4740
aacaatatta catattatca cgaaaattca ttaaataaaa tattatataa ataaaatgta    4800
atagtagtta tatgtaggaa aaaagtactg cacgcataat atatacaaaa agattaaaat    4860
gaactattat aaaataac actaaaattaa tggtgaatca tatcatagt atgaaaaagt    4920
aaataaaatt tgtaattaac ttctatatgt attacacaca caaataataa ataatagtaa    4980
aaaaaattat gataaatatt taccatctca taagatattt aaaataatga taaaaatata    5040
gattattttt tatgcaacta gctagccaaa aagagaacac gggtatatat aaaaagagta    5100
cctttaaatt ctactgtact tccttttattc ctgacgtttt tatatcaagt ggacatacgt    5160
gaagatttta attatcagtc taaatatttc attagcactt aatactttc tgttttattc    5220
ctatcctata agtagtcccg attctcccaa cattgcttat tcacacaact aactaagaaa    5280
gtcttccata gccccccaag cggccggagc tggtcatctc gctcatcgtc gagtcggcgg    5340
ccggagctgg tcatctcgct catcgtcgag tcggcggccg ctgagtgatt gctcacgagt    5400
gtggtcacca tgccttcagc aagtaccaat gggttgatga tgttgtgggt ttgacccttc    5460
actcaacact tttagtccct tatttctcat ggaaaataag ccatcgccgc catcactcca    5520
acacaggttc ccttgaccgt gatgaagtgt ttgtcccaaa accaaaatcc aaagttgcat    5580
ggttttccaa gtacttaaac aaccctctag gaagggctgt ttctcttctc gtcacactca    5640
caataggtg gcctatgtat ttagcccttca atgtctctgg tagaccctat gatagttttg    5700
caagccacta ccacccttat gctcccatat attctaaccg tgagaggctt ctgatctatg    5760
tctctgatgt tgctttgttt tctgtgactt actctctcta ccgtgttgca accctgaaag    5820
ggttggtttg gctgctatgt gtttatgggg tgcctttgct cattgtgaac ggttttcttg    5880
tgactatcac atatttgcag cacacacact ttgccttgcc tcattacgat tcatcagaat    5940
gggactggct gaagggagct ttggcaacta tggacagaga ttaagcggcc gccgactcga    6000
cgatgagcga gatgaccagc tccggccgcc gactcgacga tgagcgagat gaccagctcc    6060
ggccgcgaca caagtgtgag agtactaaat aaatgctttg ttgtacgaa atcattacac    6120
taaataaaat aatcaaagct tatatatgcc ttccgctaag gccgaatgca aagaaattgg    6180
ttctttctcg ttatcttttg ccactttac tagtacgtat taattactac ttaatcatct    6240
ttgtttacgg ctcattatat ccgtcgacgg                                    6270

SEQ ID NO: 9           moltype = DNA  length = 6638
FEATURE                Location/Qualifiers
misc_feature           1..6638
                       note = synthesized DNA of PHP29252A
source                 1..6638
                       mol_type = other DNA
                       organism = synthetic construct
SEQUENCE: 9
cgcgccaagc ttggatcctc gaagagaagg gttaataaca catttttaa catttttaac     60
acaaatttta gttatttaaa aatttattaa aaaatttaaa ataagaagag gaactcttta   120
aataaatcta acttacaaaa tttatgattt ttaataagtt ttcaccaata aaaaatgtca   180
taaaaatatg ttaaaaagta tattatcaat attctcttta tgataaataa aagaaaaaa    240
aaaataaaag ttaagtgaaa atgagattga agtgactta ggtgtgtata aatatatcaa   300
ccccgccaac aatttattta atccaaatat attgaagtat agccttattt ttatatata    360
tatttatata tttattatat aaaagcttta tttgttctag gttgttcatg aaatattttt   420
ttggttttat ctccgttgta agaaaatcat gtgctttgtg tcgccactca ctattgcagc   480
tttttcatgc attggtcaga ttgacggttg attgtatttt tgtttttat ggttttgtgt    540
tatgacttaa gtcttcatct ctttatctct tcatcaggtt tgatggttac ctaatatggt   600
ccatgggtac atgcatggtt aaattaggtg gccaactttg ttgtgaacga tagaattttt   660
ttatattaa gtaaactatt tttatattat gaaataataa taaaaaaaat attttatcat    720
tattaacaaa atcatattag ttaatttgtt aactctataa taaagaaat actgtaacat    780
tcacattaca tggtaacatc tttccaccct ttcattgtt ttttgttga tgactttttt   840
tcttgtttaa atttatttcc cttcttttaa atttggaata cattatcatc atatataaac    900
taaaatacta aaaacaggat tacacaaatg ataaataataa acacaaatat ttataaatct    960
agctgcaata tatttaaact agctatatcg atattgtaaa ataaaactag ctgcattgat   1020
actgataaaa aatatcatg tgctttctgg actgatgatg cagtatactt tgacattgc    1080
cttttattta ttttcagaa aagctttctt agttctgggt tcttcattat ttgtttccca    1140
tctccattgt gaattgaatc atttgcttcg tgtcacaaat acaatttagn taggtacatg   1200
cattggtcag attcacggtt tattatgtca tgacttaagt tcatggtagt acattacctg   1260
```

```
ccacgcatgc attatattgg ttagatttga taggcaaatt tggttgtcaa caatataaat   1320
ataaataatg ttttatatt acgaaataac agtgatcaaa acaaacagtt ttatctttat   1380
taacaagatt ttgttttgt ttgatgacgt tttttaatgt ttacgctttc cccttctt    1440
tgaatttaga acactttatc atcataaaat caaatactaa aaaattaca tatttcataa   1500
ataataacac aaatatttt aaaaaatctg aaataataat gaacaatatt acatatatc   1560
acgaaaattc attaataaaa atattatata aataaaatgt aatagtagtt atatgtagga   1620
aaaaagtact gcacgcataa tatatacaaa aagattaaaa tgaactatta taaataataa   1680
cactaaatta atggtgaatc atatcaaaat aatgaaaaag taaataaaat ttgtaattaa   1740
cttctatatg tattacacac acaaataata aataagta aaaaaaatta tgataaatat   1800
ttaccatctc ataagatatt taaaataatg ataaaaatat agattatttt ttatgcaact   1860
agctagccaa aaagagaaca cgggtatata taaaaagagt acctttaaat tctactgtac   1920
ttcctttatt cctgacgttt ttatatcaag tggacatacg tgaagatttt aattatcagt   1980
ctaaatattt cattagcact taatacttt ctgttttatt cctatcctat aagtagtccc   2040
gattctccca acattgctta ttcacacaac taactaagaa agtcttccat agccccccaa   2100
gcggccgcta gtcgactaag tcatcaacta ttccaagcta cgtatttggg agtttgtgga   2160
gtacagcaag atgatatacc tagacggtga tatccaagtt tttgacaaca ttgaccactt   2220
gtttgacttg cctgataact acttctatgc ggtgatggac tgtttctgtg agccaacttg   2280
gggccacact aaacaatatc agatcggtta ctgccagcag ctgccccata aggttcagtg   2340
gcccactcac tttgggccca aacctcctct ctatttcaat gctggcatgt ttgtgtatga   2400
gcccaatttg gctacttacc gtgacctcct tcaaacagtc caagtcaccc agcccacttc   2460
cttttgctgaa caggattttt tgaacatgta cttcaaggac aaatataggc caattcctaa   2520
tgtctacaat cttgtgctgg gcgtcaccct agaaccgttg agcttgacaa             2580
agttaaaagtg gttcactact gtgctgctgg gtcaagcct tggaggtaca ctgggaagtg   2640
actcgaggtc atcaattact ccaagctacg tattgggag ttcgtggagt acaagaagac   2700
gatatacctta gacggtgaca tccaagtatt tggaaacata gaccacttgt ttgatctgcc   2760
tgataattat ttctatgcgg tgatggattg ttttctgcga agacttgga gccacaccct   2820
tcagttccag attgggtact gccaacagtg ccctgataag gttcaatggc cctctcactt   2880
tggttccaaa cctcctctat atttcaatgc tggcatgttt gtttatgagc ctaatctcga   2940
cacctaccgt gatcttctcc aaactgtcca actcaccaag cccacttctt ttgctgagca   3000
ggactttctc aacatgtact tcaaggacaa gtacaagcca atacgaaaca tgtacaacct   3060
tgtgctggcc atgttgtggc gtcacccctga aatgttgaa cttgataaag ttcaagtggt   3120
tcattactgt gctgctgggt ctaagccttg gaggttcact gggaagtaac tgcaggtcat   3180
caactactcc aagctccgta tatgggagtt tgtggagtac agcaagatga tatacttgga   3240
cggagacatt gaggtatatg agaacataga ccacctattt gacctacctg atggtaactt   3300
ttacgctgtg atggattgtt tctgcgagaa gacatggagt cacacccctc agtacaaggt   3360
gggtactgc cagcaatgcc cggagaaggt gcggtggccc accgaattgg gtcagccccc   3420
ttctctttac ttcaacgctg gcatgttcgt gttcgaaccc aacatcgcca cctatcatga   3480
cctattgaaa acggtgcaag tcaccactcc cacctcgttc gctgaacaag atttcttgaa   3540
catgtacttc aaggacattt acaagccaat ccttaaat taccaatcttg tcctcgccat   3600
gctgtggcgc cacccggaaa acgttaaatt agaccaagtc aaggttgttc actattgcgc   3660
agcgggtcc aagccatgga gatatacggg gaagtagcct aggtgagctg atttaagatt   3720
tatcaaaagt tggggttaca aattttggaa gcttcagtgt ggaagtaata gacccagttt   3780
ctgactatct ggagctattg gagacagtat ttgattttca gctaatcaga ggtcttcttt   3840
cacgtccaga ttttaggttt atatttgatg ccatgcatgc agttactggt gcttatgcta   3900
aacccatctt cgttgataaa ctcggtgcta gtctggattc aatttcaaat ggaatccctt   3960
tggaagattt tggacatggc catcctgatc ctaatctaac atatgcgaag gatcttgtcg   4020
acattctgta tgctgaaaat ggacctgatt ttggagctgc cagtgatggg gatggtgata   4080
gaaatatgat tttaggaaga gtttcttttg taactcctt agactctgta gcagttattg   4140
cagcaaatgc aagagaagcg attccatact tcaagaacgg tgttaagggt cttgctcgat   4200
caatgccaac aagcggtgct ctggaccgtg ctgctaaaaa attgaacctc cctttctgag   4260
ctgatttaac gtacgcaggt aagtttctgc ttctaccttt gatatata taataattat   4320
cattaattag tagtaatata atatttcaaa tatttttttc aaaataaaag aatgtagtat   4380
atagcaattg ctttttctgta gtttataagt gtgtatttt taatttataa cttttctaat   4440
atatgaccaa aacatggtga tgtgcaggtc ctgcaggtta aatcagctca gaaagggagg   4500
ttcaattttt tagcagcacg gtccagagca ccgcttgttg gcattgatcg agcaagaccc   4560
ttaacaccgt tcttgaagta tggaatcgct tctcttgcat tggctgcaat aactgctaca   4620
gagtctgaag gagttacaaa gaacttctt cctaaaatca tatttctatc accatcccca   4680
tcactggcag ctccaaaatc aggtccattt tcagcataca gaatgtcgac aagatccttc   4740
gcatatgtta gattaggatc aggatggcca tgtccaaaat cttccaaagg gattccattt   4800
gaaattgaat ccagatagc accgagttta tcaacgaaga tgggttttagc ataagcacca   4860
gtaactgcat gcatgcatc aaatataaac ctaaaatctg gacgtgaaag aagacctctg   4920
attagctgaa aatcaaatac tgtctccaat agctccagat agtcagaaac tgggtctatt   4980
acttccacac tgaagcttcc aaaattttgta accccaactt ttgataaaatc ttaaaatcagc   5040
tcacctaggc tacttcccg tatatctcca tggcttgaac cccgctgcgc aataagtaac   5100
aaccttgact tggtctaatt taacgttttc cgggtggcgc cacagcatgg cgaggacaag   5160
attgtaattt aaagggattg gcttgtaaat gtccttgaag tacatgttca agaaatcttg   5220
ttcagcgaac gaggtgggag tggtgacttg caccgttttc aataggtcat gataggtggc   5280
gatgttgggt tcgaacacga acatgccagc gttgaagtaa agagaaggggg gctgacccaa   5340
ttcggtggc caccgcacct tctccgggca ttgctggcag taaacccacct tgtactgagg   5400
ggtgtgactc catgtcttct cgcagaaaca atccatcaca gcgtaaaagt taccatcagg   5460
taggtcaaat aggtggtcta tgttctcata taccttcaatg tctccgtcca agtatatcat   5520
cttgctgtac tccacaaact cccatatacg gagcttggag tagttgatga cctgcagtta   5580
cttcccagtg aacctccaag gcttagaccc agcagcacag taatgaacca cttgaacttt   5640
atcaagttca acatttcag ggtgacgcca caacatggcc agcacaaggt tgtacatgtt   5700
cggtattggc ttgtacttgt ccttgaagta catgtgaga agtcctgct cagcaaaaga   5760
agtgggcttg gtgagttgga cagtttggag aagatcacgg taggtgtcga gattaggctc   5820
ataaacaaac atgccagcat tgaaatatag aggaggtttg gaaccaaagt gagagggcca   5880
ttgaacctta tcagggcact gttggcagta cccaatctgg aactgaggg tgtggctcca   5940
agtcttctcg cagaaacaat ccatcaccgc atagaaataa ttatcaggca gatcaaacaa   6000
```

```
gtggtctatg tttccaaata cttggatgtc accgtctagg tatatcgtct tcttgtactc   6060
cacgaactcc caaatacgta gcttggagta attgatgacc tcgagtcact tcccagtgta   6120
cctccaaggc ttagacccag cagcacagta gtgaaccact ttaactttgt caagctcaac   6180
gttctcaggg tgacgccaca gcatggccag cacaagattg tagacattag gaattggcct   6240
atatttgtcc ttgaagtaca tgttcaaaaa atcctgttca gcaaaggaag tgggctgggt   6300
gacttggact gtttgaagga ggtcacggta agtagccaaa ttgggctcat acacaaacat   6360
gccagcattg aaatagagag gaggtttggg cccaaagtga gtgggccact gaaccttatg   6420
ggggcactgc tggcagtaac cgatctgata ttgtttagtg tggccccaag ttggctcaca   6480
gaaacagtcc atcaccgcat agaagtagtt atcaggcaag tcaaacaagt ggtcaatgtt   6540
gtcaaaaact tggatatcac cgtctaggta tatcatcttg ctgtactcca caaactccca   6600
aatacgtagc ttggaatagt tgatgactta gtcgacgg                           6638

SEQ ID NO: 10       moltype = DNA  length = 3984
FEATURE             Location/Qualifiers
misc_feature        1..3984
                    note = synthesized DNA of PHP19031A
source              1..3984
                    mol_type = other DNA
                    organism = synthetic construct
SEQUENCE: 10
cgcgccaagc ttggatccta gaactagaaa cgtgatgcca cttgttattg aagtcgatta   60
cagcatctat tctgttttac tatttataac tttgccattt ctgactttttg aaaactatct  120
ctggatttcg gtatcgcttt gtgaagatcg agcaaaagag acgttttgtg gacgcaatgg  180
tccaaatccg ttctacatga acaaattggt cacaatttcc actaaaagta aataaatggc  240
aagttaaaaa aggaatatgc attttactga ttgcctaggt gagctccaag agaagttgaa  300
tctacacgtc taccaaccgc taaaaaaaga aaaacattga tatgtaacct gattccatta  360
gcttttgact tcttcaacag attctctact tagatttcta acagaaatat tattactagc  420
acatcatttt cagtctcact acagcaaaaa atccaacggc acaatacaga caacaggaga  480
tatcagacta cagagataga tagatgctac tgcatgtagt aagttaaata aaggaaaat   540
aaaatgtctt gctaccaaaa ctactacaga ctatgatgct caccacaggc caaatcctgc  600
aactaggaca gcattatctt atatatattg tacaaaacaa gcatcaagga acatttggtc  660
taggcaatca gtacctcgtt ctaccatcac cctcagttat cacatcctgt aaggatccat  720
tactgggaat catcggcaac acatgctcct gatgggggcac aatgacatca agaaggtagg  780
ggccagggggt gtccaacatt ctctgaattg ccgctctaag ctcttccttc ttcgtcactc  840
gcgctgccgg tatcccacaa gcatcagcaa acttgagcat gtttgggaat atctcgctct  900
cgctagacgg atctccaaga taggtgtgag ctctattgga cttgtagaac ctatcctcca  960
actgaaccac catacccaaa tgctgattgt tcaacaacaa tatcttaact gggagattct  1020
ccactcttat agtggccaac tcctgaacat tcatgatgaa actaccatcc ccatcaatgt  1080
caaccacaac agcccaggg ttagcaacag cagcaccaat agccgcaggc aatccaaaac  1140
ccatggctcc aagaccccct gaggtcaacc actgcctcgg tctcttgtac ttgtaaaact  1200
gcgcagccca catttgatgc tgcccaaccc cagtactaac aatagcatct ccattagtca  1260
actcatcaag aacctcgata gcatgctgcg gagaaatcgc gtcctggaat gtcttgtaac  1320
ccaatgaaga cttgtgtttc tgcacattaa tctcttctct ccaacctcca agatcaaact  1380
tacccctccac tcctttctcc tccaaaatca tattaattcc cttcaaggcc aacttcaaat  1440
ccgcgcaaac cgacacgtgc gcctgcttgt tctttcccaat ctcggcagaa tcaatatcaa  1500
tgtgaacaat cttagcccta ctagcaaaag cctcaagctt cccagtaaca cggtcatcaa  1560
accttacccc aaaggcaagc aacaaatcac tattgtcaac agcatagtta gcataaacag  1620
taccatgcat acccagcatc tgaagggaat attcatcacc aataggaaaa gttccaagac  1680
ccattaaagt gctagcaacg ggaataccag tgagttcaac aaagcgcctc aattcagcac  1740
tggaattcaa actgccaccg ccgacgtaga aacgggcttt tgggcctcc atgatgagtc   1800
tgacaatgtg ttccaattgg gcctcggcgg ggggcctggg cagcctggcg aggtaaccgg   1860
ggaggttaac gggctcgtcc caattaggca cggcgagttg ctgctgaacg tctttgggaa   1920
tgtcgatgag gaccggaccg gggcggccgg aggtggcgac gaagaaagcc tcggcgacga   1980
cgcgggggat gtcgtcgacg tcgaggatga ggtagttgtg cttcgtgatg gatctgctca   2040
cctccacgat cggggtttct tggaaggcgat cggtgccgat catccggcgg cgacctggc   2100
cggtgatggc gacgactggg acgctgtcca ttaaagcgtc ggcgaggccg ctcacgaggt   2160
tggtggcgcc ggggccggag gtggcaatgc agacgccggg gaggccggag aacgcgcgt   2220
agccttcggc ggcgaagacg ccgccctgct cgtggcgcgg gagcacgttg cggatggcgg   2280
cggagcgcgt gagcgcctgg tggatctcca tcgacgcacc gccggggtac gcgaacacgt   2340
tcgtcacgcc ctgcctctcc agcgcctcca caaggatgtc cgccccttg cgaggttcgc   2400
cggaggcgaa ccgtgacacg aagggctccg tggtcggcgc ttccttggtg aagggcgccg   2460
ccgtggggggg tttggagatg aacatttga ttttgagagc gtggttgggt ttggtgaggg   2520
tttgatgaga gagagggagg gtggatctag taatgcgttt ggggaaggtg gggtgtgaag   2580
aggaagaaga gaatcgggtg gttctggaag cggtggccgc cattgtgttg tgtggcagga   2640
ttatacttca aaaactgcac aacaagccta gagttagtac ctaaacagta aatttacaac   2700
agagagcaaa gacacatgca aaatttcag ccataaaaaa agttataata gaatttaaag   2760
caaaagtttc atttttttaaa catatataca aacaaactgg atttgaagga agggattaat   2820
tcccctgctc aaagtttgaa ttcctattgt gacctatact cgaataaaat tgaagcctaa   2880
ggaatgtatg agaaacaaga aacaaaaca aaactacaga caaacaagta caattacaa   2940
attcgctaaa attctgtaat caccaaaccc catctcagtc agcacaaggc caaggttta   3000
ttttgaaata aaaaaaaagt gattttattt ctcataagct aaaagaaaga aaggcaatta   3060
tgaaatgatt tcgactagat ctgaaagtcc aacgcgtatt ccgcagatat aaagaaaga   3120
gtagagttc acatggatcc tagatggacc cagttgagga aaaagcaagg caaagcaaac   3180
gcagaagtgc agatccgaaa ttgaaccacg gaatctagaa tttggtaggg ggagaagaaa   3240
agtaccttga gaggtagaag agaagagaag agcagagaga tatatgaacg agtgtgtctt   3300
ggtctcaact ctgaagcgat acgagtttag aggggagcat tgagttccaa tttatagggaa  3360
aaccgggtgg cagggggtgag ttaatgacgg aaaagcccct aagtaacgag attggattgt   3420
gggttagatt caaccgtttg catccgcggc ttagattggg gaagtcagag tgaatctcaa   3480
ccgttgactg agttgaaaat tgaatgtagc aaccaattga gccaaccccca gccttttgccc  3540
```

```
tttgattttg atttgtttgt tgcatacttt ttatttgtct tctggttctg actctctttc    3600
tctcgtttca atgccaggtt gcctactccc acaccactca caagaagatt ctactgttag    3660
tattaaatat tttttaatgt attaaatgat gaatgctttt gtaaacagaa caagactatg    3720
tctaataagt gtcttgcaac attttttaag aaattaaaaa aaatatattt attatcaaaa    3780
tcaaatgtat gaaaaatcat gaataatata attttataca ttttttttaaa aaatcttttta   3840
atttcttaat taatatctta aaaataatga ttaatattta acccaaaata attagtatga    3900
ttggtaagga agatatccat gttatgtttg gatgtgagtt tgatctagag caaagcttac    3960
tagagtcgac cgatccgtcg acgg                                           3984
```

```
SEQ ID NO: 11           moltype = DNA   length = 3162
FEATURE                 Location/Qualifiers
misc_feature            1..3162
                        note = synthesized DNA of PHP29882A
source                  1..3162
                        mol_type = other DNA
                        organism = synthetic construct
SEQUENCE: 11
cgcgccaagc ttttgatcca tgcccttcat ttgccgctta ttaattaatt tggtaacagt     60
ccgtactaat cagttactta tccttccccc atcataatta atcttggtag tctcgaatgc    120
cacaacactg actagtctct tggatcataa gaaaaagcca aggaacaaaa gaagacaaaa    180
cacaatgaga gtatcctttg catagcaatg tctaagttca taaaattcaa acaaaaacgc    240
aatcacacac agtggacatc acttatccac tagctgatca ggatcgccgc gtcaagaaaa    300
aaaaactgga cccccaaaagc catgcacaac aacacgtact cacaaggtg tcaatcgagc    360
agcccaaaac attcaccaac tcacccatc atgagccctc acatttgttg tttctaaccc    420
aacctcaaac tcgtattctc ttccgccacc tcatttttgt ttatttcaac acccgtcaaa    480
ctgcatgcca ccccgtggcc aaatgtccat gcatgttcaa aagacctatg actataaata    540
gctgcaatct cggcccaggt tttcatcatc aagaaccagt tcaatatcct agtacaccgt    600
attaaagaat ttaagatata ctgcggcccct aggtgagctg atttaagatt tatcaaaagt   660
tggggttaca aattttggaa gcttcagtgt ggaagtaata gacccagttt ctgactatct    720
ggagctattg gagacagtat ttgatttca gctaatcaga ggtcttcttt cacgtccaga    780
ttttaggttt atatttgatg ccatgcatgc agttactggt gcttatgcta aacccatctt    840
cgttgataaa ctcggtgcta gtctggattc aatttcaaat ggaatccctt tggaagattt    900
tggacatggc catcctgatc ctaatctaac atatgcgaag gatcttgtcg acattctgta    960
tgctgaaaat ggacctgatt ttgggagctgc cagtgatggg gatggtgata gaaatatgat   1020
tttaggaaga agtttctttg taactccttc agactcttga gcagttattg cagccaatgc    1080
aagagaagcg attccatact tcaagaacgg tgttaagggt cttgctcgat caatgccaac   1140
aagcggtgct ctggaccgtg ctgctaaaaa attgaacctc cctttctgag ctgatttaac    1200
gtacgcaggt aagtttctgc ttctaccttt gatatataaaa aatgtagtat cattaattg    1260
tagtaatata atatttcaaa tatttttttc aaaataaaag aatgtagtat atagcaattg    1320
cttttctgta gtttataagt gtgtatattt taatttataa cttttctaat atatgaccaa    1380
aacatggtga tgtgcaggtc ctgcaggtta aatcagctca gaaagggagg ttcaattttt    1440
tagcagcacg gtccagagca ccgcttgttg gcattgatcg agcaagaccc ttaacaccgt    1500
tcttgaagta tggaatcgct tctcttgcat tggctgcaat aactgctaca gagtctgaaa    1560
gagttacaaa gaaacttctt cctaaaatca tatttctatc accatcccca tcactggcag    1620
ctccaaaaatc aggtccattt tcagcataca gaatgtcgac aagatccttc gcatatgtta    1680
gattaggatc aggatggcca tgtccaaaat cttccaaagg gattccattt gaaattgaat    1740
ccagactagc accgagttta tcaacgaaga tgggttttagc ataagcacca gtaactgcat    1800
gcatggcatc aaatataaac ctaaaatctg gacgtgaaag aagacctctg attagctgaa    1860
aatcaaatac tgtctccaat agctccagat agtcagaaac tgggtctatt acttccacac    1920
tgaagcttcc aaaatttgta accccaactt ttgataaatc ttaaatcagc tcacctaggg    1980
ccgcagtgtat gaactaaaat gcatgtaggt gtaagagctc atggagagca tggaatattg    2040
tatccgacca tgtaacagta taataactga gctccatctc acttcttcta tgaataaaca    2100
aaggatgtta tgatatatta acactctatc tatgcaacctt attgttctat gataaatttc    2160
ctcttattat tataaatcat ctgaatcgtg acggcttatg gaatgcttca aatagtacaa    2220
aaacaaaatgt gtactataag acttttctaaa caattctaac cttagcattg tgaacgagac    2280
ataagtgtta agaagacata acaattataa tggaagaagt ttgtctccat ttatatatta    2340
tatattaccc acttatgtat tatattagga tgttaaggag acataacaat ataaagaga    2400
gaagtttgta tccattatata tattatatac tacccatttta tatattatac ttatccactt    2460
atttaatgtc ttttaaggt ttgatccatg atattcttaa atttttagtt gatatgtata    2520
tgaaagggta ctatttgaac tctcttactc tgtataaagg ttggatcatc cttaaagtgg    2580
gtctatttaa ttttattgct tcttacagat aaaaaaaaaa ttatgagttg gtttgataaa    2640
atattgaagg atttaaaata ataataaata acatataata tatgtatata aatttattat    2700
aatataacat ttatctataa aaaagtaaat attgtcataa atctatacaa tcgtttagcc    2760
ttgctggacg aatctcaatt attttaaacga gagtaaacat atttgacttt ttggtatt    2820
aacaaattat tatttaacac tatatgaaat tttttttttt atcagcaaag aataaaatta    2880
aattaagaag acaatggtg tcccaatcct tatacaacca acttccacaa gaaagtcaag    2940
tcagagacaa caaaaaaaca agcaaaggaa atttttttaat ttgagttgtc ttgttgctgt    3000
cataatttat gcagtaaaac actacacata accctttag cagtagagca atggttgacc    3060
gtgtgcttag cttcttttat tttattttt tatcagcaaa gaataaataa aataaaatga    3120
gacacttcag ggatgtttca acaagcttgg atccgtcgac gg                       3162
```

```
SEQ ID NO: 12           moltype = DNA   length = 9744
FEATURE                 Location/Qualifiers
misc_feature            1..9744
                        note = synthesized DNA of PHP29959A
source                  1..9744
                        mol_type = other DNA
                        organism = synthetic construct
SEQUENCE: 12
```

```
cgcgccggta ccgggccccc cctcgaggtc gacggtatcg ataagcttga tatcgaattc   60
ctgcagcccg ggggatccac tagttctaga gcggccgcgc cgtcgacgg  atataatgag  120
ccgtaaacaa agatgattaa gtagtaatta atacgtacta gtaaaagtgg caaaagataa  180
cgagaaagaa ccaatttctt tgcattcggc cttagcggaa ggcatatata agctttgatt  240
attttattta gtgtaatgat ttcgtacaac caaagcattt atttagtact ctcacacttg  300
tgtcgcggcc gctagtcgac taagtcatca actattccaa gctacgtatt tgggagtttg  360
tggagtacag caagatgata tacctagacg gtgatatcca agtttttgac aacattgacc  420
acttgtttga cttgcctgat aactacttct atgcggtgat ggactgtttc tgtgagccaa  480
cttggggcca cactaaacaa tatcagatcg gttactgcca gcagtgcccc cataaggttc  540
agtggcccac tcactttggg cccaaacctc ctctctattt caatgctggc atgtttgtgt  600
atgagcccaa tttggctact taccgtgacc tccttcaaac agtccaagtc acccagccca  660
cttcctttgc tgaacaggat tttttgaaca tgtacttcaa ggacaaatat aggccaattc  720
ctaatgtcta caatcttgtg ctggccatgc tgtggcgtca ccctgagaac gttgagcttg  780
acaaagttaa agtggttcac tactgtgctg ctgggtctaa gccttggagg tacactgagg  840
agtgactcga ggtcatcaat tactccaagc tacgtatttg ggagttcgtg gagtacaaga  900
agacgatata cctagacggt gacatccaag tatttggaaa catagaccac ttgtttgatc  960
tgcctgataa ttatttctat gcggtgatgg attgttctg  cgaagagact tggagccaca 1020
cccctcagtt ccagattggg tactgccaac agtgccctga taaggttcaa tggccctctc 1080
actttggttc caaacctcct ctatatttca atgctggcat gtttgtttat gagcctaatc 1140
tcgacacccta ccgtgatctt ctccaaactg tccaactcac caagcccact tcttttgctg 1200
agcaggactt tctcaacatg tacttcaagg acaagtacaa gccaataccg aacatgtaca 1260
accttgtgct ggccatgttg tggcgtcacc ctgaaaatgt gaacttgat aaagttcaag 1320
tggttcatta ctgtgctgct gggtctaagc cttggaggtt cactgggaag taactcagg  1380
tcatcaacta ctccaagctc cgtatatggg agtttgtgga gtacagcaag atgatatact 1440
tggacgagac cattgaggta tatgagaaca tagaccacct atttgaccta cctgatggta 1500
actttttacgc tgtgatggat tgtttctgcg agaagacatg gagtcacacc cctcagtaca 1560
aggtggggtta ctgccagcaa tgcccggaga aggtgcggtg gccaccgaa ttgggtcagc  1620
cccttctct ttacttcaac gctggcatgt tcgtgttcga acccaacatc gccacctatc  1680
atgacctatt gaaaacggtg caagtcacca ctcccacctc gttcgctgaa caagatttct 1740
tgaacatgta cttcaaggac atttacaagc caatcccttt aaattacaat cttgtcctcg 1800
ccatgctgtg gcgccacccg gaaaacgtta aattagacca agtcaaggtt gttcactatt 1860
gcgcagcggg gtccaagcca tggagatata cggggaagta gcctaggacc tgcacatcac 1920
catgttttgg tcatatatta gaaaagttat aaattaaaat atacacactt ataaactaca 1980
gaaaagcaat tgctatatac tacattcttt tattttgaaa aaaatatttg aaatattata 2040
ttactactaa ttaatgataa ttattatata tatatcaaag gtagaagcag aaacttacct 2100
gcgtacgcct aggctacttc cccgtatatc tccatggctt ggaccccgct gcgcaatagt 2160
gaacaacctt gacttggtct aatttaacgt tttccgggtg gcgccacagc atggcgagga 2220
caagattgta atttaaaggg attggcttgt aaatgtcctt gaagtacatg ttcaagaaat 2280
cttgttcagc gaacgaggtg ggagtggtga cttgcaccgt tttcaatagg tcatgatagg 2340
tggcgatgtt gggttcgaac acgaacatgc cagcgttgaa gtaaagagaa ggggctgac  2400
ccaattcggt gggccaccgc accttctccg gcattgctg  gcagtaaccc accttgtact 2460
gagggtgtg  actccatgtc ttctcgcaga aacaatccat cacagcgtaa aagttaccat 2520
caggtaggtc aaataggtgg tctatgttct catataccct aatgtctccg tccaagtata 2580
tcatcttgct gtactccaca aactcccata tacggagctt ggagtagttg atgacctgca 2640
gttacttccc agtgaacctc caaggcttag acccagcagc acagtaatga accacttgaa 2700
cttatcaag ttcaacattt tcagggtgac gccacaacat ggccagcaca aggttgtaca 2760
tgttcggtat tggcttgtac ttgtccttga agtacatgt gagaaagtcc tgctcagcaa 2820
aagaagtggg cttggtgagt tggacagttt ggagaagatc acggtaggtg tcgagattag 2880
gctcataaac aaacatgcca gcattgaaat atagaggagg tttggaacca aagtgagagg 2940
gccattgaac cttatcaggg cactgttggc agtacccaat ctggaactga ggggtgtggc 3000
tccaagtctt ctcgcagaaa caatccatca ccgcatagaa ataattatca ggcagatcaa 3060
acaagtggtc tatgtttcca aatacttgga tgtcaccgtc taggtatatc gtcttcttgt 3120
actccacgaa ctcccaaata cgtagcttgg agtaattgat gacctcgagt cacttcccag 3180
tgtacctcca aggcttagac ccagcagcac agtagtgaac cactttaact ttgtcaagct 3240
caacgttctc agggtgacgc cacagcatgg ccagcacaag attgtagaca ttaggaattg 3300
gcctatattt gtccttgaag tacatgttca aaaaatcctg ttcagcaaag gaagtgggct 3360
gggtgacttg gactgtttga aggaggtcac ggtaagtagc caaattgggc tcatacacaa 3420
acatgccagc attgaaatag agaggaggtt tgggcccaaa gtgagtgggc cactgaacct 3480
tatggggca ctgctggcag taaccgatct gatattgttt agttgtggcc caagttggct 3540
cacagaaaca gtccatcacc gcatagaagt agttatcagg caagtcaaac aagtggtcaa 3600
tgttgtcaaa aacttggata tcaccgtcta ggtatatcat cttgctgtac tccacaaact 3660
cccaaatacg tagcttggaa tagttgatga cttagtcgac tagcggccgc ttgggggct   3720
atggaagact ttcttagtta gttgtgtgaa taagcaatgt tgggagaatc gggactcttt 3780
ataggatagg aataaaacag aaaagtatta agtgctcatg aaatatttag actgataatt 3840
aaaatcttca cgtatgtcca cttgatataa aaacgtcagg aataaggaa  gtacagtaga  3900
atttaaaggt actcttttta tatataccgg tgttctcttt ttggctagct agttgcataa 3960
aaaataatct atatttttat cattatttta aatatcttat gagatggtaa atatttatca 4020
taatttttt tactattatt tattatttgt gtgtgtaata catatagaag ttaattacaa 4080
attttattta cttttttcatt attttgatat gattcaccat taattagttg ttattattta 4140
taatagttca ttttaatctt tttgtatata ttatgcgtgc agtactttttt tcctacatat 4200
aactactatt acattttatt tatataatat ttttattaat gaattttcgt gataatatgt 4260
aatattgttc attattattt cagattttt  aaaaatattt gtgttattat ttatgaaata 4320
tgtaattttt ttagtatttg attttatgat gataaagtgt tctaaattca aaagaagggg 4380
gaaa acattaaaaa acgtcatcaa acaaaaacaa aatcttgtta ataagataa           4440
aactgtttgt tttgatcact gttatttcgt aatataaaaa cattatttat atttatattg 4500
ttgacaacca aatttgccta tcaaatctaa ccaatataat gcatgcgtgg caggtaatgt 4560
actaccatga acttaagtca tgacataata aaccgtgaat ctgaccaatg catgtaccta 4620
nctaaattgt atttgtgaca cgaagcaaat gattcaattc acaatggaga tgggaaacaa 4680
ataatgaaga acccagaact aagaaagctt ttctgaaaaa taaaataaag gcaatgtcaa 4740
```

```
aagtatactg catcatcagt ccagaaagca catgatattt ttttatcagt atcaatgcag    4800
ctagttttat tttacaatat cgatatagct agtttaaata tattgcagct agatttataa    4860
atatttgtgt tattatttat catttgtgta atcctgtttt tagtatttta gtttatatat    4920
gatgataatg tattccaaat ttaaaagaag ggaaataaat ttaaacaaga aaaaagtca     4980
tcaaacaaaa aacaaatgaa agggtggaaa gatgttacca tgtaatgtga atgttacagt    5040
atttcttttta ttatagagtt aacaaattaa ctaaatatgat tttgttaata atgataaaat   5100
attttttta ttattatttc ataatataaa aatagtttac ttaatataaa aaaaattcta     5160
tcgttcacaa caaagttggc cacctaattt aaccatgcat gtacccatgg accatattag    5220
gtaaccatca aacctgatga agagataaag agatgaagac ttaagtcata acacaaaacc    5280
ataaaaaaca aaaatacaat caaccgtcaa tctgaccaat gcatgaaaaa gctgcaatag    5340
tgagtggcga cacaaagcac atgattttct tacaacggag ataaaaccaa aaaaatattt    5400
catgaacaac ctagaacaaa taaagctttt atataataaa tatataaata aataaaggct    5460
atggaataat atacttcaat atatttggat taaataaatt gttggcgggg ttgatatatt    5520
tatacacacc taaagtcact tcaatctcat tttcacttaa ctttttattttt tttttcttt   5580
ttatttatca taaagagaat attgataata tactttttaa cataattttta tgacattttt   5640
tattggtgaa aacttattaa aaatcataaa ttttgtaagt tagatttatt taaagagttc    5700
ctcttcttat tttaaattttt ttaataaatt tttaaatttgt gttaaaaatg              5760
ttaaaaaagt gtgttattaa cccttctctt cgaggatcca agcttggcgc gggccgcac     5820
cgcggtgggg tcgactctag taagcttgc tctagatcaa actcacatcc aaacataaca     5880
tggatatctt ccttaccaat catactaatt attttgggtt aaatattaat cattattttt    5940
aagatattaa ttaagaaatt aaaagatttt ttaaaaaaat gtataaaatt atattattca    6000
tgattttttca tacatttgat tttgataata aatatatttt ttaaatttttc tttaaaaaatg  6060
ttgcaagaca cttattagac atagtcttgt tctgtttaca aaagcattca tcatttaata    6120
cattaaaaaa tatttaatac taacagtaga atcttcttgt gagtggtgtg ggagtaggca    6180
acctggcatt gaaacgagag aaagagagtc agaaccagaa gacaaataaa aagtatgcaa    6240
caaacaaatc aaaatcaaag ggcaaaggct ggggttggct caattggttg ctacattcaa    6300
ttttcaactc agtcaacggt tgagattcac tctgacttcc ccaatctaag ccgcggatgc    6360
aaacggttga atctaaccca caatccaatc tcgttactta ggggcttttc cgtcattaac    6420
tcaccccctgc caccggttt ccctataaat tggaactcaa tgctcccctc taaactcgta    6480
tcgcttcaga gttgagacca agacacactc gttcatatat ctctctgcct ttctcttctc    6540
ttctacctct caaggtactt ttcttctccc tctaccaaat cctagattcc gtggttcaat    6600
ttcggatctt gcacttctgg tttgctttgc cttgctttt cctcaactgg gtccatctag     6660
gatccatgtg aaactctact cttttctttaa tatctgcgga atacgcgttg gactttcaga   6720
tctagtcgaa atcatttcat aattgccttt cttttctttta gcttatgaga aataaaatca   6780
cttttttttttt atttcaaaat aaaccttggg ccttgtgctg actgagatgg ggttggtga   6840
ttacagaatt ttagcgaatt ttgtaattgt acttgtttgt ctgtagtttt gttttgtttt    6900
cttgtttctc atacattcct taggcttcaa ttttattcga gtaggtca caataggaat      6960
tcaaactttg agcaggggaa ttaatcccctt ccttcaaatc cagttgttt gtatatatgt    7020
ttaaaaaatg aaacttttgc ttttaaattct attataactt ttttttatggc tgaaatttt    7080
gcatgtgtct ttgctctctg ttgtaaattt actgtttagg tactaactct aggcttgttg    7140
tgcagttttt gaagtataac catgccacac aacacaatgg cggccaccgc ttccagaacc    7200
acccgattct cttcttcctc ttcacacccc accttcccca aacgcattac tagatccacc    7260
ctccctctct ctcatcaaac cctcaccaaa cccaaccacg ctctcaaaat caaatgttcc    7320
atctccaaac cccccacggc ggcgcccttc accaaggaag cgccgaccac ggagcccttc    7380
gtgtcacggt tcgcctccgg cgaacctcgc aagggcgcgg acatccttgt ggaggcgctg    7440
gagaggcagg gcgtgacgac ggtgttcgcg taccccggcg gtgcgtcgat ggagatccac    7500
caggcgctca cgcgctccgc cgccatccgc aacgtgctcc cacacga gcagggcggc       7560
gtcttcgccg ccgaaggcta cgcgcgttcc tccggcctcc ccggcgtctg cattgccacc    7620
tccgccccg cgccaccaa cctcgtgagc ggcctcgccg acgctttaat ggacagcgtc      7680
ccagtcgtcg ccatcaccgg ccaggtcgcc cgccggatga tcggcaccga cgccttccaa    7740
gaaaccccga tcgtggaggt gagcagatcc atcacgacgc acaactacct catcctcgac    7800
gtcgacgaca tcccccgcgt cgtcgccgag gctttcttcg tcgccacctc cggccgcccc    7860
ggtccggtcc tcatcgacat tcccaaagac gttcagcagc aactcgccgt gcctaattgg    7920
gacgagcccg ttaacctccc cggttaccctc gccaggctgc ccaggccccc cgccgaggcc    7980
caattggaac acattgtcag actcatcatg gaggcccaaa agcccgttct ctacgtcggc    8040
ggtggcagtt tgaattccag tgctgaattg aggcgctttg ttgaactcac tggtattccc    8100
gttgctagca ctttaatggg tcttggaact ttttcctattg gtgatgaata ttccccttcag   8160
atgctgggta tgcatggtac tgtttatgct aactatgctg ttgacaatag tgatttgttt    8220
cttgcctttg gggtaaggtt tgatgaccgt gttactggga agcttgaggc ttttgctagt    8280
agggctaaga ttgttcacat tgatattgat tctgccgaga ttgggaagaa caagcaggcg    8340
cacgtgtcgg tttgcgcgga tttgaagttg gccttgaagg gaattaatat gattttggag    8400
gagaaaggag tggagggtaa gtttgatctt ggaggttgga gagaagagat taatgtgcag    8460
aaacacaagt ttccatttggg ttacaagaca ttccaggacg cgatttctcc gcagcatgct    8520
atcgaggttc ttgatgagtt gactaatgga tgctctattg ttagtactgg ggttgggcag    8580
catcaaatgt gggctgcgca gttttacaag tacaagagac cgaggcagtg gttgacctca    8640
gggggtcttg gagccatggg tttttggattg cctgcggcta ttggtgctgc tgttgctaac    8700
cctgggcctg ttgtggttga cattgatggg gatggtagtt tcatcatgaa tgttcaggag    8760
ttggccacta taagagtgga gaatctccca gttaagtat tgttgttgaa caatcagcat     8820
ttgggtatgg tggttcagtt ggaggataggg ttctacaagt ccaatagagc tcacacctat    8880
cttgagatcc cgtctagcga gagcgagata ttcccaaaca tgctcaagtt tgctgatgct    8940
tgtgggatac cggcagcgcg agtgacgaag aaggaagagc ttagcgcgc aattcagaga    9000
atgttggaca cccctggccc ctaccttctt gatgtcattg tgcccatca ggagcatgtg     9060
ttgccgatga ttcccagtaa tggatccttc aaggatgtga taactgaggg tgatggtaga    9120
acgaggtact gattgccttag accaaatgtt ccttgatgct tgttttgtac aatatatata   9180
agataatgct gtcctagttg caggatttgg cctgtggtga gcatcatagt ctgtagtagt    9240
tttggtagca agacattttta ttttccttttt atttaactta ctacatgcag tagcatctat  9300
ctatctctgt agtctgatat ctcctgttgt ctgtattgtg ccgttggatt ttttgctgta    9360
gtgagactga aaatgatgtg ctagtaataa tatttctgtt agaaatctaa gtagagaatc    9420
tgttgaagaa gtcaaaagct aatggaatca ggttacatat caatgttttt cttttttttag   9480
```

-continued

```
cggttggtag acgtgtagat tcaacttctc ttggagctca cctaggcaat cagtaaaatg   9540
catattcctt ttttaacttg ccatttattt acttttagtg gaaattgtga ccaatttgtt   9600
catgtagaac ggatttggac cattgcgtcc acaaaacgtc tcttttgctc gatcttcaca   9660
aagcgatacc gaaatccaga gatagttttc aaaagtcaga aatggcaaag ttataaatag   9720
taaaacagaa tagatgctgt aatc                                          9744
```